(12) United States Patent
Chen et al.

(10) Patent No.: US 6,399,762 B1
(45) Date of Patent: Jun. 4, 2002

(54) METHODS AND COMPOSITIONS FOR DIAGNOSING AND TREATING CHROMOSOME -18P RELATED DISORDERS

(75) Inventors: Hong Chen, Brookline, MA (US); Nelson B. Freimer, San Francisco, CA (US)

(73) Assignees: The Regents of the University of California, Oakland, CA (US); Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/657,474

(22) Filed: Sep. 7, 2000

Related U.S. Application Data

(60) Division of application No. 09/268,992, filed on Mar. 16, 1999, which is a continuation-in-part of application No. 09/236,134, filed on Jan. 22, 1999.
(60) Provisional application No. 60/078,044, filed on Mar. 16, 1998, provisional application No. 60/088,312, filed on Jun. 5, 1998, and provisional application No. 60/106,056, filed on Oct. 28, 1998.

(51) Int. Cl.[7] .......................... C07H 21/04; C07K 1/00; C12N 15/00; C12N 5/00; C12Q 1/68
(52) U.S. Cl. .................. 536/23.5; 536/24.3; 536/24.33; 536/23.1; 435/6; 435/320.1; 435/325; 530/350
(58) Field of Search ......................... 435/6, 320.1, 325; 536/23.1, 24.3, 24.33, 24.32, 23.4, 23.5; 530/350; 930/10

(56) References Cited

U.S. PATENT DOCUMENTS

| | | |
|---|---|---|
| 4,190,496 A | 2/1980 | Rubenstein et al. |
| 4,376,110 A | 3/1983 | David et al. |
| 4,656,127 A | 4/1987 | Mundy |
| 4,683,202 A | 7/1987 | Mullis |
| 4,745,051 A | 5/1988 | Smith et al. |
| 4,816,397 A | 3/1989 | Boss et al. |
| 4,816,567 A | 3/1989 | Cabilly et al. |
| 4,851,331 A | 7/1989 | Vary et al. |
| 4,873,191 A | 10/1989 | Wagner et al. |
| 4,946,778 A | 8/1990 | Ladner et al. |
| 5,075,217 A | 12/1991 | Weber |
| 5,364,759 A | 11/1994 | Caskey et al. |
| 5,585,089 A | 12/1996 | regQueen et al. |

FOREIGN PATENT DOCUMENTS

| | | |
|---|---|---|
| WO | WO88/04300 | 6/1988 |
| WO | WO88/09810 | 12/1988 |
| WO | WO89/10134 | 11/1989 |
| WO | WO90/11364 | 10/1990 |
| WO | WO91/02087 | 2/1991 |
| WO | WO92/15712 | 9/1992 |
| WO | WO95/00669 | 1/1995 |
| WO | WO95/11995 | 5/1995 |
| WO | WO 97/37043 | 10/1997 |
| WO | WO 98/42362 | 10/1998 |
| WO | WO 98/42724 | 10/1998 |

OTHER PUBLICATIONS

Shimizu–Matsumoto et al. An Expression Profile of Genes in Human Retina and Isolation of a Complementary DNA for a Novel Rod Photoreceptor Protein. Investigative Opthamology and Visual Science. vol. 38, pp. 2576–2585, Nov. 1997.*
Altschul, et al., 1990, J. Molec. Biol., 215:403–410.
Altschul et al. (1997) *Nucleic Acids Res.* 25:3389–3402.
Ausubel F.M. et al., eds., 1989, Current Protocols in Molecular Biology, vol. I, Green Publishing Associates, Inc., and John Wiley & sons, Inc., New York, at pp. 6.3.1–6.3.6 and 2.10.3.
Baron, et al., 1987, Nature 326, 289–292.
Baron, et al., 1993, Nature Genet. 3, 49–55.
M. Baron, *Molecular Psychiatry*, 2, 200–210 (1997).
Been and Cech, 1986, Cell, 47:207–216.
Benoist and Chambon, 1981, Nature 290:304–310.
Berrettini et al., 1994, "Chromosome 18 DNA Markers and Manic Depressive Illness: Evidence for a Susceptibility Gene", Proc. Natl. Acad. Sci. USA 91:5918–5921.
Bertelsen, et al., 1977, Br. J. Psychiat. 130, 330–351.
Bird, 1988, Science 242:423–426.
Bitter, et al., 1987, Methods in Enzymol. 153:516–544.
Black and Dolnick, 1996, "Expression of rTS Correlates with Altered Growth Regulation of Thymidylate Synthase", Cancer Res. 56:700–705.
Brinster, et al., 1982, Nature 296:39–42.
Butler, J.E., 1981, Meth. Enzymol. 73:482–523.
Campbell, et al., 1996, Nature 380:64–66.
Chien, et al., 1991, Proc. Natl. Acad. Sci. USA, 88:9578–9582.
Cohen et al., 1993, C.R. Acad. Sci. 316:1484–1488 (Abstract).
Colbère–Garapin, et al., 1981, J. Mol. Biol. 150:1–14.
Cote et al., 1983, Proc. Natl. Acad. Sci. USA 80:2026–2030.
Cole et al., 1985, Monoclonal Antibodies And Cancer Therapy, Alan R. Liss, Inc., pp. 77–96.
Creighton, 1983, "Proteins: Structures and Molecular Principles," W.H. Freeman & Co., N.Y., pp. 34–49.
Cronin, et al., 1996, Human Mutation 7:244–255.
Dolnick and Black, 1996, "Alternate Splicing of the rTS Gene Product and Its Overexpression in a 5–Fluorouracil––Resistant Cell Line", Cancer Res. 56:3207–3210.

(List continued on next page.)

*Primary Examiner*—Stephanie W. Zitomer
*Assistant Examiner*—Cynthia B. Wilder
(74) *Attorney, Agent, or Firm*—Pennie & Edmonds LLP

(57) ABSTRACT

The present invention relates of the mammalian HKNG1 gene, a gene associated with bipolar affective disorder (BAD) in humans. The invention relates, in particular, to methods for the diagnostic evaluation, genetic testing and prognosis of HKNG1 neuropsychiatric disorders including schizophrenia, attention deficit disorder, a schizoaffective disorder, a bipolar affective disorder or a unipolar affective disorder.

12 Claims, 89 Drawing Sheets

OTHER PUBLICATIONS

Dolnick et al., 1993, "Cloning and Characterization of a Naturally Occurring Antisense RNA to Human Thymidylate Synthase mRNA", Nucl. Acids Res. 21:1747–1752.
Errabolu, et al., Cloning of a cDNA encoding human centrin, and EF–hand protein of centrosomes and mitotic spindle poles,: *J. Cell Science* (1994), 107:9–16.
H. Ewald et al., Psychiatric Genetics, 7, 1–12 (1997).
Egeland, et al., 1987, Nature 325, 783–787.
Freimer and Reus, 1993, in *The Molecular and Genetic Basis of Neurological Disease*, Rosenberg, et al., eds., Butterworths, New York, pp. 951–965.
Freimer et al., 1996, Nature Genetics 12:436–441.
Freimer et al., 1996, Neuropsychiat. Genet. 67:254–263.
Gautier, et al., 1987, Nucl. Acids Res. 15:6625–6641.
GenBank Accession No. D63813.
Goodwin, et al., 1990, *Manic Depressive Illness*, Oxford University Press, New York.
Gordon, 1989, Transgenic Animals, Intl. Rev. Cytol. 115, 171–229.
Grompe, 1993, *Nature Genetics* 5:111–117.
Gu, et al., 1994, Science 265, 103–106.
Harlow and Lane 1988, "Antibodies: A Laboratory Manual", Cold Spring Harbor Laboratory Press, Cold Spring Harbor, New York.
Haseloff and Gerlach, 1988, Nature, 334:585–591.
Helene, 1991, Anticancer Drug Des., 6(6):569–584.
Helene, et al., 1992, Ann. N.Y. Acad. Sci., 660:27–36.
Houghten, et al., 1991, Nature, 354:84–86.
Huse, et al., 1989, Science 246:1275–1281.
Huston, et al., 1988, Proc. Natl. Acad. Sci. USA 85:5879–5883.
Innis, et al., PCR Protocols: A Guide to Methods and Applications, eds. Academic Press, Inc., New York, 1990.
Inouye and Inouye, 1985, Nucleic Acids Res. 13:3101–3109.
Inoue, et al., 1987, Nucl. Acids Res. 15:6131–6148.
Inoue, et al., 1987, FEBS Lett. 215:327–330.
Ishikawa, E. et al., (eds.), 1981, Enzyme Immunoassay, Kgaku Shoin, Tokyo.
Jalanko et al., 1992, *Clin. Chem.* 38:39–43.
Janknecht, et al., 1991, Proc. Natl. Acad. Sci. USA 88:8972–8976.
Karlin and Altschul (1990) *Proc. Natl. Acad. Sci. USA* 87:2264–2268.
JP 402092286 A, Ozawa et al., Production of Calmodulin, Apr. 3, 1990, Abstract only.
JP 02092286 A, Calmodulin Prepn.—by Culturing Transforming *E. Coli*, Apr. 3, 1990, Abstract only.
Karlin and Altschul (1993)*Proc. Natl. Acad. Sci. USA* 90:5873–5877.
Kelsoe, et al., 1989, Nature 342, 238–243.
Kohler and Milstein, (1975, Nature 256:495–497.
Kozor et al., 1983, Immunology Today 4:72–79.
Krol et al., 1988, BioTechniques(6:958–976) or intercalating agents (see, e.g., Zon, 1988, Pharm. Res. 5:539–549.
Lakso, et al., 1992, Proc. Natl. Acad. Sci. USA 89:6232–6236.
Lam, et al., 1991, Nature, 354:82–84.
Landegren et al., 1988, *Science* 241:1077–1080.
Lavitrano et al., 1989, Cell 57:717–723.
Lee et al., Molecular Cloning and Centrosomal Localization of Human Caltractin, Proc. Natl. Acad. Sci., USA, Dec. 1993, vol. 90, pp. 11039–11043.
Lemaitre, et al., 1987, Proc. Natl. Acad. Sci. U.S.A. 84:648–652.
Letsinger, et al., 1989, Proc. Natl. Acad. Sci. U.S.A. 86:6553–6556.
Levinson and Levitt, 1987, Am. J. Psychiat. 144, 415–426.
Lo, 1983, Mol. Cell. Biol. 3:1803–1814.
Logan and Shenk, 1984, Proc. Natl. Acad. Sci. USA 81:3655–3659.
Lowy, et al., 1980, Cell 22:817–823.
MacKinnon et al., *Annu. Rev. Neurosci.*, 20, 355–373 (1997).
Maggio, E. (ed.), 1980, Enzyme Immunoassay, CRC Press, Boca Raton, FL.
Maher, 1992, Bioassays 14(12):807–815.
Maier, et al., 1995, Psych. Res. 59, 7–15.
McInnes and Freimer, 1995, Curr. Opin. Genet. Develop., 5, 376–381.
McInnes et al., *Proc. Natl. Acad. Scie. U.S.A.* 93:13060–13065.
Morrison, et al., 1984, Proc. Natl. Acad. Sci., 81:6851–6855.
Murray, et al., 1994, Science 265, 2049–2054.
Myers and Miller, (1988) *CABIOS* 4:11–17.
Neuberger, et al., 1984, Nature 312:604–608.
Nickerson et al., 1990, Proc. Natl. Acad. Sci. U.S.A. 87:8923–8927.
Nuovo, G.J., 1992, "PCR In Situ Hybridization: Protocols And Applications", Raven Press, NY.
Ogawa et al., CDNA Sequence for Mouse Caltractin, Biochem. Biophys. Acta., 1993, vol. 1216, pp. 126–128.
Orita et al., 1989,*Proc. Natl. Acad. Sci. USA* 86:2766–2770.
Pastinen et al., 1996, *Clin. Chem.* 42:1391–1397.
Pastinen et al., 1997, *Genome Res.* 7:606–614.
Pauls, et al., 1992, Arch. Gen. Psychiat. 49, 703–708.
Pauls, et al., 1995, Am. J. Hum. Genet. 57, 636–643.
Platt, 1994, J. Biol. Chem. 269, 28558–28562.
Roberts et al., 1989, Proc. Natil. Acad. Sci: USA 86:32–36.
Rosenthal, et al., 1980, Arch. General Psychiat. 37, 804–810.
Rossi, 1994, Current Biology 4:469–471.
Santerre, et al., 1984, Gene 30:147–156.
Sarin, et al., 1988, Proc. Natl. Acad. Sci. U.S.A. 85:7448–7451.
Sarver, et al., 1990, Science 247, 1222–1225.
Shimizu–Matsumoto, A. et al., 1997, Invest. Opthalmol. Vis. Sci. 38:2576–2585.
A. Shimizu–Matsumoto et al., Isolation and Chromosomal Localization of the Human Conge cGMP Phosphodiesterase Gamma cDNA (PDE6H), Genomics, 121–124 (1996).
Shumaker et al., 1996, *Hum. Mutation* 7:346–354.
Smith, et al., 1983, J. Virol. 46:584–593.
Smithies, et al., 1985, Nature 317:230–234.
Songyang, et al., 1993, Cell 72:767–778.
Stein, et al., 1988, Nucl. Acids Res. 16:3209–3221.
Straub, et al., 1994, Nature Genet. 8, 291–296.
Szybalska and Szybalski, 1962, Proc. Natl. Acad. Sci. USA 48:2026–2039.
Thomas and Capecchi, 1987, Cell 51:503–512.
Thompson, et al., 1989, Cell 56:313–321.
Van Heeke and Schuster, 1989, J. Biol. Chem. 264:5503–5509.
Van der Putten, et al., 1985, Proc. Natl. Acad. Sci., USA 82:6148–6152.
Voller, A. et al., 1978, J. Clin. Pathol. 31:507–520.

Voller, A., "The Enzyme Linked Immunosorbent Assay (ELISA)", 1978, Diagnostic Horizons 2:1–7, Microbiological Associates Quarterly Publication, Walkersville, MD.

Weintraub, H., 1985, Trends in Genetics, 1:22–28.

Wigler, et al., 1977, Cell 11:223–232.

Wigler, et al., 1980, Proc. Natl. Acad. Sci. USA 77:3567–3570.

Wilmut, et al., Nature 385:810–813.

Yamamoto, et al., 1980, Cell 22:787–797.

Young et al., 1998, *American Journal of Human Genetics* 63:109–119.

Zaug, et al., 1984, Science, 224:574–578.

Zaug and Cech, 1986, Science, 231:470–475.

Zaug, et al., 1986, Nature, 324:429–433.

Zon, 1988, Pharm. Res. 5:539–549.

D18S1140 Chromosomal MNW (Database ID: AFM287WE1).

D18S59 Chromosomal MNW (Database ID: AFM178XC3).

GenBank Accession No. D63813.

Accession No. AI737517, Vanderbosch et al., ESTs from uninoculated roots of Medicago truncatula (unpublished Jun. 16, 1999), 4 pages.

Ahern, H., Biochemical, Reagent Kits Offer Scientists Good Return on Investment, The Scientist, Jul. 1995, vol. 9, No. 15, 5 pages.

Hampson, R. M. et al., Mapping Studies on a Pericentric Inversion (18) (p11.31 q21.1) in a Family with Both Schizophrenia and Learning Disability, Am. J. Human Genetics, 1997, vol. 61, pp. 1397–1404.

McMahon, F. et al., Linkage of Bipolar Affective Disorder to Chromosome 18 Markers in a New Pedigree Series, Am. J. Human Genetics, 1997, vol. 61, pp. 1397–1404.

Wildenauer, D. B. et al., Do Schizophrenia and Affective Disorder Share Susceptibility Genes?, Psychiatric Genetics, 1997, vol. 7, pp. 1–12.

\* cited by examiner

```
TGCGTCACCTGCAGGCCCGGGGCCGCGGGGTTGGTTTTCCACCCTGGAGGTTGCTGACACCCTGTGCCCTCGGCTGACTTC

CAGCCGGTGGCACAGACGCCTCCAGGGGCAGCACTCAAGGCATCTTAGGAATGACAGAGTTGCGTCCCTCTGTTG

CCAGGCTGGAGTTCAGTGGCATGTTCTTAGCTCACTGAAGCCTCAAATTCCTGGGTTCAGTGACCCTCCCACCTCAGC

M   K   I   K   A   E   K   N          8
CCCATGAGGACCTGGGACTACAGGACACAGCTAAATCCCTGACACGG ATG AAA ATT AAA GCA GAG AAA AAC   24

E   G   P   S   R   S   W   W   Q   L   H   V   F   I   A   N   N   S   G    28
GAA GGT CCT TCC AGA AGC TGG TGG CAA CTT CAC GTT CAA ATT GCA AAT AAC AGC GGG     84

N   M   K   P   P   L   V   F   I   V   C   L   L   W   L   K   D   S   H    48
AAC ATG AAG CCG CCA CTC GTG TTT ATT GTG TGT CTG CTG TGG TTG AAA GAC AGT CAC    144

C   A   D   T   W   K   D   K   T   A   I   S   E   N   L   K   S   F   S    68
TGC GCA GAC ACT TGG AAG GAC AAA ACT GCT ATC AGT GAA AAC CTG AAG AGT TTT TCT    204

V   G   E   I   D   A   D   E   E   R   K   E   V   K   K   A   L   T   G    88
GTG GGG GAG ATA GAT GCA GAT GAA GAG AGA AAA GAG GTG AAG AAG GCT TTG ACT GGT    264

K   I   M   E   R   K   Q   E   A   L   K   L   N   L   M   S   T   L   K    108
AAA ATC ATG GAA AGA AAG CAG GAG GCC CTG AAA CTT AAT CTA ATG AGC ACC CTG AAG    324

C   R   E   E   K   Q   E   E   K   L   N   E   V   Q   E   H   L   E        128
TGC AGA GAA GAA AAG CAG GAG GAA GTT CAA GAA CAT CTG GAG                         384

E   E   R   L   C   R   E   S   L   A   D   S   W   G   E   C   R   S   C    148
GAA GAA AGG CTA TGC CGG GAG TCT TTG GCA GAT TCC TGG GGT GAA TGC AGG TCT TGC    444
```

FIG.1A

| | | | | | | | | | | | |
|---|---|---|---|---|---|---|---|---|---|---|---|
| L | E | N | N | C | M | R | I | Y | T | T | C | Q | P | S | W | S | S | V | K | 168 |
| CTG | GAA | AAT | AAC | TGC | ATG | AGA | ATT | TAT | ACA | ACC | TGC | CAA | CCT | AGC | TGG | TCC | TCT | GTG | AAA | 504 |
| N | K | I | E | R | F | F | R | K | I | Y | Q | F | L | F | P | F | H | E | D | 188 |
| AAT | AAG | ATT | GAA | CGG | TTT | TTT | AGG | AAG | ATA | TAT | CAA | TTT | CTA | TTT | CCT | TTC | CAT | GAA | GAT | 564 |
| N | E | K | D | L | P | I | S | E | K | L | K | L | I | E | D | A | Q | T | Q | 208 |
| AAT | GAA | AAA | GAT | CTC | CCC | ATC | AGT | GAA | AAG | CTC | AAG | CTC | ATT | GAG | GAT | GCA | CAA | ACC | CAA | 624 |
| M | E | D | V | F | S | Q | M | Q | Q | L | T | V | D | N | S | L | F | N | R | S | F | 228 |
| ATG | GAG | GAT | GTG | TTC | AGC | CAG | ATG | CAG | CAG | TTG | ACT | GTG | GAT | AAT | TCT | CTC | TTT | AAC | AGG | AGT | TTT | 684 |
| N | V | F | R | Q | E | F | D | Q | T | F | Q | A | S | H | F | I | S | 248 |
| AAC | GTC | TTC | AGA | CAG | GAG | TTT | GAC | CAG | ACT | TTT | CAA | GCT | TCA | CAT | TTC | ATA | TCA | 744 |
| D | T | D | L | T | E | P | Y | D | I | P | N | F | F | T | I | K | F | Q | L | M | T | K | 268 |
| GAT | ACA | GAC | CTA | ACT | GAG | CCT | TAC | GAC | ATT | CCC | AAC | TTC | TTT | ACT | ATT | AAG | TTC | CAG | CTG | ATG | ACA | AAA | 804 |
| A | D | Q | C | W | S | E | T | I | T | G | H | Q | L | M | I | K | A | I | E | D | 288 |
| GCA | GAT | CTT | GAG | CAA | TGT | TGG | TCT | GAA | ACA | ATT | ACT | GGA | CAC | CAG | CTG | ATG | AAG | GCA | ATA | GAA | GAT | 864 |
| V | S | I | Y | E | S | V | K | A | P | D | H | G | Q | L | S | K | M | L | I | P | G | 308 |
| GTC | TCT | ATT | TAT | GAA | AGT | GTC | AAA | GCT | CCT | GAC | CAC | GGA | CAG | CTG | TCA | AAG | ATG | TTA | CCT | GGG | 924 |
| L | P | K | Q | D | K | Q | L | G | N | L | Q | N | F | C | A | R | F | K | 328 |
| TTA | CCA | AAA | CAA | GAC | AAA | CAA | GGC | CTG | AAT | CTG | ATT | TCA | AGA | TGT | TTC | AAA | 984 |
| Q | D | R | G | L | C | Q | G | D | L | E | Q | N | L | S | R | C | F | K | H | 348 |
| CAG | GAC | AGA | GGA | CTG | TGT | CAG | GGA | GAC | CTT | GAA | CAG | AAT | TTG | TCA | AGA | TGT | TTC | AAA | CAT | 1044 |

FIG.1B

| | | | | | | | | | | | |
|---|---|---|---|---|---|---|---|---|---|---|---|
| E | K | C | Q | K | C | Q | A | H | L | S | E | D | C | P | D | V | P | A | L | 368 |
| GAA | AAA | TGC | CAA | AAA | TGT | CAG | GCT | CAC | CTA | TCT | GAA | GAC | TGT | CCT | GAT | GTA | CCT | GCT | CTG | 1104 |

| H | T | E | L | D | E | A | I | R | L | V | N | S | V | N | Q | Q | Y | G | Q | 388 |
| CAC | ACA | GAA | TTA | GAC | GAG | GCG | ATC | AGG | TTG | GTC | AAT | GTA | TCC | AAT | CAG | CAG | TAT | GGC | CAG | 1164 |

| I | L | Q | M | T | R | K | H | L | E | D | T | A | Y | L | V | E | K | M | R | 408 |
| ATT | CTC | CAG | ATG | ACC | CGG | AAG | CAC | TTG | GAG | GAC | ACC | GCC | TAT | CTG | GTG | GAG | AAG | ATG | AGA | 1224 |

| G | Q | F | G | W | V | S | E | L | A | N | Q | A | P | E | T | E | I | I | F | 428 |
| GGG | CAA | TTT | GGC | TGG | GTG | TCT | GAA | CTG | GCA | AAC | CAG | GCC | CCA | GAA | ACA | GAA | ATC | ATC | TTT | 1284 |

| N | S | I | Q | V | V | P | R | I | H | E | G | N | S | S | N | F | T | L | T | 448 |
| AAT | TCA | ATA | CAG | GTA | GTT | CCA | AGG | ATT | CAT | GAA | GGA | AAT | TCC | TCT | AAT | TTC | ACA | CTC | ACA | 1344 |

| M | M | T | D | L | S | A | E | S | S | N | F | P | G | Y | V | V | A | K | A | L | E | 468 |
| ATG | ATG | ACA | GAC | TTA | AGC | ATT | CTG | CCT | TCC | TCT | AAT | TTC | ATT | GGC | TAC | GTA | GTG | GCA | AAA | CTC | CTT | GAA | 1404 |

| E | S | A | E | S | S | N | F | I | G | Y | V | V | A | K | A | L | Q | H | F | 488 |
| GAA | AGT | GCT | GAG | AGT | TCT | AAC | TTC | ATT | GGC | TAC | GTA | GTG | GCA | AAA | GCT | CTA | CAG | CAT | TTT | 1464 |

| K | E | H | F | K | T | W | * | | | | | | | | | | | | | 496 |
| AAG | GAA | CAT | TTT | AAA | ACC | TGG | TAA | | | | | | | | | | | | | 1468 |

GAAGATCTAATGCATCCTATATCCAGTAAGTAGAATTATCTCTTCATCTGGGACCTGGAAATCCTGAAATAAAAAGGA
TAATGCAATAAACACAGTTGCAGGAAAGTATGTTAGCTATATACTATGAAGTACTCTTAGTTTACTTATGTTGAATGGC
TTAGCTATTAAATACTCAAATTGAGTTAAAATGAAAATTCCTCCTTAAAAAATCAAACGTAATATGTATTACATTTCATG
GTACATTAGTAGTTCTTTGTATATTGAATAAATACTAAATCACCTA

FIG.1C

```
TGGGTCACCTGCAGGCCCGGGCCCGCGGGGTTGGTTTCCACCCTGGAGGTTGCTGACACCCTGTGCCCTGGCTGACTTC
CAGCCGGTGGCACAGAGCCTCCAGGGGCAGCACTCAAGGCATCTTAGGAATGACAGAGTTGCGTCCCTCTCGGTTG
CCAGGGCTGGAGTTCAGTGGCATGTTCATAGCTCACTGAAGCCTCAAATTCCTGGGTTCAAGTGACCCTCCTACCTCAGC
```

| | | | | | | | | | | | | | | | | | | | | |
|---|---|---|---|---|---|---|---|---|---|---|---|---|---|---|---|---|---|---|---|---|
| M | R | T | D | Y | S | N | S | G | N | M | K | P | P | L | L | V | F | 19 | | |
| CCC | ATG | AGG | ACC | TGG | GAC | TAC | AGT | AAC | AGC | GGG | AAC | ATG | AAG | CCG | CCA | CTC | TTG | GTG | TTT | 57 |
| I | V | C | L | L | W | L | K | D | S | H | C | A | P | T | W | K | D | K | T | 39 |
| ATT | GTG | TGT | CTG | CTG | TGG | TTG | AAA | GAC | AGT | CAC | TGC | GCA | CCC | ACT | TGG | AAG | GAC | AAA | ACT | 117 |
| A | I | S | E | N | L | K | S | F | S | E | V | G | E | I | D | A | D | E | E | 59 |
| GCT | ATC | AGT | GAA | AAC | CTG | AAG | AGT | TTT | TCT | GAG | GTG | GGG | GAG | ATA | GAT | GCA | GAT | GAA | GAG | 177 |
| V | K | K | A | L | T | G | I | K | Q | M | K | R | E | E | K | Q | E | R | K | 79 |
| GTG | AAG | AAG | GCT | TTG | ACT | GGT | ATT | AAG | CAA | ATG | AAA | AGG | GAA | GAG | AAG | CAG | GAG | AGG | AAG | 237 |
| E | H | T | N | L | M | S | T | L | K | K | C | R | E | E | E | R | L | C | R | 99 |
| GAA | CAC | ACC | AAT | CTA | ATG | AGC | ACC | CTG | AAG | AAA | TGC | AGA | GAA | GAA | GAA | AGG | CTA | TGC | CGG | 297 |
| K | L | N | E | V | Q | E | C | R | S | C | L | E | N | N | C | M | R | I | Y | 119 |
| AAA | CTT | AAT | GAA | GTT | CAA | GAA | TGT | AGG | TCT | TGC | CTG | GAA | AAT | AAC | TGC | ATG | AGA | ATT | TAT | 357 |
| L | A | D | S | W | G | E | C | R | S | S | V | K | N | K | I | E | R | F | F | R | K | 139 |
| TTG | GCA | GAT | TCC | TGG | GGT | GAA | TGC | AGG | TCT | TCT | GTG | AAA | AAT | AAG | ATT | GAA | CGG | TTT | TTC | AGG | AAG | 417 |
| T | T | C | Q | P | S | W | | | | | | | | | | | | | | | | 159 |
| ACA | ACC | TGC | CAA | CCT | AGC | TGG | | | | | | | | | | | | | | | | 477 |

FIG.2A

```
I   Y   Q   F   L   F   P   F   H   E   D   N   E   K   D   L   P   I   S   E   179
ATA TAT CAA TTT CTA TTT CCT TTC CAT GAA GAT AAT GAA AAA GAT CTC CCC ATC AGT GAA  537

K   L   I   E   E   D   A   Q   L   T   Q   M   E   D   V   F   S   Q   L   T   199
AAG CTC ATT GAG GAA GAT GCA CAA TTG ACC CAA ATG GAG GAT GTG TTC AGC CAG TTG ACT  597

V   D   V   N   S   L   F   N   R   S   F   N   V   F   D   M   Q   E   Y   E   219
GTG GAT GTG AAT TCT CTC TTT AAC AGG AGT TTT AAC GTC TTC GAT ATG CAG CAA TAC GAG  657

F   D   Q   T   F   Q   S   M   F   I   S   D   T   D   L   T   E   P   Y   F   239
TTT GAC CAG ACT TTT CAA TCA CAT TTC ATA TCA GAT ACA GAC CTA ACT GAG CCT TAC TTT  717

F   P   A   S   K   E   P   M   T   K   A   D   L   E   Q   C   W   D   I   259
TTT CCA GCT TTC TCT AAA GAG CCG ATG ACA AAA GCA GAT CTT GAG CAA TGT TGG GAC ATT  777

P   N   F   F   Q   L   F   C   N   F   S   V   S   I   Y   E   S   V   S   E   279
CCC AAC TTC TTC CAG CTG TTT TGT AAT TTC AGT GTC TCT ATT TAT GAA AGT GTC AGT GAA  837

T   I   T   K   M   L   K   A   I   E   D   L   P   K   Q   D   K   A   P   D   299
ACA ATT ACT AAG ATG CTG AAG GCA ATA GAA GAT TTA CCA AAA CAA GAC AAA GCT CCT GAC  897

H   G   G   L   S   K   M   L   P   G   Q   R   G   L   C   G   E   L   319
CAC GGA GGC CTG ATT TCA AAG ATG TTA CCT GGG CAG AGA GGA CTG TGT GGG GAA CTT     957

D   Q   N   L   S   R   C   F   K   F   H   E   K   C   Q   K   C   Q   A   H   339
GAC CAG AAT TTG TCA AGA TGT TTC AAA TTT CAT GAA AAA TGC CAA AAA TGT CAG GCT CAC 1017

L   S   E   D   C   P   D   V   P   A   L   H   T   E   L   D   E   A   I   R   359
CTA TCT GAA GAC TGT CCT GAT GTA CCT GCT CTG CAC ACA GAA TTA GAC GAG GCG ATC AGG 1077
```

FIG.2B

```
  L   V   N   V   S   N   Q   Q   Y   G   Q   I   L   Q   M   T   R   K   H   L   379
 TTG GTC AAT GTA TCC AAT CAG CAG TAT GGC CAG ATT CTC CAG ATG ACC CGG AAG CAC TTG  1137

E   D   T   A   Y   L   V   E   K   M   R   G   Q   F   G   W   V   S   E   L   399
 GAG GAC ACC GCC TAT CTG GTG GAG AAG ATG AGA GGG CAA TTT GGC TGG GTG TCT GAA CTG  1197

A   N   Q   A   P   E   T   E   I   I   F   N   S   I   Q   V   V   P   R   I   419
 GCA AAC CAG GCC CCA GAA ACA GAG ATC ATC TTT AAT TCA ATA CAG GTA GTT CCA AGG ATT  1257

H   E   G   N   I   S   K   Q   D   E   T   M   M   T   D   L   S   I   L   P   439
 CAT GAA GGA AAT ATT TCC AAA CAA GAT GAA ACA ATG ATG ACA GAC TTA AGC ATT CTG CCT  1317

S   S   N   F   T   L   K   I   P   L   E   E   S   A   E   S   S   N   F   I   459
 TCC TCT AAT TTC ACA CTC AAG ATC CCT CTT GAA GAA AGT GCT GAG AGT TCT AAC TTC ATT  1377

G   Y   V   A   K   A   L   Q   H   F   K   E   H   F   K   T   W   *           478
 GGC TAC GTA GCA AAA GCT CTA CAG CAT TTT AAG GAA CAT TTT AAA ACC TGG TAA           1434

GAAGATCTAATGCATCCTATATCCAGTAAGTAGAATTATCTCTTCATCTGGGACCTGGAAATCCTGAAATAAAAAGGA

TAATGCAATAAACACAGTTGCAGGAAGTATGTTAGCTATATACTATGAAGTACTCTTAGTTTACTTATGTTGAATGGC

TTAGCTATTAATACTCAAATTGAGTTAAAATGAAAATTCCTCCTTAAAAAATCAAACGTAATATGTATTACATTTCATG

GTACATTAGTAGTTCTTTGTATATTGAATAAATACTAAATCACCTA
```

FIG.2C

```
ACATTTAAGCTACTTATAGTCCTTGGAAATAGCAACAAATATCTTAGTATTATTGGACTATTATAACCTTAGTCATCTTATTACTGCTTG
ATTATGAGACACTCTCCCTGCTAATCCTTAGAACATCTTGGTTCTTGGTTACTTGACTTTTAGCCCCTCTGACATATAGTTGATGTCAGA
GTGTCTGGCATTTCAGTAGTGCTCTATTTTACAAATCCCAGTAAACTGCTCCACTGTGTTATGTGTTAATACTGCTTGTTTTC
TGTTATAAATTATTTTTGCTTGGAGTAAGATATCATCATTTGCATAGCTACAAATCTGAAGTTAAAGAAAATTTAAAAATGTAAT
TGTGGGAAATAACAAATAGATCTGCTGAGATGGAGGCTTTGACTAATGTTTTAATAACAGGCAACAAAACAAAGAGGCAGGATATTTT
GGTCACAACTAAACCTAAATTAAATCCTCATACAAAGCCCATTAAGATAAATGCTCAAATTCTGGGAACATTTCACTTGCTTTGCCAG
CAATTTACCCTTCAGAGGGTGTGGATCTAATCAGGGGAACAAACTACCCTGGGCTTAATTCTCATTAACAGGGACTAATTGTCAAAG
CGGCAGTACTAGCTGAAGTGATGGGTATGGAAGCATTCACTGTGGAGATTTTGCTGAGGTGCCTGGCACAGGGTAGGGAACTCACCCA
GGCTGCAAGATGCTAACAGTTCAGGTTCAAGGTCTTAGTGTGGACTAAGGTGCAGTCAGGATGGGAACAGGTGCAACTTGGGCCAACAT
CAGTGAAGGGCCTGATCTGAGGGCAGGGAGGGGGCATTCTGGGAAGCAAGAGTTCCTGGTATCCTGTTGACCAGAGTCTTGG
CCCAAGGATCAACGTATGAATTAAGGTAGAAATACCAGAAACAAAGAAAAGTTGGCAGAAGAACCAGGCTGAAGCCCAGTGGTTGGGCTGGCCACA
ACTGGCTCAGCCTTGGCTACTGGCCCGGCAGATGATAGAAGAGAAAACCAGGAACCCAGGCTGAAGCCCAGTGGTTGGGCTGGCCACA
CACCATGCCAGCCATAGCCTTAAAGGGGTGGCCTAAGGCATGGTCCGCTCAATAGTGCATTCTCCTGCTTCTCAATAGGCTAATACTCTAGAGAATATTCTGAATCCACTC
ACTGCCAGGGAAGAACCTCAATTCACTCAATGTGGCGTTTGAATTTTAAGATAAGTTAATCATACATTGGCTGGGTCAGCATGTCTCTTAG
GAGGAGGGTCTAGTGGAACAGGTCTAAACTGGGAACAACACAAAAAATTCAATGAAATCTACAGACACCTATTTGCAGATGAGGAAACACGGCTATGAAGATTGGGAA
TCTTTACAAAAGTAGAACACACAAAAAATTCAATGAAATCTACAGACACCTATTTGCAGATGAGGAAACACGGCTATGAAGATTGGGAA
GATTGGGAAGAACTGGCCAGGTGTGCTCACGCTGTAATCCCAGCACTTTGGGAGGCCGAGGCTGGTGGATCACTTGAGGTCAGGA
GTTGGAGACCAGCCTGGGCAACATAGTAAAACCCTGTCTCTACTCAAATTACAAAAATTAGCCGGGCGTGGTGGTGCCACCTGTAATC
CCAGCTATGCAGGAGGCTGAGGCAGGAGAATCACTTGAACCTGGTAGGCGGAGGTTGCAGTGAGCCAAGATCACGCCACTGTACTCCAG
CCTGGGTGACAGAGCAAGACTTTGTTTAAAAAAAAAAAAAACCCATGAAGAACTAAAAATGTAATTTTCAAGGGCTATCACAAATGGT
CCCAATAACAGAGAAAGCAGGACTCATGTTTAAGAAGGGCTAAGGATGAAAATACAACAGTAATAAGGTATTAATATATTAAGAAAGCTAATGATCTA
CGTAACAGATGAAAAGCAGAGCATAGGGACTTTTTTTTTCTTAAGGATATCTTAAAGATAAAATTGAGAAGACATAGAAAGGGATAGGTCC
ACATAAGCAGAGGACATTAAAGGGACTTTTTTTTCTTAAGGATATCTTAAAGATAAAATTGAGAAGACATAGAAAGGGATAGGTCCAAC
TCTTGGGATTGTTGCAGGTTGGTTTTCCATGGAACCAGGACTGGGCAGGACTGGGCAGAGGCTGGGCTGTAACCAGTCACAACAAAGGTGTCAGCTGGTCCCA
TCACCCAGGTGGGGAGGAGGAGGGAACCAGGACTGGGCAGGACTGGGCTGTAACCAGTCACAACAAAGGTGTCAGCTGGTCCCA
TGGTGAATTCTGAGCTAGGATGGCTGATCCCAAGGCATTCCAAACTGGGGCAAGGAAGTTGTGCTTTAAAACTTCTCATTGACTGTCA
GTCACTGGGCATGGCAGTCCCCAGGAAGGGGATGACCTTGAGCAAGGTGGATGTCTTCAGCCAAGGCAAYCACTGGGAAGGAGAA
CCCAGCTATGAACTGTCAGCTGCCAACACTCCCAGCATCCCAGATGAGGGCTTCAATTCTAAGGGCAGGGGCTCAAGGGCAGGGG
TACGGATGGTGGAATCTGGGCAGTACCTTGTGGCTTCCACTACAGTCCACCCCTTGCACCACTTAGTTCCACTGGCTTTTTTTTT
```

FIG.3A

```
TTCTTTTCTGAGACAGTCTCACTCTGTCACCCAGGCTGGAGTGCGGTGGCAGATCTCGGCTCGTCGCAACCTCCGCCTCCCAGGTTCA
AGCAATTCTTGAACCTCCTGAGTAGCTGGGACTACAGATGTGTGCCACCACACCCAGCTAATTTTTGTATTTTAGTAGAGACGGGGT
TTTACCGTGTTAGCCAGGATTGGTCTCGATCTCCTGACCTCATGATCCGCCTGCTTTGCCTCCCAAAGTGCTGGGATTACAGGTGTGAG
CCACCGCACACAGCCAGATCCACTGGCTTCTATATAATTTCTGGGTGAAGCTAATTCAGGATTCTGATGGACCTGTCTTCCCGAGGGAA
ACTTGTAAAAGGAAAGTTAGAGGGACAAACTATAGCCCCTGCCACAGCAGCTGCTGTGCAGGACAAAATGGTGCTCCTCATTTCCCT
AACCACCTGACCTAGATTCCCCTAGTGGGCACCTCTGTGAATGGAAGTGGTGGCTCACYKGKKGGRWKRWYCMRRWYYCWYM
YCCCTGAGTGGTCTGAGCTCCCAGTTACCAGGCCCTTCCAGGCTGTGGCTGTTGCACTTACCTCCCCAGCCATCCCCCACTTTTTT
CTTGAGACTGGGTCTTGCTCTGTCACCCAGGCTGGAAATGCAGTGGCATAACCTCAGCTCACTGCAGCCTTGATCTCCCAAGCTCAAGCC
ATCTTCTCACCTCTGCCTCCCAAGTGGCTGGGACTACAGGCACATGCCACCATGCCCAGCTAATTTTTTATTTTTATTTTTTGTA
GCAATGGGATTTTGCCATGTTCCCAGGCTGGCTTGAACTCCTAAGCTATCCTCCCACCTCTGCTTCCCAAGTGCTGGGAT
TACAGGCTTGAGTCACTGCATCTGGCCACATTATTCCTTTAAACGTTAAAATTGAATGCAGGATCACTGAGAGACAGGTGAGTGATT
ACCAGGGTGCCAAACATACCCTTCTCCTTTCCTGCAGCTCTACCTCCTGATGATCAGGACAATCATGTATGATGACTCCTTTC
CTTGACTGCTGCTCTCTCAGAAGGAACCCATCTTTAAATGCACAGAGTCCAAAGTCGTGGGAACCAAAGCAGAAATTAAAAGGAGATGACT
AGAAGCATTCCCTCCTCTGGGGCCAAGATCTTTCCACCCTGATTTGCTGCACATGCATTCTCACTGGTGTTCTACCTAGGAGATAGCACACCATATACTGGTTATTCAT
GGGATTATGGTAAGAACTGTTTCCACCCTGATTTGCTGCACATGCATTCTCACTGGTGTTCTACCTAGGAGATAGCACACCATATACTGGTTATTCAT
TGGATTACATGCTGCATCCGGAGAATGGGCACTGCATTCATGGATTCATGGATCATGTCCCACTGCTGCACCTGCTGCACCTCCATTCTTGTAAAATGGGTCCTCTGGTTCAA
TCTGTCAGTGTGTTATAGGGTCAGTGGATTTCATGGATTCATGGATCATGTCCCACTGCTGCACCTCCATTCTTGTAAAATGGGTCCTCTGGTTCAA
TGTGATGCCATGTGGGATCTTGTGTCAATAGAATAATAACTCAGATGTTTCTGGCTGAAGCTTTACAAGCAGAAAAGGCAACCGATGAC
TGAAATAAGCGTGAGCCAGTCAAGATGAGTCTTGCTCTTCCAGGATAGACGGAGTCTAGTGTAGATCACTGACATCAAGAGACT
GGCTGGTCTCCTTGAGGGATGGTGCTGTTCTGCATTCATGTTCCTATTGCCAACACTAGGGTGTCTGTAATCACTGAAACATTATTGCTATCATTAT
TCTCTGCCACAATGAGGCGCTCCATTCATGTCCTATTGCCAACACTAGGGTGTCTGTAATCACTGAAACATTATTGCTATCATTAT
TATTATTTTTTTTGAGACAGAGTCTCGCTCTGTCCAGAGTAGCTGGGATTATAGGCATGGCCACCACGCCTGGCTAATTTTTGTATTTT
CCCGGCTTCAAGTGATTCTCCCGGCTCCAGCCTCAGCTTCCATGTCATATAGTCTGTGCCTCGGATCTCAGCCTCCCGAAGTGCTGG
TAGTAGAGACAGTCTCTTTTGCCATTAGTCTGTGTCTCGTCTCGAACTCCTGACCTCAGGTGATCTCGACCTCAGGTGCCCGGCCTTGGCCTTCCGGAGTGCT
AGGATTATAGGGCGTGAGCCACCACTTGCTATTATTGTTGAGATGTGAATTCCTGGATGGTGTCCTTGTGTCTTCTTCCACCAAG
TGCCTTTATTCCTTCTATGGTCACCACTTGCTATTATTGTTGAGATGTGAATTCCTGGATGGTGTCCTTGTGTCTTCTTCCACCAAG
AGGTTCCAGCAGGGACCACGATGATGTGGCACCTTGACCAAAGACTTGTGAATTCTGAATAGCCCTTGAACTAGCATACCCTTGTCTTGTCTATCAAGGATGGTGTCCTTGTGTCTTCTTCCACCAAG
CACACAGCTTCTGGAGGGAGCCACATGAGTGGTCAGCTCATAGCCTAGATGAAGGAACCCCGGCTAGCAGCTAGATCAAGCAGAATAAACC
CTGGTAGTCAGATGGGGTGACAGTGTGCAGCAGTGCCCTCACATCCAACTCTTAGTGATCTTCTCTTAACATTTCTTGCAGGCAG
```

FIG. 3A-1

FIG. 3A-2

```
AAACAGGCCTTTAATATGAGGTTTATGTTTATCTGGCTTGGAGTTAGGCTGTGTTTACTCTTCTTGCTGTAACTTTGGTGCCAGAGGCTA
AAATTTCCTCTGGTGCCCTTGTTTTGTCTCTCGTTATGTTTGTGTTTCCACAGAGTCTCCGTGAATATGGTGTGAGGCTTGAAGTT
CTTTAGCTGTAACCCTCTCTATTATACAGGAGCCTTACGGATGTGGTGGTAATGTGGGAGGTGGGCTTAAGTATTCAGCAGTCCTGTG
ATCAGGCCTCAGTCTTTTAATAAGCCTGAGTACTTCCCTTTCCATGTTAGAGTGCTTGGAGTTGGGGGTATCCATTACCC
CAGGTTGGTAGGCTTTGGTAAAACCACAGTCTATCAAGCTGTGGTAAAATAGTTTCCCTGCAGTCTGGCTTTGTTAAGGATAACAGAGG
GCTCTGGGGGTGTTCAAAATGCTACTTTTCCTCTCTCCCTGTCAGAAGCACAAGGAGATTTCTCTTGATCTTCACCCTGAGAGTCTG
GTGGGGTTCCTGGAGGTAAAACTCAGGAAAGTGTGAGGGCCTCCACACAAAGGGTCTGCTGAAGTTTGTTCCATAGCCTCAGTTCTCTA
ATGGATCTAAGAAGAGTTATGATTTCAATTGTCCAACTTAATTCTGTTTGAAGACAGAAGTGATGACTTCCAAGCTCTTTATAT
GTTGAACCCAACCCATATATTTTCAATTAGCATTGCATATAGCAATGGTACATTGCATTTATAGAAATAATGATGTTGCCTG
TGTATCTTTTTCCTATTATGTTGCTGAATTCATTCTTAGTTCTAGGAATTTTCTATTCTCTATTCCTTTTCTTGCCTTATGCAGTGGCTAGAA
TCATGTCATCTGCACATAGGGACAGTTTATTTCTTTTCTAGTCTGTATTCTATTCCTTTCTTGTTGCTGATCTTGGGGGAAAGTATTCAGTCTTCACC
CTTGCAGCACTATATTAAAAGTGGTAAAAGTGAACATTCTTTCTTGTTGCTGATCTTGGGGGAAAGTATTCAGTCTTCACC
ATTGAGACATAAATGTAGCTGTAGGTGTTTAAATCTTATCCAGTTGACGAAGTTACCCTTTATTCCAATTTCGAGAGTTTATATC
ATAAATGTGTTAAATTTTGTCAAATTTTTGCATGTATTGATATGATTATGTGGTTTCTCTCTTAGTTACTGCAGTGGGTGCATT
GATTGATTTCTATTATTGAACCAGCCTGCATTCCTGGAATAAACCCATTGGTCATGAGGGATCTGGGCTGGTAGGTTTTTTCCCCCTGCAATGTCTC
TCTATTTGCTAATATTTGTTAAGGATAATTTTTTTTTTTTTTTTTTGAGATGGAGTCTCGCTCTGTCTGCCTCAGGCTGGAGTGCAGTGGCAC
TGTCTGGTTTGGTATTAAGGTAATTTCCACCTCCCAGGTTAAGCGATTCTCCTGCCTCAGGCTCCTGAGTAGCTGGGACTACAGGTCACACCA
GATCTTGGCTCACTGCAACCTCCACCTCCCAGGTTAAGCGATTCTCCTGCCTCAGGCTCCTGAGTAGCTGGGACTACAGGTCACACCA
CCACGCCCGACTAATTGGTATTAAGGTAATATTATCATCATAAAATGAACTGGGAAGTGCCCTCTTCGTATTCTTTTTTTTT
TTTGAGACAGTCTTGCTGTTGCCCAGGCTACAGGGGCAGGCTACCACATCTGGCCAATTTTAAATTTCTTTTGTAGAGAGGGGTCTCACTATGT
TCCTGCCTCAGCCTTCCCAGTACAGGGCAGGCTACCACATCTGGCCAATTTTAAATTTCTTTTGTAGAGAGGGGTCTCACTATGT
TGCCCAGGAGGATCTCAAGCAATTCACCTACCTTGGCCCCTCTCTCGTATTTATGGAAGAATTATGGTGTCAATTCTTCTTGAAAGT
TTCGTTAGAATTCTTCAGTGAAGCTGTATGGGCTTGAAGATAATTTCTTTTTCTTTTTTTTGAGATGGAATTTCACTCTTGTCGCCC
AGGCTGTAGTGCAGTGGTGTGACCTCTGCTACTCACTACAACCTCTGCCTCCCACGTTCAGGTGATTCCCTGCCTTACTCAGCCTCTGGAG
GAGCTGGGATTACAGGCACCCGCCACCATGCCCGGCTAATTTTGTATTTTAGTAGAGACGGGGTTTCACCATGTTGACCAGACTGG
TCTCGAACTCCTGACCTCAAGTGATCCACCCGCCTCGGCCTCAAGTGCTGGGATTACAGGCATGAGCCACCGGCCCAGCTGAAGA
TTCTTTTGGGGAGTTTAAATTATACAATCAATTTGCTAATAGGTATAAGCTATTCAAGTTATCTATTTATACTGGATGAGTTGC
AATAGTTTGTGGTTTATGAGTTTTATATGGTCCATTTCATCTGAGGTATAAAATTTAYTTGTGTAGTATTGGTAGTATTGTTCCCTTGTT
ATCTTTTTATGTTCACATGGTATATGGTGACAGTCCTGGTTTAATTCCTAGTATTAGTAACTGGCTCTCTCTCTCTCTCT
```

FIG.3A-3

FIG. 3A-4

```
ATATTCAGGCTATTGATGTGTAATATCATACTAGGCAACTCCACTTCAATATGAGTCTCTATGATGTAAAATGAAATAGGATGTT
TCGATAGAGAGTTGCAGATTTCATTTGATGTTAGCGACCACCACAAATTACTTTCCTACATAAGAACATGTTATTACTCTAGTTGAT
GATGACTGCTTATGGGAAATGTGTCTGCTTGTTAGGAATCTTGCCTAATATGTATAATTCAAGATGGTATTATAAAGTGACATATA
TGATTTTAACATTTGCACTTAAAATAACACTTATTCTGTACCATGMASTGTCTAGGAGCTTCTACATATTCCATTATTATCTTTATTTT
ACAAGACAGGGAACTAAGGCATGAGTAATTTGTGCAATATTACCTACCTAGTAAGTGGTAAGGAAAGATTGGAACCCAT
TCTGGCTCCAGGATCCAAGGCTCAAAGCCAATATACTATCCACCACCCAACTCTTTAGTTTGATCAATTTGTCAAATTATTTTACAGTT
ATTATCTGTAAATTAAGGGGATAATTGCCCAGTCAATAAATGTGTCCCCTTCAAAGGTTACATACTTAACCAATGGTGCTACTGGCT
CAGAACATTTTTGGAACTACGATTTTGGTGGCAACCAAAAAACCTCAGTACATTCCTCTGAACATTCTCCAGAGGCAAGTCTTTCTCC
ATGGAGACTGGGCTTCATTTTTGAATTAGCCTGAAGTTGTTTGAGGTCAAATCTGATGAAAAGAGCGGCTGGGGAAGCTGGATATTT
CGTTCGTGATTTAAAACAGTAAATGCCACTTAAATGAGAAGGCTACTTCTTTGAATGTTTGTAAACTGGCTTGAAGGTACTTCTTT
AAAAAAGAAGCACAAGAAAAGACGGTGACTGGCAACAGCCTCACTGGAATACGTCTCTAATCATCAAGGCAACCACACTCATTGGATG
TGTGCATCCGGTGATGTTATTATTTTAAAGTTATGTGCCACAAAGATTCTTAGGCATTAAGTGCTCAGACAGTATAGATCTTCATTGGATGACGT
AGATATAAAAAGGGGAAAGGAGAAAGGACCAAATGGAAGATTCTTAGGCATTAAGTGCTCAGACAGTATAGATCTTCATTGAGACGT
CAGGGAGAAGAGACACAGACTTTCCTAGCTGGTCTGGGGAAAATAATTTAAAGAGGTCCAGCACGAGCAGGTCAATCAAGGAAGATGTTAAAAATAACACAGGT
GCACAGCCATTTCCTAGCTGGTCTGGGGAAAATAATTTAAAGAGGTCCAGCACGAGCAGGTCAATCAAGGAAGATGTTAAAAATAACACAGGT
TGTCAGGATGTTGTCAGAATTAGAAAAGATAAAGTGGATACATAGAACATTCCTCACACAGAGTATAATAACCTCAGAAAAATATTGCCTAGAG
GAAATGTACTCCCAAAGATAAAGTGGATACATAGAACATTCCTCACACAGAGTATGGGGGCATGAAAATTTACAATTGTAGG
TAAACATGCCTCCCAAGCCAACGTTCATCATCCAGGAATACGGAGAGGATGTTTGGGATATGGGGGCATGAAAATTTACAATTGTAGG
GCCCTTTAACAAGGGTAGACTTGCCAAGTTGCAAGTTGCAAGGCGTTCTACCTGTTCCAGACGTTCTACCATGACTCGTGGTTGTGAACCTG
GGGMCCAAGGACAGCACCCTGGCATGGGCAGGCCCCACTNGGCGACTCTCTCAGGGCTGCTGCAGCTGTGTCAGTGTCCCACAGGGAGN
CTGACATCCAGCCAGCCATGACCATCGCATTAAGCCAGGCAGGGAGGAGCAACTGCTCAGGAGGCACCTTTGACCCACTACTTTTT
CCCCTCCTGCTTTATCTGCCCAGACGGAGGCTCTCTTCTAATGTGTACAAGGCGTTCTACCTATGACTCGTGGTCCTGCCATAGAAAT
GCTTTTTTTTAACTGAATTAAGTTGCCAAGTTGAAAATCAGAATTTCACATAAGATCCCTATTTCTGTCTTCTTTTGAAAAA
CTGAATGTTCTTTCCACAGTGAGCCCACATTCCTTCCTGACGACCATCACCGTTCAGCTGAGTAGAGAGGGCTCTGCTGCTTCAGAT
CCGGACGCGCAGGTCCTCTGCAGGCCCCAGCCCGGCGTCACCTGCAGGTCCCGCCCGGTCACCTGCAGCCCCGCCACCCGGCCCACCCGG
CGTCACCTGCAGCCCCGCCACCCGGGTCGAGGCCCGCCACCCGGCCTCGAGGGCCCGCCACCCGGGTCGAGGC
CCCGCCACCCGGGTCACCTGCAGGCCCCGCCACCCGGGTCGAGGCCCTGACCCGGTCCCTGCAGGCCCAGGCGGGCCGCGG
GGTTGGTTTCCACCMTTGGAGGTTGCTGACCAGGTGAGRCATCCTCCGGCGCCCAGATTTCTCCTCGCCGCTCTTGCCCATTCTCCGGAGCCAG
AAGCGCATCTTAGGAATGACAGGTGAGRCATCCTCCGGCGCCCAGATTTCTCCTCGCCGCTCTTGCCCATTCTCCGGAGCCAG
```

FIG. 3A-5

```
AGAAAGCCGCTCCCAAGTCCAAGGCCGAGCTCCGCAGAGACGCCCGGCCCCTCCGGCGGGACAGAACAAAGCCATTGTTCTTGCGGGGA
AGGTAGAAATACTGTGGGCTGCTTCAGAGGCTGCCGAGCAAAACTCAGGCAATCTCCTGGCTGTTCCAATACGTTTATTCTCTTTTC
AAAACAGGAGGAGGTAGAGGCGGGAGAGACACCATCCTGCAAAACTAGGCGGAGCCGGGTGTGGTGGCTCA
CGCCTGTAATCTCACACTTTGGGAGGCCGAGGGGGCCGATCACTTGAGGTCAGGAGTTGGAGGCCAGCCTGGCCGGCATGGTGAAAC
ACAAAAATTAGTCGATTGTGGTGGTGCATGCTTGTAATCCCATCTACTTGGGAGGCTGAGGCAGGAGAATCGCTTGAACCCGGGAGGCG
GAGGTTGCAGTGAGCCGAGATTGCGCCACTGCACTCCAGCCTGGACAACAAGTGAGATTCTGTCTCAAAATAAATAAATAAAC
CCAAGCAGAAAAAGAATCACTCTGAAAACGATCACATCTAACTATCAATGCTCATACAGTTTATGGAATTATCAGCCAACTTGATAAA
ATCAGTATTTGAGGAAACTGTGGATAAGCCCCCTGATTTCAATCCCCATTGTGCCAGGTCCTGGTTAACTGAGGTTAACGAAGTAAAGA
GCTGCAGACACTATTACCTTAAACCGATTACTCTAGCTTAGCCTACTTCCACGTACAGATTTTACCAGTGGACAACATGAT
GCTTTATCTTGTTTTCTCTCCCTGGGACTTTTCTCCAGACATTGAAAAACAGAAAATACTAATAAGGCCACTTTTACCTGCCTGATGCAA
GAACAGAATTTCAAACTCAACATTAATGCAACTCCTCAGTCCCTGACAATGGCGGGTGGAAAAGTTTCTAAAAATATGCAGCAGCACA
ATTATCGGGAAGAGATGAGAATACTGTTACCTAATAAAAATCACTTAAACTTTGCGTGACCTTGAAGAAAGTCACGATGATCTGTTTTTCCAGGTCCCT
AGGACATGCTGGAATGTGGACAGTAAAATCACTTAAACTTTGCGTGACCTTGAAGAAAGTCACGATGATCTGTTTTTCCAGGTCCCT
CAAACAGTGAGATGTGGGCTGTTTCCCAAGTCTGAATTTGAGACGCTTGTGAGTCTTCCTTCTTCGA
CAGCCTGGAGTCTCTCTTGAGTCTCAAGGCTGCCTGAGTTCCTCTCTAACATCCTCTAGGCAGTAGAGGGTCAGATCAGCTATCAGCTAATGAGACAATGAATTCC
ATGGAGGCAGTGGTGCCACTGAGTTCTTGAGTACCATGTGTGTGAGAATGAGATCCACTCATATGTAAATGATTCCAAATAATCTTAGCAT
ACAACCAAAAAGTGGCTGTGGCACTGAGTTCTTGAGTACCAGCTGGTCACAGCTGGTCAGATCACTCATATGTAAATGATTCCAAATAATCTTAGCAT
GAATTTCTGCACTTGAAGAATTTGAAAACAAAGCCATGTGTGTGAGAATGAGATCCACTCATATGTAAATGATTCCAAATAATCTTAGCAT
TCCTTTTTCCGGACTTAAAAAAAAGCACCCCTTAAAAACTTAAAAATATGTCCATTGTTGTCTGTTAACAGCTTTTGGCAACTTTTCAGAGATTGAAA
GTGCCTATGTTGTTGTTCTGATTTACTACAGTGAGTAATTATTAGCTAGTACAATTATTAGCTAGTACAATTATTAGCAAGCGCTAAAGATACAAATACCTCTACAATACATAAA
TATGTGAGCAAATTAGAGAAATGAGTACAATTATTAGCTAGTACAATTATTAGCAAGCGCTAAAGATACAAATACCTCTACAATACATAAA
AGGAATGATTATAGTAGATTTTATAATGCCATATAAGGTTTCATTCTTAATTCTCAAAATAAAATGAAATTACATAG
AAGCAAGTAATATAGTTACCAGAATAGTATTTTACATGTCTTTAAGTGTATGTTGTTGTTAAGGTAATTATGTGATGT
TGTGGAAAGAACAGACCTGGGTTAGATAAAATTCCGGTTGTCTACCAGATTGTGATAGTGAGCAAATTACTTAACCTCTATGATCCT
TATCTTATTTATCTATGAAACAGGATTGGTAATACTCATATCATAAGGTTGAAAGGATTAAATGAGGCACTATGGAAAATTTCTAACAT
GGTGGTGCCTGGGACAGTAGAAGATGCTTAATAAGATAGCTTCATTATTATTAGCTTTTTCAGGTGATGGTGATTTTATCACCAGATTTATT
TAGGTAATTTTAAACTTTAGAAATGTCAACGACTGTCATAAAGATAAAAATTAATGATTAAGACTGCTTATTTAATCATTTATTTTATCACCAGATTTATT
TTTATTACCCAAAATGTCAACGACTGTCATAAAGATAAAAATTAATGATAAAATTGGCCAGGTGCGGTGGTTCACGCCTGTAATCCCAGCA
CTTTGGGAGCTGAGGTGGGTAGATCACAAGGTCAGGAGATTGAGACATCTCCTGGCTAACGCGGTGAAACCCCATCTCTACTAAAAATAC
```

FIG. 3A-6

```
AAAAAATTAGCTGGGTGTGTTGGCGGGCGCCTGTAGTCCTAGCTACTCATAGTCCCAGCTACTCAGGAGGCTGAGGCAGGAGAATGGTG
TGAACCCGGGAGGCGGAGCTTGCAGTGAGCCGAGATGCGCCACTGCACTCCAGTCTGGGCTACAGAGCCAGACTTCATCTCAAAAAAA
AAAAAAATTAATAATAATTAAACCGAAGTATGAACTGTTGTTAGATGATGATCACTTGCATGTTGTGACTGAACTCAGCAGTTGGTTTAT
ACTGGTTTATCTTATTCTTCCTAAAAGCAAACTGTTGTTAGATGATGATCACTTGCATGTTGTGACTGAACTCAGCAGTTGGGTTTTAT
TTTTATTTTTATTGCTTCAGTAGCATTADCCTTTCCTACCAAGATTGAACAATCCATTTGCCTTTTTTCCCTAAAATCTCTCAT
ACATTGTAAATACTACATATTGGCTAAATATTTCCTGGACAGACATGAAGGACACATAAATCAGTCTCTGTATGTTTCTCACTGTA
ATGGAGTTTATCTGCTCAAGACCAGGACATTATTGCATATCAGGTTTCTACAGTGCAGAGAATTGAAATGGTCCGTGGTACAGTAGTTGTGTCTGTATA
AAAAGTCTTCTATTGTTCTCAACCATTTCTCGCTTAGCACATGCAGTTACAGAGAAGAAGGCTTGGGGAGGTGTTTGGAAATACACTCAGAAACCTGA
TTTCTCTGTAGAATATTAGAACAAGGGATTTGCAGTTACAGAGAAATATGCTAGAGTWCGTTTTGATTGTGCACTGAGGAATTAATAGATTAAGTA
GGAAATTGTGGAAGAGAGGCTTATATTTATTTCTAGAAATATGGCTAGAGTWCGTTTTGATTGTGCACTGAGGAATTAATAGATTAAGTA
GTTTATAAGGACTGGGGTTAATAGAATACTGGCAGTGAAGTTGTCTTAGGACTTCTAATTGGATAATCAGTGAAGTCACCAGATCC
CAGTTAGAGAGACAGTTCCAAGTTTTACAAAACGCAAGATAACTGTCCAAGAGCTGTAATGCTTAATCATCTTTGATAATACCTCTCAC
TGAAGCTATATCATAAGAAGAATAAAAATCTACATTTAAAAAATTGGCTGTAATCATAGGGTGACTAACGTGCCCTGTTTACCGGACT
CAGGGTTTCCCAGCTGAGGGACAATGGTACTAAAACCAGGACAGTCCCAGGCAAACTGGACGGTTGATCACCCTACCCAATGGCCT
CATCTGTCTCATTAATTCTGGATTACTTCGTGCCTCAAAAATATCCTCGGCTTACCTGACTCACTGATGAAATATTTGTGGTTTCATGCT
ATTGTCTAATGTTGTGCTGATAGCCCACTTCTGGAGGTGATATTTCTGTCTCCTTGTGCTTGTTGTGGGATCAGGAGTTAGATATACTGGCCGGGCGGTGCTC
TGTATCTTGTGCTGATAGCCCACTTCTGGAGGTGATATTTCTGTCTCCTTGTGCTTGTTGTGGGATCAGGAGTTAGATATACTGGCCGGGCGGTGCTC
ACACCTGTAATCCCAGTACTTTGGGAGGCTGAGGCTGGGATCCCTTGAACCTGGGAGGTTGAGACCAGCCTGGCCAATATGGTGAAT
GAAGCCCTGTCTCTACTAAAAATACAAAATTAGTTGTGCGTGGTGGAAGTGCCTGTAATCCCAGCTACTCAGGAGGTGAGGCAGGA
GAACTGCTTGAACCAGGGAGGTCGGAGGTTGCAGTGAGCCGAGATCGCGCCACTGCACTCCAGCCTGGCAACAGAGTGAGACTCCATCTC
AAAAAAAAAAAAATTAGCTGGATGTGGTGGACGAGATGTGCCACTGCACTCCAGCCTGGGAGGCTGAGGAGAATCGCTTGAACCCA
GGAGACGGAGGTTGCAGTGGGACGAGATAAATAAATGAACACATAAATAGATATACCAAGAAAGTATAAAAAAGTCTTGTGTGAACATAAATGA
AAATTGGCCAAAATAGGTAACAGACCAGCTCAGGCGGTGGTGCCTCATGCCTGGTGCCTCAGGACCTCATCTCTAAATCTCTATGAAAGAAAAAATTTAAAGACGTAATGAA
ACTTGAGCCAGGAGCTCAAGACCAGCTTGGGCAACAAAGCGAGACCTCATCTCTAAAATACTAAGTAAATGCAATACATGCCCTGACATTGTAGTTTGCTTTCACAAGAT
CAACTTGCTTGCCTTCCTGCCTCTACATGTTGGGGCTAAACCTTGTGCTACATGTTGGGGCTACATGTTGGGGCTACAGGGATGAAAGARAATTGGTCTTGCCCTCCAGGAACCTT
TTACTGAATACTTACTCTAGGCTAAACCTTGTGCTACATGTTGGGGCTACAGGGATGAAAGARAATTGGTCTTGCCCTCCAGGAACCTT
TCATTTAGTACAGAGATTTAGTGTGTGCTGGTTGGTCTCGTCTCCCCTCTCTGTTCTCCCCTCTCTCTCCCCCTCTCTCCCCCTCTCCT
```

FIG.3A-7

```
GCCTCCAGGAAGGGGGGCTGGATCACTGTGGCTCATTGCTCTGTGGCTTCTGATTGAGTTCAGCCAATGGGAGGCATMATTTGGCGTG
GCAGCTCTGGCTGTTCCTCTGCAATTGCAGTTGCCTCCTCTCCAAGGCTCTGCTTCTCACTGGGTTCCTCGTATCCAATAACAGACTCCCTT
AACTGCCACTTCTGAAAACAGTTTCTGCATAAGCTATTTTCATAATTCCTCTGATGTGCCTTCGCTTCTGTTCCTGTGTAGACCTGATT
CAATAGGAAAATAAATTATTGAAATAGAGGAAGAGACAGGTAATAATAGAGGTATACACAAGTAGAATGGGGCAATAAATGGGCATT
TCGCACCATCAAGAGAGTGCCCATGTAACAGAGTAAAGTAAAATGCATCTTGAGCTGAACACTGAAGGATAAGAAACAAAGGGAGAAAGAC
CTAGAAGGGGCAATATACAAGGAGGAGGAAAATAAACTACTGTGCATTCATGCCAGTGTAGCATTTAGGACATCTGGAAGCTAGAGG
TGGAGTGGAAAAGGAGGAGAGTGATAGGAGCTGGGGCTCACTGGGGTGTCATTAGAGACTTTCAGGGTGGGCAAAGAGGTCTTGCAGGACCTTGTAGGTAATTGTAAA
GCATTTGGATTTTATTCTGAGGGTCACTGGGGTGTCATTAGAGACTTTAGAGACTATACCATGAAAGAAAATTACTTAAGATCCTTGCTACTCAAAGTATGAGCCAG
AACAATCAGAATCAACTAGATGGATTTAAGTATGGGTATACCATGAAAATGCAGAATCCCAAGTCCCCGAGACAAACTGAATCAGAACTGCACTTAA
GACCAGCTACACTGGCATMAGCTGGCCCATTTGTATGGTAGAGTTTAAGAAGCATTGGTTAAAAGATCCCTCTTGATAGGAGCATGGAAGATACATTT
CAAGATCCCAGGTGGCCCATTTGTATGGTAGAGTTTAAGAAGCATTGGTTAAAAGATCCCTCTTGATAGGAGCATGGAAGATACATTT
GAGACAGAATAGACAAGTCAGAGACAGGTGGGAAGGGCCTAAAACAGGGCAGAAGTAGGGAGGTAAATGATAGATTCACAGGAGGTGCAAAGAA
GAAAATGCACAGCACAGTGTAGACAATTCCTAAATACTTAAAAAAATTTTTTGAAATAATGACAACTATATATTTTATATCGAAACAATCAA
ATGCGTAGGGAAGAACAATGCACCCCTTTACCCAGCTCATTCAGATTCACCAGTTATTAGATGCACTCGTGTGTATGCATATAGCTCTGTGTAAT
GTGACATTGCTACAACCCATAGAGCTTATTGCTACCACAATCAAGATATTCAAGCCATTAGCAGAAGATTTCTGGTGTTACCTCCTTATAGCCACACG
TTTATCATATGTGAAGCTTTGCTACCACAATCAAGATATTCAAGCCATTAGCAGAAGATTTCTGGTGTTACCTCCTTATAGCCACACG
CATTCCCATCATTAACCCCTGGGAACAACAATCTCGTTCATCTCATCTCTATAATTATTCTATTCACGAACATTTGTAGATGGGTACATG
CAGTGTGTATCTTTTTGGATGGTAACAGAGCAAGACAGGATCTCACTCTGTCACCCAGCTGGAGTGCAGTGTGCAGTCTTGGCTCA
TGCAGCCTCCACCTCTGGGCTCAGGTGATCCTTCCACCCCAGCCTCCTGAGTAGCTGGGACTACAGACACACGCCACCTCACCTGGC
TAATTTTTTGTATTTTTATAATGATGGGGTTTCACCATTTGCCTAGCCAGGCTAGTCTAGAACTCCTGGGCTCAAGTGATCCAACCGCCTTG
GCCTCCCAAAATGCTGGGAGTACAGGCATGAGCCACCACGCCTGGCCTTTTTCATTCATACTTTCTTTGAAGTTCATCCAAGTTGTG
TGTATCAATACTTCACTCCTTCCAGTTGCTGAGTAGTATTCCATGGCTTGGAGGTGCTAGAGTTTATTCATCACCATTCAACCATTGAA
GGMCATTGGGTGGCTTCCAAGTTTCCAGTTTGGGCTATTATGAACAAAGTACTATGAACATTCATATACAAGTGATACTTTTGTA
TGAATGAATGGAATAGAATAGGATAGGATTTAGTGATCAGCTATGTGGGATGAAGAGTGGCATAAGTAGTAAAAAGTAACCCTCAATGCA
ATGTGCAGCCAGCAAGTACCACAAAAGAGTTTATTTGTTTCATACATAATAAACTATGAACTTAAATCTAAAGTAAACTTGACAACAGTGATGCAGAAT
AATAGTATCCTTCAAATGAAAACAGTAATTAACATAAACTATGAACTTAAATCTAAAGTAAACTTGACAACAGTGATGCAGAAT
TTTTGCTCCTTAGCTCAGTTAGGTCTGTGTTCTGTCTTATCTTATGACCAGGAAGAACTAGGTACCCTGACATCAAAGAATGAGTGGCATAG
AATTTATTAAGCAAAAGGAAAAGCTCTCAGGAAAGAGTGGGGTCCTGAAAGCAGGTTGCTGGTTGCCCCTTGCCTGTAGTTGAATACAAGGG
CTTCTATATAAAACCTGATGGGGCGAGTTCCCTGTTCGTATAAGGCATGAATTCCTGGTGGCTCCACGCCCTCCCCAGTGCGTATG
```

FIG. 3A-8

TGGGACCTTCGTCCACTAGGGACATGTTTAGACAAGTCCCTGTGCAGTTCCCTTATCTGCACAAAACATGGGTTGGAGGTTCTCCGG
GGACCCTTCCTTACTTCTGCCTAAAGCAAGCTGGCTAACTCCTTTCAACAATACTAAAGACATACAGACAATGGTTCTCAGTACAAT
CATTTAAATATTTAAGTAAACTTAAAATGGTGTTTGTTTGATTTGACATTTAAAAGATATCGCTGTCTAAAAATTCTGTGTTTT
AGTTGTTTGGGCTCCTATTCTACAATGTGCTATTACTATTAAGCATTCTTGTATCATGGCATTCCTCAAATAGTTTTAAATTACTTTT
AATTTGAAGAAGGAACATTCTGTACAGTCAGTGGGTGGATTGCTTGAGCCTTGAGCCTGTGGCTCACGCCTGTAATCTCCG
CACTTTGGGAGGCCTAGGTGGGTGGTGGCCCAAGCTGTAGTCCCAGCTACTTGGGAAGTTAGGGTGGGAAATCCTAGGTGACAGAATGA
AATACAAAAATTAGCCAGGTGTGGTGGCCCAAGCAGAAAAATGATAAAGGATACATATCAGGAAAACATGCATGGTATTTGTATCATCTACTTTA
GACCTGTCTCAAAAAAAAAAAGAAAAAATGATAAAGGATACATATCAGGAAAACATGCATGGTATTTGTATCATCTACTTTA
GAGTAATTCCAGTATAGTGGTTTTTGTTGTTTGTTTATTTTGAGAAAGGGTCTTGCGCTGTCACCCAGGCTGGAGTGCAGTG
GTACGATCTTGGCTCACTGCAACCTCCGCCTCAAGCCATTCTCCCAACTCAGCCTCAGCTCAGGTAGCTGGGACTACAGGTGTG
CGCCACCATGCCAGATAATTTTGTATTTTGTAGAGATGGGATTTCGCCATGTTGCCTGAATGCCTGAATGCCTGAATCCACCCTC
CTCAGCCTCCCAAAGTGCTGGGATTGCAGGCGTGAGCCACCACAGCCCAGCCTGTAGTCGTTTTCTTTTCTTTTTTATTCTATG
TTTAATGAATTTACACGTTACCCAAATGTTCCCTAGTTTTCTGCCTTCCAAGATCACTCTGGAAGATATTTAAGAATATACCAAAT
AAGAATATGCAAGTCCTCCCCTAAGGGTGGCAGGAGAAGAACACCCCTCCCCCAGATGGTATTTAGCGCCTCTGCCTGGGAACGGCTTCCC
CATGCTCCTAGGTCAGGGTCCTCTCTCTTGGCACAGTGCACAGCCTGACTCTAGGGGAAAAACAGCACAGGGCAGGAAACGATTT
ATCCCCCTTTTCCAAGATGTGCACAGCCTGACTCTAGGGGAAAAACAGCACAGGGCAGGAAACGATTT
TCCATGTCACCAACCTTCTCTGAGGGAACCTACTGGCCACTCCCACCTCCCTCTTAGGACCAGCCACAGCCCATCGTCCACAAGTGGAAGTCCAGCTTC
CGTTCAAATCGGAGTTCTTTCTTCACCCCTGGTCAGGAGAAGCCAAAACATCAGTGAGCTTCCCAGTAATCAAGCCTGGCTTTCTCACCCAGGGCT
CCATCTTCCTTGTCCTTGTCCTCAGTGTAGCCAAAAGGCTATTGGAGTCTTCTCAAATGAAAGAGATTTATCAAAGGCTTGGA
CGCCCAGAACAACCACCGGCTTCTTTCAGTGTAGCCAAAAGGCTATTGGAGTCTTCTCAAATGAAAGAGATTTATCAAAGGCTTGGA
GAAGAAAAGAAAAGAGGATTATATAATAAAACGTAAAACAACAAGCACACCCCCAGCCCCAAGGCAAGGCCAGTTCACCCTCAGTGCTCA
GGAGTGTTTAGAGCAGGAAGTGTTCTGGGCATCTGCCTTCCCCTAAAATTTCTTTCTTTCTTTCTTTCTTTCTTTAGAGTTGCG
CTACTTGCAGTGTTCATAGAATATTTGTAATAATTGTAGTGGCATGTTCATGTCAGGTCATGGCTGAAGCCTCAAATTCCTGGGTTCAAGTGACCTCTACCTC
AGCCCCATGAGGACCTGGGACTACAGGTATGCACCGCTATACCCGTCTATCTTTATTTATTTATTTAGAGACAGAGTCTAGCTC
TGTCACCCAGGCCAGAATGCAGTGACACGATCTCAGCTCACTGCAACTTCTGCCTCCCAGATTTAAGGGTTCTCTTGCCTCAGCCTCC
CTACTAGCTGGGATTACAGGCTTGCACCACTACGTCCGGCTAATTTTTTGTATTTTAGTAGAGATGGTGTTTCACCATGTTGGCAGG
CAGGTCTCGAGCTCCTGACCTCAAGTGATCCACCCGGTGCCCTCCAAAGTGCTGGGATTACAGGCGTGAGCCACTACGCCCAGCCT
ATTTATTTATAATTTATTTGTTTAGACAAGGTCTAGCTCTGTTGCCTGGGCTGGAGTGTAGTGGTGCAATCACGATTCAGTGCCCCT

FIG. 3A-9

```
GATCTCCTCGGGTTCGAGTGAGCCTTAGCCTCTGTTTAGCTGGTACTACAGGTGCATGCCACCACCTAGCTAATTTTTTAAAATTTTT
TGTAGAGACGGGGTCTCACCCTGTTGTCCAGGCTGGTCTCAAACTCCTGGGTCTCAAGCTGATCCCACATTGGCGTCCCAAGTGCTG
GGATTATAGGAGTGAACTACTGTGCCCAGTCTTTTAAAAATTTCAAGAGATTGGGGTCTTGCTATATTGCCCAGGCTGGTCTCCAC
TCCTGGTGTTAAGGCGATCCTCCCACCTCAGCCTCTTGAGTAGCTGGGATGACATTACAGGCACACTGCCACCACTGGCTCTAAAAC
TTCTTCGTGCCATTTGTGCACTTCACCCAATTGCCTCTTTGTAGTAGTAATTAGGATCTAGGGTGAAAAAAAAGTCAACAGTATAT
ATAGTCCTCAAAGTTTTGTACGTATCTGAGCAGTCATCAGTTGCACAGTGCACAGTGAGAGGATGAACTGCCGTCCCGCCACCTAAAAAGCATT
AGTGACCATCAGGGAACCGTCAGATGCATGCCAGACTAAAGCAGACTGAGGCTGTGCTGGGTCTCAGGGCTCTGCCCGTGCTCTC
ACTTCCCTGTCTTGCTCTGTGCCTTTGGGAGGTTGACCCTGCTCTGGCCTCTCACTGAGCTCCAGATTCATTGTTTCCTCCCCTACCCAAGTGA
AAGGCTACTGCTCCCACAAGGCAACCACGGTCCCCGCTCTAAAAACCCCTCTAAAATTCACTTCATCTACTGTAAGAAAAGTCATATTAAGCTTTGTCCACCAGGTGCAGTGGC
GAATAATTATGTTTATTCAGAACCCTGACAAATGAAGAGGCTAAAAACCCCTCTAAAATTCACTTCATCTACTGTAAGAAAAGTCATATTAAGCTTTGTCCACCAGGTGCAGTGGC
TTTGTTTGTTTTTTAATGCAGACACATAGTTTAAAAATTATTCACTTCATCTACTGTAAGAAAAGTCATATTAAGCTTTGTCCACCAGGTGCAGTGGC
TAAAACAAACAAACAAACAAACAACTTCTGTGACATTTGGCTAACAAGTGGTTCAATATTAAAGCTTTGTCCACCAGGTGCAGTGGC
TCATGCCTAGTCTCAGTGCTTTAGGAGGCTGAGGTGGGAGGATCACTTGAGGCCAGGAGTCGAGGCTGCAGTGAACCATGATCTCA
CTACTACACTCCAGCCTGGGCAACAGAGTGAGACTCTGTCTCTACTGCCTTTAGATAAAAATCTGGCAATAACAAAACAAATAACCAAAGAGTTTCAAGGCCTGTTGATCT
CAATCGTCTCCTTGGCCTGGGTCTCTCACTGCCTTTAGATAAAAATCTGGCAATAACAAATCTAATCTATTTCTTATCGTCTCCAATAATCCACA
ATTTATAAGACATGACATATAATTACTTGACCATTATAATACCATTATAATACCATTATAATAGGCTGAGTATCCTTATCTTACATGGTGACGCCAAAGTGTTTCAGGTTCTGGA
GAGTCAGCACACAAGGATTCTTTTTCCATATATACACAAGGTAAATTACACACACAAGGACACTCTGTAGTTGTCTTTCATTCCTGATTCATTCCTGATTCGATTCGATTATACATTGAAC
TGTTTTGGGATTTGAAATATTTGCATATACACACAAGGTAAATTACACACACAAGGACACTCTGTAGTTGTCTTTCATTCCTGATTCATTCCTGATTCGATTCGATTATACATTGAAC
ATATACACCTTATACACGTAGCCTGAAGTGACCTGAAGGTAGCCTGAAGGTAGCTGAAGGTAAATTACACACACAAGGACACTCTGTAGTTGTCTTTCATTCCTGATTCGATTCGATTATACGCTACT
CATCAGGAAGCAAGGTGTCCCTGTCTCAGCAGCAGATCACTTATTCACACAAGAGCACTTAGTAAAAAATATGACATATATATCTGGCATGCTCAGAAAAGCTATT
GACAAGCAATCATTTCTTACACTTATTCACACAAGAGCACTTAGTAAAAAATATGACATATATATCTGGCATGCTCAGAAAAGCTATT
TTGCAGCAGAAGGAGCTGGGAGGGTCCTTTTTCCCTTGTCTCTGTGCTTAAAAGTTAGATTGGCCAGGCATGGTGGCTCATGGCTG
CCCATCACATGAGGTTAAGTGTAGAATTTCCACTTGTCTCTGTGCTTAAAAGTTAGATTGGCCAGGCATGGTGGCTCATGGCTG
CAATCCATCACTTAGGAGGCCAAAGCAGGTGGTCATTTGAGGTCAGGAGTCAAAACCAGCCTGGCCAACATGGTGAAACCCTGTCT
CTACTAAAAATAAAAAAGTTAGCCTGCAGAGACAGAGATCACTCCATTGCACTTGCACTTCCAGCCTGGGTGACAAAGCGAGACTCTGTCTCAAAAAAAAA
CCTGGGAGGCAGAGGTTGCAGAGACAGAGATCACTCCATTGCACTTGCACTTCCAGCCTGGGTGACAAAGCGAGACTCTGTCTCAAAAAAAAA
AAAAAAAGGTTAGATTTGAGCATTTGGATTTTGATTTTGGATATTTGAGCATTTGTCAAGCTGAAAAGAAAATCCGATTGCTCAGGA
CAAACTTAACAAAACAAGTGAGATATTCCAATACTATACTATATATGCTCCTGTTTATATTCCTTAATTAATTTGGACTTGGAACAACTTG
GCCAATTATGGATTAGAGGATGAGACTTAAATGTACTGTACAAGGGATAGAACGATTCATTCCTCTAGTTATCAAATACTTATGGTA
```

FIG. 3A-10

FIG. 3A-11

```
TCATTCCCACTTAATTTCTTCATAACAGTTGTCATGCTTTTATACATTCTGGCTTCTATATTTATTTGTATTGTCCAGTTCCCTCC
CTTTGGAACGCAGCGTGGGCACCTGCAACGCAGAGACCACTGTATCCCGGTTGCAGAATGTAATGAGTGCCTGATACATTTGCCGAATA
AACTATTCCAAGGGTTGAACTTGCTGGAAGCAAGAGAAGCACTATTCTGGGTAAAATGGAAATTTAAATGTACTTGATATTATATAC
ATCCTAATCAATAATTAAATTTGTGTAGTGCTGATCTAAACAGATAAATCTGGCTTCATGATGATGGTGAAGTGGAATATAATTTCT
CATTTGTATTCAAACTAGATCTTTTTCATGAAAGGATTTGAAGTCTAGATTCAATGCCTACTTTTGCTACTTATGTTATATGAAACTA
AAACAATTATTTATTGTATTTTTTGAGATGGAGTCTTGCTCTCGTTGCCCAGACTGGAGTGCACTGCTGCGATCTCAGCTCACTGCA
ACCTCTACCTCCCAGGTTCAAGCGATTCTCCTGCCTCAGCTCCTGAGTGGCTGGGACTATAGGTGCGTGCCACCACACCAGCTAATT
TTTGTATTTTTAGTAAAGATGGGCTTTCACCATGTTGGCCAGGCTGGTCTTGAACTCCTGACCTCAGGTGATCTGCCTGCCTCGGCCTCC
CAAAGTGTTGGATTACAGGCATGAGCCACTGTGCCTGGCAATAATTTAGTTAGTCTGAATTTTTTTTTTGAGATGGAGTCTC
GCTCTGTTGCCCAGGCTGGAGTGCAGTGACGCTATCTCAGCTCACAGAAACCTCCGCCTCCTAGGTTTAAGCAATCTCCTGTCTCAGC
CTCCCGAGTAGCCAAGATTACAGGCACCTGCCACCACCCCAGCTAATTTTTGTATTTTAGTAGAGATGGGGTTTCACCATGTTGACC
AGGCTGGTCTCAAACTCCTGACCCAAGTGATGTGTCTACCTTCCAATGACATTGCACTCTGTGTGGCTCAATAAAACATTTCATTTATAATA
CTAGTCTGAATTTTTAAAAAGGTTATTGGTCTACCTTCCAATGACATAGAGTATGTAATTCTTCATTTACAGGTCATGTCAAATCATTTGTACATT
ACTAATTTGACCTGCTCAGCAATCTCTAAGCAAGATAGAGTATGTAATAATCACAGAACTTCAGACTTGGGAGTAACAGCTGAAATATTTCTTCCA
CCAGCTATGTACAGAGCTTGGTGAGAGGACGATGAGGTCCAAGTGGACAGACAATCGTGTGGCAAGGAAGTTGATGCAATTGAC
ATAATGCATTTTTATGAGAGAGGACGATCTTTATGTCCATCGGTCCTCTTATTATTGTGAATAATTTCTTTAAGTTTATTAAATGAATGGCAAAGGAGGAAATTTTAATTG
CTCTAAGTCAGTGATCTTTATGTCCATCGGTCCTCTTATTATTGTGAATAATTTCTTTAAGTTTATTAAATGAATGGCTGAATAAATGGACAT
AGGATTTACACTCTGCTTCTAAAATTTTGCTTATTATTGTGAATAATTTCTTTAAGTTTATTAAATGAATGGCTGAATAAATGGACAT
AAGGAAAGAAGAGAAGGAAGGAAGGGAGGGAAGGKAAGGAAGGAGGGAAGGAAGGAAGGAAGGAAGGAAGGAAGGAAGAAGGAAGAAA
AAGAAGAGAAGGAAGAAAGGAAGGAAGATAAGTCTGATGACAGCTGCTATTATATTCTACGTGGATAATTTATTAGATCTTTATACTTTAT
CTTTGTTTACTTCTCTATGCATATTCTCCTCAACTTTTTTCAGTGGGCCAGAGGAGGAGGACTGCCTCTTGTGACTGTGGAAGGA
CTTCTACCAGGCTAACACCCCTGGCCTCTCAACTTCTCACCCTCTGTCTTTTGAGACCTTACTGGTGCAAGACAGCAAATCCTAGCTGG
GGATCTCAGTTGAGGAGAACTCGTTAGAGATTTGCCCTCTCTTTGTCTTTTGAGACCTTACTGGTGCAAGACAGCAAATCCTAGCTGG
TGTCTACAGGAACACATGCACTCTTAGGTTACATAACTGCAGGGACCACTGTCATTGTATCCTGGAGCTGGTTCTCTATATAAGACACAGCC
TGAGCAGTATATAGGCTTCAAGGTGACATATTAGCAAGACCTTTATGGCCATGCATCTAAGATGCTCTGTCCAAGCTGGCAGGATG
GGCAAGTCTAACTCAAGGGTGACATATTAGCAAGACCTTTATGGCCATGCATCTAAGATGCTCATCCTTCCAAGCCTGAACTTAGCAACAAT
AAACCTGACATTTGAAATCTCCTTAATTATCAAGCAGCTATCTACAATATTTGTAATCCCTTAAATCTTGAGCATAATGTCATAATTAT
TTTGCTTCTAAATCTCCTTAATTATCAAGCAGCTATCTACAATATTTGTAATCCCTTAAATCTTGAGCATAATGTCATAATTAT
GAAAGTGMCCGWTTCACATGAAGTATTGCTTAATCTTAAGAACAAAATGGCAGCTGTGAAAACAGATGAAGTAATTAGGAAGAGCC
```

FIG. 3A-12

```
TTTTTGGAAGCTTCGAGATATTTCAAAGTAATTAGTACTAGTTAGCAATAAAGTTCTGTTCTGAGAAATTGCTCTTAAAGGAGGAACA
TGGATTAAAGAGAAAAAAATCTGCTACTAGAAGAAGTAAGCCATCTTCCTATGTGTGATTGGTTTTGCTTCCTGAAAACTGGTTCCGTTT
CAACAAAATTGGGTCTGTTGAAAAAGAACACGCAGATGCCAGCTTGATGTCAAACGGGCCAAACTTGGACAGTGGTAAACTAATGA
GCAATGGTGCACAGAGTGCAGGGTAAAGCTGGACACATTCCTATGACCAACTTTCCAGGACTCGTCTGCTCTGCTCTTCCTGAGAAAATA
CCCAAAGTGCTGCCTCTTCCATTGGCCCAACCATGCATCTTTCAGGATAGGMCACATCTGTTTATAGGTGTGGATTGTAGTTGCTCATA
AGTGACATTAGGCTGTTTAAAATAATAGTTCGAGTTTTGCTATGAGCTGATCTGTTTCCAAGGAGAGCTAAGAGTTTTCCAGCTAA
AAGAGGGAATTAGTGGGTAATCAAGGCAGCTGACATGGGGTGTGGCTGGGCCTTGAATGTGTGCACTCTCTGTGCCCAGGCAGAGCAA
AGATAAACTCCAGACTGCCATGTTGCTCAGAGACCAGGACCAACGTCATAGGGCGCCTAAAAGGCAGGTGGCCCAGTTCAGAATTGTCAA
GGTCTGACCTGCTTGGACAAGTGCTGAGTACATAGTAAGGATGGATTGGCTAGTCTCTCAAAACTTGCAAACAGGGCGCAGGTGATCTT
GAGATTTCAGGTGCCGGAGACCATCGTGTAGATTCCAGAGTTGGCTATCATCATGACAGCTGTCTAAGTTGTTTTAAATGAATC
ATTAAGGGCTACATTTCAGTTCAGCTAATCAAGTAGCAAGTTACGGTGGGTCTAAAATACTTATCTATTGCATTATGTATATGCTAGA
CTTTATCACTTTAGTTGGTTATATCGCTTCATATATCTAAGAAGTTTACTCACTTCACATGTGGCTTATAGTATTTCAATCTAAGAGACTAA
CTGTGTAAATACACTGTTTCAAACTGTTTATCTAAGAGTTTACTCACTTCACATGTGGCTTATAGTATTTCAATCTAAGAGACTAA
TTTTGCTTACATAGGAAACTACATATTTAAATTGAAAATTAAAAATATTTTAAGGTTTAATGAGTCCTATCAAAACACATTTGT
ATATAGGAAGGTAGCCCAAGGTCACTGTTGCCAATTGGGTTAATAGGATTAAACACTGTGTCATCAAATTGGGGAGATATTGCAAAGTTAGTTGATAACGGA
TCATAGTTGTAAATCTCAAAATGTTGGGTTAATAGGATTAAACACTGTGTCATCAAATTGGGGAGATATTGCAAAGTAGTGATAACGGA
TGAAAATTAAAGCAGAGAAAAACGAAGGTCCTTCCAGAAGCTGGTGCAACTTCACTGGGTGGCAACTTCACTGGGTGAGAAGAAGAGTTAGTTGAAATGATGTATGTAAAATGTGATAACTGCATAA
CTATATTAAAAAGTTTGTTTGTAAATAGACTGTATTAAAAAGACATTCCAAATGTTGATCAATAATGTTGATCAAATAATCTAACTTATTATATAGTTTTAACTTTATTA
TTACTAGTACAGTTGCTAGTTACGACTGTATTAAAAAGACATTCCAAATGTTGATCAATAATGTTGATCAAATAATCTAACTTATTATATAGTTTTAACTTTATTA
TTAAAATAGTAAATATACGTAAAGCAGATAAATATCCCTTTGTGGAGTTAAAATAATCTAACTTATTATAGTTTTAACTTTATTA
AAGCATAACGACTATTCTAACTTATTAACTTTATTCATTGAGAAGGAAATTCATTAACTGAGAAGAAAAAATTTTAACGTGCACTATTCACATAGCAACACGTAGGTAAAAACTCACTGGAGAACATAGACTTTGGAG
TAAACTCAAAGGAGGAAATTCATTAACTGAGAAGAAAAAATTTTAACGTGCACTATTCACATAGCAACACGTAGGTAAAAACTCACTGGAGAACATAGACTTTGGAG
GAAAAATGTGTGTGGTTGGTTTTGCTTTTTGCTTTTGGTGGTCCACGCGTGTAATCCCAGCCACTTGGGAGGCCGAGGCGGGATCACCTGAGGTCAGTAGTTCGAGA
CCAGCCTGACCCACATGGAGAAACTCCATCTCTACTAAAAATACAAAATTAACCGGGCTTGGTGGCGCATGCCTATAATCCCAGCTACT
TGGGAAGGCTGAGGCAGGAGAATCACTTGAACCTGGGAGGTGGAGGTTGCGGTGAGCCGAGATCACGCCATTGCACTCCAGCCTGGGCA
ACAAGAGCAAAACTCCGTCTCAAAAAAATGAAGCTGGACTCTGAGAGGATGTGATCTATCCTCCATTGCATTGAGTTCAAGTACTTCACAT
GTGTTTCGAGATGTTTAACTGTCGTGAAGTTTAAACCAAATAGGGACTAGAATTTGTTTGTTTTTTTTTTTAACTTACATTTACATTTCAAGCTTCCTTATG
GCGGGCTTTTTAACTGTCGTGAAGTTTAAACCAAATAGGGACTAGAATTTGTTTGTTTTTTTTTTTTAACTTACATTTACATTTCAAGCTTCCTTATG
```

FIG. 3A-13

```
TCTCAGGCACATTAGCATAAGTTGTCTAAAGTCATAAGGAAAAATTGACAGAAAAATGCTTTGGAGCCCCAGGTGTTTTCAATTGATGC
CAACAGAAACTAACCAAATGGAAGACATTTGATGCGGGTTTATTTTCCTTTGCAGTAACAGCGGGAACATGAAGCCGCCACTCTTGGT
GTTTATTGTGTCTGCTGTGGTTGAAAGACAGTCACTGCGCACCCACTTGGAAGGACAAAACTGCTATCAGTGAAACCTGAAGAGTA
CGTTTGGTTTCTTACCTGTGCTGTGTCCTGTTTGCATGTTGGTTGTCCTGGCGTTTATAGTGAGTCGCAGTTGAGAGATAACCATA
TTCGTGTTTTCACGGTGAAACGTTCTCAAGGCGTTAAACCAGGTCATCCTGACGCCAAACATCTGGGTAAAAATAGAAAAATTCCAAT
CACGTCTCTGCAGGGGTTCACCTTTCCAGATGTTTGTATCATGTAGATACAACTTGCCAGTTTTTCACTGCATTTTTTGTATCATCC
AGATGGTTGGTGTCATCTCAGCACAGCTCTAATGAACAGTGAAATACTTTTCTAGCATTTGAAAAATTTAAACCATTAGAGTAATCTGT
GCAATTGTCTTAAACTAGTAGTGAAAGAATGGGTTATATAATTACGTTGAATCTGGTTGTTCTGTGGCCATTAACTTGCAACTTGCTTGGTG
ATATATACTTGGGTACTTAATATATAGAAGAACAAATTAGCTAAAATGCAGCTGATTTGGGGTCTGTAATATCAGAGTCAAGAATGA
GCTCCTCAGTAGGGCCACGTTGGCTATTTGAACAGGGAATGACAATGAATTTAAACTTACTAAGGGCTTATTAAAGGTGTATAAGACA
CGTCCATTGAGTTATTAAGGAAGCTCGTATTACATGTGGGCACTTAATATAAATTGAAGAAAAATGCAAAATTTCTCTAATATAAACACA
GAGAAATTGCTGACGTGTGTTGAGGTCCCCAGCTGGGCACTTAATATAAATTGAAGAAAAATGCAAAATTTCTCTAATATAAACACA
CTTGAGTCTTAAATGAAGAAAAAAATGGATAAATGAAAACAGGGCCTGAGCAAGTGACAAGAATGAGGTTCAGTGAACTCTATTGT
TTAGGGCTCACGAAGTGAGGAGTAGAAGGTATGGTCCGTGTGTCCATGTGGCAGCTGTGTCCATGTGGCAGCTGTGACAGCTAATTCATTATGATCTGC
TTTCAGAATATGAGCCTATAAGGAGAACAATTAAGCCTCTCTCTTTAGGTTTTCTGAGGTGGGGGAGATAGATGAACCTGGTGTTTTGTAATCTGATCA
GATCTCAAAGAAAAAATTGCCACATGCTCTTTAGGTTTTCTGAGGTGGGGGAGATAGATGAGACACCCTGAAGAAATGCAGAGAAGAAA
TGGTATTAAGCAAATGAAAATCATGATGGAAGAAGAACACACCAATCTAATGAGCACCCTGAAGAAATGCAGAGAAGAAA
AGCAGGTACAGTCATTGAAAATAATGCTCTGTTCTTACACAGATCTGGACCAGAAATACTGCACTTGTTAGTGCGATTGATGAATTACTT
ATTTCCTTAGTAATAAATTTCATGGGTAGCTGCTTTTATTTGAAGAAAAGTTAAGGGAAGCTTCAGATTTCCTTGAAGAACATATTT
CGTTAGGATAGGCTTCGCAAGACTCCAACCGGAATCTGGGGGATTCATCTCTGTTAAGTGCTGCTTTCTCAAAATAGATTATTC
TTGGTCTCTTCTCTGAGTTAGGATATTGAGTCAAAAGTATTTGAAGAGTTTTTTTTTACTAGATCAGTGGTCTCCAGAGTTTTGTTTT
TGTTTTTGTGTTGTTTCTGTTCTGTTTTGAGACAGAGTCTCGCTCTGTCACCCAGGCTGGAGTTGATCCCGCTCATTGCAACCTCCACCTCC
TGGGTCAGGTGATTCTCCTGTCTCAGCCTCCTAGTAGCTGGGATTACAGGCCTGGGGCTCAAGTGATCCACCTCACCTGGCTAATTTTTTGTATTTTA
GAAGAGACGGGGTTTCACCATGCTGGCCAGGCTGGTCCCGAACTCCTGGGACCTCGTGGATTTGGTCTCTCATTCCTATGACTAAAAATTGTACCACTCACTCCTAAA
AATTACAGGCATGGACCACCGTGCTGGCCAGGAGATTTGGTCTCTCATTCCTATGACTAAAAATTGTACCACTCACTCCTAAA
TATATGCATATTCATTACTCATGAATTAGATACATGCTACCATTGCTACCAGGAATACATGCTACAAAATGACATACATATCTCAAGGCACAATATGTATTAAGGTGAGATTCA
TCATTAGCGAGTGTGGATATAAGTCCACATTCAAATAATCTTCAAATAAAGAGCTCATAATGATCAAGTGCAGCTCTGCCAGATCGATTAGAT
CACCATAGTTTTCCCTTGTCACTTGGCCAATAAGTGCCAATAAGTTTTTTTTTCAAGAATCTGTTAAGCCTCCTGTCCATTGTCCATTTGAGCT
TAAATTATTCATTTTAAAATCTGCCAAGTTTTTTTTTTTCAAGAATCTGTTAAGCCTCCTGTGTCCATTTGAGCT
```

FIG. 3A-14

FIG. 3A-15

```
AGGTATTGTTACTTGCCTTGGGAGAAACAACTTTTTTTTTTTTTGAGACAGAGTCTTACTCTTGTTGCCCAGGCTAAAGGACAATG
GCACGATCTTGGCTCACTGCAACCTCCGCCTCCTGGGTTCAAGCGATTCTCCTGCTTCAGCCTCTGAAGTGCTGGATTACAGGCACC
CACCATCATGACCAGCTAATTTTGTATTTCTAGCAGAGACAGGGTTTTACTATGTTGGCCAGGCTGTTCTCAAACTCCTGACATCAGG
TGATCCACCCGCCTCCAGCCTCCCAAATGCTGGAATTACAGTGTTGAGCCACTGCACCTGCCGAAAAACAACCACTTTAAGATGTTA
GATTCCAGCCAAGTGAAGTGGCTCATGCCTGCAATCCCAAGCACTTGGGAGGTCAACCTGGGCAGATCACTTGAGGCCAGGAGTTGA
GNTCAGCCTGGGNAAANTGGTGNAACTCCGTCTCTANTANAACATACAAAAATTNGCCCGGCATGGTGGCACGGCACCTGTACTCCAGC
TACTGGGAGGCTGAGGCAGGAGAATCTCTTAAACCTGGGAGATGGAGGTTGCAGTGAGCTGAGATTGCACCACTGCACTCCAGCCTGG
GCGACACAGCCAGACTCTGTCTCAAAAAAAAAAAAAAAGATGTAAGATTCCAAAATTGTTCTACAAAGTSCAAGGACACACA
CACACTCCTGTCTGGGTCAAAATGTATATTGGCAAGCTGGGGCCTGGGCCCTGGCAGTTTTCTTACGTGGATCATAGCAAATGCTACGTGGCTTA
GCAGCCAAACTTACAATGAGGACAACKGACAAATCCTAGCCAGGCAGAAGATGTGGAAGATTGTCAGTGCCCAGTGATTCTTTGG
GCTTAATACTCCAGGAAAGGGTCATTTCCATTAGCTCTGAGGCTGTCTTCTTATGGCCAGATCCACTATACTCACTTCATTCCCCTGCA
CGATATCTCGGCATGGAGGGGGCTGGGGTTCAGAAGTCCACACTTGCAGGAAGCCAGAGGTTTGGGCAGGGCACAGGAGAAGGTC
TGTTGCACCATGGTGCTGACCCGTGAGGCACTCCAGGGCAGGGCTGAGGCTCGCAGGGACAGGTGCCACTGCTGCTGGGCTCCTCACC
ACCCAGACAGGACTTGGCCAAGTACAGCAAGCACCACAAGGGGAGCACTGGGAATATAAACAAGAGAACAAAGCTTGTTTATATTC
CCATTTATATTTATTTAATATTACATTAATATATATTATTATTCTAATTGCAGAGATGCCATCTCGTCTCGGCA
ATTACAATGTAACTCAACGGAACATTAACTGACATCAAGAATTGTACTTTCTTGCAATGTTAAGGATATACAACAATTAAAGAC
AGCATAAATGAAAGAATTAAAATGTACCAGCTTTATAAACTGTAAAGCCACTTCCCATGCAGGGATGGCATCTTCATTGTCAGGTGATGCCATCTTCAGTCACCACACCTGGATGAGAATTGAAGACAGA
CTTACCGGTAAATAGGTAAATCACAGTTGTTCCCAGATGCAACAAATGAATGAACAGATAAGATTTACAGTCTTCAATAGGAATCAATCAGTGCT
ACATAGCAAACACTCAGTAAATACTTAGTGAACATTTGGGGAGATCTGACAGCTGCGAGGCACCTGAAGGAGAAAGATGAAAAGCAGTTTAGAATGT
CTTTTCTTAAACTAAACAGAAAGCTTTGGGGAGATCTGCACATAGATCATGAAAATGGAACTTTGTTTCTACTTTTAACTAGGAGGCCC
GTACATTTCAAAGGGTGAAATCAACTAAGGTGCACATAGAATCATGGAGGAAGAAGAAAGGCTATGCGGGAGTCTTTGGCAGATTCCTGGGGTGAATGCAGG
TGAAACTTCTGAATGAAGTTCAAGAACATCTGGAGGAAGAACATCTGGAGGAAGAACCTGCCAACCTAGCTGGTCCTCTGTGAAAATAAGGTAAGAGAAAAGAGAG
TCTTGCCTGGAAAATAACTGCATGGAAATCTGAGAATTTATACAACCTGCCAACCTAGCTGGTCCTCTGTGAAAATAAGGTAAGAGAAAAGAGAG
CTCAAGATTTCACAGTTCTTAAGGCACCTATTTCAGCTTACTTTTTATTAATTTATGTTAATATTTAGAACGGAGATGCCTGATCTGA
TAGGGGCCTTTTGCTTTCTAGAATCTAAAATATCCTGGCTTTCTGCCTTGTATTGTTATTGTGAACATGTCCCACTAGATAGTAAGCTCTT
TGGTCACTGATGCATCTCTTAAAATATCCTGGCTTTCTGCCTTGTATTGTTATTGTGAACATGTCCCACTAGATAGTAAGCTCTT
TGAGGGCAGGATCATATCTTATTGTCTTCACTTGCATTGGTGGCATCCAGTAAATGTTACCAAATTGCATTGGAATCATAGCA
TGCAGTCTCTGATTTCAATCCACATTAATTTCCTTCTGGAGGCCAAATATTTAAAGATACTCTCTGCCTCCCAAATCTTACCTTCA
ACATGCTTGCCTCTCCTTATGCATAACACACACACACACACACACCCCTTCGTGCCCTTTTGCCCTACCCATG
```

FIG. 3A-16

FIG. 3A-17

```
AGCTCTATTCTGCTAAAGCATCAGAGAGCTTCTTTAAAATTGATCTGGAATCCTCAACTCCCAGTTTGAGAAGCCCACTCTCACATATA
ACCAGAGCAATTTAGTGCCCTCCTCTGAATCACTACTAGGATGAATCATTCCTTAAATCATAAAATGTATGCATAAAACCACAAAAAATGCTCATA
AACCCCAAACTACAGAAATATTAGATAAGAAATTGCCTTCTACCAACACTAATCATGCCTCATGCATCCATGTTGGAGACACAATGCTG
CTTTATGTTTAAGGCGGCAGATATCTTCTGTGGGCTTCTATGGAGTAAGTTAGATACGGCATTCGAGAATGAGAATTGCCACGAGGGT
CAAGTGTAGGATCTGCATTTCCTTTGTCACTGTATTGACCCCTAAGCCAGGTTGAAGGCTGCTCCCCTGAGATGAAAATAAAATGG
GCTCCTTCTATCTATTTTTCTTTTCTTTTTTTTTTGAGATGGAGTGTTGCTCTGTTGTCCAGGCTGTATTGGTGTG
ATCTCGGCTCACTGCAACCTCTGCCTCTCTGGGTTCAATCAATTCTCCTGCCTCAGCTTCCGAGTAGTGGGATTACAGGTGCCGCCA
CCACGCCTGGCTAATTTTTGTATTTTTAGTAGAGACAGGGGTTTCACCATGTTGGCCAGGCTGGTCTCGAAGCTCCTGACCTCAAGTGAT
CTGCTCACCTTGGCTTCCCAAAGTGCTGGAATTACAAGCATGAGCCACCACCACCCAGCCAGCCAGCCAGCCAGCCACCACTCCT
GACCCTATCTGACTATTTTCAATTATATTAGCTGTAGCTGGCAACATCTGAATCAGATTCTCAAAATCGCCATGACATTACATAACTG
GCCTCTACATAGGAGAGGTTTACCTTCAGAAACTGAAGCTAGGAAACAGTGCATTACATCCTTCAGGTGCCATGTTCCATGAACAGA
GAACAGCCATCATTACTGGAATTGTTGGGTTCTATTTCAGAGAGTCCAGTGGACTTTTTTTATAAGTCAATTATTTGGTCTGGTAGTCCAT
TCTGAGGTTGCAAATTCATCAAATATTCAGGATAAAACACCAGGCGAGTAGACTAAATCTATCCAGGCTGGGTGGTATTAAGTGATTTA
GCCTGACTGTTTACATGGATATCAACTGTCTTGGAATAACACTGAGAATATGTTCATTAGAACAAAAGGGCTCCTCCCCTCCATGTGT
GTAGCAGCCTTACACAAGCATTGGTTACATTCCCATGTGCACAGGACTGTCAGTAGTGATTCAGACATATGTGATTGATTCAGACATGCCACCATTGCCTTCTCATTCACACAGCTGGGG
CAACCACTGTAACCCCTCCCACACACCACGGCTACGAACACATAGGTTTCCACTGTCTGCCACCCCTCGGCCACTTCCATCTCAGTGATGACCTGGAAAGCCAAGGTCC
CCAGCCCTACTCTCAGCTGCCTCACACGACCAACCAAAAACAAATAGCAACCAAAAAGTCTGTTTACACTATTGTACTTCTTTCTTCCAGTATCCC
CCTGTGAATGCAAATAGTAAAGACAAAAGACTACCGCAGAGGAGACTACCTTTTCTGGACAGGTAGTTGGTGAGGAATAAGCCTACTGCCCTAGAAAA
AGGCAGGCGCTCTACAGCACTTGAATGTGGTTTGGATGTTTGAGTTTGCCCCTTGTGTAGGCAAAATAATGACTGCCCACACATATCCCACCCTAATCCCCCAGAA
TCTGCCTAATGACTGACACTTGAGTTTGAGTTTGCGGCAAAGGGAAAGTAGCAGATGCAGATGGAAATCAATTTGTAATCAACTGACTTTATTTTATTTATTT
CCTGTGAATTTATGTGCGGCAAAGGGAAAGTAGCAGATGCAGATGGAAATCAATTTGTAATCAACTGACTTTATTTTATTTATTT
ATTTTTGAGACAGAGTCTTGCTCTGTCAGGCTGGAGTGCAGTGGCGCCATCTCGGCTCACTGCAACCTCCACCTCCGGGTTTA
AGTGATTCTCCTGCCTCAGCCTCCCGAGTAGCTGTGATTACAGGCACTCACCACCATACCTGGCTAATTTTTGTATTTTTGAGTAGAGGC
AGGGTTTCGCCATGTTGTCCAGGCTGGTCTCGAACTTCTGACCTCAAGTGATCCCAGGCCTCGGCCTCCCAAAGTGCTGGGATTACAG
GCATGAGCCACCATCATGCCCGGCCTCAACTGATTTTAAAATAGAGAGACTATGCTGGATTATCCAGATGGATTCAATGTAATCACAGGGTC
CTTAAAAGTGGAAGAAGGAGGCAGAAAATAAATGTAGGTGGCCTCGAGGAACTGGAAATTTTTTTTTGGTATAGAAATGAATTCTCCTCTAGAGCCTCGCCAAAA
AGGAAGGGGCCAGGAGCCGAGTAAGTTCATAGCGAGAACTGGAAATGGTATAGAAATGAATTGAATTCTCCTCTAGAGCCTCGCCAAAA
AACTAGCCCTACTGACATCTTTTTTTTTTTTTTTTTTTGAGACAGAGTCTCGCTCTGTCTTCAGGCTGGAGTGCAGT
```

FIG. 3A-18

```
GGTGCGATCTTGGCTCAGTACAACCTCCGCCTCCTAGGTTCAAGGCGATTCTTCTGCCTCAGCCACCTGAGTAGCTGGGACTACAGGCAC
GTGCCACCACGCCCAGCTAATTTTTGCATTTTTTTTTGAGACAGATGACATCTGATTTAGCCTAGGGAGACCCACTTCAGACT
TCTGACCTAAAAGACCAAACAATAATGAATTTGTGCTGTTCAAGCCACTGAATCTGTGGTAGCTGTAGCAGAGCTAATAATAATAGTA
ACTGACCAACATTTACTGAGCAAGTTCCGTGTGGCAAGTTCATGGATGGGCCTTATGGTCATGATTGTTTAAAGGGCCAAAATTAGA
AAAATAGCTAACACTGAATTATGAACACCAGGAGAGCGGAAATAAAAGAATCAGAAATATCTTGATAATTAATGCTATTTTT
GTTGAGTATAGGTTCATTTTGTTCTCCATATTCTTTCCTACCTTGGTCTTTCTGGACCTCAGTTCCTGAATCTGTTGAAAGCGAATAGG
TCCAGGAAAGTAGCTCTTGGAATTATCTTCATTGCCTTATGAATCCTGGAAGGAACAGATGAGATTGAGTTCTACTGTAGCTTGACC
CGTGCGGGGCCGGAGACCTGGTTCTAATGCTGCCTGCACTGGAATAGTGTCATATGGGCTAGAAGGGTCTGAGGTTCTGTCAAGGCTAGACTAAGCGAG
TGGGAGAGTAGATGATTTAGCTCAGGATGGGGAATTAGTGTCATATGGGCCTAGAATTGTCATCCTGGTGTACATCCAGGTATTAA
GTGATGGATTGTGCTGTGGCTGCAGGATAAAATGATGATTATGACACAGCCTCTGACTTCCAGGAGCTCAGTCCAGAGAATGACAAGATGACAAGATTAGTGAACA
TCTAGATGCTAGAGATAAAATGTGGGTAAAATGGCAGAGAAGATAAGAAAAGCAAAACTACATAAAGCAGGAATTAATTCTACACTGGAAATTCTCACAGGGGCTA
ATTACATCACCATATTGTGGGTAAAATGGCAGAGAAGATAAGAAAAGCAAAACTACATAAAGCAGGAATTAATTCTACACTGGAAATTCTCACAGGGGCTA
GAGGCTTACAGTCTAATGGAAAAGATAAGAAAAGCAGCTGGGAGAAACTGACTTCTGGTCACCAAATAAAACGTTTCATTTTAAATGCTGAGGATTTAAT
TACAGGGCAAAGAAGAGGGTCCAGGAAAGCAGCTGGGAGAAACTGACTTCTGGTCACCAAATAAAACGTTTCATTTTAAATGCTGAGGATTTAAT
ATCAAACAGTGCTTCACTGTTTTAAACTATGGACTTGTAAATAGTAGTACATGTTAATTCTCCTAGGGACACACAAAAAGAATAGTAATAAAATACTCGCACACATATAACCACCTATCACCCACTTAAGAAACAGACAT
ATGACAGAAATCATCAGGTGTAAATAGTAGTACATGTTAATTCTCCTAGGGACACACAAAAAGAATAGTAATAAAATACTCGCACACATATAACCACCTATCACCCACTTAAGAAACAGACAT
GACTTCTCTTTTACACATTTTATATGGATTGTAATTGTCATCTCCAAAAATGCAAAACTTCTCAAACACTCTATTGGGAAACCGCCAATTTTCTGTTGGATA
AAATCTTTGACCCCCTGTCATAACAGTATATCATATATATATGAGAAATGCAAAATGCAAAACTTCTCAAACACTCTATTGGGAAACCGCCAATTTTCTGTTGGATA
TGTGTGTGTATATACATATATATATGAGAAATGCAAAATAGCTTTTAAAAATTATAGCTTTAAAATTATAGAGATATAAAGAGTTTTTAAAATACAGAAAAGTCCAAGAGAAA
TTCTAATATCTTTGAAACTTCTCCCCAATTATAGCTTTAAAAATTATAGCTTTAAAATTATAGAGATATAAAGAGTTTTTAAAATACAGAAAAGTCCAAGAGAAA
AAGTGGTTCACAATCACCTATTTACTTAATCCTATTGACATCAGAAATACTAACTCCCTCTTAAAAGATAGTATTATTAATAATTCTTCATGACT
TATAAAGAACAAAATAAATGAAAGCTGCCCTCTCAGAAATATATGTGTATATATACATAAAGCGCATTTCTGTGTCTAAATATCTTGAGGTCAGGAGTTCAAGAAACCGGCTGGAC
CCTCCTAGAATAAAATTACATGCATTAATATATGTGTATATATACATAAAGCGCATTTCTGTGTCTAAATATCTTGAGGTCAGGAGTTCAAGAAACCGGCTGGAC
GTGCAATTTTAATAGCTGTTCAGTGTCCAGGAAGTACAAAGATTTGGGAGGCCGAGGTGCAGTGAGCCAAGATCCCGCCACTTTAAGGATAAATAAGGGCCAGGG
GCGGTGGCTCATGCCTGTAATCCCAGCACTTTGGGAGGCCGAGGTGCAGTGAGCCAAGATCCCGCCACTGCACTTAGCCTGGGCAACAAGCAAGAC
AACATGCGCAACCCCATCTCTACTAAAAGTACAAAGATTAGCTGGGCGTGGTGGCTTGCAGTGAGCCAAGATCCCGCCACTGCACTTAGCCTGGGCAACAAGCAAGAC
AGGCAGGAGAATCACTTGAACCCGGGAGGCGGAGGTTGCAGTGAGCCGAGATCGCGCCACTGCACTCCAGCCTGGGCGACAAGAGCGAAAAGCTGCGGCATTGTC
TCTGTCTCAAAAATAAATAAATTAAATACATACATAAGCACACTAAGCTCTTATGACACTCTTATGTTCCCTGTAGCTCCTGACCACGGAGGCCTGATTTCAAA
TCCACTTCTTCAAGTGCAAACTCTTATGACACTCTTATGTTCCCTGTAGCTCCTGACCACGGAGGCCTGATTTCAAA
```

```
AAAATGTAAAGAATGTCCTAATGTGCTCCCATGCTGCTTAAACTGTTATTATAAATTGCTTTTATTATAAATATATAAAGAATGATG
TAATAGGCCAGCCATGGTGGCTCATCCCTGTAATTCCAGGTCTTTGGGAGGCTGAGGCAGGTGAATCACTTGAGGTTAGGAGTTTGAGA
CCAGCCTGGCCAACATGGTGAAACCCCGTCTCTACTAAAAATATAAAATTAGCCAGGTGTGGTGGTACGCACCTGTAGTCTCAGCTAC
TCCGGAGGCTGAGGCAGGAGAATGCTTGAAACCAGAAGGCGGAGGTTGCAGTGGGTCAAGATCAAGCAACTGCACTCCAGCCTAGGTG
ACAGAGCGAGACTTTGTCTCAGGAAAAAAAAAATTCTCAGTCACCTAGATTGAGAAATAGAACATTACCAAAACAGATAAAGCCCCA
CTGTGTTCCCATCCACATCACATTCACTTATCTCCTCAAAGGAAAGTGCTATTTTTGAATTTAGTATTATTAATTATTCCTTGCATTCT
TCCTACTCATATCATGTCCTATATACATATAATATATACAAAATGCCGATATCATACATAGCAATGTTTACATTTCGATTTTTGCATT
GTCAATGTAGAATTTTAAACTTAAAAACATGCTTCATACAGCCGGGTGTGGTGGCTCATGCCTGTAATCCCAGCATTTTGGGAGGCCA
AGGCAGGCGGATCGACGAGGTCAGGAGTTCGAGACCAGCCTGACCAACATGGTGAAACCCATCTCTATTAAAAATACAAAAAAATA
TTAGCTGGTCATGGTGGCGCGTGCCTGTAATCCCAGCTACTCAGGAGGCTGAGGCAGGAGAATTGTTTGAACCCAGGAGGCAGAGGTTG
CAGTGAGCCGAGATCGCACCATTGCACTCCAGCCTGGGTGACAGAGCGAGACTCCATCTCAAAAAAAAAAAAGCTTCATACAAA
CATGAAACGGGCACATGTCTGCCTGGGTGCGGTGGCTGTAATCCCAGCACTTTGGGAGGCCAAGGCGGGCAATCACTTAAGG
CCAGGAGTTCGAGACCAGCCTGGTCAACATGGTGAAACCCGTCTCTACTAAAAATTAGCCAGGCATGGTGGCATGCGCCT
GTAGTCCCAGCTACTCGGGAGGCTGAGGCAGGAGAATCTCGTCTCAAACAAACAAACAAACAGAGGTTGCAGTGAGCCAAGATTGTGTCACTGCA
CTCCTGCCTGGGTAACAGAGTGATACTCTGTCTCAAACAAACAAACAAACAAACAAAAGAAAAAAAGAAATGGCACAT
GTCAAATGTTAATTTGACTATGTAACTTATTAATGAAGGAACCAGCAGGGTGTAGAGCTGGGTCAAGAAGTATAAGAGAGACTGGAG
TGCTTACAGTCAGTGGCAAGCAGAGACAGAATGCTGAAAGGTTATGAAAGGTTAATATTCGAAAGGGCAACTAAACTGTAAATC
TGCCATTATCTTTTCTATCAGACAGAATAATAATTACATCTCTACTAGACAACAAACATTGCCACTTTCAATCCATAATCTATGGTAAT
TTCATGGAGTCTGGCCCTAATCAACAGTAAATAGTAAAGCCAACAAACAGGATCTCTTCCCTAGACCTTGAAGTGATCTTTGGGTGGACCC
CTTAGACAATAATTTAGTATGACATTGAGAGGACACGCAAGCTGGGCAGCATAGTGAGAAATACCACTTGAGGACCCGCCTCTACAAAAAATTAAAAATTAG
CCGGGCATGGTGGTGTGAGCCTGTAGTCTCAGCTACTCAGGAGGCTAAGGTGGAAATACCACTTGAGCCGGGAGTTCGAGGCTGTAGT
GAGCTATGATCATGCCATTGCACTCCAGCCTGGGTAACAGAGCGAGAACCCTGTCTTGAAAAAAGAAAGCATGCTGCTCAGTTCATTAATTCACTGTT
AAAGGAAATGCAGCCATTTTTTTTGCCTTATTCCAAGTTCGGATAATTTTCTTTTTAACAATATAAATATTATCACTATGTA
TCTTTTGCAATATGGCTTTCACTCAGTGTAGTTGCAAGGGTTAGCCATGTGAAGTAACATTGCTTTCAAGGTATTGCTATTATAAACAAATC
GTATGTTGGTCTATGTAGGCATATCACAATWATYCATTCCTTCAATCAGCTNTGATTTACTTTGTTCNAANACNAAGCACACAACTATAATTANAAT
TCATACCTTTAATCAATAATAATTTGTCTCTTCAATCAGCTNTGATTTACTTTGTTCNAANACNAAGCACACAACTATAATTANAAT
TTCATTACTGATAAATATAAAATATTTTCCAAAACATCACAAATCTTTNTNNNTNCACTATTTACTATACACTTTNGGTCNAATTTAA
AGCGGCTTCACTATATGTGGTTCTTTCCTCTCTTCCCATACTAATTACTGGTACTGGACATATACATCCAAAATCAAATCAAATAGTARTGTC
CTTTTTAAGGGATAAATGGGATGTGATGTAGAAGGGCATAGTAGGGACTTCATCGTTTTGGCAAATTTTTCTTAATATATAGGTGGTA
```

FIG. 3A-22

```
GGCATGTGGAATTTATAACAAAGTTCTGTCTCCAGCCCAGTTTCTGTTACATAAAACCATATAATTAACAGTTAAACTGGATCTGGTT
TGACACAGATGTAGACGATATTAATAATTACTCCAGAACAACAGGCATAACTAAAAACTACCACAGGCAAAAGGGGAAAATAGAGAATG
TAAGGGCTGGGACTTAAGCCATGTTGCCCACTCCAAGTTTCATGGACTTTCCTTCTCCACATTACTTTCTCTCTGCTAGACTGT
CCTGATGTACCTGCTCTGCACACAGAATTAGACGAGGCGATCAGGTTGGTCATGTATCCAATCAGCAGTATGCCAGATTCTCCAGAT
GACCCGGAAGCACTTGGAGGACACCGCCTATCTGGTGGAAGATGAGAGGCAATTGGCTGGGTGTCGAACTGGCAAACCAGGCCC
CAGAAACAGAGATCATCTTTAATTCAATACAGGTAAAGGAGGAGACCCAAGAGCAGATACGGAAATGACACGTGCATACCTTGATTCAC
TGTTAATTACTTATGAATTGTGTCTGAATTTGAAAACAAGAAAGTCTCATATAATTCCATTGTGATTGCCTTCAGGCTGACTT
GATTAACGTAGTTCATGGTCTTTAGAGAAACAAGAAAGTCCATAAAGAAAATCAATTAAAACACAAAATACTTTCTAATCTAGAAATG
GCTATTTCTGCTTAGAGTTATAGGGCTATAACTGATAGAGGTAACCTTGAAGAAATATGCCAATGTAGGTTTTAGGAGAGAAGACTTA
CAAATAAAGCAATTTGAGTTCAAAATTTGACTCTGAAACTTACCAGCTGAGTAAGCTTGGGAAAGTACCTCAACCATTCTAGGCCTCAG
TGTTCCACCTGTAAATGGTAACAATCATAGTCTATCTTAAGCGTGTACACCTATAAAGTGATTAGTAGTATAGATTCTTATACAAAACAAGA
GCTCTGTAAATTATAGCTCTTATTAGTTGCTGACACAATAAAGCCACTGAGTTATCTGAGAATAAACATTTATATGTTACTCGTCAC
ATAAAATACATTGCCAGCTGGGCGCAGTGGCTCATGCCTGTAATCCAGCACTTTGGGAGGCTGAGGTGGTGGATCACTTGAGGTCA
GGAGTTTGAGACGAGCCAGCCTGGGCTAATGTGGGCGAAACCCGTCTCTACCAAAAACATAAAAATTAGCCAAGTGTGATGCCACTGT
AATCCCAGCTACTCAGGAGGCTGAGGCAGAGGACTCTGTCTCAAAAAAACAAGTGACTTTTCTCCTAAGACATCCCCCCTCCAACACACAAAAATTACTGGGCAGAGCA
CCAGCCTGGGCGACAGAAGGAGACTTGCATAACATGCAAGTGGCTGGGTTAGGTTATGTTGGTAGCCCTATCCAGATCCCTTGGAGCACTTATGCCCCAGAGCTTCCTGCAGG
CCAGATTCAGTCAATAACTTTTGCATAACATGATGAGGCTGGTTTAGGTTATGTTGGTAGCCCTATCCAGATCCCTTGGAGCACTTATGCCCCAGAGCTTCCTGCAGG
CTACAAATGCGCCAGGCTAGTGATTCCTGACATATCTGAAACTTTCTCCCAAAGATTGCCCTTGGAGCACTTATGCCCCAGAGCTTCCTGCAGG
ATGAAGATGCATATTCTGTGTAGTATGTTAGGTTATGTTGGTAGCCCTATCCAGATCCCTTGGAGCACTTATGCCCCAGAGCTTCCTGCAGG
GGTGCTGGTGCTGCTGACTGCTATCTGAAACTTTCTCCCAAAGATTGCCCTTCACTTCTCTAGTTGCTTTCCTCATCCCTTAAAAGT
ATCAGGCTGAGGCTAACAGTCATCTGAAGCCATATCTGAAGCACTGCTTCAGGAAGTCCTAGAGAAATAAGCACTTATGGCATTCTATAATCCA
TGCACCTGAGAGCATTCTTTATAAACCACTTCTGTCAGAATCTCAGGCACTGCTTCAGGAAGATAAGTTTAGAAAGTCACGAAGCTCATTAAAAA
GCATTTCCCTCTTTTTCAAACTACAAGCTGTGATCATGCCTGATTGAGAAATATTAGCATGCATTCATAAGTCATATGCACATCATG
ACAAATTAAAAACCATACAAAATAGAATAGGACAAAGTAGAACATATACACATATGAGACATACGTGTGTTTGAATCATGATGTCA
GAATTTCATTTCCATTTGTATGTGTATATGTGTAAACATATATTTGAAAGCCACTGTCCAATCCCTGCCAGCTCCTCTGATTCTATAACTCTATTA
AGTGTATTCATTACTGCAGACCACAGTCAAAGGGTTTGAAAGCCACTGTCCAATCCCTGCCAGCTCCTCTGATTCTATAACTCTATTA
GATTACACTTGAGGAAGTAAAATAATTCAATATTTGATCATCCTCGGCATATATAGACTTTAGTTAACGAGGAAAAAGTCTTGTA
TGAAGAATAAAACTTGAAGAAATTTAGCAGTGCTTCAACCTTTAGAAATCTACAGTCAATAACATAACATAACAGATTTTATCTAAAATTCTTAATGTGTCA
GTATTTCTATTCTGTGCTTTGATTTACTTGCGTCTCTTGAGTAACATAACATAACAGATTTTATCTAAAATTCTTTATGCTGATAA
```

FIG. 3A-23

```
CAAAGGCACTTCTATATAAAAACCTCCACATAAAATAAAATTATGGTTTCAATTATACATTTTATATAACAATTATTACCACTTAAGAG
CATTTACTGGGTGTCAGGCAATGTTCTAAGACTTTTTCCATATATCAGATCATTTAATACCCTCAATGACCCTATAAGGGAAGTAGAAT
TCTTTCCCCAGTTTTTCAAATGAGGCACAGAGAGGAGGTTAAGCAACTTGTCTGAGCTCACACAGCTAGTAAATGGTAGAAACTAGAATTCA
AACTCAAGCAGTATTTCTCTAGAATCAGTGAACGTAACCACTTTGCTAAACTGCCTGTGAAGTTACTTTTCTCAAAACAGCTCCTATT
CACCATGTAAAGAAAAGTACAAACCCATAAATAGTTACATGGGTGTTGACTTTACAATTATTTAAACCAAAACATAAATACTTTATGCAGTTTTA
ACGGTTGTGGTCCCGTGGTTGTATAATAGTTACATGGGTGTTGACTTTACAATTATTTAAACCAAAACATAAATACTTTATGCAGTTTTA
TGTATGTTATACTCACAGAAAGAGAAGGGAAAATTTTAAATCATTCTCTTAAGGTTACATCAAGTTGCGTATCAGTTCAGTTCCAT
TAAATGATTCAAATCAAAGTCTGTGCATTTGAGAATTCATTAAGAGAGTAACATACATGTTATTCATTAAGAGTAACATAAATTTTGCA
TTGATTCTTGCCAAATCACACCTACAACCATAAATTGTAAATTTCTAGGAAAACTCAGTACAAAACTTGGTGCAATGCAATAAAGTTT
GTGGCACAGACAGTAATACTCAGCAAACATCCCACCTCCTCCATATTTTCCAGCTCCCCTTGTGGTTAAACGTTGCCATGTGGCAA
GTTCTGGCCAGTGAGGGCACAAGAAAGTCCTGAAACTGAGATATGAGATAACTTTGCTACCAGGCTTCTCAGTGTTTA
TTTCTGCTGAGGGCACAAGAAAGTCCTGAAACTGAGATATGAGATAACTTTGCTACCAGGCTTCTCAGTGTTTA
CTGGTGTGGAGCCCTTGTAATGACACATAACATGAACAAGAATAAATCTTTGTTGCATGAAGCCCTAGGAATGCCAGGACTAATCTG
TTACCTCAGCACACAAACCCAGCCTATCCTGACTAAGGTGTATTAAATTACTATTGAATGTGTATTAGTAAACTTCTACTGT
ATAATCCTTCTTCTGTAGGTAGTTCACACTCAAGATCCCTCTTGAAGAATATTCCAAACAAGATGAAACAATGATGACAGACTTAAGCATTCT
GCCTTCCTCCTCTAATTTCACACTCAAGATCCCTCTTGAAGACAGAGTGCTGAGAGTTCTAACTTCATTGGCTACGTAGTGGCAAAAGCTCTAC
AGCATTTTAAGGAACATTTAAAACCTGGTAAGCAGAGTGCCTGGTTAGGAATGCCTTGTTGACAGGAATAGTTAATTCTCAAAAGGGA
AAAACAAAACTTGTTTCAAATACCTGGAAAACATGTTAACCTCATTAATAAGACATGAAAACAAGATGGCATTTCTGCCTA
TCAGATTTGCAAATTAAAAAAAAACCCAGGAAATCCTGATAGGAATGTGATGAAGAGCCATAAAATTCCTTTGATATCATGTATTGGTGGAAC
ATAATTGGTTTGCATTTTGAAAGCTATTTGATTGATGAAMKTCTCCCCCAAGATCTAGATTTGCAGCATTATTAAATATTAAAAGTTGGCC
ATCAATCCTAAGGRATAAATCTAAATTTGAATGAAMKTCTCCCCCAAGATCTAGATTTGCAGCATTATTAAATATTAAAAGTTGGCC
GGGCGCAGTGGCTCATGCCTGTAATCCCAGCACACTTGGGAGGCTGAGGCGGGATCACGAGGTCAGGAGATTGAGACCATCCTGGAT
AACACGGAGAAACTGCGTCTCTACTAAAATAAAAAATTAGCCGGGCATGGTGGCGGGCGCCCTAGTCCCAGCTACTCGGGAGGCTG
AGGCAGGAGAATGGCGTGAACCCGGGAGGCAGARCTTGCAGTGAGCAGAGATCGGGCCACTGCCACTGCACTGCCAGCCTGGGCGACAGAGCAAGA
CTCTGTTTAAAAAAAAACAAGAGAATGATTAAGTAKATTATGACTAAATACACCTCAATACATTTTGGAGGTAATAGTATTATCATGATTTTCAGAAAAGATC
TGTGTAAAACAAGAGAATGATTAAGTAKATTATGACTAAATACACCTCAATACATTTTGGAGGTAATAGTATTATCATGATTTTCAGAAAAGATC
ATAATGACTTGCTAACTACTTTAACAAGAGCTTTATTATCAGCTAGTCTTGGAGGTAGAGCAGCATGTGGAGCCAGTTCTCTCCGACTCGTCA
CTGAGGCTCAGTGTCCAAGGTCCAATGAACTACTCAGGTCGGAGGTGGTAGAGCAGCATGTGGAGCCAGTTCTCTCCGACTCGTCA
TCACACTGCACGGCTTCCTGTTAAGATATTTGCTCAAAAAAATGCGAGATATAAAATCTGGGTAATATGATCAACCTTAAAGAATAATT
```

FIG. 3A-24

```
ACATTTTAAATTATTCATGAGACCTTGTTAGTAGTCACCATCAATGTGTAATTAAGCCAGATGTGACAGGATTTGTTGCCTCTCCTT
TACTTCTGAATTTTGGAGGCCTTTTTTTTTTCTAGTTGTATCAGTCAGCCAACCAATATCTTTTAGCATCTACTAAGTTTAGATACG
GGAACTGGTACTCTGAAAGAGAAAATGAGAAATTTGACAAGATCCTGTCCCCAAGGAGCTTCCTATCCAACAGGGCACAAGACAGATA
GATAGACACACACACACACACACACACACACTTGTCCCCAAGGCAAGATTTAGAGAGTGCACAGGAGTGGG
CTCTGGGAGTTCAGGGAGGGTCGTTCACATTCTGGTAGGGAAGATACTTCTGAGCTCAGTATATTCCCTTTCTACTGTCCTTCTATC
CCCTCTCTTCCTCCTCTGTCTTGTTCTGTCACCCATACTGGAGTACAGTGGCACGATCTCGGCTCACTGCAACCTCGGCCTCCCAGGT
TTTTTTTTTGAGACAGAGTCTTGTTCTGTGCCTCAGCCTCCTGAGTGCTGGGATTACAGGCGCACACCACCATGCCTGGCTAATTTTGTGTTTTTAGTAG
TCAAATGATTCTTGTGCCTCAGCCTCCTGAGTGCTGGCAGGCTGGGCTCTTGAACTCCTGACCTCAAGTAATCCACCCACCTTGGCCTCCCAAAGTGCTGGGATC
AGACAGGGTTTCACCATGTTGGCCAGGCTGGTCTTGAACTCCTGACCTCAAGTAATCCTGACCTCAAGTATATATAAAGTAGATACACACAGGC
ACAGGCATGAGCCACCACTGGGTCCTCCTCCCTTTCTTAAAAATACATCAATTAATATAAAGTAGATACACACAGGC
AGAATCAAAGTGTATAGGTTGGAGAGAGACTGTTCCAAAGGGGATGGCAATGGGCAAATACGGCAAGAAAGAGTAGAGCATCTAGG
TACTGAGGGTGCTGGGAAGTCCTGCTAAAAATACGGCAAGAAAGATAGAGCATCTAGGTACTGAGGGTGCTGGGAAGTCCTGCTAAAG
TGGTCCCCTCCACTGTGGGGGCCTTTGAGTTTCCCTGTGCCAGGTACCTCATGAGTCAGAGGGGAAGCTGGACGTCTATGCCCAGAGCCAGGCAGA
ACCAAGACCAGCTCAGCTAAAAGAATGGATGGAGGAGGAAACCGATGGACAGCTGCTTCAGGGCCCAGGCTGAAGCAGTCGCAGTTGTTT
AACGGGTCAGGTCTAGAGTCACTCTGCTCAAGATGTGACTTGCCAGGAGGAATCTGGCTGGGACATGTGTGTCTACCTCTAGACCA
TTAGTCTCAGATCACTCTGCTCAAGATGTGACTTGCCAGGAGGAATCTGGCTGGGACATGTGTGTCTACCTCTAGACCA
GGAGAGAGGAGAGTCTTGGTTGACAGTCCCATGTAGTAACATAAACTAGGGGCAACATACCCTCTCCCTTTCACACATGACCATAACACCATG
ACTTCTTCAGGGCAATATACCCTCTTGGTTGACACTTTATAGTGACCACATACCCTCTCCCTTTCACACATGACCATAACACCATG
TAGCACTCAACTCTTGGGTTTTGCTCTTCTTGTCAGTTGACATTACCATGTCAGTGGGACTTAGGACTCTGCCTGGCACAGGGCAAACCCTCAATATTTGTTGAAT
CCACCGTTCTAGGGTTTTGCTCTCTTTGTCAGTTGACATTAGACCATGTCAGTGGGACTTAGGACTCTGCCTGGCACAGGGCAAACCCTCAATATTTGTTGAAT
AAATTAATTAATAAAACAGTGTAAATGAATATCAGTAGACTACAACAAGAGTAACAGTAGGCGAAGGTGGAAGGCAAAGGTGGAAGAG
GTCAGGGCTCTGAGTGCTGGGCTGTGGGAGTCTGAGGTTCACTCTGAGGTCTGAGGTTCACTCTGAGGTCTGAGAGCACAGGTAGGTTTAGAGAAAGGAAGCCTCA
TGCTGGTGCCCCAGTGGGTACTGACTATGCATTTGTAGCCAAATCAAAGTATTTGTAGCCAAATCAAGTCATCTATCTCTTCCCAGTTGTTGGG
ACTTCCAATGGCAATGGGAATTAAGATACTGAGTAATGGGAGATCAAGAATTATTACTAACAGGCACACAAGGCACGAAGTGATTTTCAC
AGGCAATGTTAATGTTTTCTTTTATGTAGTTTTAAAATTCTAAAAGTAACAAAATCACAACATCACAAACATTAGACGACAAAAAT
TATCCATAATCCCACCATCTTAACACCACTATTCATTATTTGTTTCCTTATTCACATTCACATTTTCTACCTATTTCTTAGATTYCCAAGA
AATAGAATTACTTGTTTAGAGGTTATTAACATCTTATTGTTCTGGATATATAATATATAGCTATATATAGCTAAATTAATAACAG
CAATGTCTGCAGTACCACTTCTCAAATGCTAACTGGCATTTCAATTTTTTGAGACAGTCTCTCTCTGTTGCCCAGGCAGGATTGCAGT
GGCATGATCTCGGCTCACGGCAACCTCCACCTCCCAGGTTCAAGCGACTCTCATGCCTCAGCCTCCCAAGTAGCTGGGATTACAGGTGT
```

FIG. 3A-25

GCACCACCACACTTGGCTAATTTTTGTATTTTTAGTAGAGATGTGTTTTACCATGTTGGCCGGGCTGGTCTCAAACTCCTGCCTCA
AGTGATCCTTCCACCTCAGCCTCCCAAGGCTGGTATTACAGGCATGAGCCACTGCCTGGCCATTTAAAATCTTCA
GTAATAAATGAAAATTTTATCTTATTGTTATAATTTTATGGTTTTTATTATTCATGAGAATAAACATTTCCAAGTTGTTACTG
ACTGAATTTCTTTTGTGCACCTTACTTGGTATCATGGATAAAATTTGTCAATTTCTGATTATATCATGCATTCAGGGTCCCAAA
CCTGCCAAAGTTTAAAGAGAAAGATACTAAGGGAAAAACCAGGAAAACATGGTAGAAAAGAATCACCCTGGCATTTCAATCAGTAAA
CATTTGCTAGGTGCCCTAGCTGCAGGTATACAGCTCACTGAAACATGAAATTCCAATTTTATAGGGTGAAATATATATTTAGAACCCTCT
TCTGGAACTTTCTTCTAGTATCTAGCATCCTAAGTGCCTGGACGTTCCTGATTGGTTGCAATGTGTTTGTTTATTTCCCATCCCAAGTT
TCATAGCTGCCGGCCCTGGGATCTACAGTCACAGGCTGTAACACAATATCTTGCACATCCTGAGTCTTTAATAAGCTTTTGTAGATGGG
CTCTTACCATCATCATCGTGAAAGGCAAATAAACACTTTATTATCACATCAGAGAGAAAAGACCATCTTAGAGGCTCAACAACCCAGGAAAG
AACACTACGTGCATGTAGAGTTCAGAATAAATTGTTAAGAATATCCATGCATATGGGTTTCACATTATTTGCTACACACAGTACCAATTTTCCAAAGC
CTGTGACGATTTCTTCAAATTGTTAAGAATATCCATGCATATGGGTTTCACATTATTTGCTACACACAGTACCAATTTTATTAGTATTTGATCA
CAACAGCAGGTATTCTATTACCCATCCTGGACTTTACTCCAAGAAAAATACACTGAGTCTGTGAGTAGAATTATCTCTTCATCTGGGACCTGGAA
TGCTGCTTTTTTTTTTTAAGGTAAGAAGATCTAATGCATCCTATATCCAGTAGCATCCTATATCCAGTAGCTATATACTGAAGTACTCTTAGTTCTTACTTATG
ATCCTGAAATAAAAAAGGATAATAATGCAATAAACACAGTTGCAGGAAAGTATGTTAGCTATATACATGAAGTACTCTTAGTTCTTACTTATG
TTGAATGGCTTAGCTATTAATACTCAAATTGAGTTAAAATGAAAATTCCTCCTTAAAAAATCAAACGTAATATGTAATATGTATTACATTTCATGG
TACATTAGTAGTTCTTTGTATATTGATAATTACTAAATCACCTAGTGTCTATGTCTATGTCTATGTTCTATCACATCACAAACATGCACATCACTTGCTTTG
TAACAAATGTCTTCTTCTTGTAGTTTGCACTTAAATATATATATTGCACTTTTTGGAAAAAATCTAAGATTCATTGCTTTG
TTTTGTAAAGACCAATAGGTTCTGTATAGTCTTTTTTAAATTGTGGTAAAATACACATGGCATTAAATACACATGGCATTAATTACCATTTTAACCATTTTAA
AGTGCACAATTGTGGCATTAAGTACACTCACGTTGCTGTGCAACCATCACCACCGTCCATCTTCAGAACCTTTTATCTTCCTAAACT
GAAACTCTGTACTCGTTAAGCACTCACTTCCCGTTCCCCATCCCCAGCCTGCTCAACACGACTGTACTTCTCTATGAATTTGACTA
CTCTAGGTACTGCATGTAGGTGGAATCATACAGTATTTGTCTTTGTTCATTTGTTTTGTTTTTCACTTAGTGCCATGTTTTCAAGGTTCA
TCTGTCGCCCAGCTGGAGTGCAGTGGTGCAGTGTCCTTTTAGGCTAATATTCTTGCATGTATATTGCTTATCCATTCAGCCATTG
TCCATGTGTTGCATGTCTCAGAACTTCCTTTTAGGCTAATATTCTTGCATGTATATTGCTTATCCATTCAGCCATTG
ATGGACACTTGGGTTGCTTCCATCTTTGACATACGTATTTTATGGCTATGTGAATAATGCTGTTTGAACGTGGGTGCTACATAGTTACTTTTAAAATTG
GCAACAACAGGCGTGTCTTTGACATACGTATTTATGGAAAAACACAAGATTTTCCTGGCTGACGCTCAACCTCATAATTGGACCTTGG
TGCAACACAATAATAGGCCAGGCACGGTGCCTCACACGTGGTGCTCCTCACACGTGGTGCTCACGTGGTGCTCAATGAGCCAACTGGAATTACGTGGGTGGATTACCTGGATTACCAGTCAGTTATACAGTCAGTATTCACAAATTATAAA
AAGAAATGTAGGCCAGGCACGGTGGCTCACACCTGTAAATCCCAGCACTTTGGGAGGCCAAGTGGGTGGATCACCTGAGGTCAGGAGAGTT
CGAACCAGCCTGGCCAACATGGTGAAACCCGTCTCTACTAAAAATACAAAAATTGGCCAGGTGTGGTGGCGCATGCCTGTAATCCCA
GCTACTCAGGAGGCTGAGATGGGAGAATTGCTTGAACCTGGGAGGCAGAGGTTGCACTGAGCCGAGATCGCGCCACTGTACTCCAGCCT

FIG. 3A-26

```
GGGCAACAGAGGGAGACTCTTTTTTAATAAATAAATAAATAAATATAAAGAAACGTAATGAAAGAGAGAACTCTGAACTT
TAAAGAACTTTCACCCAGTCTTGATCTATCTGACAGAAAGGCTTGTCAGAGAAAGTTAGAGTTCAGAGGCAGCCAATTGAATATAAT
TAACTCCAAATGAAGATAAACCTTTTCTAAATCATACTGAAGGCTATAAAAAAATGAGAATTATGTTATTTTTTGAGACAGGGTCT
TACTCTATTGCCCAGGCTGGAGTGCAGTGGCATGATCTGGCTCACTGAAGCCTGACCTCCTTGGCTCAGGTGATCCTCCCACCTCAGC
CTCCTGAGTAGCTGGGACTACAGGTACTACCATGCCCGCCTCATTTTTGTATTTTTTAGTAGAGATGGGGTTTCTCCATGTTGTCCAGG
CTGGTCTCAAACTCCCAGGCTCAAGCAATCTGCCCGCCTCAGCCTCCAAAAGTGCTGTAATTACAGGCATGAGCCACTGCTCCTGCCAG
GGAACTAATAGAATCCTGGGTTCTCGGTGTGCAATAAAYCTCAATGAGCTATCAAAAGCTTATAGAGTGGAAAGAGAGTGGGGAAGTGA
TGACAAAAAAATAAGTGATTAAGAGAACCTATTTCTATCCAATGAGCTATCAAAAGCTTATAGAGTGGAAAGAGAGTGGGGAAGTGA
GGCTCAAAACAGCTAAATGGAAGAAGATTTGCATGCAGGCTGAACTGGATTTCATCCTGGCTACTATATTCTCCAGATGTGTCACT
TTGGCCAAGATCCTTAATCTCAGTGTCATCTATAAGGTAATTAAAGTACACTAGTGCCCACTAATACATAGTAAGTTTTCAATGCATGCCAAATGTTCT
TCAGTTACCCGAGATCAACTGCGGTTTTTAAAATATATATGGAAAATTCCAGAAATACATAGTAAGTTTTCAATGCATGCCATTAAAT
CTCATGCTGTCCTGACCCCTTCCTCCCGGAGGTGAATGCTCCCTTTGTCCAGTGGCTCCAGATGACTACATTCCCAAATGTTCT
CTTAGGAACCCTTTCTGTGTTCAAGGAACCCTTACTTCATCTCTACCTGTGACTAATTTATGACATATCATTATCCAAGACATAGGATGCCGGCATACTGTTATA
ATTGTTCTATTTTATTAGTTATGTATAAGGTTCAGTAGTACTATCTGCAGTTTCAGACATCTCCCTTGGGGTCTTGGAACATATCCCCGTGGATAASG
GAAAAAAACATGGTATGTAAAAGTTTGTSTTTATAGAGTAGTTSTSAGAACTACATTCATCCATAATGTGTGSCTCATGATACTCATTGATAGA
GGAAACTACTGTAAAGTTTGTSTTTATAGAGTAGTTSTSAGAACTACATTCATCCATAATGTGTGSCTCATGATACTCATTGATAGA
TGGTAGTAGCAACAATAAAAATAATATTATCAAGTAACTGATTCATAATGACTCTCAAAACGTTAATTTTGCTCTCATACTTCCTTTACCT
AAGTTTACCTACATGTTTGAATTTGTAAAGGGAAGGTTTTTCTAGACCAATAATCATCCAAATCTAATATCATCGCAATTTGACCCAGCATCATCCATTAATTCCCACGCATCGTAAAG
AAACTGAAAAAGTTGCAACATACTGCATGTCATTTTAAATGTACCAAATGGAATCTAAATATCATCGCAATTTGACCCAGCATCATCCATTAATTCCCACGCATCGTAAAG
ATTAGCAGGTCATCATCCCTCTTTAAAATGAGAAATTTATCTCAATACATCTTTGTTGATCAACACAATTTGATCATTTTAAATTTAAAAATTAAGAACATCCTGT
CAAGTTTCTTAACAATGAGAAATTTATCTCAATACATCTTTGTTGATCAACACAATTTGATCATTTTAAATTTAAAAATTAAGAACATCCTGT
TAATGTAGTATAATTTTATGCTTAAATATTTATTCTAGAATATGAAAATATCTAGAATTCTATGACTACTAAACATACTAATAAACAATATATCTCTTAATGAGAAGGAAGAGCTTTTATAC
GACATCAAATTCTAGTATGAAATATTATTCTAGAATATGAAAATATCTAGAATTCTATGACTACTAAACATACTAATAAACAATATATCTCTTAATGAGAAGGAAGAGCTTTTATAC
TATACTACAAATTCTATGACTACTAAACATACTAATAAACAATATATCTCTTAATGAGAAGGAAGAGCTTTTATAC
TCCAATAAGTAAGTATCCACTATAATATTATTTCTTCCTAGAACAAGACAGGATTAAGCATCATGACCGTCCCTATTGGGGATG
TTTTTATAGATGCAAGCACTGTGGCACCTCAGCTCAAATGTGACTTCCTCAATGCACCTGCTGATTGGAATGTCTTCCCCAGATCTTCCCTGCTGGTT
TCTTCCCAGTATTCAGGTCTCAGCTCAAATGTGACTTCCTCAATGCACCTGCTGATTGGAATGTCTTCCCCAGATCTTCCCTGCTGGTT
TGTTTAGTGCTATACCCATTAATTTACTATCATCACACTTGTCACTATCTGCAGATGTCTTGTTGGTTACTTTGTNGTGTTTGTCAC
TGCCAGAATATCAGTTCTATGAAGAAAAGGGCCTTGTCTATTTGACACTTATGAGANATGTGNAGGNACATACAAATGGCCAATG
```

FIG. 3A-27

```
GGCATATGGAAAAACGCTTGACTTCAAGAGTACTNATGGNTATNACCAACATTTATGGAGTAACTACTTTGAAAAGAACCATTCTGTCT
TTACTATCAAGCCAAGATACTCAAGGAAGGCAGCAGAAGTGGAAGCTCCATGTGGGCAGAGAGCCTAGTCTTGAGATGTGATTTAGCT
GGTATTTGGGTGAAACAAATAAACCAGCCTCAAAATAACACAAGGGGCCGGGTGCAGTGCCTCACGCCTGTATCCCAGCACTTTGGGAG
GCTCGAGGCAGGCAGATTACTTCAGGTGAGGAGTTCGAGACCAGCCTGGCTAACATGGTGAACCTCCAT
```

FIG. 3A-28

| Brain Regions | HKNG 1 mRNA expression in normal brain | | | | |
|---|---|---|---|---|---|
| | Gray Matter | White Matter | Neuron | Astrocytes | Oligodendrocytes |
| Frontal cortex(1) | +++ | - | ++ | - | - |
| Motor cortex(2) | +++ | - | ++ | - | - |
| Parietal cortex(3) | +++ | - | ++ | - | - |
| Occipital cortex(4) | +++ | - | ++ | - | - |
| Hippocampal formation(5) | | | | | |
| CA1 | +++ | - | ++ | - | - |
| CA2 | +++ | - | ++ | - | - |
| CA3 | na | na | na | na | na |
| CA4 | ++ | - | ++ | - | - |
| Dentate gyrus | +++ | - | + | - | - |
| subiculum | +++ | - | ++ | - | - |
| parahippocampal gyri | +++ | - | ++ | - | - |
| Caudate/Putamen(6) | +/- | - | +/- | - | - |
| GPi/GPe/Putamen(7) | | | | | |
| GPi | + | - | + | - | - |
| GPe | + | - | + | - | - |
| Putamen | +/- | - | +/- | - | - |
| Amygdala(8) | ++ | - | + | - | - |
| Thalamus(9)medial | ++ | - | + | - | - |
| Substantia nigra level(10) | | | | | |
| SNc(substantia nigra pars compacta) | ++ | - | ++ | - | - |
| SNr(substantia nigra pars reticulata) | + | - | + | - | - |
| Red Nucleus | + | - | + | - | - |
| 3rd cranial nerve nuclei | + | - | + | - | - |
| superior colliculus | | | | | |
| Upper pons(11) | | | | | |
| Locus coeruleus | + | - | + | - | - |

FIG.4A

| Region | Col1 | Col2 | Col3 | Col4 |
|---|---|---|---|---|
| pontine nuclei | - | - | +++ | - |
| Lower pons(12) | - | - | + | + |
| locus coeruleus | - | - | +++ | ++ |
| pontine nuclei | - | - | ++ | + |
| raphe nucleus(midline) | - | - | ++ | ++ |
| Medulla(13) | - | - | + | + |
| Inferior olivary nucleus | - | - | ++ | ++ |
| 12th cranial nerve nuclei | - | - | + | + |
| nucleus ambiguus(multipolar lower motor neurons) | - | - | ++ | ++ |
| Cerebellum(14) | | | | |
| Purkinje cells | - | - | ++ | +/- |
| Granular layer | - | - | + | + |
| Molecular layer | - | - | + | ++ |
| Temporal pole(15) | - | - | +++ | ++ |
| Cingulate cortex(16) | - | - | +++ | ++ |
| Anterior thalamus(17) | - | - | ? | ? |
| Subthalamic nucleus | - | - | ++ | ++ |
| Ventral anterior N.(VA),Ventral lateral N.(VL) | na | na | na | na |
| Hippocampal formation(18) | na | na | na | na |
| CA1 | - | - | +++ | ++ |
| CA2 | - | - | +++ | ++ |
| CA3 | - | - | +++ | ++ |
| CA4 | - | - | +++ | ++ |
| subiculum | - | - | +++ | ++ |
| parahippocampal gyri | - | - | ++ | + |
| cervical cord (rostral position) | - | - | ++ | + |
| anterior motor nuclei | - | - | | |
| sensory nuclei group | - | - | | |

FIG.4B

| pedigree | Affected Individuals | Phenotype | a.a. change | exon | comment | nt change | nt position |
|---|---|---|---|---|---|---|---|
| 30124 | 3010189 | scz | R331T | 8 | 3 of 4 affected individuals | AGA -> ACT | 51,641 51,642 |
|  | 3010185 | scz |  |  |  |  |  |
|  | 3010184 | scz |  |  |  |  |  |
| 30105 | 3010027 | scz | I23T | 3 | the only affected individual | ATT -> ACT | 35,044 |
| 31102 | 3110017 | major depr | E202K | 7 | all three affected individual (also seen once in Costa Rica) | GAA -> AAA | 45,487 |
|  | 3110014 | scz |  |  |  |  |  |
|  | 3110003 | scz |  |  |  |  |  |
| 30120 | 3010155 | scz | E202K | 7 | one of the two affected individuals | GAA -> AAA | 45,487 |
| 30126 | 3010203 | scz | intronic | 10 | 3 of 4 affected individuals | insertion: GAATGCCTGGTTAG 21 base pairs 3' of exon 10 | after 63,417 |
|  | 3010210 | scz |  |  |  |  |  |
|  | 3010204 | scz |  |  |  |  |  |
| 30140 | 3011486 | scz | intronic | 6 | one of the two affected individuals | A -> T (24bp downstream of exon 6) | 43,450 |
| 32301 | 3210041 | scz |  |  | two of the three affected individuals |  |  |
|  | 3210051 | scz |  |  |  |  |  |

FIG. 5A

| pedigree | Affected Individuals | Phenotype | a.a. change | exon | comment | nt change | nt position |
|---|---|---|---|---|---|---|---|
| 30120 | 3010155 | scz | L34L | 4 | one of the two affected individuals | CTC -> CTA | 36,307 |
| 32200 | 3210104 | scz | L34L | 4 | both affected individuals | CTC -> CTA | 36,307 |
| | 3210009 | scz | | | | | |
| 31109 | 3110013 | scz | I23T | 3 | one of the two affected individuals | ATT -> ACT | 35,044 |

FIG.5B

| a.a. change | exon | nt change | position |
|---|---|---|---|
| non-coding 5'-UTR | 1 | G→C (35 bp upstream from 3' endo of exon 1) | 15,385 |
| L42L (silent) | 4 | CTG → CTA | 36,331 |
| V123G | 6 | GTT → GGT | 43,184 |
| non-coding (intronic) | 6 | A → T (24 bp downstream from exon 6) | 43,350 |
| V301I | 7 | GTC → ATC | 45,571 |

FIG. 5C

```
AGTTGCGTCCCTCTCTGTTGCCAGGCTGGAGTTCAGTGGCATGTTCATAGCTC
ACTGAAGCCTCAAATTCNTGGGTTCAAGTGACCCTCCTACCTCAGCCCCATGA
GGACCTGGGACTACAGTTCCCTCCCTTTGGAACGCAGCGTGGGCACCTGCAA
CGCAGAGACCACTGTATCTCCGGTGCAGAATGTAATGAGTGCCTGATACATT
TGCCGAATAAACTATTCCAAGGGTTGAACTTGCTGGAAGCAANAGAAGCACT
ATTCTGGTAACAGCGGGAACATGAAGCCGCCACTCTTGGTGTTTATTGTGTGT
CTGCTGTGGTTGAAAGACAGTCACTGCGCACCCACTTGGAAGGACAAAACTG
CTATCAGTGAAAACCTGAAGAGTTTTTCTGA
```

FIG.6A

```
AGTTGCGTCCCTCTCTGTTGCCAGGCTGGAGTTCAGTGGCATGTTCTTAGCTC
ACTGAAGCCTCAAATTCCTGGGTTCAAGTGACCCTCCCACCTCAGCCCCATGA
GGACCTGGGACTACAGATGGAGTCTTGCTCTCGTTGCCCAGACTGGAGTGCA
CTGCTGCGATCTCAGCTCACTGCAACCTCTACCTCCCAGGTTCAAGCGATTCT
CCTGCCTCAGCCTCTCGAGTGGCTGGGACTATAGTAACAGCGGGAACATGAA
GCCGCCACTCTTGGTGTTTATTGTGTGTCCGCTGTGGTTGAAAGACAGTCACT
GCGCACCCACTTGGAAGGACAAAACTGCTATCAGTGAAAACCTGAAGAGTTT
TTCT
```

FIG.6B

```
                                                                                                    79
                                                                            M   K   L               3
CTTGGAGTCAACTGAGTGTGGACTGAAACTTCCAAAAACTGACATGAGGAGTCACTGGAGAATCATGATCAAGGAGCTA
                                                                            ATG AAG CTG
                  M   K   L                                                                         153
CACACTCTGACTTAACTTTATTCTGTGGACAATGAGAGACAACTGCAAGGATTAACAGTGAGAAC

P   L   L   M   F   P   V   C   L   L   W   L   K   D   C   H   C   A   P   T                     23
CCA CTT TTG ATG TTT CCC GTG TGT CTG CTA TGG TTG AAA GAC TGT CAT TGT GCA CCT ACT                     213

W   K   D   K   T   A   I   S   E   N   A   N   S   F   S   E   A   G   E   I                     43
TGG AAG GAC AAA ACT GCC ATC AGT GAA AAC GCG AAC AGT TTT TCT GAG GCT GGG GAG ATA                     273

D   V   D   G   E   V   K   I   A   L   I   G   I   K   Q   M   K   I   M   M                     63
GAC GTA GAT GGA GAG GTG AAG ATA GCT TTG ATT GGC ATT AAA CAG ATG AAA ATC ATG ATG                     333

E   R   E   E   E   H   S   K   L   M   K   T   L   K   K   C   K   E   E                         83
GAA AGG GAG GAG GAA CAC AGC AAA CTA ATG AAA ACC TTG AAG AAG TGC AAA GAA GAA                         393

K   Q   E   A   L   K   L   M   N   E   V   H   E   H   L   E   E   E   S                         103
AAG CAG GAG GCC CTG AAA CTT ATG AAT GAA GTT CAT GAA CAC CTG GAG GAG GAA AGC                         453

L   C   Q   V   S   L   A   D   S   W   D   E   C   R   A   C   L   E   S   N                     123
TTA TGC CAG GTT TCT CTG GCA GAT TCC TGG GAT GAA TGC AGG GCT TGC CTG GAA AGT AAC                     513

C   M   R   F   D   T   T   C   Q   P   A   W   S   S   V   K   N   M   V   E                     143
TGC ATG AGG TTT GAT ACC ACC TGC CAA CCT GCA TGG TCC TCT GTG AAA AAT ATG GTG GAA                     573

Q   F   F   R   K   I   Y   Q   F   L   F   P   L   Q   E   N   D   R   S   G                     163
CAG TTT TTC AGG AAG ATC TAT CAG TTT CTG CCT CTC CAG GAA AAT GAC AGA AGT GGC                         633

P   V   S   K   G   V   T   E   E   D   A   Q   V   S   H   I   E   H   V   F                     183
CCT GTC AGC AAA GGG GTC ACT GAG GAA GAT GCG CAG GTG TCA CAC ATA GAG CAT GTG TTC                     693
```

FIG.7A

| S   | Q   | L   | S   | A   | D   | V   | T   | S   | L   | F   | N   | R   | S   | L   | Y   | V   | F   | K   | Q   | 203  |
|-----|-----|-----|-----|-----|-----|-----|-----|-----|-----|-----|-----|-----|-----|-----|-----|-----|-----|-----|-----|------|
| AGC | CAG | CTG | AGC | GCA | GAT | GTG | ACA | TCT | CTC | TTC | AAC | AGA | AGC | CTT | TAC | GTC | TTC | AAA | CAG | 753  |
| L   | R   | E   | F   | D   | Q   | A   | F   | S   | Q   | Y   | F   | T   | S   | G   | T   | D   | V   | T   |     | 223  |
| CTG | CGG | GAA | TTT | GAC | CAG | GCT | TTT | CAG | TCA | TAT | TTC | ACA | TCG | GGG | ACT | GAC | GTT | ACA |     | 813  |
| E   | P   | F   | F   | P   | S   | L   | S   | K   | E   | P   | A   | Y   | R   | A   | D   | A   | E   | P   |     | 243  |
| GAG | CCT | TTC | TTT | CCA | TCT | TTG | TCC | AAG | GAG | CCA | GCC | TAC | AGA | GCA | GAT | GCT | GAG | CCA |     | 873  |
| S   | W   | A   | I   | P   | N   | V   | F   | Q   | L   | C   | N   | L   | S   | F   | S   | V   | Y   | Q   |     | 263  |
| AGC | TGG | GCC | ATT | CCC | AAT | GTC | TTC | CAG | CTG | CTC | TGC | AAC | TTG | AGT | TTC | TCA | GTT | TAT | CAA | 933  |
| S   | V   | S   | E   | K   | L   | I   | T   | T   | L   | R   | A   | T   | E   | D   | P   | P   | K   | Q   | D   | 283  |
| AGT | GTC | AGT | GAA | AAA | CTC | ATC | ACA | ACC | CTG | CGT | GCC | ACA | GAG | GAC | CCT | CCA | AAA | CAA | GAC | 993  |
| K   | D   | S   | N   | Q   | G   | P   | I   | S   | K   | I   | L   | P   | E   | Q   | D   | R   | G   | S   |     | 303  |
| AAA | GAC | TCC | AAC | CAG | GGC | CCG | ATT | TCA | AAG | ATA | CTA | CCT | GAG | CAA | GAC | AGA | GGC | TCA |     | 1053 |
| D   | G   | K   | L   | G   | Q   | N   | L   | S   | D   | D   | C   | V   | N   | F   | R   | K   | R   | C   | Q   | K   | 323 |
| GAT | GGG | AAA | CTT | GGC | CAG | AAT | TTG | TCT | GAT | GAC | TGC | GTT | AAT | TTT | CGC | AAG | AGA | TGC | CAG | AAA | 1113 |
| D   | G   | Y   | L   | S   | R   | S   | N   | P   | E   | L   | Y   | R   | E   | L   | N   |     | 343  |
| GAT | GGG | AAA | CTT | GGC | CAG | AAT | TTG | TCT | GAT | GAC | TGC | GTT | AAT | TTT | CGC | AAG | AGA | TGC | CAG | AAA | 1113 |



FIG.7B

```
V   S   E   L   A   Y   Q   S   P   G   A   E   D   I   F   N   P   V   K   V    403
GTT TCT GAA CTG GCA TAC CAG TCC CCA GGA GCT GAG GAC ATC TTT AAT CCA GTG AAA GTA  1353

M   V   A   L   S   A   H   E   G   N   S   S   D   D   T   V   V   P           423
ATG GTA GCC CTA AGT GCT CAT GAA GGA AAT TCT TCT GAT GAC ACA GTG GTT CCT          1413

S   S   L   L   P   S   S   N   F   T   L   S   S   P   L   E   K   S   A   G   443
TCA AGC CTC CTG CCT TCC TCT AAC TTC ACA CTC AGC CCT CTT GAA AAG AGT GCT GGC      1473

N   A   N   F   I   D   H   V   E   K   V   L   Q   H   F   K   E   H   F       463
AAC GCT AAC TTC ATT GAT CAC GTG GAG AAG GTT CTT CAG CAC TTT AAG GAG CAC TTT      1533

K   T   W   *                                                                    467
AAA ACT TGG TAA                                                                  1545

GAAGATTTAGTCCATCCTATAATCAGCAAGAATTACACCCTTCGGCCAAGACCTGAGAATTCTGAAAATACAAAGCAGGC 1624

TAACACAATGAACACAGCTGCATGAAAGTTAGGTATATATTAGGAAGCACTATTGGTTTACTTTGTTGAATGGAAGTTT 1703

AATAGCTATTCAAATTGAGTTAATATAAAAATTTCTTCCTAAAAAGTAAAATGTACATATGTAGAATATGATGCATTAG 1782

TTCTTTGTATACTAAATAAAATACTGAGTCCCCT                                               1815
```

FIG.7C

```
CTTGGAGTCAACTGAGTGTGGACTGAAACTTCCAAAAACTGACATGAGGAGTCACTGGAGAATCATGATCAAGGAGCTA      79
                                                                      M  K  L   3
CACACTCTGACTTAACTTTATTCTGTGGACAATGAGAGACAACTGCAAGGATTAACAGTGAGAAC ATG AAG CTG       153
 P  L  L  M  F  P  V  C  L  L  W  L  L  K  D  C  H  C  A  P  T                      23
CCA CTT TTG ATG TTT CCC GTG TGT CTG CTA TGG TTG AAA GAC TGT CAT TGT GCA CCT ACT      213
 W  K  D  K  T  A  I  S  E  N  A  N  S  F  S  E  A  G  E  I                         43
TGG AAG GAC AAA ACT GCC ATC AGT GAA AAC GCG AAC AGT TTT TCT GAG GCT GGG GAG ATA      273
 D  V  D  G  E  E  V  K  I  A  L  I  G  I  K  Q  M  K  I  M  M                      63
GAC GTA GAT GGA GAG GAG GTG AAG ATA GCT TTG ATT GGC ATT AAA CAG ATG AAA ATC ATG ATG  333
 E  R  R  E  E  E  H  S  K  L  M  K  T  L  K  K  C  K  E  E                         83
GAA AGG AGA GAA GAA GAA CAC AGC AAA CTA ATG AAA ACC TTG AAG AAG TGC AAA GAA GAA      393
 K  Q  E  A  L  K  L  M  N  E  V  H  E  H  L  E  E  E  S                            103
AAG CAG GAG GCC CTG AAA CTT ATG AAT GAA GTT CAT GAA CAC CTG GAG GAG GAA AGC          453
 L  C  Q  V  S  L  A  D  S  W  D  E  C  R  A  C  L  E  S  N                         123
TTA TGC CAG GTT TCT CTG GCA GAT TCC TGG GAT GAA TGC AGG GCT TGC CTG GAA AGT AAC      513
 C  M  R  F  D  T  T  C  Q  P  A  W  S  S  V  K  N  M  E  N                         143
TGC ATG AGG TTT GAT ACC ACC TGC CAA CCT GCA TGG TCC TCT GTG AAA AAT ATG GAA AAT      573
 D  R  S  G  P  V  S  K  G  V  T  E  E  D  A  Q  V  S  H  I                         163
GAC AGA AGT GGC CCT GTC AGC AAA GGG GTC ACT GAG GAA GAT GCG CAG GTG TCA CAC ATA      633
 E  H  F  S  Q  L  S  A  D  V  T  S  L  F  N  R  S  L  Y                            183
GAG CAT GTG TTC AGC CAG CTG AGC GCA GAT GTG ACA TCT CTC TTC AAC AGA AGC CTT TAC      693
```

FIG.8A

```
V   F   K   Q   L   R   R   E   F   D   Q   A   F   Q   S   Y   F   T   S   G   203
GTC TTC AAA CAG CTG CGG CGA GAA TTT GAC CAG GCT TTT CAG TCA TAT TTC ACA TCG GGG   753

T   D   V   T   E   P   F   F   P   S   L   S   K   E   P   A   Y   R   A         223
ACT GAC GTT ACA GAG CCT TTC TTT CCA TCT TTG TCC AAG GAG CCA TAC AGA GCA         813

D   A   E   P   S   W   A   I   P   N   V   F   Q   L   L   C   N   L   S   F   243
GAT GCT GAG CCA AGC TGG GCC ATT CCC AAT GTC TTC CAG CTG CTC TGC AAC TTG AGT TTC   873

S   V   Y   Q   S   V   S   E   K   K   L   I   T   T   L   R   A   T   E   D   P   263
TCA GTT TAT CAA AGT GTC AGT GAA AAA CTC ATC ACA ACC CTG CGT GCC ACA GAG GAC CCT   933

P   K   Q   D   K   D   S   N   Q   G   G   P   I   S   K   I   L   P   E   Q   283
CCA AAA CAA GAC AAA GAC TCC AAC CAG GGA GGC CCG ATT TCA AAG ATA CTA CCT GAG CAA   993

D   R   G   S   D   G   K   L   G   Q   N   L   S   D   C   V   N   F   R   K   303
GAC AGA GGC TCA GAT GGG AAA CTT GGC CAG AAT TTG TCT GAT TGC GTT AAT TTT CGC AAG   1053

R   C   Q   K   C   Q   D   Y   L   S   D   C   P   N   V   P   E   L   Y   323
AGA TGC CAG AAA TGC CAG GAT TAT CTA TCT GAT TGC CCT AAT GTG CCT GAA CTA TAC TAC   1113

R   E   L   N   E   A   L   R   L   V   S   R   S   N   Q   Q   Y   D   Q   V   343
AGA GAA CTC AAT GAG GCC CTC CGA CTG GTC AGT AGA TCC AAT CAG CAA TAC GAC CAG GTG   1173

V   Q   M   T   Q   Y   H   L   E   D   T   T   L   L   M   E   K   M   R   E   363
GTG CAG ATG ACC CAG TAT CAC CTG GAA GAC ACC ACG CTT CTG ATG GAG AAG ATG AGA GAG   1233

Q   F   G   W   V   S   E   L   A   Y   Q   S   P   G   A   E   D   I   F   N   383
CAG TTT GGC TGG GTT TCT GAA CTG GCA TAC CAG TCC CCA GGA GCT GAG GAC ATC TTT AAT   1293
```

FIG. 8B

```
P   V   K   V   M   V   A   L   S   A   H   E   G   N   S   S   D   Q   D   D    403
CCA GTG AAA GTA ATG GTA GCC CTA AGT GCT CAT GAA GGA AAT TCT TCT GAT CAA GAT GAC  1353

T   V   P   S   S   L   L   P   S   S   N   F   T   L   S   S   P   L   E        423
ACA GTG GTT CCT TCA AGC CTC CTG CCT TCC TCT AAC TTC ACA CTC AGC AGC CCT CTT GAA  1413

K   S   A   G   N   A   N   F   I   D   H   V   V   E   K   V   L   Q   H   F    443
AAG AGT GCT GGC AAC GCT AAC TTC ATT GAT CAC GTG GTA GAG AAG GTT CTT CAG CAC TTT  1473

K   E   H   F   K   T   W   *                                                     451
AAG GAG CAC TTT AAA ACT TGG TAA                                                   1497

GAAGATTTAGTCCATCCTATAATCAGCAAGAATTACACCTTCGGCCAAGACCTGAGAATTCTGAAAATACAAAGCAGGC  1576

TAACACAATGAACACAGCTGCATGAAAGTTAGGTATATATTAGGAAGCACTATTGGTTTACTTTGTTGAATGGAAGTTT 1655

AATAGCTATTCAAATTGAGTTAATATAAAATTTCTTCCTAAAAAGTAAAATGTACATATGTAGAATATGATGCATTAG  1734

TTCTTTGTATACTAAATAAATACTGAGTCCCCT                                                1767
```

FIG.8C

CTTGGAGTCAACTGAGTGTGACTGAAACTTCCAAAAACTGACATGAGGAGTCACTGGAGAATCATGATCAAGGAGCTA 79

```
                                                             M   K   L          3
CACACTCTGACTTAACTTTATTCTGTGACAATGAGAGACAACTGCAAGGATTAACAGTGAGAAC ATG AAG CTG  153
```

| | | | | | | | | | | | | | | | | | | | | |
|---|---|---|---|---|---|---|---|---|---|---|---|---|---|---|---|---|---|---|---|---|
|P|L|M|F|P|V|C|L|L|K|D|C|H|C|A|P|T| | | | 23 |
|CCA|CTT|ATG|TTT|CCC|GTG|TGT|CTG|CTA|AAA|GAC|TGT|CAT|TGT|GCA|CCT|ACT| | | | 213 |
|W|K|D|K|T|A|I|S|E|N|A|N|S|F|S|E|A|G|E|I| 43 |
|TGG|AAG|GAC|AAA|ACT|GCC|ATC|AGT|GAA|AAC|GCG|AAC|AGT|TTT|TCT|GAG|GCT|GGG|GAG|ATA| 273 |
|D|V|D|G|E|V|K|I|A|L|I|G|Q|M|K|I|M|M| | | 63 |
|GAC|GTA|GAT|GGA|GAG|GTG|AAG|ATA|GCT|TTG|ATT|GGC|CAG|ATG|AAA|ATC|ATG|ATG| | | 333 |
|E|R|E|E|H|S|K|L|M|K|T|L|K|C|K|E|E|E| | | 83 |
|GAA|AGG|GAG|GAA|CAC|AGC|AAA|CTA|ATG|AAA|ACC|TTG|AAG|TGC|AAA|GAA|GAA|GAA| | | 393 |
|K|Q|E|A|L|K|L|M|N|E|V|H|E|C|R|A|C|L|E|S|103|
|AAG|CAG|GAG|GCC|CTG|AAA|CTT|ATG|AAT|GAA|GTT|CAT|GAA|TGC|AGG|GCT|TGC|CTG|GAA|AGC|453|
|L|C|Q|V|S|L|A|D|S|W|D|E|P|A|W|S|S|V|K|N|123|
|TTA|TGC|CAG|GTT|TCT|CTG|GCA|GAT|TCC|TGG|GAT|GAA|CCT|GCA|TGG|TCC|TCT|GTG|AAA|AAT|513|
|C|M|R|F|D|T|T|C|Q|A|E|P|S|W|A|I|P|N|M|E|P|143|
|TGC|ATG|AGG|TTT|GAT|ACC|ACC|TGC|CAA|GCT|GAG|CCA|AGC|TGG|GCC|ATT|CCC|AAT|ATG|GAG|CCA|573|
|A|Y|R|A|D|A|E|P|S|V|Q|S|V|Y|Q|N|V|F|Q|L|163|
|GCC|TAC|AGA|GCA|GAT|GCT|GAG|CCA|AGC|GTG|CAG|AGC|GTT|TAT|CAA|AAT|GTC|TTC|CAG|CTG|633|
|N|L|S|F|S|V|Y|Q|V|S|E|K|L|I|T|T|L|R|A| | 183|
|AAC|TTG|AGT|TTC|TCA|GTT|TAT|CAA|GTC|AGT|GAA|AAA|CTC|ATC|ACA|ACC|CTG|CGT|GCC| | 693|

FIG.9A

```
T   E   D   P   P   K   Q   D   K   D   S   N   Q   G   G   P   I   S   K   I    203
ACA GAG GAC CCT CCA AAA CAA GAC AAA GAC TCC AAC CAG GGA GGC CCG ATT TCA AAG ATA   753

L   P   E   Q   D   R   G   S   D   G   K   L   G   Q   N   L   S   D   C   V    223
CTA CCT GAG CAA GAC AGA GGC TCA GAT GGG AAA CTT GGC CAG AAT TTG TCT GAT TGC GTT   813

N   F   R   K   R   C   Q   K   C   Q   D   Y   L   S   D   D   C   P   N   V    243
AAT TTT CGC AAG AGA TGC CAG AAA TGC CAG GAT TAT CTA TCT GAT GAC TGC CCT AAT GTG   873

P   E   L   Y   R   E   L   N   E   A   L   R   L   V   S   R   S   N   Q   Q    263
CCT GAA CTA TAC AGA GAA CTC AAT GAG GCC CTC CGA CTG GTC AGT AGA TCC AAT CAG CAA   933

Y   D   Q   V   Q   M   T   Q   Y   H   L   E   D   T   L   T   L   M   E        283
TAC GAC CAG GTG CAG ATG ACC CAG TAT CAC CTG GAA GAC ACC ACG CTT CTG ATG GAG       993

K   M   R   E   Q   F   G   W   V   S   E   L   A   Y   Q   S   P   G   A   E    303
AAG ATG AGA GAG CAG TTT GGC TGG GTT TCT GAA CTG GCA TAC CAG TCC CCA GGA GCT GAG   1053

D   I   F   N   P   V   K   V   M   V   A   L   S   A   H   E   G   N   S   S    323
GAC ATC TTT AAT CCA GTG AAA GTA ATG GTA GCC CTA AGT GCT CAT GAA GGA AAT TCT TCT   1113

D   Q   D   D   T   V   V   P   S   S   L   P   S   N   F   T   L   S            343
GAT CAA GAT GAC ACA GTG GTT CCT TCA TCA CTC CCT TCC AAC TTC ACA CTC AGC           1173

S   P   L   E   K   S   A   G   N   A   N   F   I   D   H   V   V   E   K   V    363
AGC CCT CTT GAA AAG AGT GCT GGC AAC GCT AAC TTC ATT GAT CAC GTG GTA GAG AAG GTT   1233

L   Q   H   F   K   E   H   F   K   T   W   *                                    375
CTT CAG CAC TTT AAG GAG CAC TTT AAA ACT TGG TAA                                  1269
```

FIG.9B

GAAGATTTAGTCCATCCTATAATCAGCAAGAATTACACCCTTCGGCCAAGACCTGAGAATTCTGAAAATACAAAGCAGGC 1348

TAACACAATGAACACAGCTGCATGAAAGTTAGGTATATATTAGGAAGCACTATTGGTTTACTTGTTGAATGGAAGTTT 1427

AATAGCTATTCAAATTGAGTTAATATAAAAATTTCTTCCTAAAAAGTAAAATGTACATATGTAGAATATGATGCATTAG 1506

TTCTTTGTATACTAAATAAATACTGAGTCCCCT 1539

FIG.9C

```
CTTGGAGTCAACTGAGTGTGGACTGAAACTTCCAAAAACTGACATGAGGAGTCACTGGAGAATCATGATCAAGGAGCTA  79
                                                     M   K   L                      3
CACACTCTGACTTAACTTTATTCTGTGGACAATGAGAGACAACTGCAAGGATTAACAGTGAGAAC ATG AAG CTG    153
 P   L   L   M   F   P   V   C   L   L   W   L   L   K   D   C   A   P   T          23
CCA CTT TTG ATG TTT CCC GTG TGT CTG CTA TGG TTG AAA GAC TGT GCA CCT ACT            213
 W   K   D   K   T   A   I   S   E   N   A   N   S   F   S   E   A   G   E   I     43
TGG AAG GAC AAA ACT GCC ATC AGT GAA AAC GCG AAC AGT TTT TCT GAG GCT GGG GAG ATA    273
 D   V   D   G   E   V   K   I   A   L   I   G   I   K   Q   M   K   I   M   M     63
GAC GTA GAT GGA GAG GTG AAG ATA GCT TTG ATT GGC ATT AAA CAG ATG AAA ATC ATG ATG    333
 E   R   R   E   E   E   E   H   S   K   L   M   K   T   L   K   K   C   K   E   E  83
GAA AGG AGA GAG GAA GAA GAA CAC AGC AAA CTA ATG AAA ACC TTG AAG AAG TGC AAA GAA GAA 393
 K   Q   E   A   L   K   L   S   L   M   N   E   V   H   E   H   L   E   E   E   S 103
AAG CAG GAG GCC CTG AAA CTT ATG AAT GAA GTT CAT GAA CAC CTG GAG GAA GAA AGC       453
 L   C   Q   V   S   L   A   D   S   W   D   E   C   R   A   C   L   E   S   N    123
TTA TGC CAG GTT TCT CTG GCA GAT TCC TGG GAT GAA TGC AGG GCT TGC CTG GAA AGT AAC   513
 C   M   R   F   D   T   T   C   Q   P   A   W   S   S   V   K   N   M   P   A   143
TGC ATG AGG TTT GAT ACC ACC TGC CAA CCT GCA TGG TCC TCT GTG AAA AAT ATG CCA GCC   573
 Y   R   A   D   A   E   P   S   W   A   I   P   N   V   F   Q   L   L   C   N    163
TAC AGA GCA GAT GCT GAG CCA AGC TGG GCC ATT CCC AAT GTC TTC CAG CTG CTC TGC AAC   633
 L   S   F   S   V   Y   Q   S   V   S   E   K   L   I   T   T   L   R   A   T    183
TTG AGT TTC TCA TAT CAA AGT GTC AGT GAA AAA CTC ATC ACA ACC CTG CGT GCC ACA       693
```

FIG.10A

| | | | | | | | | | | | |
|---|---|---|---|---|---|---|---|---|---|---|---|
| E | D | P | P | K | Q | D | K | D | S | N | Q | G | G | P | I | S | K | I | L | 203 |
| GAG | GAC | CCT | CCA | AAA | CAA | GAC | AAA | GAC | TCC | AAC | CAG | GGA | GGC | CCG | ATT | TCA | AAG | ATA | CTA | 753 |

| P | E | Q | D | R | G | S | D | G | K | L | G | Q | N | L | S | D | C | V | N | 223 |
|---|---|---|---|---|---|---|---|---|---|---|---|---|---|---|---|---|---|---|---|---|
| CCT | GAG | CAA | GAC | AGA | GGC | TCA | GAT | GGG | AAA | CTT | GGC | CAG | AAT | TTG | TCT | GAT | TGC | GTT | AAT | 813 |

| F | R | K | C | Q | K | C | Q | D | Y | L | S | D | D | C | P | N | V | P | 243 |
|---|---|---|---|---|---|---|---|---|---|---|---|---|---|---|---|---|---|---|---|
| TTT | CGC | AAG | TGC | CAG | AAA | TGC | CAG | GAT | TAT | CTA | TCT | GAT | GAC | TGC | CCT | AAT | GTG | CCT | 873 |

| E | L | Y | R | E | L | N | E | A | L | R | L | V | S | R | S | N | Q | Q | Y | 263 |
|---|---|---|---|---|---|---|---|---|---|---|---|---|---|---|---|---|---|---|---|---|
| GAA | CTA | TAC | AGA | GAA | CTC | AAT | GAG | GCC | CTC | CGA | CTG | GTC | AGT | AGA | TCC | AAT | CAG | CAA | TAC | 933 |

| D | Q | V | V | Q | M | T | Q | Y | H | L | E | D | T | T | L | M | E | K | 283 |
|---|---|---|---|---|---|---|---|---|---|---|---|---|---|---|---|---|---|---|---|
| GAC | CAG | GTG | GTG | CAG | ATG | ACC | CAG | TAT | CAC | CTG | GAA | GAC | ACC | ACG | CTT | ATG | GAG | AAG | 993 |

| M | R | E | Q | F | G | W | V | S | E | L | A | Y | Q | S | P | G | A | E | D | 303 |
|---|---|---|---|---|---|---|---|---|---|---|---|---|---|---|---|---|---|---|---|---|
| ATG | AGA | GAG | CAG | TTT | GGC | TGG | GTT | TCT | GAA | CTG | GCA | TAC | CAG | TCC | CCA | GGA | GCT | GAG | GAC | 1053 |

| I | F | N | P | V | K | V | M | V | P | S | S | A | H | E | G | N | S | D | 323 |
|---|---|---|---|---|---|---|---|---|---|---|---|---|---|---|---|---|---|---|---|
| ATC | TTT | AAT | CCA | GTG | AAA | GTA | ATG | GTA | CCT | TCA | AGC | GCT | CAT | GAA | GGA | AAT | TCT | GAT | 1113 |

| Q | D | D | T | V | P | S | S | N | A | N | F | T | L | S | 343 |
|---|---|---|---|---|---|---|---|---|---|---|---|---|---|---|---|
| CAA | GAT | GAC | ACA | GTT | CCT | TCC | AGC | AAC | GCT | AAC | TTC | ACA | CTC | AGC | AGC | 1173 |

| P | L | E | K | S | A | G | N | A | F | I | D | H | V | V | E | K | V | L | 363 |
|---|---|---|---|---|---|---|---|---|---|---|---|---|---|---|---|---|---|---|---|
| CCT | CTT | GAA | AAG | AGT | GCT | GGC | AAC | GCT | TTC | ATT | GAT | CAC | GTG | GTA | GAG | AAG | GTT | CTT | 1233 |

| Q | H | F | K | E | H | F | K | T | W | * | 374 |
|---|---|---|---|---|---|---|---|---|---|---|---|
| CAG | CAC | TTT | AAG | GAG | CAC | TTT | AAA | ACT | TGG | TAA | 1266 |

FIG.10B

GAAGATTTAGTCCATCCTATAATCAGCAAGAATTACACCTTCGGCCAAGACCTGAGAATTCTGAAAATACAAAGCAGGC 1345

TAACACAATGAACACAGCTGCATGAAAGTTAGGTATATATTAGGAAGCACTATTGGTTACTTTGTTGAATGGAAGTTT 1424

AATAGCTATTCAAATTGAGTTAATATAAAAATTTCTTCCTAAAAAGTAAAAATGTACATATGTAGAATATGATGCATTAG 1503

TTCTTTGTATACTAAATAAATACTGAGTCCCCT 1536

FIG.10C

```
                                                       M   K   P   P   L   L   V   F      8
GCAACCTCGTTGGTGAGAGCCTGCAGTTAGTGTCACGGGCGGAAAC ATG AAG CCG CCA CTC TTG GTG TTT            69

I   V   Y   L   L   R   D   C   Q   C   A   P   T   G   K   D   R   T                  28
ATT GTG TAT CTG CTG CGG AGA GAC TCT CAG TGT GCG CCT ACA GGG AAG GAC CGA ACT              129

S   I   R   E   D   P   K   G   F   S   K   A   G   E   I   D   V   D   E   E          48
TCC ATC CGT GAA GAC CCG AAG GGT TTT TCC AAG GCT GGG GAG ATA GAC GTA GAT GAA GAG          189

V   K   K   A   L   I   G   M   K   Q   M   K   I   L   M   E   R   R   E   E          68
GTG AAG AAG GCT TTG ATT GGC ATG AAG CAG ATG AAA ATC CTG ATG GAA AGA AGA GAG GAG          249

E   H   S   K   L   M   R   T   L   K   K   C   R   E   E   E   K   Q   E   A   L      88
GAA CAT AGC AAA CTA ATG AGA ACA CTG AAG AAA TGC AGA GAA GAA GAA AAG CAG GAG GCC CTG      309

K   L   M   N   E   V   Q   E   H   L   L   E   E   E   R   L   C   Q   V   S          108
AAG CTT ATG AAT GAA GTT CAA GAA CAT CTA CTA GAA GAG GAA AGG CTA TGC CAG GTG TCT          369

L   M   G   S   S   W   D   E   C   K   S   L   E   S   D   C   M   R   F   Y          128
CTG ATG GGT TCC TGG GAC GAA TGC AAA TCT CTG GAA AGT GAC TGC ATG AGA TTT TAT              429

T   T   C   Q   F   L   F   P   F   H   E   D   D   E   K   E   L   P   V   F   R   K  148
ACA ACC TGC CAA AGC AGT TGG TCC TCT ATG AAA TCC ACG ATT GAA CGG GTT TTC CGG AAG          489

I   Y   Q   F   L   F   P   F   H   E   D   D   E   K   E   N   V   F   E              168
ATA TAT CAG TTT CTC TTC CCT TTC CAT GAA GAC GAT GAA AAA GAG CTT CCT GTT GGT GAG          549

K   F   T   E   E   D   V   Q   L   M   Q   I   E   N   V   F   S   Q   L   T          188
AAG TTC ACT GAG GAA GAT GTA CAG CTG ATG CAG ATA GAG AAT GTG TTC AGC CAG CTG ACC          609
```

FIG.11A

```
V   D   V   G   F   L   Y   N   M   S   F   H   V   F   K   Q   M   Q   Q   E         208
GTG GAT GTG GGA TTT CTC TAT AAC ATG AGC TTT CAC GTC TTC AAA CAG ATG CAG CAA GAA        669

F   D   L   A   F   Q   S   Y   F   M   S   D   T   D   S   M   E   P   Y   F         228
TTT GAC CTG GCT TTT CAA TCA TAC TTT ATG TCA GAC ACA GAC TCC ATG GAG CCT TAC TTT        729

F   P   A   F   S   K   E   P   A   K   K   A   H   P   M   Q   S   W   D   I         248
TTT CCA GCT TTT TCC AAA GAG CCA GCA AAA AAA GCA CAT CCT ATG CAG AGT TGG GAC ATT        789

P   S   F   Q   L   F   C   N   F   S   L   S   V   Q   Y   Q   K   D   S   A         268
CCC AGC TTC CAG CTG TTT TGT AAT TTC AGC CTC TCT GTT TAT CAA AAA GAC AGT GTC AGC GCA    849

T   V   T   E   M   L   K   A   I   E   D   L   S   K   Q   D   R   G   L   A         288
ACA GTT ACA GAG ATG CTG AAG GCC ATT GAG GAC TTA TCC AAA CAA GAC AGA GGG CTG TGT GCC    909

H   G   P   S   S   T   W   P   V   R   G   F   H   A   R   C   Q   K   E   P         308
CAC GGT GGA CCG AGT TCC ACG TGG CCT GTG CGG GGC AGA TGC CAG AAA GAG GAA CCT            969

G   Q   N   S   S   E   C   L   Q   F   H   A   L   Y   T   K   A   D   E   Y         328
GGC CAG AAC TCG GAA TGT CTC CAA TTT CAT GCA CTA TAC ACA AAG GCG GAT GAG TAC            1029

L   W   A   D   C   P   A   V   P   Q   V   L   Q   M   T   Q   H   H   L   E         348
CTA TGG GCA GAC TGC CCT GCT GTT CCT CAA CAG CAG ATG ACC CAG CAT CAC CTT GAG            1089

L   V   N   I   S   N   Q   Q   Y   A   Q   M   R   E   Q   F   G   W   V   T   L     368
TTG GTC AAC ATA TCC AAT CAG CAG TAT GCC CAG ATG AGA GAG CAG TTT GGT TGG GTA ACA CTG    1149

E   D   T   T   Y   L   M   E   K   M   R   E   Q                                      388
GAG GAC ACC ACG TAT CTG ATG GAG AAG ATG AGA GAG CAG                                    1209
```

FIG. 11B

FIG. 11C

```
                                                          M   K   P   P   L     5
CAGAAGCTGGTGGCAACCTCGTTGGTGAGAGCCTGCAGTTAGTGTCACGGCGAAAC ATG AAG CCG CCA CTC    72

L   V   F   I   V   Y   L   L   R   D   C   Q   C   A   P   T   G   K        25
 TTG GTG TTT ATT GTG TAT CTG CTG CGG AGA GAC TGT CAG CCT ACA GGG AAG           132

D   R   T   S   I   R   E   D   P   K   G   F   S   K   A   G   E   I   D   V  45
 GAC CGA ACT TCC ATC CGT GAA GAC CCG AAG GGT TTT TCC AAG GCT GGG GAG ATA GAC GTA 192

D   E   E   V   K   K   A   L   I   G   M   K   Q   M   K   I   L   M   E   R  65
 GAT GAA GAG GTG AAG AAG GCT TTG ATT GGC ATG AAG CAG ATG AAA ATC CTG ATG GAA AGA 252

R   E   E   H   S   K   L   M   R   T   L   K   K   C   R   E   E   K   Q      85
 AGA GAG GAG CAT AGC AAA CTA ATG AGA ACA CTG AAG AAA TGC AGA GAA GAA AAG CAG    312

E   A   L   K   L   M   N   E   V   Q   E   H   L   E   E   E   R   L   C     105
 GAG GCC CTG AAG CTT ATG AAT GAA GTT CAA GAA CAT CTA GAA GAG GAA AGG CTA TGC    372

Q   V   S   L   M   G   S   S   W   D   E   C   K   S   L   E   S   T   I   M  125
 CAG GTG TCT CTG ATG GGT TCC TGG GAC GAA TGC AAA TCT CTG GAA AGT GAC TGC ATG    432

R   F   Y   T   T   C   Q   F   L   F   P   F   H   E   D   D   E   K   L   P  145
 AGA TTT TAT ACA ACC TGC CAA AGC TTT CTC TTT CCT TTC CAT GAA GAC GAT GAA AAG CTT CCT 492

F   R   K   I   Y   Q   F   T   Q   K   F   T   E   E   D   E   K   E   L   P  165
 TTC CGG AAG ATA TAT CAG TTC ACA CAG AAG TTC ACT GAA GAG GAT GAA AAA GAG CTT CCT 552

V   G   E   K   F   T   E   E   D   V   Q   L   M   Q   I   E   N   V   F   S  185
 GTT GGT GAG AAG TTC ACT GAG GAA GAT GTA CAG CTG ATG CAG ATA GAG AAT GTG TTC AGC 612
```

FIG.12A

```
Q   L   T   V   D   V   G   F   L   Y   N   M   S   F   H   V   F   K   Q   M   205
CAG CTG ACC GTG GAT GTG GGA TTT CTC TAT AAC ATG AGC TTT CAC GTC TTC AAA CAG ATG 672

Q   Q   F   E   P   D   L   A   F   Q   S   Y   F   M   S   D   T   D   S   E   225
CAA CAA GAA TTT GAC CTG GCT TTT CAA TCA TAC TTT ATG TCA GAC ACA GAC TCC ATG GAG 732

P   Y   F   F   P   A   F   S   K   E   P   A   K   K   A   H   P   M   Q   S   245
CCT TAC TTT TTT CCA GCT TTT TCC AAA GAG CCA GCA AAA AAA GCA CAT CCT ATG CAG AGT 792

W   D   I   P   S   F   F   Q   L   C   N   F   S   L   S   V   Y   Q   S   265
TGG GAC ATT CCC AGC TTC TTC CAG CTG TGT AAT TTC AGC CTC TCT GTT TAT CAA AGT 852

V   S   A   T   V   T   E   M   L   K   A   I   E   D   L   S   K   Q   D   K   285
GTC AGC GCA ACA GTT ACA GAG ATG CTG AAG GCC ATT GAG GAC TTA TCC AAA CAA GAC AAA 912

D   S   A   H   G   P   S   S   E   C   L   Q   T   W   P   V   R   G   L   C   305
GAT TCT GCC CAC GGA CCG AGT TCC GAA TGT CTC CAA ACG TGG CCT GTG CGG GGC CTG TGT 972

G   E   P   G   Q   N   S   A   D   C   P   A   V   P   E   L   Y   T   K   C   325
GGA GAA CCT GGC CAG AAC TCG GCA GAC TGC CCT GCT GTT CCT GAA CTA TAC ACA AAG TGC 1032

Q   D   Y   L   W   I   S   N   Q   Y   A   Q   V   L   Q   M   T   A   D   E   345
CAG GAT TAC CTA TGG ATA TCC AAT CAG TAT GCC CAG GTA CTC CAG ATG ACC GCG GAT GAG 1092

A   L   E   L   V   N   I   S   Y   L   M   E   K   M   R   E   Q   F   G   Q   365
GCC CTT GAG TTG GTC AAC ATA TCC TAC CTG ATG GAG AAG ATG AGA GAG CAG TTT GGT CAG 1152

H   H   L   E   D   T   T   Y   L   M   E   D   T   Y   L   M   E   Q   V   385
CAT CAC TTG GAG GAC ACC ACG TAT CTG ATG GAG GAC ACC TAT CTG ATG GAG CAG GTA 1212
```

FIG.12B

| | | | | | | | | | | | | |
|---|---|---|---|---|---|---|---|---|---|---|---|---|
| T | E | L | A | S | Q | T | P | G | S | E | N | I | F | S | F | I | K | V | V | 405 |
| ACA | GAG | CTG | GCC | AGC | CAG | ACC | CCA | GGA | AGC | GAG | AAC | ATC | TTC | AGT | TTC | ATA | AAG | GTA | GTT | 1272 |

| P | G | V | H | E | G | N | F | S | K | Q | D | E | K | M | I | D | I | S | I | 425 |
|---|---|---|---|---|---|---|---|---|---|---|---|---|---|---|---|---|---|---|---|---|
| CCA | GGT | GTT | CAC | GAA | GGA | AAT | TTC | TCC | AAA | CAA | GAT | GAA | AAG | ATG | ATA | GAC | ATA | AGC | ATT | 1332 |

| L | P | S | S | N | F | T | L | T | I | P | L | E | E | S | A | E | S | S | D | 445 |
|---|---|---|---|---|---|---|---|---|---|---|---|---|---|---|---|---|---|---|---|---|
| CTG | CCT | TCC | TCT | AAT | TTC | ACA | CTC | ACC | ATC | CCT | CTT | GAA | GAA | AGT | GCT | GAG | AGT | TCC | GAC | 1392 |

| F | I | S | Y | M | L | A | K | A | V | Q | H | F | K | E | H | F | K | S | W | 465 |
|---|---|---|---|---|---|---|---|---|---|---|---|---|---|---|---|---|---|---|---|---|
| TTC | ATT | AGC | TAC | ATG | CTG | GCC | AAA | GCT | GTA | CAG | CAT | TTT | AAG | GAA | CAT | TTT | AAA | TCT | TGG | 1452 |

| * | | 466 |
|---|---|---|
| TAA | | 1455 |

GCAGAGTATTTGATTAGGGACGTTTGCTGATAGGAATAGATGGTTCTTAAAAGGGAAAAATGACAAAACTAGCTTTTGA 1534

ATACCTTGAAAACGTATTCAACCTCATTAATAATCAAAGGCATGAAAACTAAGACAAGTTAGCAGTTTTTACCTATTGA 1613

ATTTTCAAATTAAAAAAAAAAATCCTGATAGAATGCAATGAAATGAGAATTCTTATATGTGATTGCCAGAAACAAACTG 1692

GTTTGTCTTTTGAAAAGTTATTCAATTATACATATCAAGAGTCATCAAATTTCTTTTAATATAATAATTCCACTTC 1771

TGGAATCAATCCAAAGGAGTAAATCTAAAATTGAAGTTCCCACCCCAAGATCAATATTTGCAAATTATTTAAAA 1850

TAGTAAACTGTTAAAAACTGAATGTCATCTGAATGTCTAAAAACCAGAAATGGTTAAAAGCTGTGGCTAAATATGCTCC 1929

AAATATCTTATAAACCATTAAAAATTTATAAAATTTAAATCATGACATGACATCTGCTGGAACAAGAGTTTATTCT 2008

AAGCCTATCTATAAGGCAAATATTATTACTATCTTCCAGAAAAGAAACTTGAGACTCAGGGTCCAAGTGTTAGTTG 2087

CTCAGTCATGTCTGACTCTTTGAGACCCCTTGGACTGTGGCCCACCAGGCTCCTCTGTCCATGGGATTCTTCAGACAAG 2166

FIG.12C

```
AATACTGGAGCAGGTTGCTATTTCCTTCTCCAGGAAATCTTCCCTATCCAGGGATGGAACCCAGGTCTCCTGCATTGCA     2245

GGTAGATGCTTTACTATCTGAGCAACCAAATGAATTACTCAAGTCAGTAGGGGGTAGAGGCAAATTTAACTTAGTTTT     2324

CTCTGAATCATAATTGCCACATTGGTTCCTGTTGGGACATTTGGTTGAAAAAAATAAAGTGAAAAATGAGTATA        2403

AAACTCTATAAATGTAATGATCAAAACGAAAAAAATCTACAATCTGCATTAAAAATAAAAAGGGTTGGCAGGAATTAC     2482

GGTTGGAAATGGATGATTTTTTAACCTTTCATCTTTGATATTTTACAATTTTCTATAATGAATAATTTTGA           2561

GATTTCAAAATTAGAGAGATATGTTGCTAAAATAGCTAGGTAAATGTAGATTGAACACTGTATCAATGTGTTCTCATCTTT  2640

AAACTTTAGTATAAGTACTTCTATTCCATGGTAATCCTACAGTAAGACGAAAATGTAAATCTGTTCGGTCTACAGGAAAA   2719

ACAACTAAATGACATTCAGACGTACATTACCATCTCTGTTAGGATAATCTTCTGAATTAATGGCACAATTAGAACTGT     2798

ACATAGTATTCCTTTGGTAAAATGGTCAATCTTAAAGAAGCATTAAATGTAATTCTAAGTATTACTCATAAGGGA        2877

CCTTGTAGGTAGGTCCCTATCAATGTATAATTAAGCTGGGTATTTCTAGATTCGCTGCCTCTCCCTTTATCTCTGAATG    2956

TTGGAGAGGTTGTTGGTCATCAATCAACCAATATCTTTTAGCATCTTCTAAGTGAAGGC                        3016
```

FIG. 12D

```
                                                                                    M   K     2
GTGAAGGTCCTTACAGAAGCTGGTGGCAACCTCGTTGGTGAGAGCCTGCAGTTAGTGTCACGGGCGGAAAC ATG AAG    76

P   P   I   L   V   F   I   V   Y   L   L   Q   L   R   D   C   Q   C   A   P     22
CCG CCA ATC TTG GTG TTT ATC GTG TAT CTG CTG CAG CTG AGA GAC TGT CAG TGT GCG CCT   136

T   G   K   D   R   T   S   I   R   E   D   P   K   G   F   S   K   A   G   E     42
ACA GGG AAG GAC CGA ACT TCC ATC CGT GAA GAC CCG AAG GGT TTT TCC AAG GCT GGG GAG   196

I   D   V   D   E   E   V   K   K   A   L   I   G   M   M   K   Q   M   K   I   L  62
ATA GAC GTA GAT GAA GAG GTG AAG AAG GCT TTG ATT GGC ATG ATG AAG CAG ATG AAA ATC CTG 256

M   E   R   R   E   E   E   H   S   K   L   M   R   T   L   K   K   C   R   E     82
ATG GAA AGA AGA GAG GAA GAA CAT AGC AAA CTA ATG AGA ACC CTG AAG AAA TGC AGA GAA   316

E   K   Q   E   A   L   K   L   M   N   E   V   Q   E   H   L   E   E   E   E    102
GAA AAG CAG GAG GCC CTG AAG CTT ATG AAT GAA GTT CAA GAA CAT CTA GAA GAG GAA GAA   376

R   L   C   Q   V   S   L   M   G   S   W   D   E   C   K   S   C   L   E   S    122
AGG CTA TGC CAG GTG TCT CTG ATG GGT TCC TGG GAC GAA TGC AAA TCT TGC CTG GAA AGT   436

D   C   M   R   F   Y   T   T   C   Q   S   S   M   K   S   T   I    142
GAC TGC ATG AGA TTT TAT ACA ACC TGC CAA AGC AGT TGG TCC TCT ATG AAA TCC ACG ATT   496

E   R   V   F   R   K   I   Y   Q   F   L   P   F   H   E   D   D   E   K        162
GAA CGG GTT TTC CGG AAG ATA TAT CAG TTT CTC CCT TTC CAT GAA GAC GAT GAA AAA        556

E   L   P   V   G   E   K   F   T   E   E   D   V   Q   L   M   Q   I   E   N    182
GAG CTT CCT GTT GGT GAG AAG TTC ACT GAG GAA GAT GTA CAG CTG ATG CAG ATA GAG AAT   616
```

FIG. 13A

```
V   F   S   Q   L   T   V   D   V   G   F   L   Y   N   M   S   F   H   V   F   202
GTG TTC AGC CAG CTG ACC GTG GAC GTG GGA TTT CTC TAT AAC ATG AGC TTT CAC GTC TTC  676

K   Q   M   Q   Q   E   F   Y   F   P   A   L   A   F   Q   S   Y   M   S   D   222
AAA CAG ATG CAG CAA GAA TTT TAC TTT CCA GCT CTG GCT TTT CAA TCA TAC TTT ATG TCA GAC  736

S   M   E   P   Y   F   F   P   A   F   F   S   K   E   P   A   K   A   H   P   242
TCC ATG GAG CCT TAC TTT TTT CCA GCT TTT TCC AAA GAG CCA AAA GCA CAT CCT  796

M   Q   D   I   P   S   F   F   Q   L   F   C   N   F   A   K   S   L   S   V   262
ATG CAG GAC ATT CCC AGC TTC TTC CAG CTG TTT TGT AAT TTC GCC AAA AGC CTC TCT GTT  856

Y   Q   S   V   S   A   T   V   T   E   M   L   K   A   I   E   D   L   S   K   282
TAT CAA AGT GTC AGC GCA ACA GTT ACA GAG ATG CTG AAG GCC ATT GAG GAC TTA TCC AAA  916

Q   D   K   D   S   A   H   G   G   P   S   S   T   T   W   P   V   R   G   R   302
CAA GAC AAA GAT TCT GCC CAC GGT GGA CCG AGT TCC ACG TGG CCT GTG CGG GGC AGA  976

G   L   C   G   E   P   N   S   D   C   L   Q   F   H   A   V   P   E   L   Y   322
GGG CTG TGT GGA GAA CCT GGC AAC TCG GAC TGC CTC CAA TTT CAT GCA GTA CCT GAA CTA TAC 1036

Q   K   C   Q   D   Y   L   V   N   I   S   N   Q   Q   Y   A   Q   V   T   K   342
CAG AAA TGT CAG GAT TAC CTA GTC AAC ATA TCC AAT CAG CAG TAT GCC CAG GTA ACA AAG 1096

A   D   E   A   L   E   D   T   T   Y   L   M   E   K   M   R   E   Q   L   Q   362
GCG GAT GAG GCC CTT GAG GAC ACC ACG TAT CTG ATG GAG AAG ATG AGA GAG CAG CTC CAG 1156

M   T   Q   H   H   L   E   D   T   T   Y   L   M   E   K   M   R   E   Q   F   382
ATG ACC CAG CAT CAC TTG GAG GAC ACC ACG TAT CTG ATG GAG AAG ATG AGA GAG CAG TTT 1216
```

FIG. 13B

```
G   W   V   T   E   L   A   S   Q   T   P   G   S   E   N   I   F   S   F   I    402
GGT TGG GTA ACA GAG CTG GCC AGC CAG ACC CCA GGA AGC GAG AAC ATC TTC AGT TTC ATA   1276

K   V   V   P   G   V   H   E   G   N   F   S   K   Q   D   E   K   M   I   D    422
AAG GTA GTT CCA GGT GTT CAC GAA GGA AAT TTC TCC AAA CAA GAT GAA AAG ATG ATA GAC   1336

I   S   I   L   P   S   S   N   F   T   L   T   I   P   L   E   E   S   A   E    442
ATA AGC ATT CTG CCT TCC TCT AAT TTC ACA CTC ACC ATC CCT CTT GAA GAA AGT GCT GAG   1396

S   S   D   F   I   S   Y   M   L   A   K   A   V   Q   H   F   K   E   H   F    462
AGT TCC GAC TTC ATT AGC TAC ATG CTG GCC AAA GCT GTA CAG CAT TTT AAG GAA CAT TTT   1456

K   S   W   *                                                                     466
AAA TCT TGG TAA                                                                  1468

GCAGAGTATTGATTAGGGACGTTTGCTGATAGGAATAGATGGTTCTTAAAAGGGAAAAATGACAAAACTAGCTTTTGA   1547
ATACCTTGAAAACGTATTCAACCTCATTAATAATCCTGATAGAATGCATGAAAACTAAGACAAGTTAGCAGTTTTACCTATTGA 1626
ATTTCAAATTAAAAAAAAATCCTGATAGAATGCAATGAGAATTCTTATATGTGATTGCCAGAAACAAACTGG        1705
TTTTGTCTTTTGAAAAGTTATTCAATTATACATATCAAGAGTCATCAAATTTCTTTTTAATATAATAATTCCACTTCT   1784
GGAATCAATCCAAAGGAGTAAATCTAAAATTGAATTGAAGTTCCCACCCCAAGATCAATATTTGCAAATTATTAAAT   1863
AGTAAACTGTTAAAAACTGAATGTCATCTGAATGTCTAAAAACCAGAAATGGTTAAAAGCTGTGGCTAAATATGCTCCA  1942
AATATCTTATAAACCATTAAGCAAATATTTATAATTTAAATCATGACATGACAAACTTGAGACTCAGGGTCCAAGTGTTAGTTGC 2021
AGCCTATCTATAAGGCAAATATTATTATTACTATCTTCCAGAAAGAAACTTGAGACTCAGGGTCCAAGTGTTAGTTGC   2100
TCAGTCAGTCTGACTCTTTGAGACCCCTTGGACTGTAGCCACCTGTAGCCCACCAGGCTCTCGTCCATGGATTCTTCAGACAAGA 2179
ATACTGGAGCAGGTTGCTATTTCCTTCTCCAGGAAATCTTCCCATCCCAGGATGGAACCCAGGTCTCCTGCATTGCAG   2258
GTAGATGCTTACTATCTGAGCAACCAAATGAATTACTCAAGTCAGTAGGGGGTAGAGGCAAATTTAACTTAGTTTTC   2337
TCTGAATCATAATTGCCACATTAAACTGGTTCCTGTTGGGACATTTGGTTGAAAAAATAAAGTGAAAAATGAGTATAA   2416
AACTCTATAAATGTAATGATCAAAACGAAAAAAAATCTACAATCTGCATTAAAAAATAAAAAGGGTTGGCAGG        2488
```

```
     GAAAATCATGATGGAAAGCAGAGAGGAAGAACACAGCAAA   Majority
                330          340          350           360
321  GAAAATCATGATGGAAAGCAGAGAGGAAGAACACAGCAAA   gphkng1815-1.
321  GAAAATCATGATGGAAAGCAGAGAGGAAGAACACAGCAAA   gp7b-1.
321  GAAAATCATGATGGAAAGCAGAGAGGAAGAACACAGCAAA   gp7c-1.
321  GAAAATCATGATGGAAAGCAGAGAGGAAGAACACAGCAAA   gp7d-1.

CTAATGAAAACCTTGAAGAAGTGCCAAAGAAAAAGCAGG    Majority
                370          380          390           400
361  CTAATGAAAACCTTGAAGAAGTGCCAAAGAAAAAGCAGG    gphkng1815-1.
361  CTAATGAAAACCTTGAAGAAGTGCCAAAGAAAAAGCAGG    gp7b-1.
361  CTAATGAAAACCTTGAAGAAGTGCCAAAGAAAAAGCAGG    gp7c-1.
361  CTAATGAAAACCTTGAAGAAGTGCCAAAGAAAAAGCAGG    gp7d-1.

AGGCCCTGAAAACTTATGAATGAAGTTCATGAACACCTGGA  Majority
                410          420          430           440
401  AGGCCCTGAAAACTTATGAATGAAGTTCATGAACACCTGGA  gphkng1815-1.
401  AGGCCCCTGAAAACTTTATGAATGAAGTTCATGAACACCTGGA gp7b-1.
401  AGGCCCCTGAAAACTTATGAATGAAGTTCATGAACACCTGGA gp7c-1.
401  AGGCCCCTGAAAACTTATGAATGAAGTTCATGAACACCTGGA gp7d-1.

GGAGGAAGAAAAGCTTATGCCCAGGTTTCTCTGGCCAGATTCC Majority
                450          460          470           480
441  GGAGGAAGAAAAGCTTATGCCCAGGTTTCTCTGGCCAGATTCC gphkng1815-1.
441  GGAGGAAGAAAAGCTTATGCCCAGGTTTCTCTGGCCAGATTCC gp7b-1.
441  GGAGGAAGAAAAGCTTATGCCCAGGTTTCTCTGGCCAGATTCC gp7c-1.
441  GGAGGAAGAAAAGCTTATGCCCAGGTTTCTCTGGCCAGATTCC gp7d-1.
```

| | | | | | | | | | | | | Majority |
|---|---|---|---|---|---|---|---|---|---|---|---|---|
| | | A T T A T C T A T C T G A T G A C T G C C C T A A T G T G C C T G A A C T A T A | | | | | | | | | | |
| | | 1130 | | 1140 | | 1150 | | 1160 | | | | |
| 1121 | | A T T A T C T A T C T G A T G A C T G C C C T A A T G T G C C T G A A C T A T A | | | | | | | | | | gphkng1815-1. |
| 1073 | | A T T A T C T A T C T G A T G A C T G C C C T A A T G T G C C T G A A C T A T A | | | | | | | | | | gp7b-1. |
| 845 | | A T T A T C T A T C T G A T G A C T G C C C T A A T G T G C C T G A A C T A T A | | | | | | | | | | gp7c-1. |
| 842 | | A T T A T C T A T C T G A T G A C T G C C C T A A T G T G C C T G A A C T A T A | | | | | | | | | | gp7d-1. |
| | | | | | | | | | | | | Majority |
| | | C A G A G A A C T C A A T G A G G C C C T C C G A C T G G T C A G T A G A T C C | | | | | | | | | | |
| | | 1170 | | 1180 | | 1190 | | 1200 | | | | |
| 1161 | | C A G A G A A C T C A A T G A G G C C C T C C G A C T G G T C A G T A G A T C C | | | | | | | | | | gphkng1815-1. |
| 1113 | | C A G A G A A C T C A A T G A G G C C C T C C G A C T G G T C A G T A G A T C C | | | | | | | | | | gp7b-1. |
| 885 | | C A G A G A A C T C A A T G A G G C C C T C C G A C T G G T C A G T A G A T C C | | | | | | | | | | gp7c-1. |
| 882 | | C A G A G A A C T C A A T G A G G C C C T C C G A C T G G T C A G T A G A T C C | | | | | | | | | | gp7d-1. |
| | | | | | | | | | | | | Majority |
| | | A A T C A G C A A T A C G A C C A G G T G G T G C A G A T G A C C C A G T A T C | | | | | | | | | | |
| | | 1210 | | 1220 | | 1230 | | 1240 | | | | |
| 1201 | | A A T C A G C A A T A C G A C C A G G T G G T G C A G A T G A C C C A G T A T C | | | | | | | | | | gphkng1815-1. |
| 1153 | | A A T C A G C A A T A C G A C C A G G T G G T G C A G A T G A C C C A G T A T C | | | | | | | | | | gp7b-1. |
| 925 | | A A T C A G C A A T A C G A C C A G G T G G T G C A G A T G A C C C A G T A T C | | | | | | | | | | gp7c-1. |
| 922 | | A A T C A G C A A T A C G A C C A G G T G G T G C A G A T G A C C C A G T A T C | | | | | | | | | | gp7d-1. |
| | | | | | | | | | | | | Majority |
| | | A C C T G G A A G A C A C C A C C G C T T C T G A T G G A G A A G A T G A G A G A | | | | | | | | | | |
| | | 1250 | | 1260 | | 1270 | | 1280 | | | | |
| 1241 | | A C C T G G A A G A C A C C A C C G C T T C T G A T G G A G A A G A T G A G A G A | | | | | | | | | | gphkng1815-1. |
| 1193 | | A C C T G G A A G A C A C C A C C G C T T C T G A T G G A G A A G A T G A G A G A | | | | | | | | | | gp7b-1. |
| 965 | | A C C T G G A A G A C A C C A C C G C T T C T G A T G G A G A A G A T G A G A G A | | | | | | | | | | gp7c-1. |
| 962 | | A C C T G G A A G A C A C C A C C G C T T C T G A T G G A G A A G A T G A G A G A | | | | | | | | | | gp7d-1. |

FIG. 14H

```
        GCAGTTTGGCCTGGGTTTCTGAACTGCCATACCAGTCCCCA  Majority
             1290           1300          1310         1320
1281    GCAGTTTGGCCTGGGTTTCTGAACTGCCATACCAGTCCCCA  gphkng1815-1.
1233    GCAGTTTGGCCTGGGTTTCTGAACTGCCATACCAGTCCCCA  gp7b-1.
1005    GCAGTTTGGCCTGGGTTTCTGAACTGCCATACCAGTCCCCA  gp7c-1.
1002    GCAGTTTGGCCTGGGTTTCTGAACTGCCATACCAGTCCCCA  gp7d-1.

GGAGCTGAGGACATCTTTAATCCAGTGAAAGTAATGGTAG  Majority
             1330          1340          1350         1360
1321    GGAGCTGAGGACATCTTTAATCCAGTGAAAGTAATGGTAG  gphkng1815-1.
1273    GGAGCTGAGGACATCTTTAATCCAGTGAAAGTAATGGTAG  gp7b-1.
1045    GGAGCTGAGGACATCTTTAATCCAGTGAAAGTAATGGTAG  gp7c-1.
1042    GGAGCTGAGGACATCTTTAATCCAGTGAAAGTAATGGTAG  gp7d-1.

CCCTAAGTGCTCATGAAGGAAATTCTTCTGATCAAGATGA  Majority
             1370          1380          1390         1400
1361    CCCTAAGTGCTCATGAAGGAAATTCTTCTGATCAAGATGA  gphkng1815-1.
1313    CCCTAAGTGCTCATGAAGGAAATTCTTCTGATCAAGATGA  gp7b-1.
1085    CCCTAAGTGCTCATGAAGGAAATTCTTCTGATCAAGATGA  gp7c-1.
1082    CCCTAAGTGCTCATGAAGGAAATTCTTCTGATCAAGATGA  gp7d-1.

CACAGTGGTTCCTTCAAGCCCTCCTGCCCTTCCTCTAACTTC  Majority
             1410          1420          1430         1440
1401    CACAGTGGTTCCTTCAAGCCCTCCTGCCCTTCCTCTAACTTC  gphkng1815-1.
1353    CACAGTGGTTCCTTCAAGCCCTCCTGCCCTTCCTCTAACTTC  gp7b-1.
1125    CACAGTGGTTCCTTCAAGCCCTCCTGCCCTTCCTCTAACTTC  gp7c-1.
1122    CACAGTGGTTCCTTCAAGCCCTCCTGCCCTTCCTCTAACTTC  gp7d-1.
```

FIG.14I

```
                                                                                                       Majority
        ACACTCAGCAGCCCTCTCTTGAAAAGAGTGCTGGCAACGGCTA
                    1450              1460             1470             1480
1441    ACACTCAGCAGCCCTCTCTTGAAAAGAGTGCTGGCAACGGCTA            gphkng1815-1.
1393    ACACTCAGCAGCCCCCTCTTGAAAAGAGTGCTGGCAACGGCTA            gp7b-1.
1165    ACACTCAGCAGCCCCCTCTTGAAAAGAGTGCTGGCAACGGCTA            gp7c-1.
1162    ACACTCAGCAGCCCCCTCTTGAAAAGAGTGCTGGCAACGGCTA            gp7d-1.

Majority
        ACTTCATTGATCACGTGGTAGAGAAGGTTCTTCAGCACTT
                    1490              1500             1510             1520
1481    ACTTCATTGATCACGTGGTAGAGAAGGTTCTTCAGCACTT              gphkng1815-1.
1433    ACTTCATTGATCACGTGGTAGAGAAGGTTCTTCAGCACTT              gp7b-1.
1205    ACTTCATTGATCACGTGGTAGAGAAGGTTCTTCAGCACTT              gp7c-1.
1202    ACTTCATTGATCACGTGGTAGAGAAGGTTCTTCAGCACTT              gp7d-1.

Majority
        TAAGGAGCACTTTAAAAACTTGGTAAGAAGATTTAGTCCAT
                    1530              1540             1550             1560
1521    TAAGGAGCACTTTAAAAACTTGGTAAGAAGATTTAGTCCAT             gphkng1815-1.
1473    TAAGGAGCACTTTAAAAACTTGGTAAGAAGATTTAGTCCAT             gp7b-1.
1245    TAAGGAGCACTTTAAAAACTTGGTAAGAAGATTTAGTCCAT             gp7c-1.
1242    TAAGGAGCACTTTAAAAACTTGGTAAGAAGATTTAGTCCAT             gp7d-1.

Majority
        CCTATAATCAGCAAGAATTACACCTTCCGGCCAAGACCTGA
                    1570              1580             1590             1600
1561    CCTATAATCAGCAAGAATTACACCTTCCGGCCAAGACCTGA             gphkng1815-1.
1513    CCTATAATCAGCAAGAATTACACCTTCCGGCCAAGACCTGA             gp7b-1.
1285    CCTATAATCAGCAAGAATTACACCTTCCGGCCAAGACCTGA             gp7c-1.
1282    CCTATAATCAGCAAGAATTACACCTTCCGGCCAAGACCTGA             gp7d-1.
```

FIG.14J

FIG.14K

```
        TATGTAGAATATGATGCATTAGTTCTTTGTATACTAAAATA  Majority
                 1770           1780          1790          1800

1761    TATGTAGAATATGATGCATTAGTTCTTTGTATACTAAAATA  gphkng1815-1.
1713    TATGTAGAATATGATGCATTAGTTCTTTGTATACTAAAATA  gp7b-1.
1485    TATGTAGAATATGATGCATTAGTTCTTTGTATACTAAAATA  gp7c-1.
1482    TATGTAGAATATGATGCATTAGTTCTTTGTATACTAAAATA  gp7d-1.

AATACTGAGTCCCCT                            Majority
                 1810

1801    AATACTGAGTCCCCT                            gphkng1815-1.
1753    AATACTGAGTCCCCT                            gp7b-1.
1525    AATACTGAGTCCCCT                            gp7c-1.
1522    AATACTGAGTCCCCT                            gp7d-1.
```

FIG. 14L

```
gphkng1815_aa_   1 MKLPLLMFPVCLLWLKDCHCAPTWKDKTAISENANSFSEAGEIDVDGEVKIALIGIKQMKIMMERREEHSKLMKTLKKC  80
gp7b_aa_           MKLPLLMFPVCLLWLKDCHCAPTWKDKTAISENANSFSEAGEIDVDGEVKIALIGIKQMKIMMERREEHSKLMKTLKKC
gp7c_aa_           MKLPLLMFPVCLLWLKDCHCAPTWKDKTAISENANSFSEAGEIDVDGEVKIALIGIKQMKIMMERREEHSKLMKTLKKC
gp7d_aa_           MKLPLLMFPVCLLWLKDCHCAPTWKDKTAISENANSFSEAGEIDVDGEVKIALIGIKQMKIMMERREEHSKLMKTLKKC gphkng1815_aa_  81 KEEKQEALKLMNEVEHLEEEESLCQVSLADSWDECRACLESNCMRFDTTCQPAWSSVKNMVEQFFRKIYQFLFPLQEND 160
gp7b_aa_           KEEKQEALKLMNEVEHLEEEESLCQVSLADSWDECRACLESNCMRFDTTCQPAWSSVKN..................
gp7c_aa_           KEEKQEALKLMNEVEHLEEEESLCQVSLADSWDECRACLESNCMRFDTTCQPAWSSVKN................MEND
gp7d_aa_           KEEKQEALKLMNEVEHLEEEESLCQVSLADSWDECRACLESNCMRFDTTCQPAWSSVKN..................

gphkng1815_aa_ 161 RSGPVSKGVTEEDAQVSHIEHVFSQLSADVTSLFNRSLYVFKQLRREFDQAFQSYFTSGTDVTEPFFFPSLSKEPAYRAD 240
gp7b_aa_           RSGPVSKGVTEEDAQVSHIEHVFSQLSADVTSLFNRSLYVFKQLRREFDQAFQSYFTSGTDVTEPFFFPSLSKEPAYRAD
gp7c_aa_           ...............................................................MEPAYRAD
gp7d_aa_           ...............................................................MPAYRAD gphkng1815_aa_ 241 AEPSWAIPNVFQLLCNLSFSVYQSVSEKLITTLRATEDPPKQDKDSNQGGPISKILPEQDRGSDGKLGQNLSDCVNFRKR 320
gp7b_aa_           AEPSWAIPNVFQLLCNLSFSVYQSVSEKLITTLRATEDPPKQDKDSNQGGPISKILPEQDRGSDGKLGQNLSDCVNFRKR
gp7c_aa_           AEPSWAIPNVFQLLCNLSFSVYQSVSEKLITTLRATEDPPKQDKDSNQGGPISKILPEQDRGSDGKLGQNLSDCVNFRKR
gp7d_aa_           AEPSWAIPNVFQLLCNLSFSVYQSVSEKLITTLRATEDPPKQDKDSNQGGPISKILPEQDRGSDGKLGQNLSDCVNFRKR gphkng1815_aa_ 321 CQKCQDYLSDDCPNVPELYRELNEALRLVSRSNQQYDQVVQMTQYHLEDTTLLMEKMREQFGWVSELAYQSPGAEDIFNP 400
gp7b_aa_           CQKCQDYLSDDCPNVPELYRELNEALRLVSRSNQQYDQVVQMTQYHLEDTTLLMEKMREQFGWVSELAYQSPGAEDIFNP
gp7c_aa_           CQKCQDYLSDDCPNVPELYRELNEALRLVSRSNQQYDQVVQMTQYHLEDTTLLMEKMREQFGWVSELAYQSPGAEDIFNP
gp7d_aa_           CQKCQDYLSDDCPNVPELYRELNEALRLVSRSNQQYDQVVQMTQYHLEDTTLLMEKMREQFGWVSELAYQSPGAEDIFNP gphkng1815_aa_ 401 VKVMVALSAHEGNSSDQDDTVVPSSLLPSSNFTLSSPLEKSAGNANFIDHVVEKVLQHFKEHFKTW 466
gp7b_aa_           VKVMVALSAHEGNSSDQDDTVVPSSLLPSSNFTLSSPLEKSAGNANFIDHVVEKVLQHFKEHFKTW
gp7c_aa_           VKVMVALSAHEGNSSDQDDTVVPSSLLPSSNFTLSSPLEKSAGNANFIDHVVEKVLQHFKEHFKTW
gp7d_aa_           VKVMVALSAHEGNSSDQDDTVVPSSLLPSSNFTLSSPLEKSAGNANFIDHVVEKVLQHFKEHFKTW
```

FIG. 14M

```
         1                                                                GCAACCTCGTTGGTGAGAGCCTGCAGTTAGTGTCACGGCGGAAACATGAAGCCGC
bhkng1
bhkng2                                                   CAGAAGCTGGTGGCAACCTCGTTGGTGAGAGCCTGCAGTTAGTGTCACGGCGGAAACATGAAGCCGC
bhkng3   GTGAAGGTCCTTACAGAAGCTGGTGGCAACCTCGTTGGTGAGAGCCTGCAGTTAGTGTCACGGCGGAAACATGAAGCCGC
         81                                                                                                                      160
bhkng1   CACTCTTGGTGTTTATTGTGTATCTGCTGCGGCTGAGAGACTGTCAGTGTGCGCTACAGGGAAGGACCGAACTTCCATC
bhkng2   CACTCTTGGTGTTTATTGTGTATCTGCTGCGGCTGAGAGACTGTCAGTGTGCGCTACAGGGAAGGACCGAACTTCCATC
bhkng3   CAATCTTGGTGTTTATCGTGTATCTGCTGCAGCTGAGAGACTGTCAGTGTGCGCTACAGGGAAGGACCGAACTTCCATC
         161                                                                                                                     240
bhkng1   CGTGAAGACCCGAAGGGTTTTCCAAGGCTGGGGAGATAGACGTAGATGAAGAGGTGAAGAAGGCTTTGATTGGCATGAA
bhkng2   CGTGAAGACCCGAAGGGTTTTTCCAAGGCTGGGGAGATAGACGTAGATGAAGAGGTGAAGAAGGCTTTGATTGGCATGAA
bhkng3   CGTGAAGACCCGAAGGGTTTTTCCAAGGCTGGGGAGATAGACGTAGATGAAGAGGTGAAGAAGGCTTTGATTGGCATGAA
         241                                                                                                                     320
bhkng1   GCAGATGAAAATCCTGATGGAAAGAGAGAGAGGAGGAACATAAGCAAACTGAAGAACACTGAAGAAATGCAGAGAAGAAA
bhkng2   GCAGATGAAAATCCTGATGGAAAGAGAGAGAGGAGGAACATAGCAAACTGAAGAACACTGAAGAAATGCAGAGAAGAAA
bhkng3   GCAGATGAAAATCCTGATGGAAAGAGAGAGAGGAGGAACATAGCAAACTGAAGAACACTGAAGAAATGCAGAGAAGAAA
         321                                                                                                                     400
bhkng1   AGCAGGAGGCCCTGAAGCTTATGAATGAAGTTCAAGAACATCTAGAAGAGGAAGAAGAAAGGCTATGCCAGGTGTCTCTGATG
bhkng2   AGCAGGAGGCCCTGAAGCTTATGAATGAAGTTCAAGAACATCTAGAAGAGGAAGAAGAAAGGCTATGCCAGGTGTCTCTGATG
bhkng3   AGCAGGAGGCCCTGAAGCTTATGAATGAAGTTCAAGAACATCTAGAAGAGGAAGAAGAAAGGCTATGCCAGGTGTCTCTGATG
         401                                                                                                                     480
bhkng1   GGTTCCTGGGACGAATGCAAATCTTGCCTGGAAAGTGACTGCATGAGATTTATACAACCTGCCAAAGCAGTTGGTCCTC
bhkng2   GGTTCCTGGGACGAATGCAAATCTTGCCTGGAAAGTGACTGCATGAGATTTATACAACCTGCCAAAGCAGTTGGTCCTC
bhkng3   GGTTCCTGGGACGAATGCAAATGCAAATCTTGCCTGGAAAGTGACTGCATGAGATTTATACAACCTGCCAAAGCAGTTGGTCCTC
         481                                                                                                                     560
bhkng1   TATGAAATCCACGATTGAACGGGTTTTCCGGAAGATATATCAGTTTCTCTTTCCTTTCCTTTCCATGAAGACGATGAAAAAGAGC
bhkng2   TATGAAATCCACGATTGAACGGGTTTTCCGGAAGATATATCAGTTTCTCTTTCCTTTCCTTTCCATGAAGACGATGAAAAAGAGC
bhkng3   TATGAAATCCACGATTGAACGGGTTTTCCGGAAGATATATCAGTTTCTCTTTCCTTTCCTTTCCATGAAGACGATGAAAAAGAGC
```

FIG. 15A

```
         561                                                            640
bhkng1   TTCCTGTGTTGGTGAGAAGTTCACTGAGGAAGATGTACAGCTGATGCAGATAGAGAATGTGTTCAGCCAGCTGACGTGGAT
bhkng2   TTCCTGTGTTGGTGAGAAGTTCACTGAGGAAGATGTACAGCTGATGCAGATAGAGAATGTGTTCAGCCAGCTGACGTGGAT
bhkng3   TTCCTGTGTTGGTGAGAAGTTCACTGAGGAAGATGTACAGCTGATGCAGATAGAGAATGTGTTCAGCCAGCTGACGTGGAC
         641                                                            720
bhkng1   GTGGGATTTCTCTATAACATGAGCTTTCACGTCTTCAAACAGATGCAGCAAGAATTTGACCTGGCTTTTCAATCATACTT
bhkng2   GTGGGATTTCTCTATAACATGAGCTTTCACGTCTTCAAACAGATGCAGCAAGAATTTGACCTGGCTTTTCAATCATACTT
bhkng3   GTGGGATTTCTCTATAACATGAGCTCTTCAAACAGATGCAGCAAGAATTTGACCTGGCTTTTCAATCATACTT
         721                                                            800
bhkng1   TATGTCAGACACAGACTCCATGGAGCCTTACTTTTTCCAGCTTTTTCCAAAGAGCCAGCAAAAAAGCACATCCTATGC
bhkng2   TATGTCAGACACAGACTCCATGGAGCCTTACTTTTTCCAGCTTTTTCCAAAGAGCCAGCAAAAAAGCACATCCTATGC
bhkng3   TATGTCAGACACAGACTCCATGGAGCCTTACTTTTTCCAGCTTTTTCCAAAGAGCCAGCAAAAAAGCACATCCTATGC
         801                                                            880
bhkng1   AGAGTTGGGACATTCCCAGCTTCTTCCAGCTGTGTTTGTAATTTCAGCTTCAGCCTCTCGTTTATCAAAGTGTCAGCGCAACAGTT
bhkng2   AGAGTTGGGACATTCCCAGCTTCTTCCAGCTGTGTTTGTAATTTCAGCTTCAGCCTCTCGTTTATCAAAGTGTCAGCGCAACAGTT
bhkng3   AGAGTTGGGACATTCCCAGCTTCTTCCAGCTGTGTTTGTAATTTCAGCTTCAGCCTCTCGTTTATCAAAGTGTCAGCGCAACAGTT
         881                                                            960
bhkng1   ACAGAGATGCTGAAGGCCATTGAGGACTTATCCAAACAAGACAAAGATTCTGCCCACGGTGACCGAGTTCCACGACGTG
bhkng2   ACAGAGATGCTGAAGGCCATTGAGGACTTATCCAAACAAGACAAAGATTCTGCCCACGGTGACCGAGTTCCACGACGTG
bhkng3   ACAGAGATGCTGAAGGCCATTGAGGACTTATCCAAACAAGACAAAGATTCTGCCCACGGTGACCGAGTTCCACGACGTG
         961                                                            1040
bhkng1   GCCTGTGCGGGGCAGAGGGCTGTGTGGAGAAACCTGGCCAGAACTCGTCGAATGTCTCCAATTTCATGCAAGATGCCAGA
bhkng2   GCCTGTGCGGGGCAGAGGGCTGTGTGGAGAAACCTGGCCAGAACTCGTCGAATGTCTCCAATTTCATGCAAGATGCCAGA
bhkng3   GCCTGTGCGGGGCAGAGGGCTGTGTGGAGAAACCTGGCCAGAACTCGTCGAATGTCTCCAATTTCATGCAAGATGCCAGA
         1041                                                           1120
bhkng1   AATGTCAGGATTACCTATGGGCAGACTGCCCTGCTGTTCCTGAACTATACACAAAGGCGGATGAGGCCCTTGAGTTGGTC
bhkng2   AATGTCAGGATTACCTATGGGCAGACTGCCCTGCTGTTCCTGAACTATACACAAAGGCGGATGAGGCCCTTGAGTTGGTC
bhkng3   AATGTCAGGATTACCTATGGGCAGACTGCCCTGCTGTTCCTGAACTATACACAAAGGCGGATGAGGCCCTTGAGTTGGTC
```

FIG.15B

```
        1121                                                                    1200
bhkng1  AACATATCCAATCAGCAGTATGCCCAGTACTCCAGATGACCCAGCATCACTTGGAGGACACCAGTATCTGATGGAGAA
bhkng2  AACATATCCAATCAGCAGTATGCCCAGTACTCCAGATGACCCAGCATCACTTGGAGGACACCAGTATCTGATGGAGAA
bhkng3  AACATATCCAATCAGCAGTATGCCCAGTACTCCAGATGACCCAGCATCACTTGGAGGACACCAGTATCTGATGGAGAA
        1201                                                                    1280
bhkng1  GATGAGAGAGCAGTTTGGTTGGGTAACAGAGCTGGCCAGCCAGACCCCAGGAAGCGAGAACATCTTCAGTTTCATAAAGG
bhkng2  GATGAGAGAGCAGTTTGGTTGGGTAACAGAGCTGGCCAGCCAGACCCCAGGAAGCGAGAACATCTTCAGTTTCATAAAGG
bhkng3  GATGAGAGAGCAGTTTGGTTGGGTAACAGAGCTGGCCAGCCAGACCCCAGGAAGCGAGAACATCTTCAGTTTCATAAAGG
        1281                                                                    1360
bhkng1  TAGTTCCAGGTGTTCACGAAGGAAATTTCTCCAAACAAGATGAAAAGATGATAGACATAAGCATTCTGCCTTCCTCTAAT
bhkng2  TAGTTCCAGGTGTTCACGAAGGAAATTTCTCCAAACAAGATGAAAAGATGATAGACATAAGCATTCTGCCTTCCTCTAAT
bhkng3  TAGTTCCAGGTGTTCACGAAGGAAATTTCTCCAAACAAGATGAAAAGATGATAGACATAAGCATTCTGCCTTCCTCTAAT
        1361                                                                    1440
bhkng1  TTCACACTCACCATCCCCTCTTGAAGAAAGTGCTGAGAGTTCCGACTTCATTAGCTACACATGCTGGCCAAAGCTGTACAGCA
bhkng2  TTCACACTCACCATCCCCTCTTGAAGAAAGTGCTGAGAGTTCCGACTTCATTAGCTACACATGCTGGCCAAAGCTGTACAGCA
bhkng3  TTCACACTCACCATCCCCTCTTGAAGAAAGTGCTGAGAGTTCCGACTTCATTAGCTACACATGCTGGCCAAAGCTGTACAGCA
        1441                                                                    1520
bhkng1  TTTTAAGGAACATTTTAAATCTTGGTAAGCAGAGTATTTGATTAGGGACGTTTGCTGATAGGAATAGATGGTTCTTAAAA
bhkng2  TTTTAAGGAACATTTTAAATCTTGGTAAGCAGAGTATTTGATTAGGGACGTTTGCTGATAGGAATAGATGGTTCTTAAAA
bhkng3  TTTTAAGGAACATTTTAAATCTTGGTAAGCAGAGTATTTGATTAGGGACGTTTGCTGATAGGAATAGATGGTTCTTAAAA
        1521                                                                    1600
bhkng1  GGGAAAAATGACAAAACTAGCTTTTGAATACCTTGAAAACGTATTCAACCTCATTAATAATCAAAGGCATGAAAACTAAG
bhkng2  GGGAAAAATGACAAAACTAGCTTTTGAATACCTTGAAAACGTATTCAACCTCATTAATAATCAAAGGCATGAAAACTAAG
bhkng3  GGGAAAAATGACAAAACTAGCTTTTGAATACCTTGAAAACGTATTCAACCTCATTAATAATCAAAGGCATGAAAACTAAG
        1601                                                                    1680
bhkng1  ACAAGTTAGCAGTTTTTACCTATTGAATTTTCAAATTAAAAAAAAAATCCTGATAGAATGCAATGAAATGAGAATTCTT
bhkng2  ACAAGTTAGCAGTTTTTACCTATTGAATTTTCAAATTTCAAATTAAAAAAAAAAATCCTGATAGAATGCAATGAAATGAGAATTCTT
bhkng3  ACAAGTTAGCAGTTTTTACCTATTGAATTTTCAAATTTCAAATTAAAAAAAAAA.TCCTGATAGAATGCAATGAAATGAGAATTCTT
```

FIG. 15C

```
            1681                                                                1760
bhkng1  ATATGTGATTGCCAGAAACAAACTGGTTTGTCTTTTTGAAAAGTTATTCAATTATACATATCAAGAGTCATCAAATTTC
bhkng2  ATATGTGATTGCCAGAAACAAACTGGTTTGTCTTTTTGAAAAGTTATTCAATTATACATATCAAGAGTCATCAAATTTC
bhkng3  ATATGTGATTGCCAGAAACAAACTGGTTTGTCTTTTTGAAAAGTTATTCAATTATACATATCAAGAGTCATCAAATTTC
            1761                                                                1840
bhkng1  TTTTAATAATAATTCCACTTCTGGAATCAATCCAAAGGAGTAAATCTAAAATTGAATTGAAGTTCCCACCCCAAGAT
bhkng2  TTTTAATAATAATTCCACTTCTGGAATCAATCCAAAGGAGTAAATCTAAAATTGAATTGAAGTTCCCACCCCAAGAT
bhkng3  TTTTAATAATAATTCCACTTCTGGAATCAATCCAAAGGAGTAAATCTAAAATTGAATTGAAGTTCCCACCCCAAGAT
            1841                                                                1920
bhkng1  CAATATTTGCAAATTATTTAAAATAGTAAACTGTTAAAAACTGAATGTCATCTGAATGTCTAAAAACCAGAAATGGTTAA
bhkng2  CAATATTTGCAAATTATTTAAAATAGTAAACTGTTAAAAACTGAATGTCATCTGAATGTCTAAAAACCAGAAATGGTTAA
bhkng3  CAATATTTGCAAATTATTTAAAATAGTAAACTGTTAAAAACTGAATGTCATCTGAATGTCTAAAAACCAGAAATGGTTAA
            1921                                                                2000
bhkng1  AAGCTGTGGCTAAATATGCTCCAAATATCTTATAAACCATTAAAATATTTATAAATTTAAATCATGACATCT
bhkng2  AAGCTGTGGCTAAATATGCTCCAAATATCTTATAAACCATTAAAATATTTATAAATTTAAATCATGACATCT
bhkng3  AAGCTGTGGCTAAATATGCTCCAAATATCTTATAAACCATTAAAATATTTATAAATTTAAATCATGACATCT
            2001                                                                2080
bhkng1  GCTGGAACAAGAGTTTATTCTAAGCCTATCTATAAGGCAAATATTATTATTACTATCTTCCAGAAAAGAAACTTGAGACT
bhkng2  GCTGGAACAAGAGTTTATTCTAAGCCTATCTATAAGGCAAATATTATTATTACTATCTTCCAGAAAAGAAACTTGAGACT
bhkng3  GCTGGAACAAGAGTTTATTCTAAGCCTATCTATAAGGCAAATATTATTATTACTATCTTCCAGAAAAGAAACTTGAGACT
            2081                                                                2160
bhkng1  CAGGGTCCAAGTGTTAGTTGCTCAGTCATGTCTGACTCTTGGACTGTAGCCCACCAGGCTCCTCTGTCC
bhkng2  CAGGGTCCAAGTGTTAGTTGCTCAGTCATGTCTGACTCTTGGACTGTAGCCCACCAGGCTCCTCTGTCC
bhkng3  CAGGGTCCAAGTGTTAGTTGCTCAGTCATGTCTGACTCTTGGACTGTAGCCCACCAGGCTCCTCTGTCC
            2161                                                                2240
bhkng1  GTGGGATTCTTCAGACAAGAATACTGGGGCAGGTTGCTATTTCCTTCTCCAGGAAATCTTCCCTATCCAGGGATGGAACC
bhkng2  ATGGGATTCTTCAGACAAGAATACTGGAGCAGGTTGCTATTCCCTATCCTCCAGGAAATCTTCCCTATCCAGGGATGGAACC
bhkng3  ATGGGATTCTTCAGACAAGAATACTGGAGCAGGTTGCTATTCCCTATCCTCCAGGAAATCTTCCCTATCCAGGGATGGAACC
```

FIG.15D

```
bhkng1  2241
bhkng2  CAGGTCTCCTGCATTGCAGGTAGATGCTTTACTATCTGAGCAACCAAATGAATTACTCAAGTCAGTAGGGGGTAGAGGCA
bhkng3  CAGGTCTCCTGCATTGCAGGTAGATGCTTTACTATCTGAGCAACCAAATGAATGAATTACTCAAGTCAGTAGGGGGTAGAGGCA
        CAGGTCTCCTGCATTGCAGGTAGATGCTTTACTATCTGAGCAACCAAATGAATTACTCAAGTCAGTAGGGGGTAGAGGCA   2320
        2321                                                                            2400 bhkng1  AATTTAACTTAGTTTCTCTGAATCATAATTGCCACATTAAACTGGTTCCTGTTGGGACATTTGGTTGAAAAAAATAAA
bhkng2  AATTTTAACTTAGTTTCTCTGAATCATAATTGCCACATTAAACTGGTTCCTGTTGGGACATTTGGTTGAAAAAAATAAA
bhkng3  AATTTAACTTAGTTTCTCTGAATCATAATTGCCACATTAAACTGGTTCCTGTTGGGACATTTGGTTGAAAAAAATAAA
        2401                                                                            2480 bhkng1  GTGAAAAATGAGTATAAAACTCTATAAATGTAATGATCAAAACGAAAAAAATCTACAATCTGCATTAAAAATAAAAGG
bhkng2  GTGAAAAATGAGTATAAAACTCTATAAATGTAATGATCAAAACGAAAAAAATCTACAATCTGCATTAAAAATAAAAGG
bhkng3  GTGAAAAATGAGTATAAAACTCTATAAATGTAATGATCAAAACGAAAAAAATCTACAATCTGCATTAAAAATAAAAGG
        2481                                                                            2560 bhkng1  GTTGGCAGG...............................................................
bhkng2  GTTGGCAGGAATTACGGTTGGGAAATGGATGATTTTTTTAACCTTTTCATCTTTGATATTTTACAATTTTCTATAATGA
bhkng3  GTTGGCAGG...............................................................
        2561                                                                            2640 bhkng1  ........................................................................
bhkng2  ATAAATAATTTTGAGATTTCAAATTAGAAGATATGTTGCTAAAAATAGCTAGGTAAATGTAGATTGAACACTGTATCAATG
bhkng3  ........................................................................
                                                                                        2720 bhkng1  ........................................................................
bhkng2  TGTTCTCATCTTTAAACTTTAGTATAAGTACTTCTATTCCATGGTAATCCTACAGTAAGACGAAATGTAAATCTGTTCGG
bhkng3  ........................................................................
                                                                                        2800 bhkng1  ........................................................................
bhkng2  TCTACAGGAAAAAACAACTAAATGACATTTCAGACGTACATTACCATCTCTGTTAGGATAATCTTCTGAATTAATGGCACA
bhkng3  ........................................................................
```

FIG. 15E

```
           2880
bhkng1   ..................................................................................
bhkng2   ATTAGAACTGTACATAGTATTCTCCTTTGGTAAAAATGGTCAATCTTAAAGAAGCATTAAATGTTAATTCTAAGTTATTAC
bhkng3   ..................................................................................

2960
bhkng1   ..................................................................................
bhkng2   TCATAAGGGACCTTGTAGGTAGGTCCCTATCAATGTATAATTAAGCTGGGTATTTCTAGATTCGCTGCCTCTCCCTTTAT
bhkng3   ..................................................................................

3029
bhkng1   ..................................................................................
bhkng2   CTCTGAATGTTGGAGAGGTTGTTGGTCATCAATCAACCAATATCTTTTAGCATCTTCTAAGTGAAGGC
bhkng3   ..................................................................................
```

FIG. 15F

```
                                                                                                              80
hmhkng_aa        1   MKIKAEKNEGPSRSWWQLHWGDIANNSGNMKPPLLVFIVCLLWLKDSHCAPTWKDKTAISENLKSFSEVGEIDADEEVKK
bhkng1_aa                                    ---------MKPPLLVFIVYLLRLRDCQCAPTGKDRTSIREDPKGFSKAGEIDVDEEVKK
phkng1815_aa                                 ---------MKLPLLMFPVCLLWLKDCHCAPTWKDKTAISENANSFSEAGEIDVDGEVKI
                                                                                                             160
hmhkng_aa       81   ALTGIKQMKIMMERKEKEHTNLMSTLKKCREEKQEALKLLNEVQEHLEEEERLCRESLADSWGECRSCLENNCMRIYTTC
bhkng1_aa            ALIGMKQMKILMERREEHSKLMRTLKKCREEKQEALKLMNEVQEHLEEEERLCQVSLMGSWDECKSCLESDCMRFYTTC
gphkng1815_aa        ALIGIKQMKIMMERREEHSKLMKTLKKCKEEKQEALKLMNEVHEHLEEEESLCQVSLADSWDECRACLESNCMRFDTTC
                                                                                                             240
hmhkng_aa      161   QPSWSSVKNKIERFFRKIYQFLFPFHEDNEKDLPISEKLIEEDAQLTQMEDVFSQLTVDVNSLFNRSFNVFRQMQQEFDQ
bhkng1_aa            QSSWSSMKSTIERVFRKIYQFLFPFHEDDEKELPVGEKFTEEDVQLMQIENVFSQLTVDVGFLYNMSFHVFKQMQQEFDL
gphkng1815_aa        QPAWSSVKNMVEQFFRKIYQFLFPLQE.NDRSGPVSKGVTEEDAQVSHIEHVFSQLSADVTSLFNRSLYVFKQLRREFDQ
                                                                                                             320
hmhkng_aa      241   TFQSHFISDTDLTEPYFFPAFSKEPMTKADLEQCWDIPNFFQLFCNFSVSIYESVSETITKMLKAIEDLPKQDKAPDHGG
bhkng1_aa            AFQSYFMSDTDSMEPYFFPAFSKEPSKEPAKKAHPMQSWDIPSFFQLFCNFSLSVYQSVSATVTEMLKAIEDLSKQDKDSAHGG
gphkng1815_aa        AFQSYFTSGTDVTEPFFFPSLSKEPAYRADAEPSWAIPNVFQLLCNLSFSVYQSVSEKLITTLRATEDPPKQDKDSNQGG
                                                                                                             400
hmhkng_aa      321   LISKMLPGQDRGLCGELDQNLSRCFKFHEKCQKCQAHLSEDCPDVPALHTELDEAIRLVNVSNQQYGQILQMTRKHLEDT
bhkng1_aa            PSSTTWPVRGRGLCGEPGQNSSECLQFHARCQKCQDYLWADCPAVPELYTKADEALELVNISNQQYAQVLQMTQHHLEDT
gphkng1815_aa        PISKILPEQDRGSDGKLGQNLSDCVNFRKRCQKCQDYLSDDCPNVPELYRELNEALRLVSRSNQQYDQVVQMTQYHLEDT
                                                                                                             480
hmhkng_aa      401   AYLVEKMRGQFGWVSELANQAPETEIIFNSIQVVPRI..HEGNISKQDETMMTDLSILPSSNFTLKIPLEESAESSNFIG
bhkng1_aa            TYLMEKMREQFGWVTELASQTPGSENIFSFIKVVPGV..HEGNFSKQDE.KMIDISILPSSNFTLTIPLEESAESSDFIS
gphkng1815_aa        TLLMEKMREQFGWSELAYQSPGAEDIFNPVKVMVALSAHEGNSSDQDD.TVVPSSLLPSSNFTLSSPLEKSAGNANFID
                                                                                                             497
hmhkng_aa      481   YVVAKALQHFKEHFKTW
bhkng1_aa            YMLAKAVQHFKEHFKSW
gphkng1815_aa        HVVEKVLQHFKEHFKTW
```

FIG. 16

```
matureHKNG        ----------------------------------------------------APTWKDTAIS
HKNG1-V1-IPF3     -------------MRTWDYSNSGNMKPPLLVFIVCLLWLKDSHCAPTWKDTAIS
HKNG1/1-V1-IPF2   ----------------MKPPLLVFIVCLLWLKDSHCAPTWKDTAIS
HKNG1-IPF1        MKIKAEKNEGPSRSWWQLHWGDIANNSGNMKPPLLVFIVCLLWLKDSHCAPTWKDTAIS
                                                                    ********** matureHKNG        ENLKSFSEVGEIDADEEVKKALTGIKQMKIMMEREKEHTNLMSTLKKCREEKQEALKLL
HKNG1-V1-IPF3     ENLKSFSEVGEIDADEEVKKALTGIKQMKIMMEREKEHTNLMSTLKKCREEKQEALKLL
HKNG1/1-V1-IPF2   ENLKSFSEVGEIDADEEVKKALTGIKQMKIMMEREKEHTNLMSTLKKCREEKQEALKLL
HKNG1-IPF1        ENLKSFSEVGEIDADEEVKKALTGIKQMKIMMEREKEHTNLMSTLKKCREEKQEALKLL
                  *********************************************************** matureHKNG        NEVQEHLEEEERLCRESLADSWGECRSCLENNCMRIYTTCQPSWSSVKNKIERFFRKIYQ
HKNG1-V1-IPF3     NEVQEHLEEEERLCRESLADSWGECRSCLENNCMRIYTTCQPSWSSVKNKIERFFRKIYQ
HKNG1/1-V1-IPF2   NEVQEHLEEEERLCRESLADSWGECRSCLENNCMRIYTTCQPSWSSVKNKIERFFRKIYQ
HKNG1-IPF1        NEVQEHLEEEERLCRESLADSWGECRSCLENNCMRIYTTCQPSWSSVKNKIERFFRKIYQ
                  *********************************************************** matureHKNG        FLFPFHEDNEKDLPISEKLIEEDAQLTQMEDVFSQLTVDVNSLFNRSFNVFRQMQQEFDQ
HKNG1-V1-IPF3     FLFPFHEDNEKDLPISEKLIEEDAQLTQMEDVFSQLTVDVNSLFNRSFNVFRQMQQEFDQ
HKNG1/1-V1-IPF2   FLFPFHEDNEKDLPISEKLIEEDAQLTQMEDVFSQLTVDVNSLFNRSFNVFRQMQQEFDQ
HKNG1-IPF1        FLFPFHEDNEKDLPISEKLIEEDAQLTQMEDVFSQLTVDVNSLFNRSFNVFRQMQQEFDQ
                  *********************************************************** matureHKNG        TFQSHFISDTDLTEPYFFPAFSKEPMTKADLEQCWDIPNFFQLFCNFSVSIYESVSETIT
HKNG1-V1-IPF3     TFQSHFISDTDLTEPYFFPAFSKEPMTKADLEQCWDIPNFFQLFCNFSVSIYESVSETIT
HKNG1/1-V1-IPF2   TFQSHFISDTDLTEPYFFPAFSKEPMTKADLEQCWDIPNFFQLFCNFSVSIYESVSETIT
HKNG1-IPF1        TFQSHFISDTDLTEPYFFPAFSKEPMTKADLEQCWDIPNFFQLFCNFSVSIYESVSETIT
                  ***********************************************************
```

FIG. 17A

```
matureHKNG         KMLKAIEDLPKQDKAPDHGGLISKMLPGQDRGLCGELDQNLSRCFKFHEKCQKCQAHLSE
HKNG1-V1-IPF3      KMLKAIEDLPKQDKAPDHGGLISKMLPGQDRGLCGELDQNLSRCFKFHEKCQKCQAHLSE
HKNG1/1-V1-IPF2    KMLKAIEDLPKQDKAPDHGGLISKMLPGQDRGLCGELDQNLSRCFKFHEKCQKCQAHLSE
HKNG1-IPF1         KMLKAIEDLPKQDKAPDHGGLISKMLPGQDRGLCGELDQNLSRCFKFHEKCQKCQAHLSE
                   ************************************************************ matureHKNG         DCPDVPALHTELDEAIRLVNVSNQQYGQILQMTRKHLEDTAYLVEKMRGQFGWVSELANQ
HKNG1-V1-IPF3      DCPDVPALHTELDEAIRLVNVSNQQYGQILQMTRKHLEDTAYLVEKMRGQFGWVSELANQ
HKNG1/1-V1-IPF2    DCPDVPALHTELDEAIRLVNVSNQQYGQILQMTRKHLEDTAYLVEKMRGQFGWVSELANQ
HKNG1-IPF1         DCPDVPALHTELDEAIRLVNVSNQQYGQILQMTRKHLEDTAYLVEKMRGQFGWVSELANQ
                   ************************************************************ matureHKNG         APETEIIFNSIQVVPRIHEGNISKQDETMMTDLSILPSSNFTLKIPLEESAESSNFIGYV
HKNG1-V1-IPF3      APETEIIFNSIQVVPRIHEGNISKQDETMMTDLSILPSSNFTLKIPLEESAESSNFIGYV
HKNG1/1-V1-IPF2    APETEIIFNSIQVVPRIHEGNISKQDETMMTDLSILPSSNFTLKIPLEESAESSNFIGYV
HKNG1-IPF1         APETEIIFNSIQVVPRIHEGNISKQDETMMTDLSILPSSNFTLKIPLEESAESSNFIGYV
                   ************************************************************ matureHKNG         VAKALQHFKEHFKTW
HKNG1-V1-IPF3      VAKALQHFKEHFKTW
HKNG1/1-V1-IPF2    VAKALQHFKEHFKTW
HKNG1-IPF1         VAKALQHFKEHFKTW
                   ***************
```

FIG. 17B

FIG. 18A

```
        R   H   L   Q   A   R   A   A   G   L   V   S   T   L   E   V   A   D   T     19
    TG CGT CAC CTG CAG GCC CGG GCC GCG GGG TTG GTT TCC ACC CTG GAG GTT GCT GAC ACC     57

L   C   P   R   L   T   S   S   R   W   H   R   L   Q   G   A   A   L   K         39
   CTG TGC CCT CGG CTG ACT TCC AGC CGG TGG CAC AGA CGC CTC CAG GGG GCA GCA CTC AAG    117

R   I   L   G   M   T   E   L   R   P   S   L   L   P   G   W   S   V   A         59
   CGC ATC TTA GGA ATG ACA GAG TTG CGT CCC TCT CTG TTG CCA GGC TGG AGT TCA GTG GCA    177

C   S   *   L   T   E   A   S   N   S   W   V   Q   V   T   L   P   P   Q         79
   TGT TCT TAG CTC ACT GAA GCC TCA AAT TCC TGG GTT CAA GTG ACC CTC CCA CCT CAG CCC    237

H   E   D   L   G   L   Q   D   T   A   K   S   L   T   R   M   K   I   A         99
   CAT GAG GAC CTG GGA CTA CAG GAC ACA GCT AAA TCC CTG ACA CGG ATG AAA ATT GCA        297

E   K   N   E   G   P   S   R   S   W   Q   L   F   I   V   C   L   W   N        119
   GAG AAA AAC GAA GGT CCT TCC AGA AGC TGG CAA CTT ATT GTG TGT CTG TGG AAT            357

N   S   G   N   M   K   P   P   T   W   K   D   K   T   A   I   S   E   N        139
   AAC AGC GGG AAC ATG AAG CCG CCA ACT TGG AAG GAC AAA ACT GCT ATC AGT GAA AAC        417

D   S   H   C   A   P   I   D   A   D   E   E   V   K   K   A   L   T   G        159
   GAC AGT CAC TGC GCA CCC ATA GAT GCA GAT GAA GAG GTG AAG AAG GCT TTG ACT GGT        477

F   S   E   V   G   E   M   M   E   R   K   E   K   H   T   N   L   M   S        179
   TTT TCT GAG GTG GGG GAG ATG ATG GAA AGA AAA GAG AAA CAC ACC AAT CTA ATG AGC        537

K   Q   M   K   I   M   M   E   R   K   E   K   H   T   N   L   M   S   T        199
   AAG CAA ATG AAA ATC ATG ATG GAA AGA AAA GAG AAA CAC ACC AAT CTA ATG AGC ACC        597
```

FIG.18A

FIG. 18B

```
 L   K   K   C   R   E   E   K   Q   E   A   L   K   L   L   N   E   V   Q   E   219
CTG AAG AAA TGC AGA GAA GAA AAG CAG GAG GCC CTG AAA CTT CTG AAT GAA GTT CAA GAA  657

H   L   E   E   E   R   L   C   R   E   S   L   A   D   S   W   G   E   C       239
CAT CTG GAG GAA GAA AGG CTA TGC CGG GAG TCT TTG GCA GAT TCC TGG GGT GAA TGC      717

R   S   C   L   E   N   N   C   M   R   I   Y   T   T   C   Q   P   S   W   S   259
AGG TCT TGC CTG GAA AAT AAC TGC ATG AGA ATT TAT ACA ACC TGC CAA CCT AGC TGG TCC  777

S   V   K   N   K   L   L   T   E   *   A   E   R   I   C   Q   *   F   Y   R   279
TCT GTG AAA AAT AAG CTC CTG ACC GAG TGA GCC GAG ACG ATA TGT CAA TGA TTT TAC AGA  837

T   E   D   C   V   G   N   L   T   Y   W   R   S   G   W   S   M   Y   P   I   299
ACA GAG GAC TGT GTG GGG AAC TTG ACC TAT TGG CGA TCA GGT TGG TCA ATG TAT CCA ATC  897

S   S   M   A   R   *   E   G                                                   319
AGC AGT ATG GCC AGA TGA GAG GGC                                                  957

N   A   K   N   V   R   L   T   Y   L   M   F   L   C   T                       
AAT GCC AAA AAT GTC AGG CTC TAC CTG ATG TTC CTG TGC ACA

Q   *   N   T   R   R   S   G   W   R   T   W   R   P   I   W   R   R   S   F   339
CAG AAT TAG ACG AGG CGA TCA GGT TGG AGA ACA TGG AGA CCA ATC TGG AGA AGA TCT TTC  1017

S   R   *   P   G   S   T   W   R   T   Q   R   P   Q   K   Q   R   S   L   I   359
TCC AGA TGA CCC GGA AGC ACT TGG AGG ACA CAG AGG CCC CAG AAA CAG AGA TCA TTA ATT  1077

N   L   A   G   C   L   N   W   Q   N   W   Q   F   M   K   E   F   P   N   K   379
AAT TTG GCT GGG TGT CTG AAC TGG CAA AAC TGG CAA TTC ATG AAG GAA TTT CCA AAC AAG  1137

Q   Y   R   R   *   F   Q   F   M   K   E   I   F   P   N   K   M   K   Q   *   399
CAA TAC AGG TAG TTC CAA TTC ATG AAG GAA ATA TTT CCA AAC AAG ATG AAA CAA TGA     1197
```

```
  *   Q   T   *   A   F   C   L   P   L   I   S   H   S   R   S   L   L   K   K   419
 TGA CAG ACT TAA GCA TTC TGC CTT CCT CTA ATT TCA CAC TCA AGA TCC CTC TTG AAG AAA 1257

V   L   R   V   L   T   S   L   A   T   *   W   Q   K   L   Y   S   I   L   R   439
 GTG CTG AGA GTT CTA ACT TCA CTT GCT ACG TAG TGG CAA AAG CTC TAC AGC ATT TTA AGG 1317

N   I   L   K   P   G   K   K   I   *   C   I   L   Y   P   V   S   R   I   I   459
 AAC ATT TTA AAA CCT GGT AAG AAG ATC TAA TGC ATC CTA TAT CCA GTA AGT AGA ATT ATC 1377

S   S   S   G   T   W   K   S   *   N   K   K   G   *   C   N   K   H   S   C   479
 TCT TCA TCT GGG ACC TGG AAA TCC TGA AAT AAA AAA GGA TAA TGC AAT AAA CAC AGT TGC 1437

R   K   V   C   *   L   Y   T   M   K   Y   S   *   F   T   Y   V   E   W   L   499
 AGG AAA GTA TGT TAG CTA TAT ACT ATG AAG TAC TCT TAG TTT ACT TAT GTT GAA TGG CTT 1497

S   *   Y   S   N   *   V   K   M   K   I   P   P   *   K   I   K   R   N   519
 AGC TAT TAA TCA AAT TGA GTT AAA ATG AAA ATT CCT CCT TAA AAA ATC AAA CGT AAT 1557

M   Y   I   S   W   Y   I   S   S   S   L   Y   I   E   *   I   L   N   H   539
 ATG TAT TAC ATT TCA TGG TAC ATT AGT AGT TCT TTG TAT ATT GAA TAA ATA CTA AAT CAC 1617

L                                                                           540
 CTA                                                                          1620
```

FIG. 18C

METHODS AND COMPOSITIONS FOR DIAGNOSING AND TREATING CHROMOSOME -18P RELATED DISORDERS

This is a divisional of application Ser. No. 09/268,992, filed Mar. 16, 1999.

This is a continuation-in-part of U.S. application Ser. No. 09/236,134, filed on Jan. 22, 1999 which claims priority under 35 U.S.C. §119(e)(1) of provisional application No. 60/078,044 filed on Mar. 16, 1998, of provisional application No. 60/088,312 filed on Jun. 5, 1998, and of provisional application No. 60/106,056 filed on Oct. 28, 1998, each of which is incorporated herein by reference in its entirety.

1. INTRODUCTION

The present invention relates, first, to the HKNG1 gene, shown herein to be associated with central nervous system-related disorders, e.g., neuropsychiatric disorders, in particular, bipolar affective disorder and schizophrenia and with myopia-related disorders. The invention includes recombinant DNA molecules and cloning vectors comprising sequences of the HKNG1 gene, and host cells and non-human host organisms engineered to contain such DNA molecules and cloning vectors. The present invention further relates to HKNG1 gene products, and to antibodies directed against such HKNG1 gene products. The present invention also relates to methods of using the HKNG1 gene and gene product, including drug screening assays, and diagnostic and therapeutic methods for the treatment of HKNG1-mediated disorders, including HKNG1-mediated neuropsychiatric disorders such as bipolar affective disorder, as well as HKNG1-mediated myopia disorders such as early-onset autosomal dominant myopia.

2. BACKGROUND OF THE INVENTION

There are only a few psychiatric disorders in which clinical manifestations of the disorder can be correlated with demonstrable defects in the structure and/or function of the nervous system. Well-known examples of such disorders include Huntington's disease, which can be traced to a mutation in a single gene and in which neurons in the striatum degenerate, and Parkinson's disease, in which dopaminergic neurons in the nigro-striatal pathway degenerate. The vast majority of psychiatric disorders, however, presumably involve subtle and/or undetectable changes, at the cellular and/or molecular levels, in nervous system structure and function. This lack of detectable neurological defects distinguishes "neuropsychiatric" disorders, such as schizophrenia, attention deficit disorders, schizoaffective disorder, bipolar affective disorders, or unipolar affective disorder, from neurological disorders, in which anatomical or biochemical pathologies are manifest. Hence, identification of the causative defects and the neuropathologies of neuropsychiatric disorders are needed in order to enable clinicians to evaluate and prescribe appropriate courses of treatment to cure or ameliorate the symptoms of these disorders.

One of the most prevalent and potentially devastating of neuropsychiatric disorders is bipolar affective disorder (BAD), also known as bipolar mood disorder (BP) or manic-depressive illness, which is characterized by episodes of elevated mood (mania) and depression (Goodwin, et al., 1990, Manic Depressive Illness, Oxford University Press, New York). The most severe and clinically distinctive forms of BAD are BP-I (severe bipolar affective (mood) disorder), which affects 2–3 million people in the United States, and SAD-M (schizoaffective disorder manic type). They are characterized by at least one full episode of mania, with or without episodes of major depression (defined by lowered mood, or depression, with associated disturbances in rhythmic behaviors such as sleeping, eating, and sexual activity). BP-I often co-segregates in families with more etiologically heterogeneous syndromes, such as with a unipolar affective disorder such as unipolar major depressive disorder (MDD), which is a more broadly defined phenotype (Freimer and Reus, 1992, in The Molecular and Genetic Basis of Neurological Disease, Rosenberg, et al., eds., Butterworths, New York, pp. 951–965; McInnes and Freimer, 1995, Curr. Opin. Genet. Develop., 5, 376–381). BP-I and SAD-M are severe mood disorders that are frequently difficult to distinguish from one another on a cross-sectional basis, follow similar clinical courses, and segregate together in family studies (Rosenthal, et al., 1980, Arch. General Psychiat. 37, 804–810; Levinson and Levitt, 1987, Am. J. Psychiat. 144, 415–426; Goodwin, et al., 1990, Manic Depressive Illness, Oxford University Press, New York). Hence, methods for distinguishing neuropsychiatric disorders such as these are needed in order to effectively diagnose and treat afflicted individuals.

Currently, individuals are typically evaluated for BAD using the criteria set forth in the most current version of the American Psychiatric Association's Diagnostic and Statistical Manual of Mental Disorders (DSM). While many drugs have been used to treat individuals diagnosed with BAD, including lithium salts, carbamazepine and valproic acid, none of the currently available drugs are adequate. For example, drug treatments are effective in only approximately 60–70% of individuals diagnosed with BP-I. Moreover, it is currently impossible to predict which drug treatments will be effective in, for example, particular BP-I affected individuals. Commonly, upon diagnosis, affected individuals are prescribed one drug after another until one is found to be effective. Early prescription of an effective drug treatment, therefore, is critical for several reasons, including the avoidance of extremely dangerous manic episodes, the risk of progressive deterioration if effective treatments are not found, and the risk of substantial side effects of current treatments.

The existence of a genetic component for BAD is strongly supported by segregation analyses and twin studies (Bertelson, et al., 1977, Br. J. Psychiat. 130, 330–351; Freimer and Reus, 1992, in The Molecular and Genetic Basis of Neurological Disease, Rosenberg, et al., eds., Butterworths, New York, pp. 951–965; Pauls, et al., 1992, Arch. Gen. Psychiat. 49, 703–708). Efforts to identify the chromosomal location of genes that might be involved in BP-I, however, have yielded disappointing results in that reports of linkage between BP-I and markers on chromosomes X and 11 could not be independently replicated nor confirmed in the re-analyses of the original pedigrees, indicating that with BAD linkage studies, even extremely high lod scores at a single locus, can be false positives (Baron, et al., 1987, Nature 326, 289–292; Egeland, et al., 1987, Nature 325, 783–787; Kelsoe, et al., 1989, Nature 342, 238–243; Baron, et al., 1993, Nature Genet. 3, 49–55).

Recent investigations have suggested possible localization of BAD genes on chromosomes 18p and 21q, but in both cases the proposed candidate region is not well defined and no unequivocal support exists for either location (Berrettini, et al., 1994, Proc. Natl. Acad. Sci. USA 91, 5918–5921; Murray, et al., 1994, Science 265, 2049–2054; Pauls, et al., 1995, Am. J. Hum. Genet. 57, 636–643; Maier, et al., 1995, Psych. Res. 59, 7–15; Straub, et al., 1994, Nature Genet. 8, 291–296).

Mapping genes for common diseases believed to be caused by multiple genes, such as BAD, may be complicated by the typically imprecise definition of phenotypes, by etiologic heterogeneity, and by uncertainty about the mode of genetic transmission of the disease trait. With neuropsychiatric disorders there is even greater ambiguity in distinguishing individuals who likely carry an affected genotype from those who are genetically unaffected. For example, one can define an affected phenotype for BAD by including one or more of the broad grouping of diagnostic classifications that constitute the mood disorders: BP-I, SAD-M, MDD, and bipolar affective (mood) disorder with hypomania and major depression (BP-II).

Thus, one of the greatest difficulties facing psychiatric geneticists is uncertainty regarding the validity of phenotype designations, since clinical diagnoses are based solely on clinical observation and subjective reports. Also, with complex traits such as neuropsychiatric disorders, it is difficult to genetically map the trait-causing genes because: (1) neuropsychiatric disorder phenotypes do not exhibit classic Mendelian recessive or dominant inheritance patterns attributable to a single genetic locus, (2) there may be incomplete penetrance, i.e., individuals who inherit a predisposing allele may not manifest disease; (3) a phenocopy phenomenon may occur, i.e., individuals who do not inherit a predisposing allele may nevertheless develop disease due to environmental or random causes; (4) genetic heterogeneity may exist, in which case mutations in any one of several genes may result in identical phenotypes.

Despite these difficulties, however, identification of the chromosomal location, sequence and function of genes and gene products responsible for causing neuropsychiatric disorders such as bipolar affective disorders is of great importance for genetic counseling, diagnosis and treatment of individuals in affected families.

3. SUMMARY OF THE INVENTION

The present invention relates, first, to the discovery, identification, and characterization of novel nucleic acid molecules that are associated with central nervous system-related disorders and processes, e.g., human neuropsychiatric disorders, such as schizophrenia, attention deficit disorder, schizoaffective disorder, dysthymic disorder, major depressive disorder, and bipolar affective disorder (BAD) including severe bipolar affective (mood) disorder (BP-I), bipolar affective (mood) disorder with hypomania and major depression (BP-II). The invention further relates to the discovery, identification, and characterization of proteins encoded by such nucleic acid molecules, or by degenerate, e.g., allelic or homologous, variants thereof. The invention further relates to the discovery, identification, and characterization of novel nucleic acid molecules that are associated with human myopia or nearsightedness, such as early-onset, autosomal dominant myopia, as well as to the discovery, identification, and characterization of proteins encoded by such nucleic acid molecules or by degenerate variants thereof.

In particular, the nucleic acid molecules of the present invention represent, first, nucleic acid sequences corresponding to the gene referred to herein as HKNG1. As demonstrated in the Examples presented below in Sections 6, 8 and 14, the HKNG1 gene is associated with human CNS-related disorders, e.g., neuropsychiatric disorders, in particular BAD. The HKNG1 gene is associated with other human neuropsychiatric disorders as well, such as schizophrenia. As demonstrated in the Example presented below in Section 14, the HKNG1 gene is also associated with human myopia, such as early-onset autosomal dominant myopia.

In addition to the positive correlation between mutations within the HKNG1 gene and individuals exhibiting symptoms of BAD, described in Section 6 and 8, the present invention is further based, in part, on Applicants' discovery of novel HKNG1 cDNA sequences. Applicants' discovery of such cDNA sequences has led to the elucidation of the HKNG1 genomic (that is, upstream untranslated, intron/exon, and downstream untranslated) structure, and to the discovery of full-length and alternately spliced HKNG1 variants and the polypeptides encoded by such variants. These discoveries are described in Sections 7 and 10, below. Applicants' discovery of such cDNA sequences has also led to the elucidation of novel mammalian (e.g., guinea pig and bovine) HKNG1 sequences, and to the discovery of novel allelic variants and polymorphisms of such sequences. These discoveries are described in Section 10 below.

The invention encompasses nucleic acid molecules which comprise the following nucleotide sequences: (a) nucleotide sequences (e.g., SEQ ID NOS: 1, 3, 5, 6, 36, and 37) that comprise a human HKNG1 gene and/or encode a human HKNG1 gene product (e.g., SEQ ID NO: 2; SEQ ID NO: 4), as well as allelic variants, homologs and orthologs thereof, including nucleotide sequences (e.g., SEQ ID NOS:38, 40, 42, 44, and 46–48) that encode non-human HKNG1 gene products (e.g., SEQ ID NOS:39, 41, 43, 45, and 49); (b) nucleotide sequences comprising the novel HKNG1 sequences disclosed herein that encode mutants of the HKNG1 gene product in which sequences encoding all or a part of one or more of the HKNG1 domains is deleted or altered, or fragments thereof; (c) nucleotide sequences that encode fusion proteins comprising a HKNG1 gene product (e.g., SEQ ID NO: 2; SEQ ID NO: 4), or a portion thereof fused to a heterologous polypeptide; and (d) nucleotide sequences within the HKNG1 gene, as well as chromosome 18p nucleotide sequences flanking the HKNG1 gene, which can be utilized, e.g., as primers, in the methods of the invention for identifying and diagnosing individuals at risk for or exhibiting an HKNG1-mediated disorder, such as BAD or schizophrenia, or for diagnosing individuals at risk for or exhibiting a form of myopia such as early-onset autosomal dominant myopia. The nucleic acid molecules of (a) through (d), above, can include, but are not limited to, cDNA, genomic DNA, and RNA sequences.

The invention also encompasses the expression products of the nucleic acid molecules listed above; i.e., peptides, proteins, glycoproteins and/or polypeptides that are encoded by the above HKNG1 nucleic acid molecules.

The compositions of the present invention further encompass agonists and antagonists of the HKNG1 gene product, including small molecules (such as small organic molecules), and macromolecules (including antibodies), as well as nucleotide sequences that can be used to inhibit HKNG1 gene expression (e.g., antisense and ribozyme molecules, and gene or regulatory sequence replacement constructs) or to enhance HKNG1 gene expression (e.g., expression constructs that place the HKNG1 gene under the control of a strong promoter system).

The compositions of the present invention further include cloning vectors and expression vectors containing the nucleic acid molecules of the invention, as well as hosts which have been transformed with such nucleic acid molecules, including cells genetically engineered to contain the nucleic acid molecules of the invention, and/or cells genetically engineered to express the nucleic acid molecules of the invention. In addition to host cells and cell lines, hosts also include transgenic non-human animals (or progeny thereof), particularly non-human mammals, that have been engineered to express an HKNG1 transgene, or "knock-outs" that have been engineered to not express HKNG1.

Transgenic non-human animals of the invention include animals engineered to express an HKNG1 transgene at higher or lower levels than normal, wild-type animals. The transgenic animals of the invention also include animals engineered to express a mutant variant or polymorphism of an HKNG1 transgene which is associated with HKNG1-mediated disorder, for example an HKNG1-mediated neuropsychiatric disorders, such as BAD and schizophrenia, or, alternatively, a myopia disorder such as early-onset autosomal dominant myopia. The transgenic animals of the invention further include the progeny of such genetically engineered animals.

The invention further relates to methods for the treatment of HKNG1-mediated disorders in a subject, such as HKNG1-mediated neuropsychiatric disorders and HKNG1-mediated myopia disorders, wherein such methods comprise administering a compound which modulates the expression of a HKNG1 gene and/or the synthesis or activity of a HKNG1 gene product so symptoms of the disorder are ameliorated.

The invention further relates to methods for the treatment of HKNG1-mediated disorders in a subject, such as HKNG1-mediated neuropsychiatric disorders and HKNG1-mediated myopia disorders, resulting from HKNG1 gene mutations or aberrant levels of HKNG1 expression or activity, wherein such methods comprise supplying the subject with a nucleic acid molecule encoding an unimpaired HKNG1 gene product such that an unimpaired HKNG1 gene product is expressed and symptoms of the disorder are ameliorated.

The invention further relates to methods for the treatment of HKNG1-mediated disorders in a subject, such as HKNG1-mediated neuropsychiatric disorders and HKNG1-mediated myopia disorders, resulting from HKNG1 gene mutations or from aberrant levels of expression or activity, wherein such methods comprise supplying the subject with a cell comprising a nucleic acid molecule that encodes an unimpaired HKNG1 gene product such that the cell expresses the unimpaired HKNG1 gene product and symptoms of the disorder are ameliorated.

The invention also encompasses pharmaceutical formulations and methods for treating HKNG1-mediated disorders, including neuropsychiatric disorders, such as BAD and schizophrenia, and myopia disorders, such as early-onset autosomal dominant myopia, involving HKNG1 gene.

In addition, the present invention is directed to methods that utilize the HKNG1 nucleic acid sequences, chromosome 18p nucleotide sequences flanking the HKNG1 human gene and/or HKNG1 gene product sequences for mapping the chromosome 18p region, and for the diagnostic evaluation, genetic testing and prognosis of a HKNG1-mediated disorder, such as a HKNG1-mediated neuropsychiatric disorder or a HKNG1-mediated myopia disorder. For example, in one embodiment, the invention relates to methods for diagnosing HKNG1-mediated disorders, wherein such methods comprise measuring HKNG1 gene expression in a patient sample, or detecting a HKNG1 polymorphism or mutation in the genome of a mammal, including a human, suspected of exhibiting such a disorder. In one embodiment, nucleic acid molecules encoding HKNG1 can be used as diagnostic hybridization probes or as primers for diagnostic PCR analysis for the identification of HKNG1 gene mutations, allelic variations and regulatory defects in the HKNG1 gene which correlate with neuropsychiatric disorders such as BAD or schizophrenia.

The invention still further relates to methods for identifying compounds which modulate the expression of the HKNG1 gene and/or the synthesis or activity of the HKNG1 gene products, including therapeutic compounds, which reduce or eliminate the symptoms of HKNG1-mediated disorders, including HKNG1-mediated neuropsychiatric disorders such as BAD and schizophrenia. In particular, cellular and non-cellular assays are described that can be used to identify compounds that interact with the HKNG1 gene product, e.g., modulate the activity of the HKNG1 and/or bind to the HKNG1 gene product. Such cell-based assays of the invention utilize cells, cell lines, or engineered cells or cell lines that express the HKNG1 gene product.

In one embodiment, such methods comprise contacting a compound to a cell that expresses a HKNG1 gene, measuring the level of HKNG1 gene expression, gene product expression or gene product activity, and comparing this level to the level of HKNG1 gene expression, gene product expression or gene product activity produced by the cell in the absence of the compound, such that if the level obtained in the presence of the compound differs from that obtained in its absence, a compound that modulates the expression of the HKNG1 gene and/or the synthesis or activity of the HKNG1 gene products has been identified.

In another embodiment, such methods comprise contacting a compound to a cell that expresses a HKNG1 gene and also comprises a reporter construct whose transcription is dependent, at least in part, on HKNG1 expression or activity.

In such an embodiment, the level of reporter transcription is measured and compared to the level of reporter transcription in the cell in the absence of the compound. If the level of reporter transcription obtained in the presence of the compound differs from that obtained in its absence, a compound that modulates expression of HKNG1 or genes involved in HKNG1-related pathways or signal transduction has been identified.

In yet another embodiment, such methods comprise administering a compound to a host, such as a transgenic animal, that expresses an HKNG1 transgene or a mutant HKNG1 transgene associated with an HKNG1-mediated disorder such as a neuropsychiatric disorder (e.g., BAD or schizophrenia), or to an animal, e.g., a knock-out animal, that does not express HKNG1, and measuring the level of HKNG1 gene expression, gene product expression, gene product activity, or symptoms of an HKNG1-mediated disorder such as an HKNG1-mediated neuropsychiatric disorder (e.g., BAD or schizophrenia). The measured level is compared to the level obtained in a host that is not exposed to the compound, such that if the level obtained when the host is exposed to the compound differs from that obtained in a host not exposed to the compound, a compound modulates the expression of the mammalian HKNG1 gene and/or the synthesis or activity of the mammalian HKNG1 gene products, and/or the symptoms of an HKNG1-mediated disorder such as a neuropsychiatric disorder (e.g., BAD or schizophrenia), has been identified.

The present invention still further relates to pharmacogenomic and pharmacogenetic methods for selecting an effective drug to administer to an individual having a HKNG1-mediated disorder. Such methods are based on the detection of genetic polymorphisms in the HKNG1 gene or variations in HKNG1 gene expression due to, e.g., altered methylation, differential splicing, or post-translational modification of the HKNG1 gene product which can affect the safety and efficacy of a therapeutic agent.

As briefly discussed above, the present invention is based, in part, on the genetic and physical mapping of the HKNG1 gene to a specific portion of the short arm of human chromosome 18 that is associated with human neuropsychiatric disorders, in particular, bipolar affective disorder. These results are described in the Example presented, below, in Section 6. The invention is also based on the elucidation of the HKGN1 nucleotide sequence, amino acid sequence and expression pattern, as described in the Example presented, below, in Section 7. The invention is further based on the identification of specific mutations and/or polymorphisms within the HKNG1 gene which positively correlate with neuropsychiatric disorders, in particular, BAD, as described in the Example presented below in Section 8. These mutations include a point mutation discovered in an individual affected by BAD which is absent from the corresponding wild-type nucleic acid derived from non-affected individuals and linkage disequilibrium of three markers showing cosegregation with a population of individuals with BAD. This mutation is single base mutation which results in a mutant HKNG1 gene product comprising substitution of a lysine residue for the wild-type glutamic acid residue at HKNG1 amino acid position 202 of the polypeptide of SEQ ID NO:2 or the HKNG1 amino acid residue 184 of the polypeptide of SEQ ID NO:4. These mutations further include the mutations discovered in schizophrenic and BAD patients that are detailed in FIGS. 5A–5C.

3.1. Definitions

As used herein, the following terms shall have the abbreviations indicated.

BAC, bacterial artificial chromosomes
BAD, bipolar affective disorder(s)
BP, bipolar mood disorder
BP-I, severe bipolar affective (mood) disorder
BP-II, bipolar affective (mood) disorder with hypomania and major depression
bp, base pair(s)
EST, expressed sequence tag
HKNG1, Hong Kong new gene 1
lod, logarithm of odds
MDD, unipolar major depressive disorder
ROS, reactive oxygen species
RT-PCR, reverse transcriptase PCR
SSCP, single-stranded conformational polymorphism
SAD-M, schizoaffective disorder manic type
STS, sequence tagged site
YAC, yeast artificial chromosome "HKNG1-mediated disorders" include disorders involving an aberrant level of HKNG1 gene expression, gene product synthesis and/or gene product activity relative to levels found in clinically normal individuals, and/or relative to levels found in a population whose level represents a baseline, average HKNG1 level. While not wishing to be bound by any particular mechanism, it is to be understood that disorder symptoms can, for example, be caused, either directly or indirectly, by such aberrant levels. Alternatively, it is to be understood that such aberrant levels can, either directly or indirectly, ameliorate disorder symptoms, (e.g., as in instances wherein aberrant levels of HKNG1 suppress the disorder symptoms caused by mutations within a second gene).

HNKG1-mediated disorders include, for example, central nervous system (CNS) disorders. CNS disorders include, but are not limited to cognitive and neurodegenerative disorders such as Alzheimer's disease, senile dementia, Huntington's disease, amyotrophic lateral sclerosis, and Parkinson's disease, as well as Gilles de la Tourette's syndrome, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as bipolar affective disorder, e.g., severe bipolar affective (mood) disorder (BP-I), bipolar affective (mood) disorder with hypomania and major depression (BP-II). Further CNS-related disorders include, for example, those listed in the American Psychiatric Association's Diagnostic and Statistical manual of Mental Disorders (DSM), the most current version of which is incorporated herein by reference in its entirety.

"HKNG1-mediated processes" include processes dependent and/or responsive, either directly or indirectly, to levels of HKNG1 gene expression, gene product synthesis and/or gene product activity. Such processes can include, but are not limited to, developmental, cognitive and autonomic neural and neurological processes, such as, for example, pain, appetite, long term memory and short term memory.

4. BRIEF DESCRIPTION OF THE FIGURES

FIGS. 1A–1C. The nucleotide sequence of human HKNG1 cDNA (SEQ ID NO: 1) is depicted on the bottom line. The top line depicts the full length amino acid sequence of human HKNG1 polypeptide (SEQ ID NO: 2) encoded by the human HKNG1 cDNA sequence. The nucleotide sequence encoding SEQ ID NO:2 corresponds to SEQ ID NO:5.

FIGS. 2A–2C. Nucleotide sequence of an alternately spliced human HKNG1 variant, referred to as HKNG1-V1 (SEQ ID NO: 3) is depicted on the bottom line. The derived amino acid sequence of the human HKNG1 gene product (SEQ ID NO: 4) encoded by this alternately spliced cDNA variant is depicted on the top line. The nucleotide sequence encoding SEQ ID NO:4 corresponds to SEQ ID NO:6

FIGS. 3A–3A-28. Genomic sequence of the human HKNG1 gene (SEQ ID NO. 7). Exons are in bold and the 3' and 5' UTRs (untranslated regions) are underlined.

FIGS. 4A–4B. Summary of in situ hybridization analysis of HKNG1 mRNA distribution in normal human brain tissue.

FIGS. 5A–5C. HKNG1 polymorphisms relative to the HKNG1 wild-type sequence. These polymorphisms were isolated from a collection of schizophrenic patients of mixed ethnicity from the United States (FIG. 5A) and from the San Francisco BAD collection (FIG. 5B).

FIGS. 6A–B. Nucleotide sequence of the RT-PCR products for HKNG1-V2 (FIG. 6A; SEQ ID NO:36) and HKNG1-V3 (FIG. 6B; SEQ ID NO:37).

FIGS. 7A–7C. The cDNA sequence (SEQ ID NO:38) and the predicted amino acid sequence (SEQ ID NO:39) of the guinea pig HKNG1 ortholog gphkng1815.

FIGS. 8A–8C. The cDNA sequence (SEQ ID NO:40) and the predicted amino acid sequence (SEQ ID NO:41) of gphkng 7b, an allelic variant of the guinea pig HKNG1 ortholog gphkng1815.

FIGS. 9A–9C. The cDNA sequence (SEQ ID NO:42) and the predicted amino acid sequence (SEQ ID NO:43) of gphkng 7c, an allelic variant of the guinea pig HKNG1 ortholog gphkng1815.

FIGS. 10A–10C. The cDNA sequence (SEQ ID NO:44) and the predicted amino acid sequence (SEQ ID NO:45) of gphkng 7d, an allelic variant of the guinea pig HKNG1 ortholog gphkng1815.

Figure 11C:
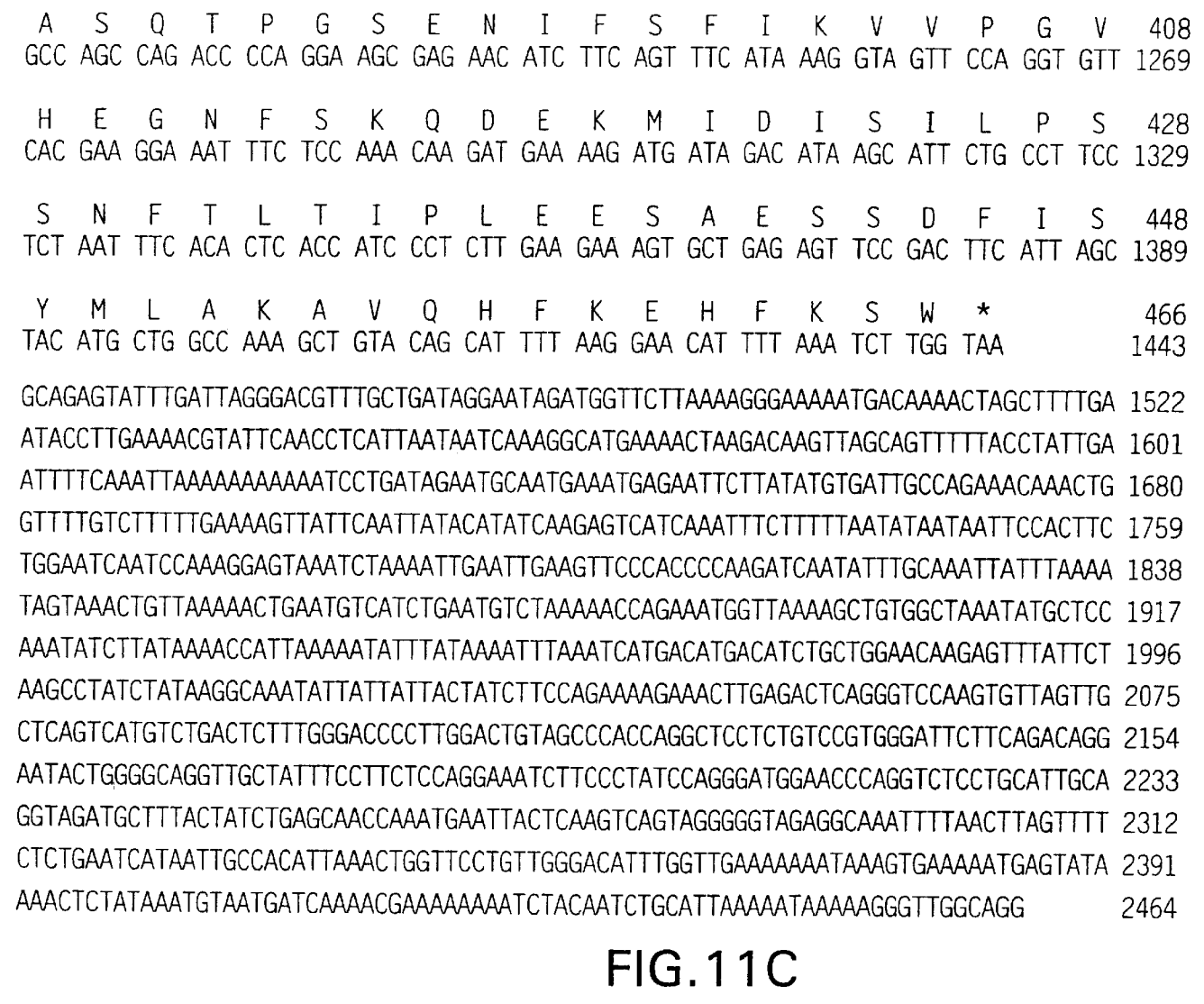

FIGS. 11A–11C. The cDNA sequence (SEQ ID NO:46) and the predicted amino acid sequence (SEQ ID NO:49) of the allelic variant bhkng1 of the bovine HKNG1 ortholog.

FIGS. 12A–12D. The cDNA sequence (SEQ ID NO:47) and the predicted amino acid sequence (SEQ ID NO:49) of the allelic variant bhkng2 of the bovine HKNG1 homolgue.

FIGS. 13A–13C. The cDNA sequence (SEQ ID NO:48) and the predicted amino acid sequence (SEQ ID NO:49) of the allelic variant bhkng3 of the bovine HKNG1 homolgue.

Figure 14A:
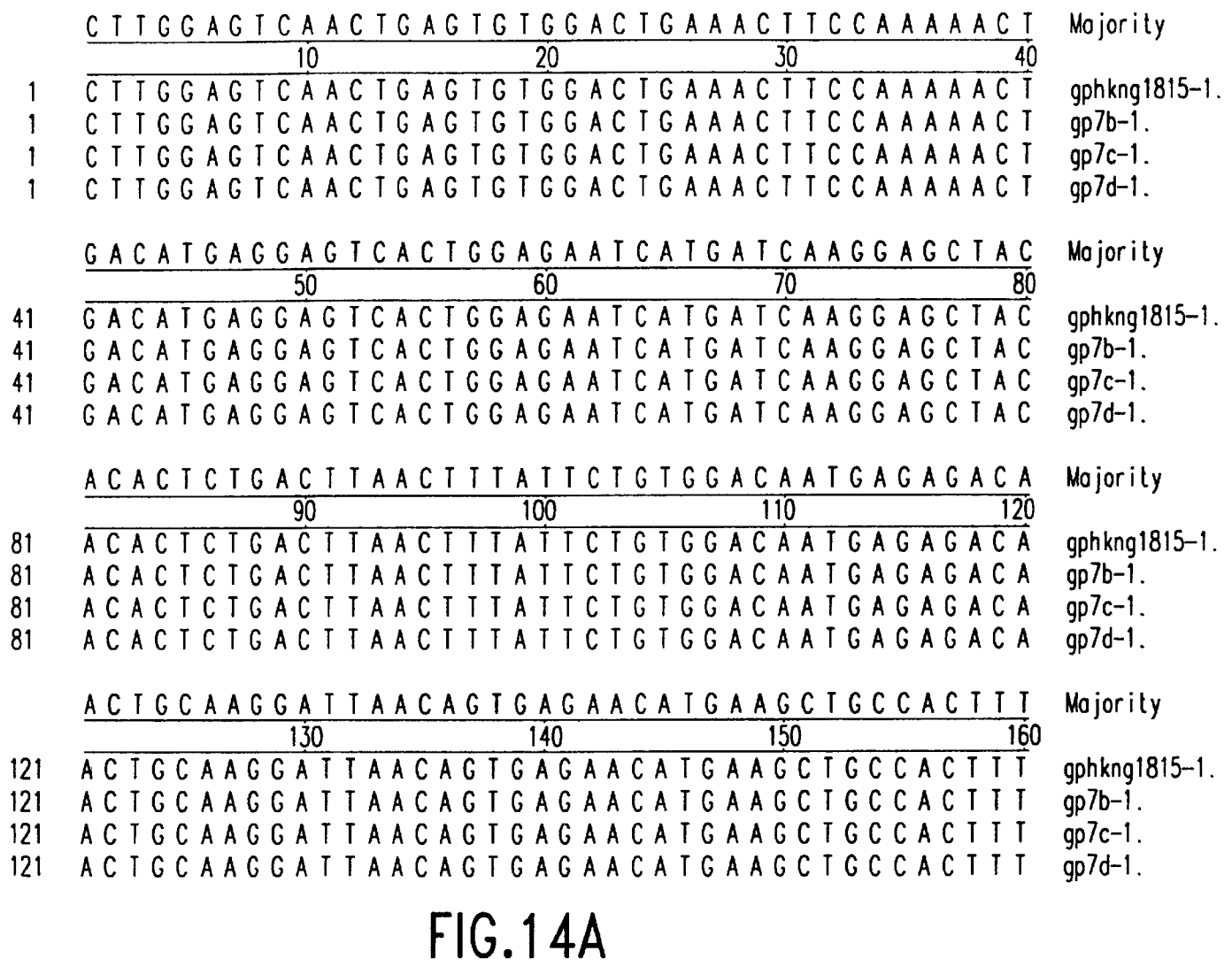
Figure 14B:
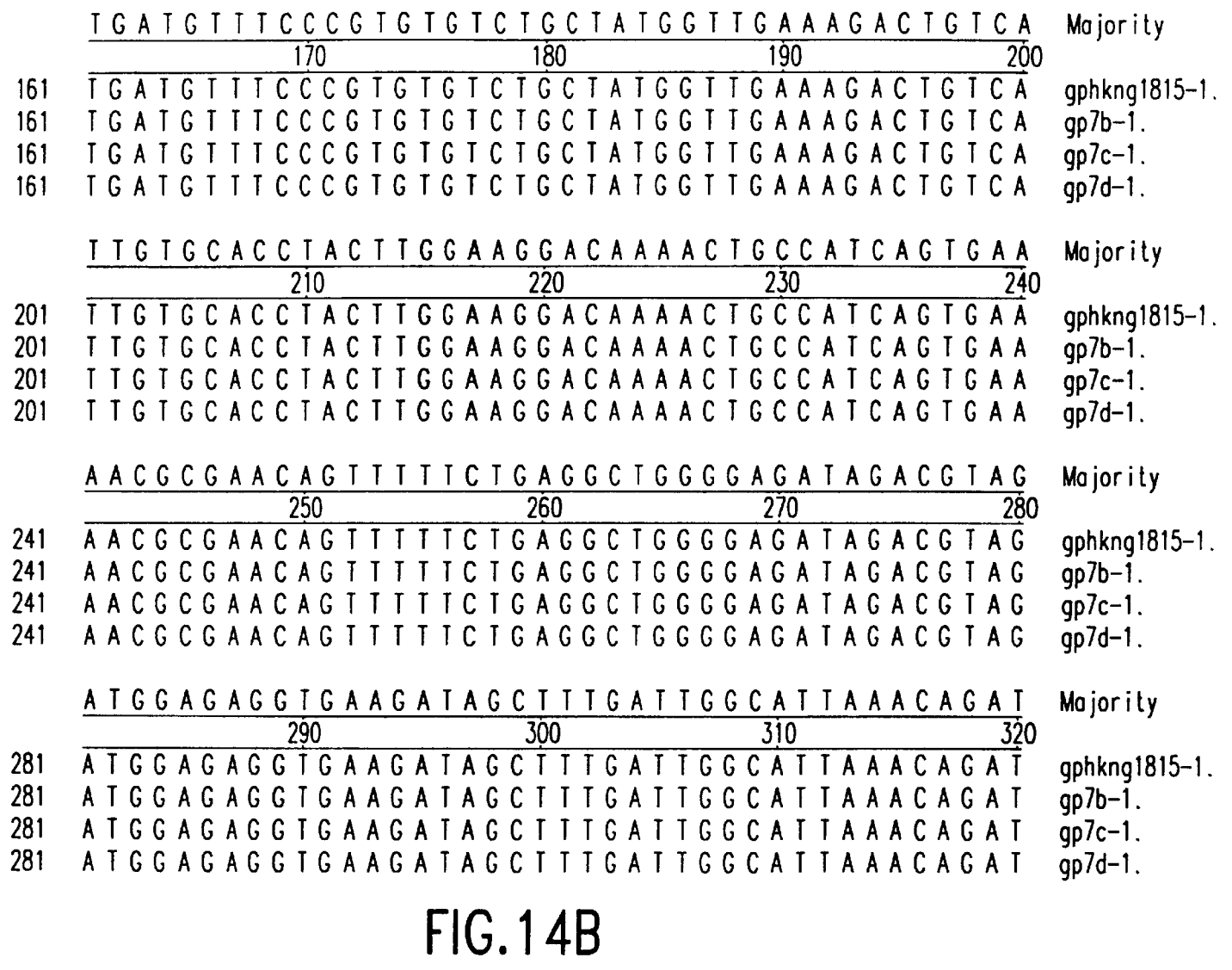
Figure 14D:
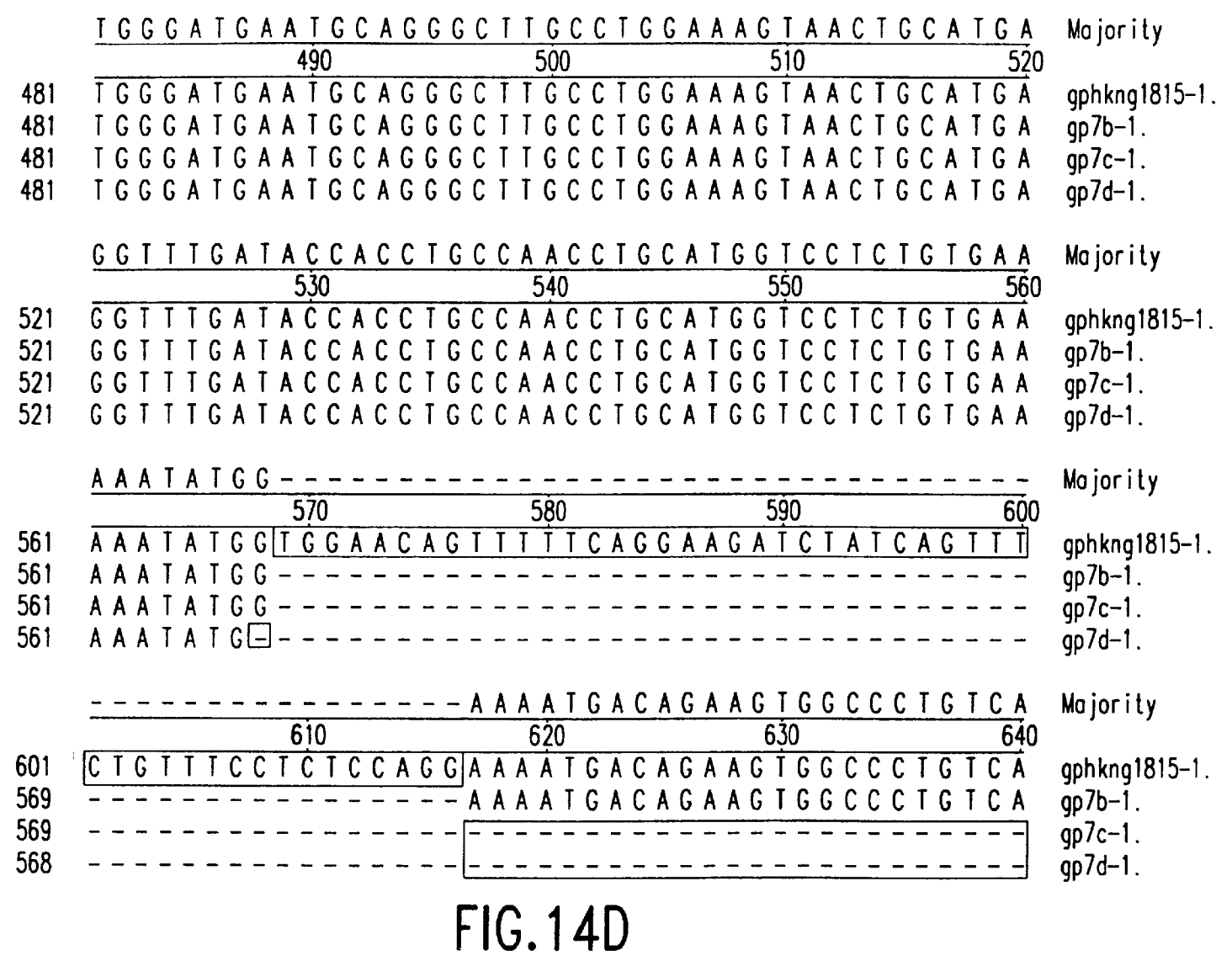
Figure 14E:
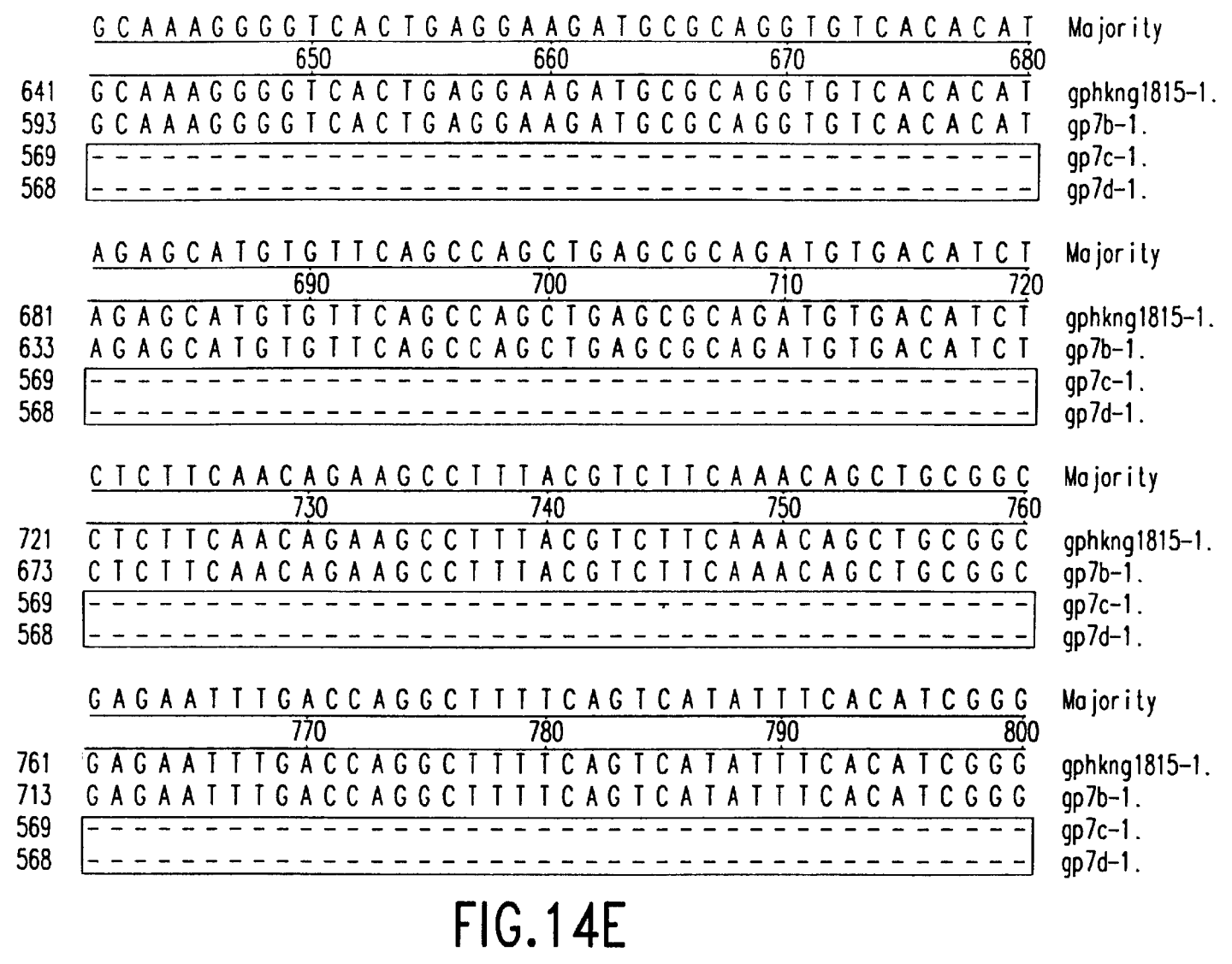
Figure 14F:
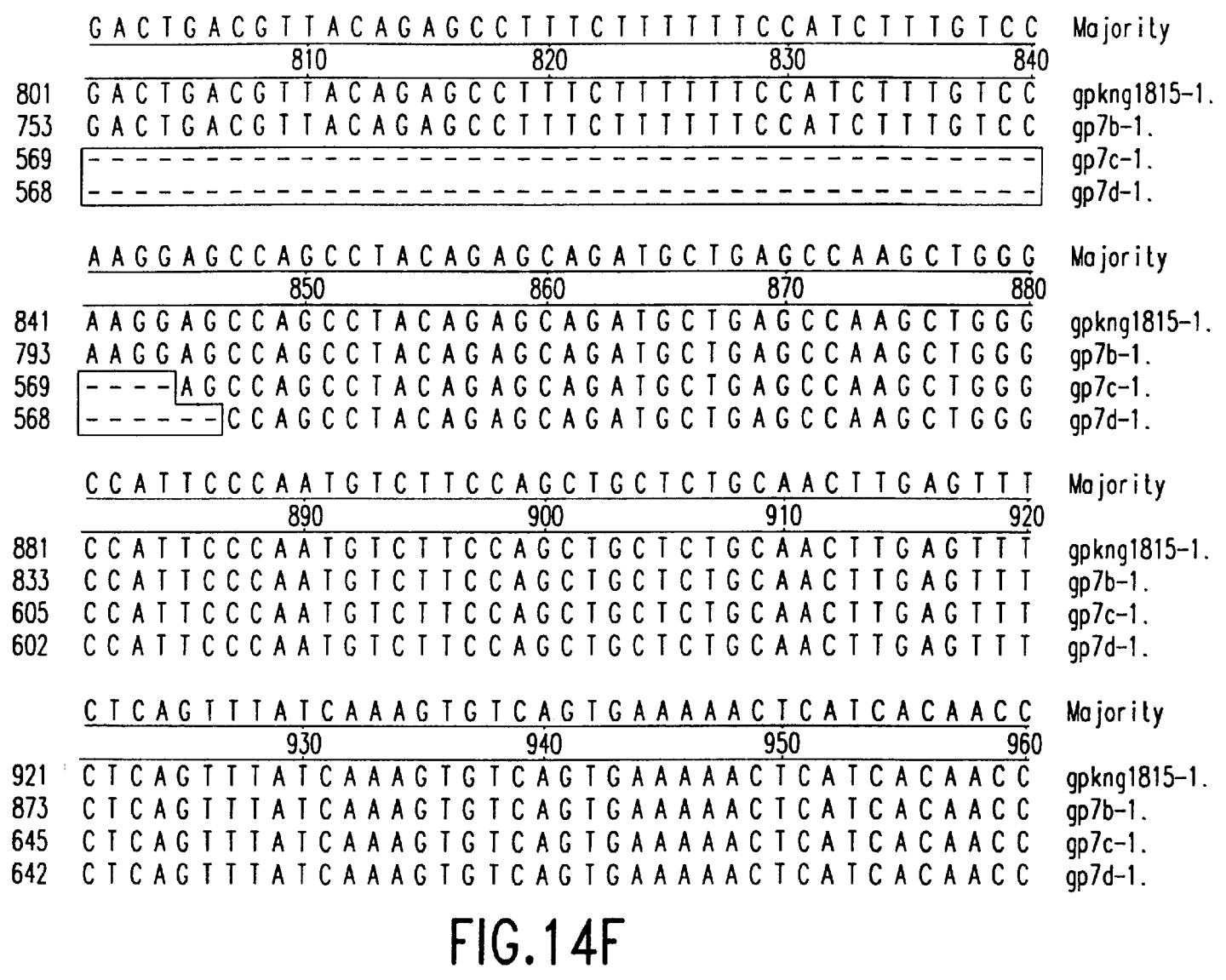
Figure 14G:
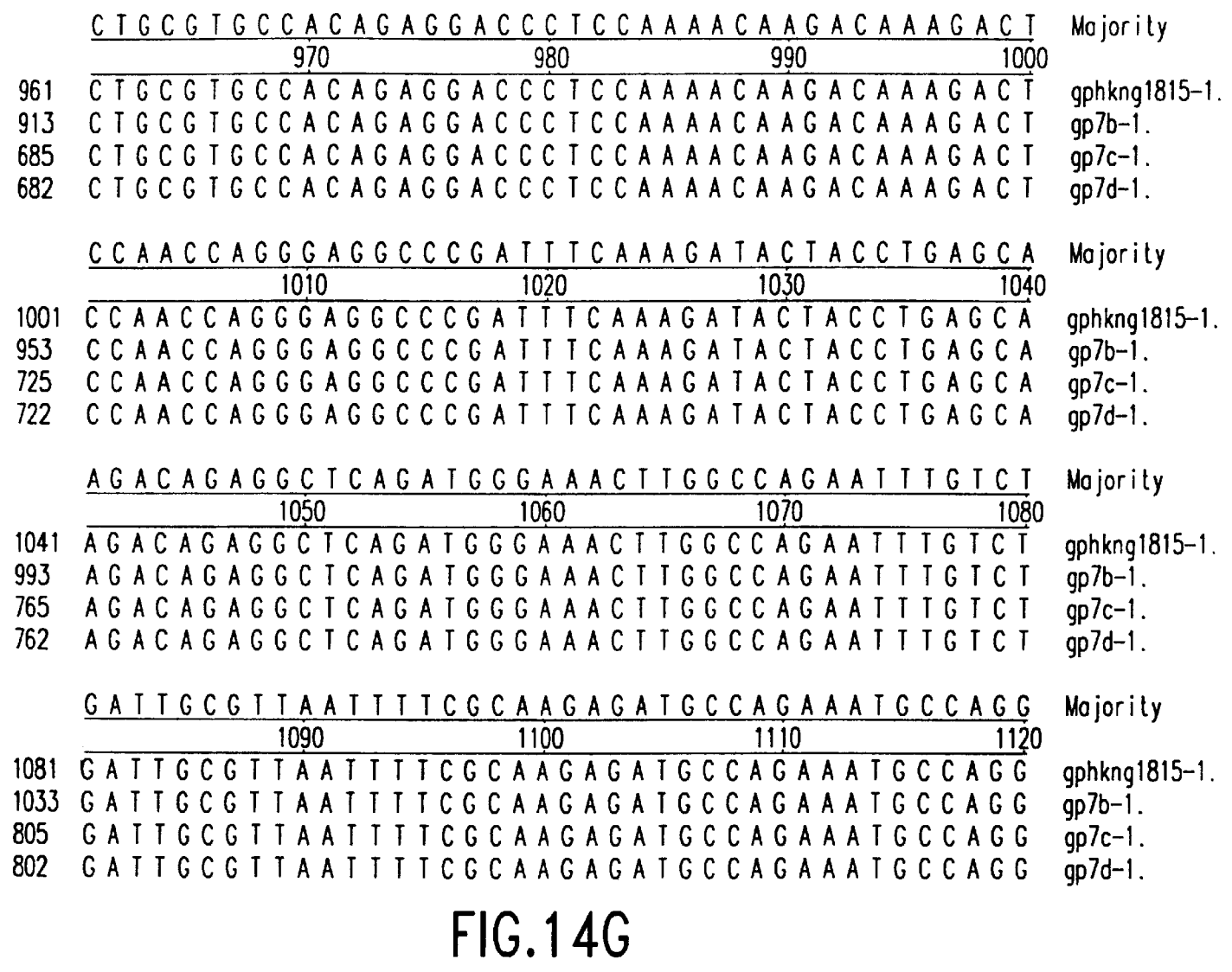
Figure 14K:
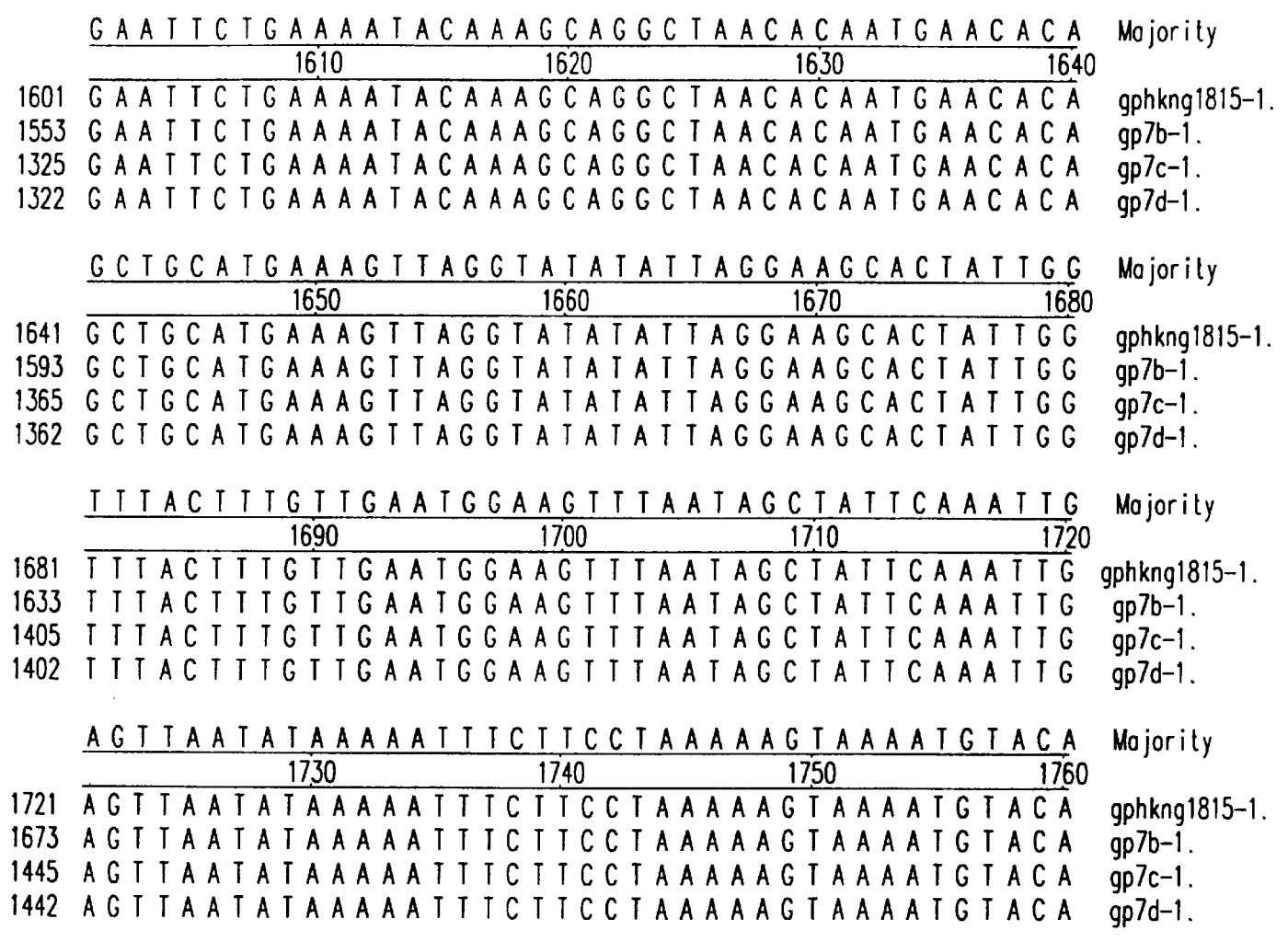

FIGS. 14A–14M. Alignments of the guinea pig HKNG1 cDNA (FIG. 14A) and predicted amino acid (FIG. 14B) sequences for gphkng1815, gphkng 7b, gphkng7c, and gphkng 7d.

FIGS. 15A–15F. Alignments of the cDNA sequences of the bovine HKNG1 allelic variants bhkng1, bhkng2, and bhkng3.

FIG. 16. Alignments of the human (hkng_aa), bovine (bhkng1_aa) and guinea pig (gphkng1815_aa) HKNG1 amino acid sequences.

FIGS. 17A–17B. Alignments of the human HKNG1 protein sequences; top line: the mature secreted HKNG1 protein sequence (SEQ ID NO:51); second line: immature HKNG1 protein form 1 (IPF1; SEQ ID NO:2); third line: immature HKNG1 protein form 2 (IPF2; SEQ ID NO:64); bottom line: immature HKNG1 protein form 3 (IPF3; SEQ ID NO:4).

FIGS. 18A–18C. The nucleotide sequence of human HKNG1 splice variant HKNG1Δ7 cDNA (SEQ ID NO: 65) is depicted on the bottom line. The top line depicts the full length amino acid sequence of human HKNG1Δ7 polypeptide (SEQ ID NO: 66) encoded by the human HKNG1Δ7 cDNA sequence.

5. DETAILED DESCRIPTION OF THE INVENTION

5.1. The HKNG1 Gene

HKNG1 nucleic acid molecules are described in the section. Unless otherwise stated, the term "HKNG1 nucleic acid" refers collectively to the sequences described herein.

A human HKNG1 cDNA sequence (SEQ ID NO: 1) encoding the full length amino acid sequence (SEQ ID NO: 2) of the HKNG1 polypeptide is shown in FIGS. 1A–1C. The human HKNG1 gene encodes a secreted polypeptide of 495 amino acid residues, as shown in FIGS 1A–1B, and SEQ ID NO: 2. The nucleotide sequence of the portion of the cDNA corresponding to the coding sequence for HKNG1 (SEQ ID NO:2) is depicted as SEQ ID NO:5.

The HKNG1 sequences of the invention also include splice variants of the HKNG1 sequences described herein. For example, an alternately spliced human HKNG1 cDNA sequence, referred to as HKNG1-V1 (SEQ ID NO: 3) encoding a human HKNG1 variant gene product (i.e., the HKNG1-V1 gene product) is shown in FIGS. 2A–2C. This splice variant of a human HKNG1 gene encodes a secreted polypeptide of 477 amino acid residues, as shown in FIGS. 2A–2C, and SEQ ID NO:4. The nucleotide sequence of the portion of the cDNA corresponding to the coding sequence for HKNG1 (SEQ ID NO:4) is depicted in SEQ ID NO:6.

Another alternately spliced human HKNG1 cDNA sequence (SEQ ID NO:65), referred to as HKNG1Δ7, encodes a second HKNG1 variant gene product (the HKNG1Δ7 gene product) which is depicted in FIGS. 18A–18C. This splice variant of the human HKNG1 gene encodes the variant polypeptide shown in FIGS. 18A–18C (SEQ ID NO:66).

The genomic structure of the human HKNG1 gene has been elucidated and is depicted in FIGS. 3A–3CC, with the HKNG1 exons indicated in bold type, and the 5'- and 3'-untranslated regions indicated by underlining. The wild-type genomic sequence of the HKNG1 gene is depicted in FIGS. 3A–3CC and SEQ ID NO:7.

Non-human homologues or orthologs mammalian orthologs, e.g., of the human HKNG1 sequences discussed above are also provided. Specifically, a guinea pig cDNA sequence (SEQ ID NO:38), referred to herein as gphkng1815, encoding the full length amino acid sequence (SEQ ID NO:39) of a guinea pig HKNG1 ortholog is shown in FIGS. 7A–7C. This guinea pig cDNA sequence encodes a gene product of 466 amino acid residues, as shown in FIGS. 7A–7C and in SEQ ID NO:39.

Allelic variants of this guinea pig HKNG1 ortholog, referred to as gphkng 7b, gphkng 7c, and gphkng 7d (SEQ ID NOS:40, 42, and 44, respectively), are shown in FIGS. 8A–10C, respectively. The allelic variants gphkng7b, gphkng7c, and gphkng7d each encode variants of the guinea pig gphkng1815 HKNG1 gene product which contain deletions of 16, 92, and 93 amino acids, respectively, as shown in FIGS. 8A–10C, in SEQ ID NOS:41, 43, and 45, respectively, and in the sequence alignment in FIG. 14B.

Bovine HKNG1 ortholog cDNA sequences (SEQ ID NOS: 46–48), referred to herein as bhkng1, bhkng2, and bhkng3, and each encoding the same bovine ortholog gene product are shown in FIGS. 11A–13C, respectively. The bovine HKNG1 allelic variants encode the same gene product, i.e., a 465 amino acid protein, as shown in FIGS. 11A–13C and in SEQ ID NO:49.

The HKNG1 gene nucleic acid molecules of the invention include: (a) nucleotide sequences and fragments thereof (e.g., SEQ ID NOS: 1, 3, 5, 6, 7, 36, 37, and 65) that encode a HKNG1 gene product (e.g., SEQ ID NOS: 2, 4 and 66), as well as homologues, orthologs and allelic variants of such sequences and fragments thereof (e.g., SEQ ID NOS:38, 40, 42, 44, and 46–48) which encode homologue or ortholog HKNG1 gene products (e.g., SEQ ID NOS:39, 41, 43, 45, and 49); (b) nucleotide sequences that encode one or more functional domains of a HKNG1 gene product including, but not limited to, nucleic acid sequences that encode a signal sequence domain, or one or more clusterin domains as described in Section 5.2 below; (c) nucleotide sequences that comprise HKNG1 gene sequences of upstream untranslated regions, intronic regions, and/or downstream untranslated regions or fragments thereof of the HKNG1 nucleotide sequences in (a) above; (d) nucleotide sequences comprising the novel HKNG1 sequences disclosed herein that encode mutants of the HKNG1 gene product in which all or a part of one or more of the domains is deleted or altered, as well as fragments thereof; (e) nucleotide sequences that encode fusion proteins comprising a HKNG1 gene product (e.g., SEQ ID NO: 2, 4, 39, 41, 43, 45, 49 and 65), or a portion thereof fused to a heterologous polypeptide; and (f) nucleotide sequences (e.g., primers) within the HKNG1 gene, and chromosome 18p nucleotide sequences flanking the HKNG1 gene which can be utilized as part of the methods of the invention for identifying and diagnosing individuals at risk for or exhibiting an HKNG1-mediated disorder, such as BAD, or myopia.

The HKNG1 nucleotide sequences of the invention further include nucleotide sequences corresponding to the nucleotide sequences of (a)–(f) above wherein one or more of the exons, or fragments thereof, have been deleted. In one preferred embodiment, the HKNG1 nucleotide sequence of the invention is a sequence wherein the exon corresponding to exon 7 of SEQ ID NO:7, or a fragment thereof, has been deleted.

The HKNG1 nucleotide sequences of the invention also include nucleotide sequences that have at least 65%, 70%, 75%, 80%, 85%, 90%, 95%, 98%, or more nucleotide sequence identity to the HKNG1 nucleotide sequences of (a)–(f) above. The HKNG1 nucleotide sequences of the invention further include nucleotide sequences that encode polypeptides having at least 65%, 70%, 75%, 80%, 85%, 90%, 95%, 98%, or higher amino acid sequence identity to the polypeptides encoded by the HKNG1 nucleotide sequences of (a)–(f), e.g., SEQ ID NOS: 2, 4, 39, 41, 43, 45, 49, and 66 above.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.*25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

The HKNG1 nucleotide sequences of the invention further include: (a) any nucleotide sequence that hybridizes to a HKNG1 nucleic acid molecule of the invention under stringent conditions, e.g., hybridization to filter-bound DNA in 6×sodium chloride/sodium citrate (SSC) at about 45° C. followed by one or more washes in 0.2×SSC/0.1% SDS at about 50–65° C., or (b) under highly stringent conditions, e.g., hybridization to filter-bound nucleic acid in 6×SSC at about 45° C. followed by one or more washes in 0.1×SSC/0.2% SDS at about 68° C., or under other hybridization conditions which are apparent to those of skill in the art (see, for example, Ausubel F. M. et al., eds., 1989, Current Protocols in Molecular Biology, Vol. I, Green Publishing Associates, Inc., and John Wiley & sons, Inc., New York, at pp. 6.3.1–6.3.6 and 2.10.3). Preferably the HKNG1 nucleic acid molecule that hybridizes to the nucleotide sequence of (a) and (b), above, is one that comprises the complement of a nucleic acid molecule that encodes a HKNG1 gene product. In a preferred embodiment, nucleic acid molecules comprising the nucleotide sequences of (a) and (b), above, encode gene products, e.g., gene products functionally equivalent to an HKNG1 gene product.

Functionally equivalent HKNG1 gene products include naturally occurring HKNG1 gene products present in the same or different species. In one embodiment, HKNG1 gene sequences in non-human species map to chromosome regions syntenic to the human 18p chromosome location within which human HKNG1 lies. Functionally equivalent HKNG1 gene products also include gene products that retain at least one of the biological activities of the HKNG1 gene products, and/or which are recognized by and bind to antibodies (polyclonal or monoclonal) directed against the HKNG1 gene products.

Among the nucleic acid molecules of the invention are deoxyoligonucleotides ("oligos") which hybridize under highly stringent or stringent conditions to the HKNG1 nucleic acid molecules described above. In general, for probes between 14 and 70 nucleotides in length the melting temperature (TM) is calculated using the formula: $Tm(°C.)=81.5+16.6(\log[\text{monovalent cations(molar)}])+0.41(\%\ G+C)-(500/N)$ where N is the length of the probe. If the hybridization is carried out in a solution containing formamide, the melting temperature is calculated using the equation $Tm(°C.)=81.5+16.6(\log[\text{monovalent cations (molar)}])+0.41(\%\ G+C)-(0.61\%\ \text{formamide})-(500/N)$ where N is the length of the probe. In general, hybridization is carried out at about 20–25 degrees below Tm (for DNA-DNA hybrids) or 10–15 degrees below Tm (for RNA-DNA hybrids).

Exemplary highly stringent conditions may refer, e.g., to washing in 6×SSC/0.05% sodium pyrophosphate at 37° C. (for about 14-base oligos), 48° C. (for about 17-base oligos), 55° C. (for about 20-base oligos), and 60° C. (for about 23-base oligos).

These nucleic acid molecules may encode or act as antisense molecules, useful, for example, in HKNG1 gene regulation, and/or as antisense primers in amplification reactions of HKNG1 gene nucleic acid sequences. Further, such sequences may be used as part of ribozyme and/or triple helix sequences, also useful for HKNG1 gene regulation. Still further, such molecules may be used as components of diagnostic methods whereby, for example, the presence of a particular HKNG1 allele involved in a HKNG1-related disorder, e.g., a neuropsychiatric disorder, such as BAD, may be detected.

Fragments of the HKNG1 nucleic acid molecules can be at least 10 nucleotides in length. In alternative embodiments, the fragments can be about 20, 30, 40, 50, 60, 70, 80, 90, 100, 200, 300, 400, 500, 1000, 1500, 2000, 2500, 3000, 3500, 4000, 4500, 5000, or more contiguous nucleotides in length. Alternatively, the fragments can comprise sequences that encode at least 10, 20, 30, 40, 50, 100, 150, 200, 250, 300, 350, 400, 450 or more contiguous amino acid residues of the HKNG1 gene products. Fragments of the HKNG1 nucleic acid molecules can also refer to HKNG1 exons or introns, and, further, can refer to portions of HKNG1 coding regions that encode domains (e.g., clusterin domains) of HKNG1 gene products.

The HKNG1 nucleotide sequences of the invention can be readily obtained, for example, by standard sequencing and the sequence provided herein.

As will be appreciated by those skilled in the art, DNA sequence polymorphisms of a HKNG1 gene will exist within a population of individual organisms (e.g., within a human population). Such polymorphisms may exist, for example, among individuals within a population due to natural allelic variation. Such polymorphisms include ones that lead to changes in amino acid sequence. An allele is one of a group of genes which occur alternatively at a given genetic locus.

As used herein, the phrase "allelic variant" refers to a nucleotide sequence which occurs at a given locus or to a gene product encoded by that nucleotide sequence. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. As used herein, the terms "gene" and "recombinant gene" refer to nucleic acid molecules comprising an open reading frame encoding a polypeptide of the invention. The term can further include nucleic acid molecules comprising upstream and/or exon/intron sequences and structure.

With respect to HKNG1 allelic variants, any and all such nucleotide variations and resulting amino acid polymorphisms or variations that are the result of natural allelic variation of the HKNG1 gene are intended to be within the scope of the present invention. Such allelic variants include, but are not limited to, ones that do not alter the functional activity of the HKNG1 gene product. Variants include, but are not limited to, variants comprising the polymorphisms summarized in FIGS. 5A–5C and a variant which encodes a full length HKNG1 polypeptide comprising a substitution of a lysine amino acid at amino acid residue 202 of the HKNG1 polypeptide shown in FIGS. 1A–1C and SEQ ID NO:2 or the HKNG1 amino acid residue 184 of the polypeptide of SEQ ID NO:4.

With respect to the cloning of additional allelic variants of the human HKNG1 gene and homologues and orthologs from other species (e.g., guinea pig, cow, mouse), the isolated HKNG1 gene sequences disclosed herein may be labeled and used to screen a cDNA library constructed from mRNA obtained from appropriate cells or tissues (e.g., brain or retinal tissues) derived from the organism (e.g., guinea pig, cow, and mouse) of interest. The hybridization conditions used should generally be of a lower stringency when the cDNA library is derived from an organism different from the type of organism from which the labeled sequence was derived, and can routinely be determined based on, e.g., relative relatedness of the target and reference organisms.

Alternatively, the labeled fragment may be used to screen a genomic library derived from the organism of interest, again, using appropriately stringent conditions. Appropriate stringency conditions are well known to those of skill in the art as discussed above, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., 1989–1999, Current Protocols in Molecular Biology, Green Publishing Associates and Wiley Interscience, N.Y., both of which are incorporated herein by reference in their entirety.

Further, a HKNG1 gene allelic variant may be isolated from, for example, human nucleic acid, by performing PCR using two degenerate oligonucleotide primer pools designed on the basis of amino acid sequences within the HKNG1 gene product disclosed herein. The template for the reaction may be cDNA obtained by reverse transcription of mRNA prepared from, for example, human or non-human cell lines or tissue known or suspected to express a wild type or mutant HKNG1 gene allele (such as, for example, brain cells, including brain cells from individuals having BAD). In one embodiment, the allelic variant is isolated from an individual who has a HKNG1-mediated disorder. Such variants are described in the examples below.

The PCR product may be subcloned and sequenced to ensure that the amplified sequences represent the sequences of a HKNG1 gene nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the HKNG1 gene, such as, for example, brain tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., 1989, supra, or Ausubel et al., supra.

A cDNA of an allelic, e.g., mutant, variant of the HKNG1 gene may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying a mutant HKNG1 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant HKNG1 allele to that of the normal HKNG1 allele, the mutation(s) responsible for the loss or alteration of function of the mutant HKNG1 gene product can be ascertained.

Alternatively, a genomic library can be constructed using DNA obtained from an individual suspected of or known to carry a mutant HKNG1 allele, or a cDNA library can be constructed using RNA from a tissue known, or suspected, to express a mutant HKNG1 allele. An unimpaired HKNG1 gene or any suitable fragment thereof may then be labeled and used as a probe to identify the corresponding mutant HKNG1 allele in such libraries. Clones containing the mutant HKNG1 gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant HKNG1 allele in an individual suspected of or known to carry such a mutant allele. In this manner, gene products made by the putatively mutant tissue may be expressed and screened using standard antibody screening techniques in conjunction with antibodies raised against the normal HKNG1 gene product, as described, below, in Section 5.3. (For screening techniques, see, for example, Harlow and Lane, eds., 1988, "Antibodies: A Laboratory Manual", Cold Spring Harbor Press, Cold Spring Harbor.)

In cases where a HKNG1 mutation results in an expressed gene product with altered function (e.g., as a result of a missense or a frameshift mutation), a polyclonal set of anti-HKNG1 gene product antibodies are likely to cross-react with the mutant HKNG1 gene product. Library clones detected via their reaction with such labeled antibodies can be purified and subjected to sequence analysis according to methods well known to those of skill in the art.

HKNG1 mutations or polymorphisms can further be detected using PCR amplification techniques. Primers can routinely be designed to amplify overlapping regions of the whole HKNG1 sequence including the promoter regulating region. In one embodiment, primers are designed to cover the exon-intron boundaries such that, coding regions can be scanned for mutations. Exemplary primers for analyzing HKNG1 exons are provided in Table 1, of Section 5.6, below.

The invention also includes nucleic acid molecules, preferably DNA molecules, that are the complements of the nucleotide sequences of the preceding paragraphs.

In certain embodiments, the nucleic acid molecules of the invention are present as part of nucleic acid molecules comprising nucleic acid sequences that do not contain heterologous (e.g., cloning vector or expression vector) sequences. In other embodiments, the nucleic acid molecules of the invention further comprise vector sequences, e.g., cloning vectors or expression vectors.

5.2. Protein Products of the HKNG1 Gene

HKNG1 gene products or peptide fragments thereof, can be prepared for a variety of uses. For example, such gene products, or peptide fragments thereof, can be used for the generation of antibodies, in diagnostic assays, or for the identification of other cellular or extracellular gene products involved in the regulation of HKNG1-mediated disorders, e.g., neuropsychiatric disorders, such as BAD.

The HKNG1 gene products of the invention include, but are not limited to, human HKNG1 gene products, e.g., polypeptides comprising the amino acid sequences depicted in FIGS. 1A–1C, 2A–2C, 17A–17B, and 18A–18C (i.e., SEQ ID NOS:2, 4, 51, and 66). The HKNG1 gene products of the invention also include non-human, e.g., mammalian (such as bovine or guinea pig), HKNG1 gene products. These include, but are not limited to, polypeptides comprising the amino acid sequences depicted in FIGS. 7A–13C (i.e., SEQ ID NOS:39, 41, 43, 45, and 49).

HKNG1 gene product, sometimes referred to herein as an "HKNG1 protein" or "HKNG1 polypeptide," includes those gene products encoded by the HKNG1 gene sequences depicted in FIGS. 1A–1C, 2A–2C, 7A–13C, 17A–17B, and 18A–C, as well as gene products encoded by other human allelic variants and non-human variants of HKNG1 that can be identified by the methods herein described. Among such HKNG1 gene product variants are gene products comprising HKNG1 amino acid residues encoded by the polymorphisms depicted in FIGS. 5A–5C. Such gene product variants also include a variant of the HKNG1 gene product depicted in FIGS. 1A–1C (SEQ ID NO:2) wherein the amino acid residue Lys202 is mutated to a glutamic acid residue. Such HKNG1 gene product variants also include a variant of the HKNG1 gene product depicted in FIGS. 2A–2C (SEQ ID NO:4) wherein the amino acid residue Lys184 is mutated to a glutamic acid residue.

In addition, HKNG1 gene products may include proteins that represent functionally equivalent gene products. Functionally equivalent gene products may include, for example, gene products encoded by one of the HKNG1 nucleic acid molecules described in Section 5.1, above. In preferred embodiments, such functionally equivalent HKNG1 gene products are naturally occuring gene products. Functionally equivalent HKNG1 gene products also include gene products that retain at least one of the biological activities of the HKNG1 gene products described above, and/or which are recognized by and bind to antibodies (polyclonal or monoclonal) directed against HKNG1 gene products.

Equivalent HKNG1 gene product may contain deletions, including internal deletions, additions, including additions yielding fusion proteins, or substitutions of amino acid residues within and/or adjacent to the amino acid sequence encoded by the HKNG1 gene sequences described, above, in Section 5.1. Generally, deletions will be deletions of single amino acid residues, or deletions of no more than about 2, 3, 4, 5, 10 or 20 amino acid residues, either contiguous or non-contiguous. Generally, additions or substitutions, other than additions that yield fusion proteins, will be additions or substitutions of single amino acid residues, or additions or substitutions of no more than about 2, 3, 4, 5, 10 or 20 amino acid residues, either contiguous or non-contiguous. Preferably, these modifications result in a "silent" change, in that the change produces a HKNG1 gene product with the same activity as the HKNG1 gene product depicted in FIGS. 1A–1C, 2A–2C, 7A–13C, or 17A–17B.

Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, where alteration of function is desired, addition(s), deletion(s) or non-conservative alterations can produce altered, including reduced-activity, HKNG1 gene products. Such alterations can, for example, alter one or more of the biological functions of the HKNG1 gene product. Further, such alterations can be selected so as to generate HKNG1 gene products that are better suited for expression, scale up, etc. in the host cells chosen. For example, cysteine residues can be deleted or substituted with another amino acid residue in order to eliminate disulfide bridges.

As another example, altered HKNG1 gene products can be engineered that correspond to variants of the HKNG1 gene product associated with HKNG1-mediated neuropsychiatric disorders such as BAD. Such altered HKNG1 gene products include, but are not limited to, HKNG1 proteins or peptides comprising substitution of a lysine residue for the wild-type glutamic acid residue at HKNG1 amino acid position 202 in FIGS. 1A–1C (SEQ ID NO:2) or amino acid position 184 (SEQ ID NO:4) in FIGS. 2A–2C.

HKNG1 protein fragments and/or HKNG1 peptides comprise at least as many contiguous amino acid residues as necessary to represent an epitope fragment (that is to be recognized by an antibody directed to the HKNG1 protein). For example, such protein fragments or peptides comprise at least about 8 contiguous HKNG1 amino acid residues from a full length HKNG1 protein. In alternate embodiments, the HKNG1 protein fragments and peptides of the invention can comprise about 10, 20, 30, 40, 50, 60, 70, 80, 90, 100, 150, 200, 250, 300, 350, 400, 450 or more contiguous amino acid residues of a HKNG1 protein.

Peptides and/or proteins corresponding to one or more domains of the HKNG1 protein as well as fusion proteins in which a HKNG1 protein, or a portion of a HKNG1 protein such as a truncated HKNG1 protein or peptide or a HKNG1 protein domain, is fused to an unrelated protein are also within the scope of this invention. Such proteins and peptides can be designed on the basis of the HKNG1 nucleotide sequence disclosed in Section 5.1, above, and/or on the basis of the HKNG1 amino acid sequence disclosed in the Section. Fusion proteins include, but are not limited to, IgFc fusions which stabilize the HKNG1 protein or peptide and prolong half life in vivo; or fusions to any amino acid sequence that allows the fusion protein to be anchored to the cell membrane; or fusions to an enzyme, fluorescent protein, luminescent protein, or a flag epitope protein or peptide which provides a marker function.

The HKNG1 protein, the HKNG1 protein sequences described above can include a domain which comprises a signal sequence that targets the HKNG1 gene product for secretion. As used herein, a signal sequence includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19–34 amino acid residues, and has at least about 60–80%, more preferably 65–75%, and more preferably at least about 70% hydrophobic residues. A signal sequence serves to direct a protein containing such a sequence to a lipid bilayer.

In one embodiment, a HNKNG1 protein contains a signal sequence at about amino acids 1 to 49 of SEQ ID NO:2. In another embodiment, a HKNG1 protein contains a signal sequence at about amino acids 30–49 of SEQ ID NO:2. In yet another embodiment, a HKNG1 protein contains a signal sequence at about amino acid residues 1 to 31 of SEQ ID NO:4. In yet another embodiment, a HKNG1 protein contains a signal sequence at about amino acids 12–31 of SEQ ID NO:4. The signal sequence is cleaved during processing of the mature protein.

A signal sequence of a polypeptide of the invention can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described HKNG1 polypeptides having a signal sequence (that is, "immature" polypeptides), as well as to the HKNG1 signal sequences themselves and to the HNKG1 polypeptides in the absence of a signal sequence (i.e., the "mature" HKNG1 cleavage products). It is to be understood that HKNG1 polypeptides of the invention can further comprise polypeptides comprising any signal sequence having characteristics as described above and a mature HKNG1 polypeptide sequence.

In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The HKNG1 protein sequences described above can also include one or more domains which comprise a clusterin domain, i.e., domains which are identical to or substantially homologous to (i.e., 65%, 75%, 80%, 85%, 90%, 95% or more identical to) the domain corresponding to amino acid residues 134 to 160 or amino acid residues 334 to 362 of SEQ ID NO:2, or to the domain corresponding to amino acid residues 105–131 or amino acid residues 305–333 of SEQ ID No:39, or to the domain corresponding to amino acid residues 105–131 or amino acid residues 304–332 of SEQ ID NO:49. Preferably, such domains comprise cysteine amino acid residues at positions corresponding to conserved cysteine residues of the clusterin domains of SEQ ID NOS: 2, 39 or 49.

In particular, HKNG1 protein sequences described above can also include one or more domains which comprise a conserved cysteine domain. Such a domain corresponds, for example, to the domain of cysteines corresponding to Cys134, Cys145, Cys148, Cys158 and Cys160; or to Cys334, Cys344, Cys351, Cys354, and Cys362 of SEQ ID NO:2. In an alternative embodiment, a conserved cystein domain corresponds to one or more of the domains of SEQ ID NO:39 which comprises Cys105, Cys116, Cys119, Cys124, and Cys131; or Cys305, Cys315, Cys322, Cys325, and Cys333. In yet another alternative embodiment, a conserved cysteine domain corresponds to one or more of the domains of SEQ ID NO:49 which comprises Cys105, Cys116, Cys119, Cys124, and Cys131; or Cys314, Cys321, Cys324, and Cys332.

Finally, the HKNG1 proteins of the invention also include HKNG1 protein sequences wherein domains encoded by one or more exons of the cDNA sequence, or fragments thereof, have been deleted. In one particularly preferred embodiment, the HKNG1 proteins of the invention are proteins in which the domain(s) corresponding the those domains encoded by exon 7 of SEQ ID NO:7, or fragments thereof, have been deleted.

The HKNG1 polypeptides of the invention can further comprise posttranslational modifications, including, but not limited to glycosylations, acetylations, and myrisalations.

The HKNG1 gene products, peptide fragments thereof and fusion proteins thereof, may be produced by recombinant DNA technology using techniques well known in the art. Thus, methods for preparing the HKNG1 gene products, polypeptides, peptides, fusion peptide and fusion polypeptides of the invention by expressing nucleic acid containing HKNG1 gene sequences are described herein. Methods that are well known to those skilled in the art can be used to construct expression vectors containing HKNG1 gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding HKNG1 gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the HKNG1 gene product coding sequences of the invention. Such host-expression systems represent vehicles by which the coding sequences of interest may be produced and subsequently purified, but also represent cells that may, when transformed or transfected with the appropriate nucleotide coding sequences, exhibit the HKNG1 gene product of the invention in situ. These include but are not limited to microorganisms such as bacteria (e.g., *E. coli, B. subtilis*) transformed with recombinant bacteriophage DNA, plasmid DNA or cosmid DNA expression vectors containing HKNG1 gene product coding sequences; yeast (e.g., Saccharomyces, Pichia) transformed with recombinant yeast expression vectors containing the HKNG1 gene product coding sequences; insect cell systems infected with recombinant virus expression vectors (e.g., baculovirus) containing the HKNG1 gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing HKNG1 gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the HKNG1 gene product being expressed. For example, when a large quantity of such a protein is to be produced, for the generation of pharmaceutical compositions of HKNG1 gene product or for raising antibodies to HKNG1 gene product, for example, vectors that direct the expression of high levels of fusion protein products that are readily purified may be desirable. Such vectors include, but are not limited, to the *E. coli* expression vector pUR278 (Ruther et al., 1983, EMBO J. 2:1791), in which the HKNG1 gene product coding sequence may be ligated individually into the vector in frame with the lacZ coding region so that a fusion protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica,* nuclear polyhidrosis virus (AcNPV) is used as a vector to express foreign genes. The virus grows in *Spodoptera frugiperda* cells. The HKNG1 gene product coding sequence may be cloned individually into non-essential regions (for example the polyhedrin gene) of the virus and placed under control of an AcNPV promoter (for example the polyhedrin promoter). Successful insertion of HKNG1 gene product coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., 1983, J. Virol. 46:584; Smith, U.S. Pat. No. 4,215,051).

In mammalian host cells, a number of viral-based expression systems may be utilized. In cases where an adenovirus is used as an expression vector, the HKNG1 gene product coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing HKNG1 gene product in infected hosts. (e.g., See Logan and Shenk, 1984, Proc. Natl. Acad. Sci. USA 81:3655–3659). Specific initiation signals may also be required for efficient translation of inserted HKNG1 gene product coding sequences. These signals include the ATG initiation codon and adjacent sequences. In cases where an entire HKNG1 gene, including its own initiation codon and adjacent sequences, is inserted into the appropriate expression vector, no additional translational control signals may be needed. However, in cases where only a portion of the HKNG1 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and W138.

For long-term, high-yield production of recombinant proteins, stable expression is preferred. For example, cell lines that stably express the HKNG1 gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the HKNG1 gene product. Such engineered cell lines may be particularly useful in screening and evaluation of compounds that affect the endogenous activity of the HKNG1 gene product.

A number of selection systems may be used, including but not limited to the herpes simplex virus thymidine kinase (Wigler, et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, the expression characteristics of an endogenous HKNG1 gene within a cell line or microorganism may be modified by inserting a heterologous DNA regulatory element into the genome of a stable cell line or cloned microorganism such that the inserted regulatory element is operatively linked with the endogenous HKNG1 gene. For example, an endogenous HKNG1 gene which is normally "transcriptionally silent", i.e., an HKNG1 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous HKNG1 gene may be activated by insertion of a promiscuous regulatory element that works across cell types.

A heterologous regulatory element may be inserted into a stable cell line or cloned microorganism, such that it is operatively linked with an endogenous HKNG1 gene, using techniques, such as targeted homologous recombination, which are well known to those of skill in the art, and described e.g., in Chappel, U.S. Pat. No. 5,272,071; PCT publication No. WO 91/06667, published May 16, 1991.

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$.nitriloacetic acid-agarose columns and histidine-tagged proteins are selectively eluted with imidazole-containing buffers.

The HKNG1 gene products can also be expressed in transgenic animals. Animals of any species, including, but not limited to, mice, rats, rabbits, guinea pigs, pigs, micro-pigs, goats, sheep, cows, and non-human primates, e.g., baboons, monkeys, and chimpanzees may be used to generate HKNG1 transgenic animals. The term "transgenic," as used herein, refers to animals expressing HKNG1 gene sequences from a different species (e.g., mice expressing huma HKNG1 gene sequences), as well as animals that have been genetically engineered to overexpress endogenous (i.e., same species) HKNG1 sequences or animals that have been genetically engineered to no longer express endogenous HKNG1 gene sequences (i.e., "knock-out" animals), and their progeny.

Any technique known in the art may be used to introduce a HKNG1 gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82:6148–6152); gene targeting in embryonic stem cells (Thompson, et al., 1989, Cell 56:313–321); electroporation of embryos (Lo, 1983, Mol. Cell. Biol. 3:1803–1814); and sperm-mediated gene transfer (Lavitrano et al., 1989, Cell 57:717–723) (For a review of such techniques, see Gordon, 1989, Transgenic Animals, Intl. Rev. Cytol. 115, 171–229)

Any technique known in the art may be used to produce transgenic animal clones containing a HKNG1 transgene, for example, nuclear transfer into enucleated oocytes of nuclei from cultured embryonic, fetal or adult cells induced to quiescence (Campbell, et al., 1996, Nature 380:64–66; Wilmut, et al., Nature 385:810–813).

The present invention provides for transgenic animals that carry a HKNG1 transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89:6232–6236). The regulatory sequences required for such a cell-type specific activation will depend upon the particular cell type of interest, and will be apparent to those of skill in the art. When it is desired that the HKNG1 transgene be integrated into the chromosomal site of the endogenous HKNG1 gene, gene targeting is preferred. Briefly, when such a technique is to be utilized, vectors containing some nucleotide sequences homologous to the endogenous HKNG1 gene are designed for the purpose of integrating, via homologous recombination with chromosomal sequences, into and disrupting the function of the nucleotide sequence of the endogenous HKNG1 gene. The transgene may also be selectively introduced into a particular cell type, thus inactivating the endogenous HKNG1 gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant HKNG1 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of HKNG1 gene-expressing tissue, may also be evaluated immunocytochemically using antibodies specific for the HKNG1 transgene product.

HKNG1 proteins can be used, e.g., to treat CNS-related disorders, e.g., neuropsychiatric disorders. Such HKNG1 gene products include but are not limited to soluble derivatives such as peptides or polypeptides corresponding to one or more domains of the HKNG1 gene product, particularly HKNG1 gene products, that are modified such that they are deleted for one or more hydrophobic domains. Alternatively, antibodies to the HKNG1 protein or anti-idiotypic antibodies that mimic the HKNG1 gene product (including Fab fragments), antagonists or agonists can be used to treat neuropsychiatric disorders involving HKNG1. In yet another approach, nucleotide constructs encoding such HKNG1 gene products can be used to genetically engineer host cells to express such HKNG1 gene products in vivo; these genetically engineered cells can function as "bioreactors" in the body delivering a continuous supply of HKNG1 gene product, HKNG1 peptides, soluble HKNG1 polypeptides.

5.3. Antibodies to HKNG1 Gene Products

Described herein are methods for the production of antibodies capable of specifically recognizing one or more HKNG1 gene product epitopes or epitopes of conserved variants or peptide fragments of the HKNG1 gene products. Further, antibodies that specifically recognize mutant forms of HKNG1, are encompassed by the invention. The terms "specifically bind" and "specifically recognize" refer to antibodies that bind to HKNG1 gene product epitopes at a higher affinity than they bind to non-HKNG1 (e.g., random) epitopes.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above, including the polyclonal and monoclonal antibodies described in Section 12 below. Such antibodies may be used, for example, in the detection of a HKNG1 gene product in an biological sample and may, therefore, be utilized as part of a diagnostic or prognostic technique whereby patients may be tested for abnormal levels of HKNG1 gene products, and/or for the presence of abnormal forms of such gene products. Such antibodies may also be utilized in conjunction with, for example, compound screening schemes, as described, below, in Section 5.8, for the evaluation of the effect of test compounds on HKNG1 gene product levels and/or activity. Additionally, such antibodies can be used in conjunction with the gene therapy techniques described, below, in Section 5.9.2 to, for example, evaluate the normal and/or engineered HKNG1-expressing cells prior to their introduction into the patient.

Anti-HKNG1 gene product antibodies may additionally be used in methods for inhibiting abnormal HKNG1 gene product activity. Thus, such antibodies may, therefore, be utilized as part of treatment methods for a HKNG1-mediated neuropsychiatric disorder, such as BAD or schizophrenia.

For the production of antibodies against a HKNG1 gene product, various host animals may be immunized by injection with a HKNG1 gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a HKNG1 gene product, or an antigenic functional derivative thereof. For the production of polyclonal antibodies, host animals such as those described above, may be immunized by injection with HKNG1 gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81:6851–6855; Neuberger, et al., 1984, Nature 312:604–608; Takeda, et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983) ). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242:423–426; Huston, et al., 1988, Proc. Natl. Acad. Sci. USA 85:5879–5883; and Ward, et al., 1989, Nature 334:544–546) can be adapted to produce single chain antibodies against HKNG1 gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, which can be produced by pepsin digestion of the antibody molecule and the Fab fragments, which can be generated by reducing the disulfide bridges of the F(ab')$_2$ fragments. Alternatively, Fab expression libraries may be constructed (Huse, et al., 1989, Science 246:1275–1281) to allow rapid and easy identification of monoclonal Fab fragments with the desired specificity.

5.4. Uses of HKNG1 Gene Sequences Gene Products, and Antibodies

Described herein are various applications of HKNG1 gene sequences, HKNG1 gene products, including peptide fragments and fusion proteins thereof, and of antibodies directed against HKNG1 gene products and peptide fragments thereof. Such applications include, for example, mapping of chromosome 18p, prognostic and diagnostic evaluation of HKNG1-mediated disorders, including CNS-related disorders, e.g., neuropsychiatric disorders, such as BAD or schizophrenia, modulation of HKNG1-related processes, and the identification of subjects with a predisposition to such disorders, as described, below, in Section 5.5.

Additionally, such applications include methods for the treatment of a HKNG1-mediated disorders, such as BAD or schizophrenia, as described, below, in Section 5.9, and for the identification of compounds that modulate the expression of the HKNG1 gene and/or the synthesis or activity of the HKNG1 gene product, as described below, in Section 5.8. Such compounds can include, for example, other cellular products that are involved in such processes as mood regulation and in HKNG1-mediated disorders, e.g., neuropsychiatric disorders such as BAD or schizophrenia. These compounds can be used, for example, in the amelioration of HKNG1-mediated disorders and for the modulation of HKNG1-mediated processes.

Uses of the HKNG1 gene sequences, HKNG1 gene products, including peptide fragments and fusion proteins thereof, and of antibodies directed against HKNG1 gene products and/or peptide fragments thereof also include prognostic and diagnostic evaluation of a HKNG1-mediated myopia disorder such as early-onset autosomal dominant myopia, methods for the treatment of a HKNG1-mediated myopia disorder, and for the identification of compound that modulate the expression of the HKNG1 gene and/or the synthesis or activity of the HKNG1 gene product and could therefore be used in the amelioration of a HKNG1-mediated myopia such as early-onset autosomal dominant myopia. Indeed, such methods are substantially identical to the methods described, below, in Sections 5.5, 5.8, and 5.9 for the diagnosis and treatment of HKNG1-mediated disorders.

5.5. Diagnosis of HKNG1-Mediated Disorders

A variety of methods can be employed for the diagnostic and prognostic evaluation of HKNG1-mediated disorders, e.g., neuropsychiatric disorders and for the identification of subjects having a predisposition to such disorders.

Such methods may, for example, utilize reagents such as the HKNG1 gene nucleotide sequences described in Sections 5.1, and antibodies directed against HKNG1 gene products, including peptide fragments thereof, as described, above, in Section 5.3. Specifically, such reagents may be used, for example, for:

(1) the detection of the presence of HKNG1 gene mutations, or the detection of either over- or under-expression of HKNG1 gene relative to wild-type HKNG1 levels expression;

(2) the detection of over- or under-abundance of HKNG1 gene product relative to wild-type abundance of HKNG1 gene product; and (3) the detection of an aberrant level of HKNG1 gene product activity relative to wild-type HKNG1 gene product activity levels.

HKNG1 gene nucleotide sequences can, for example, be used to diagnose a HKNG1-mediated neuropsychiatric disorder using, for example, the techniques for HKNG1 mutation/polymorphism detection described above in Section 5.1, and in Section 5.6 below.

Mutations at a number of different genetic loci may lead to phenotypes related to neuropsychiatric disorders. Ideally, the treatment of patients suffering from such neuropsychiatric disorder will be designed to target the particular genetic loci containing the mutation mediating the disorder. Genetic polymorphisms have been linked to differences in drug effectiveness. Thus, identification of alterations in the HKNG1 gene, protein or gene flanking regions, can be utilized in pharmacogenetic methods to optimize therapeutic drug treatments.

In one embodiment of the present invention, therefore, alterations, i.e., polymorphisms, in the HKNG1 gene or protein encoded by genes comprising such polymorphisms, are associated with a drug or drugs' efficacy, tolerance, or toxicity, and may be used in pharmacogenomic methods to optimize therapeutic drug treatments, including therapeutic drug treatments for one of the disorders described herein, e.g., HKNG1-mediated disorders such as schizophrenia and BAD. Such polymorphisms can be used, for example, to refine the design of drugs by decreasing the incidence of adverse events in drug tolerance studies, e.g., by identifying patient subpopulations of individuals who respond or do not respond to a particular drug therapy in efficacy studies, wherein the subpopulations have a HKNG1 polymorphism associated with drug responsiveness or unresponsiveness. The pharmacogenomic methods of the present invention can also provide tools to identify new drug targets for designing drugs and to optimize the use of already existing drugs, e.g., to increase the response rate to a drug and/or to identify and exclude non-responders from certain drug treatments (e.g., individuals having a particular HKNG1 polymorphism associated with unresponsiveness or inferior responsiveness to the drug treatment) or to decrease the undersireable side effects of certain drug treatments and/or to identify and exclude individuals with marked susceptibility to such side effects (e.g., individuals having a particular HKNG1 polymorphism associated with an undersirable side effect to the drug treatment).

In an embodiment of the present invention, polymorphisms in the HKNG1 gene sequence or flanking this sequence, or variations in HKNG1 gene expression, or activity, e.g., variations due to altered methylation, differential splicing, or post-translational modification of the HKNG1 gene product, may be utilized to identify an individual having a disease or condition resulting from a HKNG1-mediated disorder and thus define the most effective and safest drug treatment. Assays such as those described herein may be used to identify such polymorphisms or variations in HKNG1 gene expression or activity. Once a polymorphism in the HKNG1 gene or in a flanking sequence in linkage disequilibrium with a disorder-causing allele, or a variation in HKNG1 gene expression has been identified in an individual, an appropriate drug treatment can be prescribed to the individual.

For the detection of HKNG1 gene mutations or polymorphisms, any nucleated cell can be used as a starting source for genomic nucleic acid. For the detection of HKNG1 gene expression or HKNG1 gene products, any cell type or tissue in which the HKNG1 gene is expressed may be utilized.

Nucleic acid-based detection techniques are described, below, in Section 5.6. Peptide detection techniques are described, below, in Section 5.7.

The methods described herein may be performed, for example, by utilizing pre-packaged diagnostic kits. The invention therefore also encompasses kits for detecting the presence of a polypeptide or nucleic acid of the invention in a biological sample (i.e., a test sample). Such kits can be used, e.g., to determine if a subject is suffering from or is at increased risk of developing a disorder associated with a disorder-causing allele, or aberrant expression or activity of a polypeptide of the invention (e.g., a CNS disorder, including a neuropsychiatric disorder such as BAD or schizophrenia). For example, the kit can comprise a labeled compound or agent capable of detecting the polypeptide or mRNA or DNA or HKNG1 gene sequences, e.g., encoding the polypeptide in a biological sample. The kit can further comprise a means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level, or if the DNA correlates with presence of a HKNG1 allele that causes a disorder.

For antibody-based kits, the kit can comprise, for example: (1) a first antibody (e.g., attached to a solid support) which binds to a polypeptide of the invention; and, optionally, (2) a second, different antibody which binds to either the polypeptide or to the first antibody and is conjugated to a detectable agent.

For oligonucleotide-based kits, the kit can comprise, for example: (1) an oligonucleotide (e.g., a detectably labeled oligonucleotide) which hybridizes to a nucleic acid sequence encoding a polypeptide of the invention, or (2) a pair of primers, such as the primers recited in Table 1, useful for amplifying a nucleic acid molecule encoding a polypeptide of the invention.

The kit can also comprise, for example, one or more buffering agents, preservatives, or protein stabilizing agents. The kit can also comprise components necessary for detecting the detectable agent (e.g., an enzyme or a substrate). The kit can also contain a control sample or a series of control samples which can be assayed and compared to the test sample. Each component of the kit is usually enclosed within an individual container and all of the various containers are within a single package along with instructions for observing whether the tested subject is suffering from or is at risk of developing a disorder associated with polymorphisms that correlate with alleles that cause HKNG1-related disorders, and/or aberrant levels of HKNG1 mRNA, polypeptides or activity.

5.6. Detection of HKNG1 Nucleic Acid Molecules

A variety of methods can be employed to screen for the presence of HKNG1 gene-specific mutations or polymorphisms (including polymorphisms flanking HKNG1 gene) and to detect and/or assay levels of HKNG1 nucleic acid sequences.

Mutations or polymorphisms within or flanking the HKNG1 gene can be detected by utilizing a number of techniques. Nucleic acid from any nucleated cell can be used as the starting point for such assay techniques, and may be isolated according to standard nucleic acid preparation procedures that are well known to those of skill in the art.

HKNG1 nucleic acid sequences may be used in hybridization or amplification assays of biological samples to detect abnormalities involving HKNG1 gene structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of HKNG1 gene-specific mutations or polymorphisms can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such as described in Section 5.1, above, under conditions favorable for the specific annealing of these reagents to their complementary sequences within or flanking the HKNG1 gene. The diagnostic methods of the present invention further encompass contacting and incubating nucleic acids for the detection of single nucleotide mutations or polymorphisms of the HKNG1 gene. Preferably, these nucleic acid reagent sequences within the HKNG1 gene, or chromosome 18p nucleotide sequences flanking the HKNG1 gene are 15 to 30 nucleotides in length.

After incubation, all non-annealed nucleic acids are removed from the nucleic acid:HKNG1 molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled HKNG1 nucleic acid reagents is accomplished using standard techniques well-known to those in the art. The HKNG1 gene sequences to which the nucleic acid reagents have annealed can be compared to the annealing pattern expected from a normal HKNG1 gene sequence in order to determine whether a HKNG1 gene mutation is present.

In a preferred embodiment, HKNG1 mutations or polymorphisms can be detected by using a microassay of HKNG1 nucleic acid sequences immobilized to a substrate or "gene chip" (see, e.g. Cronin, et al., 1996, Human Mutation 7:244–255).

Alternative diagnostic methods for the detection of HKNG1 gene-specific nucleic acid molecules (or HKNG1 flanking sequences), in patient samples or other appropriate cell sources, may involve their amplification, e.g., by PCR (the experimental embodiment set forth in Mullis, 1987, U.S. Pat. No. 4,683,202), followed by the analysis of the amplified molecules using techniques well known to those of skill in the art, such as, for example, those listed above. The resulting amplified sequences can be compared to those that would be expected if the nucleic acid being amplified contained only normal copies of the HKNG1 gene in order to determine whether a HKNG1 gene mutation or polymorphism in linkage disequilibrium with a disease-causing HKNG1 allele exists.

Among those HKNG1 nucleic acid sequences which are preferred for such amplification-related diagnostic screening analyses are oligonucleotide primers which amplify HKNG1 exon sequences. The sequences of such oligonucleotide primers are, therefore, preferably derived from HKNG1 intron sequences so that the entire exon, or coding region, can be analyzed as discussed below. Primer pairs useful for amplification of HKNG1 exons are preferably derived from adjacent introns. Appropriate primer pairs can be chosen such that each of the eleven HKNG1 exons are amplified. Primers for the amplification of HKNG1 exons can be routinely designed by one of ordinary skill in the art by utilizing the exon and intron sequences of HKNG1 shown in FIGS. 3A–3CC.

As an example, and not by way of limitation, Table 1, below, lists primers and primer pairs which can be utilized for the amplification of each of the human HKGN1 exons one through eleven. In this table, a primer pair is listed for each exon which consists of a forward primer derived from intron sequence upstream of the exon to be amplified, and a reverse primer derived from intron sequence downstream of the exon to be amplified. For exons greater than about 300 base pairs in length, i.e., exons 4 and 7, two primer pairs are listed (marked 4a, 4b, 7a and 7b). Each of the primer pairs can be utilized, therefore, as part of a standard PCR reaction to amplify an individual HKNG1 exon (or portion thereof). Primer sequences are depicted in a 5' to 3' orientation.

TABLE 1

| | Primer Sequence | | |
|---|---|---|---|
| 1 | cggggttggtttccacc | (SEQ ID NO:8) | forward |
|   | gcgaggagagaaatctggg | (SEQ ID NO:9) | reverse |

TABLE 1-continued

| | Primer Sequence | | |
|---|---|---|---|
| 2 | tgctcactactttgcagtgttc | (SEQ ID NO:10) | forward |
|   | tgagatcgtgtcactgcattct | (SEQ ID NO:11) | reverse |
| 3 | gtaaatctcaaaatgttgggttaatag | (SEQ ID NO:12) | forward |
|   | ctaactcttcttctatcattactc | (SEQ ID NO:13) | reverse |
| 4A | tgtttattgtgtgtctgctgtg | (SEQ ID NO:14) | forward |
|   | ggacaaccaacatgcaaacag | (SEQ ID NO:15) | reverse |
| 4B | cccaggtgttttcaattgatgc | (SEQ ID NO:16) | forward |
|   | agcagttttgtccttccaagtg | (SEQ ID NO:17) | reverse |
| 5 | gtgttttgtaatctgatcagatctc | (SEQ ID NO:18) | forward |
|   | gcagtatttctggtccagatc | (SEQ ID NO:19) | reverse |
| 6 | ggtgcacatagatcatgaaatgg | (SEQ ID NO:20) | forward |
|   | taagctgaaataggtgccttaag | (SEQ ID NO:21) | reverse |
| 7A | ttttattccatttctgtcccctac | (SEQ ID NO:22) | forward |
|   | aaggctcagttaggtctgtatc | (SEQ ID NO:23) | reverse |
| 7B | caggagttttaacgtcttcagac | (SEQ ID NO:24) | forward |
|   | gactcagaaatgtctaccatttc | (SEQ ID NO:25) | reverse |
| 8 | tgtctccacttcttcaaagtgc | (SEQ ID NO:26) | forward |
|   | caaaatgtacctgagaacttaaag | (SEQ ID NO:27) | reverse |
| 9 | cacctccaagtttcatggac | (SEQ ID NO:28) | forward |
|   | caaggtatgcacgtgtcatttc | (SEQ ID NO:29) | reverse |
| 10 | gaatgtgtattgggatttagtaaac | (SEQ ID NO:30) | forward |
|   | ttgagaattaactattcctgtcaac | (SEQ ID NO:31) | reverse |
| 11 | ccatcctggacttttactcc | (SEQ ID NO:32) | forward |
|   | ctttcctgcaactgtgtttattg | (SEQ ID NO:33) | reverse |

Each primer pair above can be used to generate an amplified sequence of about 300 base pairs. This is especially desirable in instances in which sequence analysis is performed using SSCP gel electrophoretic procedures, in that such procedures work optimally using sequences of about 300 base pairs or less.

Additional HKNG1 nucleic acid sequences which are preferred for such amplification-related analyses are those which will detect the presence of an HKNG1 polymorphism which differs from the HKNG1 sequence depicted in FIGS. 3A–3CC. Such polymorphisms include ones which represent mutations associated with an HKNG1-mediated neuropsychiatric disorder, such as BAD or schizophrenia. For example, a single base mutation identified in the Example presented in Section 8, below, results in a mutant HKNG1 gene product comprising substitution of a lysine residue for the wild-type glutamic acid residue at amino acid position 202 of the HKNG1 amino acid sequence shown in FIGS. 1A–1C (SEQ ID NO:2) or amino acid position 184 of the HKNG1 amino acid sequence shown in FIGS. 2A–2C (SEQ ID NO:4). Such polymorphisms also include ones that correlate with the presence of a HKNG1-mediated neuropsychiatric disorder, e.g., polymorphisms that are in linkage disequilibrium with disorder-causing HKNG1 alleles.

Amplification techniques are well known to those of skill in the art and can routinely be utilized in connection with primers such as those listed in Table 1 above. In general, hybridization conditions can be as follows. In general, for probes between 14 and 70 nucleotides in length the melting temperature TM is calculated using the formula: $Tm(°C.)=81.5+16.6(\log[\text{monovalent cations}])+0.41(\% \text{ G+C})-(500/N)$ where N is the length of the probe. If the hybridization is carried out in a solution containing formamide, the melting temperature is calculated using the equation $Tm(°C.)=81.5+16.6(\log[\text{monovalent cations}])+0.41(\% \text{ G+C})-(0.61\% \text{ formamide})-(500/N)$ where N is the length of the probe.

Additionally, well-known genotyping techniques can be performed to identify individuals carrying HKNG1 gene mutations. Such techniques include, for example, the use of restriction fragment length polymorphisms (RFLPs), which involve sequence variations in one of the recognition sites for the specific restriction enzyme used.

Further, improved methods for analyzing DNA polymorphisms, which can be utilized for the identification of HKNG1 gene-specific mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the HKNG1 gene, and the diagnosis of diseases and disorders related to HKNG1 mutations.

Also, Caskey et al. (U.S. Pat. No. 5,364,759) describe a DNA profiling assay for detecting short tri and tetra nucleotide repeat sequences. The process includes extracting the DNA of interest, such as the HKNG1 gene, amplifying the extracted DNA, and labelling the repeat sequences to form a genotypic map of the individual's DNA.

Other methods well known in the art may be used to identify single nucleotide polymorphisms (SNPs), including biallelic SNPs or biallelic markers which have two alleles, both of which are present at a fairly high frequency in a population. Conventional techniques for detecting SNPs include, e.g., conventional dot blot analysis, single stranded conformational polymorphism (SSCP) analysis (see, e.g., Orita et al., 1989, *Proc. Natl. Acad. Sci. USA* 86:2766–2770), denaturing gradient gel electrophoresis (DGGE), heterodulex analysis, mismatch cleavage detection, and other routine techniques well known in the art (see, e.g., Sheffield et al., 1989, *Proc. Natl. Acad. Sci.* 86:5855–5892; Grompe, 1993, *Nature Genetics* 5:111–117). Alternative, preferred methods of detecting and mapping SNPs involve microsequencing techniques wherein an SNP site in a target DNA is detecting by a single nucleotide primer extension reaction (see, e.g., Goelet et al., PCT Publication No. WO92/15712; Mundy, U.S. Pat. No. 4,656, 127; Vary and Diamond, U.S. Pat. No. 4,851,331; Cohen et al., PCT Publication No. WO91/02087; Chee et al., PCT Publication No. WO95/11995; Landegren et al., 1988, *Science* 241:1077–1080; Nicerson et al., 1990, *Proc. Natl. Acad. Sci. U.S.A.* 87:8923–8927; Pastinen et al.,1997, *Genome Res.* 7:606–614; Pastinen et al., 1996, *Clin. Chem.* 42:1391–1397; Jalanko et al., 1992, *Clin. Chem.* 38:39–43; Shumaker et al., 1996, *Hum. Mutation* 7:346–354; Caskey et al., PCT Publication No. WO 95/00669).

The level of HKNG1 gene expression can also be assayed. For example, RNA from a cell type or tissue known, or suspected, to express the HKNG1 gene, such as brain, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the HKNG1 gene. Such analyses may reveal both quantitative and qualitative aspects of the expression pattern of the HKNG1 gene, including activation or inactivation of HKNG1 gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the HKNG1 gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such HKNG1 gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the HKNG1 gene.

5.7. Detection of HKNG1 Gene Products

Antibodies directed against unimpaired or mutant HKNG1 gene products or conserved variants or peptide fragments thereof, which are discussed, above, in Section 5.3, may also be used as diagnostics and prognostics for a HKNG1-mediated disorder, e.g., a neuropsychiatric disorder such as BAD or schizophrenia. Such methods may be used to detect abnormalities in the level of HKNG1 gene product synthesis or expression, or abnormalities in the structure, temporal expression, and/or physical location of HKNG1 gene product. The antibodies and immunoassay methods described herein have, for example, important in vitro applications in assessing the efficacy of treatments for HKNG1-mediated disorders. Antibodies, or fragments of antibodies, such as those described below, may be used to screen potentially therapeutic compounds in vitro to determine their effects on HKNG1 gene expression and HKNG1 gene product production. The compounds that have beneficial effects on a HKNG1-mediated disorder, such as BAD or schizophrenia.

In vitro immunoassays may also be used, for example, to assess the efficacy of cell-based gene therapy for a HKNG1-mediated disorder, e.g., a neuropsychiatric disorder, such as BAD schizophrenia. Antibodies directed against HKNG1 gene products may be used in vitro to determine, for example, the level of HKNG1 gene expression achieved in cells genetically engineered to produce HKNG1 gene product. In the case of intracellular HKNG1 gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the HKNG1 gene. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the HKNG1 gene.

Preferred diagnostic methods for the detection of HKNG1 gene products, conserved variants or peptide fragments thereof, may involve, for example, immunoassays wherein the HKNG1 gene products or conserved variants or peptide fragments are detected by their interaction with an anti-HKNG1 gene product-specific antibody.

For example, antibodies, or fragments of antibodies, such as those described, above, in Section 5.3, may be used to quantitatively or qualitatively detect the presence of HKNG1 gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred for HKNG1 gene products that are expressed on the cell surface.

The antibodies (or fragments thereof) useful in the present invention may, additionally, be employed histologically, as in immunofluorescence or immunoelectron microscopy, for in situ detection of HKNG1 gene products, conserved variants or peptide fragments thereof. In situ detection may be accomplished by removing a histological specimen from a patient, and applying thereto a labeled antibody that binds to an rTs polypeptide. The antibody (or fragment) is preferably applied by overlaying the labeled antibody (or fragment) onto a biological sample. Through the use of such a procedure, it is possible to determine not only the presence of the HKNG1 gene product, conserved variants or peptide fragments, but also its distribution in the examined tissue. Using the present invention, those of ordinary skill will readily recognize that any of a wide variety of histological methods (such as staining procedures) can be modified in order to achieve in situ detection of a HKNG1 gene product.

Immunoassays for HKNG1 gene products, conserved variants, or peptide fragments thereof will typically comprise incubating a sample, such as a biological fluid, a tissue extract, freshly harvested cells, or lysates of cells in the presence of a detectably labeled antibody capable of identifying HKNG1 gene product, conserved variants or peptide fragments thereof, and detecting the bound antibody by any of a number of techniques well-known in the art.

The biological sample may be brought in contact with and immobilized onto a solid phase support or carrier, such as nitrocellulose, that is capable of immobilizing cells, cell particles or soluble proteins. The support may then be washed with suitable buffers followed by treatment with the detectably labeled HKNG1 gene product specific antibody. The solid phase support may then be washed with the buffer a second time to remove unbound antibody. The amount of bound label on the solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which the HKNG1 gene product-specific antibody can be detectably labeled is by linking the same to an enzyme, such as for use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect HKNG1 gene products through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.8. Screening Assays for Compounds that Modulate HKNG1 Gene Activity

The following assays are designed to identify compounds that bind to a HKNG1 gene product, compounds that bind to proteins, or portions of proteins that interact with a HKNG1 gene product, compounds that modulate, e.g., interfere with, the interaction of a HKNG1 gene product with proteins and compounds that modulate the activity of the HKNG1 gene (i.e., modulate the level of HKNG1 gene expression and/or modulate the level of HKNG1 gene product activity). Assays may additionally be utilized that identify compounds that bind to HKNG1 gene regulatory sequences (e.g., promoter sequences; see e.g., Platt, 1994, J. Biol. Chem. 269, 28558–28562), and that can modulate the level of HKNG1 gene expression. Such compounds may include, but are not limited to, small organic molecules, such as ones that are able to cross the blood-brain barrier, gain to and/or entry into an appropriate cell and affect expression of the HKNG1 gene or some other gene involved in a HKNG1 regulatory pathway.

Methods for the identification of such proteins are described, below, in Section 5.8.2. Such proteins may be involved in the control and/or regulation of mood. Further, among these compounds are compounds that affect the level of HKNG1 gene expression and/or HKNG1 gene product activity and that can be used in the therapeutic treatment of HKNG1-mediated disorders, e.g., neuropsychiatric disorders such as BAD and schizophrenia as described, below, in Section 5.9.

Compounds may include, but are not limited to, peptides such as, for example, soluble peptides, including but not limited to, Ig-tailed fusion peptides, and members of random peptide libraries; (see, e.g., Lam, et al., 1991, Nature 354:82–84; Houghten, et al., 1991, Nature 354:84–86), and combinatorial chemistry-derived molecular library made of D- and/or L-configuration amino acids, phosphopeptides (including, but not limited to members of random or partially degenerate, directed phosphopeptide libraries; see, e.g., Songyang, et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Such compounds may further comprise compounds, in particular drugs or members of classes or families of drugs, known to ameliorate the symptoms of a HKNG1-mediated disorder, e.g., a neuropsychiatric disorder such as BAD or schizophrenia.

Such compounds include families of antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone.

Compounds identified via assays such as those described herein may be useful, for example, in elaborating the biological function of the HKNG1 gene product and for ameliorating HKNG1-mediated neuropsychiatric disorders, such as BAD and schizophrenia. Assays for testing the effectiveness of compounds identified by, for example, techniques such as those described in Sections 5.8.1–5.8.3, are discussed, below, in Section 5.8.4.

5.8.1. In Vitro Screening Assays for Compounds that Bind to the HKNG1 Gene Product In vitro systems may be designed to identify compounds capable of binding the HKNG1 gene products of the invention. Compounds identified may be useful, for example, in modulating the activity of unimpaired and/or mutant HKNG1 gene products, may be useful in elaborating the biological function of the HKNG1 gene product, may be utilized in screens for identifying compounds that disrupt normal HKNG1 gene product interactions, or may in themselves disrupt such interactions.

The principle of the assays used to identify compounds that bind to the HKNG1 gene product involves preparing a reaction mixture of the HKNG1 gene product and the test compound under conditions and for a time sufficient to allow the two components to interact and bind, thus forming a complex that can be removed and/or detected in the reaction mixture. These assays can be conducted in a variety of ways. For example, one method to conduct such an assay involves anchoring a HKNG1 gene product or a test substance onto a solid support and detecting HKNG1 gene product/test compound complexes formed on the solid support at the end of the reaction. In one embodiment of such a method, the HKNG1 gene product may be anchored onto a solid support, and the test compound, which is not anchored, may be labeled, either directly or indirectly.

In practice, microtiter plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for HKNG1 gene product or the test compound to anchor any complexes formed in solution, and a labeled antibody specific for the other component of the possible complex to detect anchored complexes.

5.8.2. Assays for Proteins that Interact with HKNG1 Gene Products

Any method suitable for detecting protein-protein interactions may be employed for identifying HKNG1 gene product-protein interactions.

Among the traditional methods that may be employed are co-immunoprecipitation, cross-linking and co-purification through gradients or chromatographic columns. Utilizing procedures such as these allows for the identification of proteins, including intracellular proteins, that interact with HKNG1 gene products. Once isolated, such a protein can be identified and can be used in conjunction with standard techniques, to identify proteins it interacts with. For example, at least a portion of the amino acid sequence of a protein that interacts with the HKNG1 gene product can be ascertained using techniques well known to those of skill in the art, such as via the Edman degradation technique (see, e.g., Creighton, 1983, "Proteins: Structures and Molecular Principles," W.H. Freeman & Co., N.Y., pp.34–49). The amino acid sequence obtained may be used as a guide for the generation of oligonucleotide mixtures that can be used to screen for gene sequences encoding such proteins. Screening made be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode a protein which interacts with a HKNG1 gene product. These methods include, for example, probing expression libraries with labeled HKNG1 gene product, using HKNG1 gene product in a manner similar to the well known technique of antibody probing of λgt11 libraries.

One method that detects protein interactions in vivo, the two-hybrid system, is described in detail for illustration only and not by way of limitation. One version of this system has been described (Chien, et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the HKNG1 gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites.

Interaction of the two hybrid proteins reconstitutes the functional activator protein and results in expression of the reporter gene, which is detected by an assay for the reporter gene product.

The two-hybrid system or related methodologies may be used to screen activation domain libraries for proteins that interact with the "bait" gene product. By way of example, and not by way of limitation, HKNG1 gene products may be used as the bait gene product. Total genomic or cDNA sequences are fused to the DNA encoding an activation domain. This library and a plasmid encoding a hybrid of a bait HKNG1 gene product fused to the DNA-binding domain are co-transformed into a yeast reporter strain, and the resulting transformants are screened for those that express the reporter gene. For example, a bait HKNG1 gene sequence, such as the open reading frame of the HKNG1 gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait HKNG1 gene product are to be detected can be made using methods routinely practiced in the art. According to the particular system described herein, for example, the cDNA fragments can be inserted into a vector such that they are translationally fused to the transcriptional activation domain of GAL4. Such a library can be co-transformed along with the bait HKNG1 gene-GAL4 fusion plasmid into a yeast strain that contains a lacZ gene driven by a promoter that contains GAL4 activation sequence. A cDNA encoded protein, fused to a GAL4 transcriptional activation domain that interacts with bait HKNG1 gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait HKNG1 gene product-interacting protein using techniques routinely practiced in the art.

5.8.3. Assays for Compounds that Interfere with or Potentiate HKNG1 Gene Product Macromolecule Interaction The HKNG1 gene products may, in vivo, interact with one or more macromolecules, including intracellular macromolecules, such as proteins. Such macromolecules may include, but are not limited to, nucleic acid molecules and those proteins identified via methods such as those described, above, in Sections 5.8.1–5.8.2. For purposes of this discussion, the macromolecules are referred to herein as "binding partners". Compounds that disrupt HKNG1 gene product binding to a binding partner may be useful in regulating the activity of the HKNG1 gene product, especially mutant HKNG1 gene products. Such compounds may include, but are not limited to molecules such as peptides, and the like, as described, for example, in Section 5.8.2 above.

The basic principle of an assay system used to identify compounds that interfere with or potentiate the interaction between the HKNG1 gene product and a binding partner or partners involves preparing a reaction mixture containing the HKNG1 gene product and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of HKNG1 gene product and its binding partner. Control reaction mixtures are incubated without the test compound or with a compound which is known not to block complex formation. The formation of any complexes between the HKNG1 gene product and the binding partner is then detected. The formation of a complex in the control reaction, but not in the reaction mixture containing the test compound, indicates that the compound interferes with the interaction of the HKNG1 gene product and the binding partner. Additionally, complex formation within reaction mixtures containing the test compound and normal HKNG1 gene product may also be compared to complex formation within reaction mixtures containing the test compound and a mutant HKNG1 gene product. This comparison may be important in those cases wherein it is desirable to identify compounds that disrupt interactions of mutant but not normal HKNG1 gene product.

In order to test a compound for potentiating activity, the reaction mixture is prepared in the presence and absence of the test compound. The test compound may be initially included in the reaction mixture, or may be added at a time subsequent to the addition of HKNG1 gene product and its binding partner. Control reaction mixtures are incubated without the test compound or with a compound which is known not to block complex formation. The formation of any complexes between the HKNG1 gene product and the binding partner is then detected. Increased formation of a complex in the reaction mixture containing the test compound, but not in the control reaction, indicates that the compound enhances and therefore potentiates the interaction of the HKNG1 gene product and the binding partner. Additionally, complex formation within reaction mixtures containing the test compound and normal HKNG1 gene product may also be compared to complex formation within reaction mixtures containing the test compound and a mutant HKNG1 gene product. This comparison may be important in those cases wherein it is desirable to identify compounds that enhance interactions of mutant but not normal HKNG1 gene product.

In alternative embodiments, the above assays may be performed using a reaction mixture containing the HKNG1 gene product, a binding partner, and a third which disrupts or enhances HKNG1 gene product binding to the binding partner. The reaction mixture is prepared and incubated in the presence and absence of the test compound, as described above, and the formation of any complexes between the HKNG1 gene product and the binding partner is detected. In this embodiment, the formation of a complex in the reaction mixture containing the test compound, but not in the control reaction, indicates that the test compound interferes with the ability of the second compound to disrupt HKNG1 gene product binding to its binding partner.

The assays for compounds that interfere with or potentiate the interaction of the HKNG1 gene products and binding partners can be conducted in a heterogeneous or homogeneous format. Heterogeneous assays involve anchoring either the HKNG1 gene product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For example, test compounds that interfere with or potentiate the interaction between the HKNG1 gene products and the binding partners, e.g., by competition, can be identified by conducting the reaction in the presence of the test substance; i.e., by adding the test substance to the reaction mixture prior to or simultaneously with the HKNG1 gene product and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the HKNG1 gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the HKNG1 gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. In this approach, a preformed complex of the HKNG1 gene product and the interactive binding partner is prepared in which either the HKNG1 gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt HKNG1 gene product/binding partner interaction can be identified.

In another embodiment of the invention, these same techniques can be employed using peptide fragments that correspond to the binding domains of the HKNG1 product and/or the binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments is engineered to express peptide fragments of the protein, it can then be tested for binding activity and purified or synthesized.

For example, and not by way of limitation, a HKNG1 gene product can be anchored to a solid material as described, above, in this Section by making a GST-HKNG1 fusion protein and allowing it to bind to glutathione agarose beads. The binding partner can be labeled with a radioactive isotope, such as $^{35}S$, and cleaved with a proteolytic enzyme such as trypsin. Cleavage products can then be added to the anchored GST-HKNG1 fusion protein and allowed to bind. After washing away unbound peptides, labeled bound material, representing the binding partner binding domain, can be eluted, purified, and analyzed for amino acid sequence by well-known methods. Peptides so identified can be produced synthetically or produced using recombinant DNA technology.

5.8.4. Assays for Identification of Compounds that Ameliorate a HKNG1-Mediated Disorder Compounds, including but not limited to binding compounds identified via assay techniques such as those described, above, in Sections 5.8.1–5.8.4, can be tested for the ability to ameliorate symptoms of a HKNG1-mediated disorder, e.g., a CNS-related disorder, such as a neuropsychiatric disorder, including schizophrenia and bipolar affective (mood) disorders, including severe bipolar affective (mood) disorder (BP-I), bipolar affective (mood) disorder with hypomania and major depression (BP-II), and myopia disorders.

It should be noted that the assays described herein can identify compounds that affect HKNG1 activity by either affecting HKNG1 gene expression or by affecting the level of HKNG1 gene product activity. For example, compounds may be identified that are involved in another step in the pathway in which the HKNG1 gene and/or HKNG1 gene product is involved and, by affecting this same pathway may modulate the effect of HKNG1 on the development of a HKNG1-mediated disorder. Such compounds can be used, e.g., as part of a therapeutic method for the treatment of the disorder.

Described below are cell-based and animal model-based assays for the identification of compounds exhibiting such an ability to ameliorate symptoms of a HKNG1-mediated disorder, e.g., neuropsychiatric disorder, such as BAD or schizophrenia.

First, cell-based systems can be used to identify compounds that may act to ameliorate symptoms of a HKNG1-mediated disorder. Such cell systems can include, for example, recombinant or non-recombinant cell, such as cell lines, that express the HKNG1 gene.

In utilizing such cell systems, cells that express HKNG1 may be exposed to a compound suspected of exhibiting an ability to ameliorate symptoms of a HKNG1-mediated disorder, e.g., a neuropsychiatric disorder, such as BAD or schizophrenia, at a sufficient concentration and for a sufficient time to elicit such an amelioration of such symptoms in the exposed cells. After exposure, the cells can be assayed to measure alterations in the expression of the HKNG1 gene, e.g., by assaying cell lysates for HKNG1 mRNA transcripts (e.g., by Northern analysis) or for HKNG1 gene products expressed by the cell; compounds that modulate expression of the HKNG1 gene are good candidates as therapeutics.

In addition, animal-based systems or models for a HKNG1-mediated disorder, e.g., neuropsychiatric disorder, for example, transgenic mice containing a human or altered form of HKNG1 gene, may be used to identify compounds capable of ameliorating symptoms of the disorder. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of symptoms of a HKNG1-mediated disorder. The response of the animals to the exposure may be monitored by assessing the reversal of the symptoms of the disorder.

With regard to intervention, any treatments that reverse any aspect of symptoms of a HKNG1-mediated disorder, should be considered as candidates for human therapeutic intervention in such disorders. Dosages of test agents may be determined by deriving dose-response curves, as discussed in Section 5.10.1, below.

5.9. Compounds and Methods for the Treatment of HKNG1-Mediated Disorders

Described below are methods and compositions whereby a HKNG1-mediated disorder described herein, e.g., a HKNG1-mediated neuropsychiatric disorder, such as BAD or schizophrenia, may be treated. For example, such methods can comprise administering compounds which modulate the expression of a mammalian HKNG1 gene and/or the synthesis or activity of a mammalian HKNG1 gene product (e.g., a recombinant HKNG1 gene product) so symptoms of the disorder are ameliorated.

Alternatively, in those instances whereby the HKNG1-mediated disorders result from HKNG1 gene mutations, such methods can comprise supplying the subject with a nucleic acid molecule encoding an unimpaired HKNG1 gene product such that an unimpaired HKNG1 gene product is expressed and symptoms of the disorder are ameliorated.

In another embodiment of methods for the treatment of HKNG1-mediated disorders resulting from HKNG1 gene mutations, such methods can comprise supplying the subject with a cell comprising a nucleic acid molecule that encodes an unimpaired HKNG1 gene product such that the cell expresses the unimpaired HKNG1 gene product and symptoms of the disorder are ameliorated.

In cases in which a loss of normal HKNG1 gene product function results in the development of a HKNG1-mediated disorder an increase in HKNG1 gene product activity would facilitate progress towards an asymptomatic state in individuals exhibiting a deficient level of HKNG1 gene expression and/or HKNG1 gene product activity. Methods for enhancing the expression or synthesis of HKNG1 can include, for example, methods such as those described below, in Section 5.9.2.

Alternatively, symptoms of HKNG1-mediated neuropsychiatric disorders, may be ameliorated by administering a compound that decreases the level of HKNG1 gene expression and/or HKNG1 gene product activity. Methods for inhibiting or reducing the level of HKNG1 gene product synthesis or expression can include, for example, methods such as those described in Section 5.9.1.

In one embodiment of treatment methods, the compounds administered comprise compounds, in particular drugs, which ameliorate the symptoms of a disorder described herein as a neuropsychiatric disorder, such as BAD or schizophrenia. Such compounds include drugs within the families of antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone.

In another embodiment, symptoms of a disorder described herein, e.g., a HKNG1-mediated neuropsychiatric disorder such as BAD or schizophrenia, may be ameliorated by HKNG1 protein therapy methods, e.g., decreasing or increasing the level and/or of HKNG1-activity using the HKNG1 protein, fusion protein, and peptide sequences described in Section 5.2, above, or by the administration of proteins or protein fragments (e.g., peptides) which interact with an HKNG1 gene or gene product and thereby inhibit or potentiate its activity.

Such protein therapy may include, for example, the administration of a functional HKNG1 protein or fragments of an HKNG1 protein (e.g., peptides) which represent functional HKNG1 domains.

In one embodiment, HKNG1 fragments or peptides representing a functional HKNG1 binding domain are administered to an individual such that the peptides bind to an HKNG1 binding protein, e.g., an HKNG1 receptor. Such fragments or peptides may serve to inhibit HKNG1 activity in an individual by competing with, and thereby inhibiting, binding of HKNG1 to the binding protein, thereby ameliorating symptoms of a disorder described herein.

Alternatively, such fragments or peptides may enhance HKNG1 activity in an individual by mimicking the function of HKNG1 in vivo, thereby ameliorating the symptoms of a disorder described herein.

The proteins and peptides which may be used in the methods of the invention include synthetic (e.g., recombinant or chemically synthesized) proteins and peptides, as well as naturally occurring proteins and peptides. The proteins and peptides may have both naturally occurring and non-naturally occuring amino acid residues (e.g., D-amino acid residues) and/or one or more non-peptide bonds (e.g., imino, ester, hydrazide, semicarbazide, and azo bonds). The proteins or peptides may also contain additional chemical groups (i.e., functional groups) present at the amino and/or carboxy termini, such that, for example, the stability, bioavailability, and/or inhibitory activity of the peptide is enhanced. Exemplary functional groups include hydrophobic groups (e.g. carbobenzoxyl, dansyl, and t-butyloxycarbonyl, groups), an acetyl group, a 9-fluorenylmethoxy-carbonyl group, and macromolecular carrier groups (e.g., lipid-fatty acid conjugates, polyethylene glycol, or carbohydrates) including peptide groups.

5.9.1. Inhibitory Antisense, Ribozyme and Triple Helix Approaches

In another embodiment, symptoms of HKNG1-mediated neuropsychiatric disorders may be ameliorated by decreasing the level of HKNG1 gene expression and/or HKNG1 gene product activity by using HKNG1 gene sequences in conjunction with well-known antisense, gene "knock-out," ribozyme and/or triple helix methods to decrease the level of HKNG1 gene expression. Among the compounds that may exhibit the ability to modulate the activity, expression or synthesis of the HKNG1 gene, including the ability to ameliorate the symptoms of a HKNG1-mediated neuropsychiatric disorder, such as BAD or schizophrenia, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, although preferred, is not required.

A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the HKNG1 gene could be used in an antisense approach to inhibit translation of endogenous HKNG1 mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86:6553–6556; Lemaitre, et al., 1987, Proc. Natl. Acad. Sci. U.S.A. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15:6625–6641). The oligonucleotide is a 2'-O-methylribonucleotide (Inoue, et al., 1987, Nucl. Acids Res. 15:6131–6148), or a chimeric RNA-DNA analogue (Inoue, et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16:3209), methylphosphonate oligonucleotides can be prepared by use of controlled pore glass polymer supports (Sarin, et al., 1988, Proc. Natl. Acad. Sci. U.S.A. 85:7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

A preferred approach to achieve intracellular concentrations of the antisense sufficient to suppress translation of endogenous mRNAs utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner, et al., 1981, Proc. Natl. Acad. Sci. U.S.A.

78:1441–1445), the regulatory sequences of the metallothionein gene (Brinster, et al., 1982, Nature 296:39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4:469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference,* VCH Publishers, New York, (see especially FIG. 4, page 833) and in Haseloff and Gerlach, 1988, Nature, 334:585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317:230–234; Thomas and Capecchi, 1987, Cell 51:503–512; Thompson, et al., 1989, Cell 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6):569–584; Helene, et al., 1992, Ann. N.Y. Acad. Sci., 660:27–36; and Maher, 1992, Bioassays 14(12):807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.9.2. Gene Replacement Therapy

HKNG1 gene nucleic acid sequences, described above in Section 5.1, can be utilized for transferring recombinant HKNG1 nucleic acid sequences to cells and expressing said sequences in recipient cells. Such techniques can be used, for example, in marking cells or for the treatment of a HKNG1-mediated neuropsychiatric disorder. Such treatment can be in the form of gene replacement therapy. Specifically, one or more copies of a normal HKNG1 gene or a portion of the HKNG1 gene that directs the production of a HKNG1 gene product exhibiting normal HKNG1 gene function, may be inserted into the appropriate cells within a patient, using vectors that include, but are not limited to adenovirus, adeno-associated virus, and retrovirus vectors, in addition to other particles that introduce DNA into cells, such as liposomes.

Because the HKNG1 gene is expressed in the brain, such gene replacement therapy techniques should be capable of delivering HKNG1 gene sequences to these cell types within patients. Thus, in one embodiment, techniques that are well known to those of skill in the art (see, e.g., PCT Publication No. WO89/10134, published Apr. 25, 1988) can be used to enable HKNG1 gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration, e.g., by stereotactic delivery of such HKNG1 gene sequences to the site of the cells in which the HKNG1 gene sequences are to be expressed.

Additional methods that may be utilized to increase the overall level of HKNG1 gene expression and/or HKNG1 gene product activity include using targeted homologous recombination methods, discussed in Section 5.2, above, to modify the expression characteristics of an endogenous HKNG1 gene in a cell or microorganism by inserting a heterologous DNA regulatory element such that the inserted regulatory element is operatively linked with the endogenous HKNG1 gene in question. Targeted homologous recombination can thus be used to activate transcription of an endogenous HKNG1 gene that is "transcriptionally silent", i.e., is not normally expressed or is normally expressed at very low levels, or to enhance the expression of an endogenous HKNG1 gene that is normally expressed.

Further, the overall level of HKNG1 gene expression and/or HKNG1 gene product activity may be increased by the introduction of appropriate HKNG1-expressing cells, preferably autologous cells, into a patient at positions and in numbers that are sufficient to ameliorate the symptoms of a HKNG1-mediated neuropsychiatric disorder. Such cells may be either recombinant or non-recombinant.

Among the cells that can be administered to increase the overall level of HKNG1 gene expression in a patient are normal cells, preferably brain cells, that express the HKNG1 gene. Alternatively, cells, preferably autologous cells, can be engineered to express HKNG1 gene sequences, and may then be introduced into a patient in positions appropriate for the amelioration of the symptoms of a HKNG1-mediated neuropsychiatric disorder. Alternately, cells that express an unimpaired HKNG1 gene and that are from a MHC matched individual can be utilized, and may include, for example, brain cells. The expression of the HKNG1 gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.8, that are capable of modulating HKNG1 gene product activity can be administered using standard techniques that are well known to those of skill in the art. In instances in which the compounds to be administered are to involve an interaction with brain cells, the administration techniques should include well known ones that allow for a crossing of the blood-brain barrier.

5.10. Pharmaceutical Preparations and Methods of Administration

The compounds that are determined to affect HKNG1 gene expression or gene product activity can be administered to a patient at therapeutically effective doses to treat or ameliorate a HKNG1-mediated disorder or modulate a HKNG1-related process described herein. A therapeutically effective dose refers to that amount of the compound sufficient to result in amelioration of symptoms of such a disorder.

5.10.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of antibody, protein, or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

5.10.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral rectal or topical administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In certain embodiments, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the compounds may be combined with a carrier so that an effective dosage is delivered, based on the desired activity A topical formulation for treatment of some of the eye disorders discussed infra (e.g., myopia) consists of an effective amount of the compounds in a ophthalmologically acceptable excipient such as buffered saline, mineral oil, vegetable oils such as corn or arachis oil, petroleum jelly, Miglyol 182, alcohol solutions, or liposomes or liposome-like products. Any of these compositions may also include preservatives, antioxidants, antibiotics, immunosuppressants, and other biologically or pharmaceutically effective agents which do not exert a detrimental effect on the compound.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

The HKNG1 Gene of Chromosome 18 is Associated with the Neuropsychiatric Disorder BAD In the Example presented in this Section, studies are described that define a narrow interval of approximately 27 kb on the short arm of human chromosome 18 which is associated with the neuropsychiatric disorder BAD. The interval is demonstrated to lie within the gene referred to herein as the HKNG1 gene.

6.1. Materials and Methods

6.1.1. Linkage Disequilibrium

Linkage disequilibrium (LD) studies were performed using DNA from a population sample of neuropsychiatric disorder (BP-I) patients. The population sample and LD techniques were as described in Escamilla et al., 1996, *Am J. Med. Genet.* 67:244–253. The present LD study took advantage of the additional population sample collection and the additional physical markers identified via the physical mapping techniques described below.

6.1.2. Yeast Artificial Chromosome (YAC) Mapping

For physical mapping, yeast artificial chromosomes (YACs) containing human sequences were mapped to the region being analyzed based on publicly available maps (Cohen et al., 1993, C.R. Acad. Sci. 316:1484–1488). The YACs were then ordered and contig reconstructed by performing standard short tag sequence (STS)-content mapping with microsatellite markers and non-polymorphic STSs available from databases that surround the genetically defined candidate region.

6.1.3. Bacterial Artificial Chromosome (BAC) Mapping

STSs from the short arm of human chromosome 18 were used to screen a human BAC library (Research Genetics, Huntsville, Ala.). The ends of the BACs were cloned or directly sequenced. The end sequences were used to amplify the next overlapping BACs. From each BAC, additional microsatellites were identified. Specifically, random sheared libraries were prepared from overlapping BACs within the defined genetic interval. BAC DNA was sheared with a nebulizer (CIS-US Inc., Bedford, Mass.). Fragments in the size range of 600 to 1,000 bp were utilized for the sublibrary production. Microsatellite sequences from the sublibraries were identified by corresponding microsatellite probes. Sequences around such repeats were obtained to enable development of PCR primers for genomic DNA.

6.1.4. Radiation Hybrid (RH) Mapping

Standard RH mapping techniques were applied to a Stanford G3 RH mapping panel (Research Genetics, Huntsville,. Ala.) to order all microsatellite markers and non-polymorphic STSs in the region being analyzed.

6.1.5. Sample Sequencing

Random sheared libraries were made from all the BACs within the defined genetic region. Approximately 9,000 subclones within the approximately 340 kb region containing the BAD interval were sequenced with vector primers in order to achieve an 8-fold sequence coverage of the region. All sequences were processed through an automated sequence analysis pipeline that assessed quality, removed vector sequences and masked repetitive sequences. The resulting sequences were then compared to public DNA and protein databases using BLAST algorithms (Altschul, et al., 1990, J. Molec. Biol., 215:403–410).

All sequences were contiged using Sequencher 3.0 (Gene Code Corp.) and PHRED and PHRAP (Phill Green, Washington University) into a single DNA fragment of 340 kb.

6.2. Results

Genetic regions involved in bipolar affective disorder (BAD) human genes had previously been reported to map to portions of the long (18q) and short (18p) arms of human chromosome 18 (Freimer et al., 1996, Neuropsychiat. Genet. 67:254–263; Freimer et al., 1996, Nature Genetics 12:436–441; and McInnis et al., *Proc. Natl. Acad. Scie. U.S.A.* 93:13060–13065).

High resolution physical mapping using YAC, BAC and RH techniques. In order to provide the precise order of genetic markers necessary for linkage and LD mapping, and to guide new microsatellite marker development for finer mapping, a high resolution physical map of the 18p candidate region was developed using YAC, BAC and RH techniques.

For such physical mapping, first, YACs were mapped to the chromosome 18 region being analyzed. Using the mapped YAC contig as a framework, the region from publicly available markers spanning the 18p region were also mapped and contiged with BACs. Sublibraries from the contiged BACs were constructed, from which microsatellite marker sequences were identified and sequenced.

To ensure development of an accurate physical map, the radiation hybrid (RH) mapping technique was independently applied to the region being analyzed. RH was used to order all microsatellite markers and non-polymorphic STSs in the region. Thus, the high resolution physical map ultimately constructed was obtained using data from RH mapping and STS-content mapping.

Linkage Disequilibrium. Prior to attempting to identify gene sequences, studies were performed to further narrow the neuropsychiatric disorder region. Specifically, a linkage disequilibrium (LD) analysis was performed using population samples and techniques as described in Section 6.1, above, which took advantage of the additional physical markers identified via the physical mapping techniques described below.

Initial LD analysis narrowed the interval which associates with BAD disorders to a 340 kb region of 18p. BAC clones within this newly identified neuropsychiatric disorder region were analyzed to identify specific genes within the region. A combination of sample sequencing, cDNA selection and transcription mapping analyses were used to arrange sequences into tentative transcription units, that is, tentatively delineating the coding sequences of genes within this genomic region of interest.

Subsequent LD analyses further narrowed the BAD region of 18p to a narrow interval of approximately 27 kb. This was accomplished by identifying the maximum haplotype shared among affected individuals using additional markers. Statistical analysis of the entire 18p candidate region indicated that the 27 kb haplotype was significantly elevated in frequency among affected Costa Rican individuals (LOD=2.2; p=0.0005).

This newly identified narrow interval was found to map completely within one of the transcription units identified as described above. The gene corresponding to this transcription unit is referred to herein as the HKNG1 gene. Thus, the results of the mapping analyses presented in this Section demonstrate that the HKNG1 gene of human chromosome 18 is associated with the neuropsychiatric disorder BAD.

Analysis of the BAD interval indicated that the 27 kb BAD disease-associated chromosomal interval identified in the linkage disequilibrium studies is contained within an approximately 60 kb genomic region which contains a sequence referred to as GS4642 or rod photoreceptor protein (RPP) gene (Shimizu-Matsumoto, A. et al., 1997, Invest. Ophthalmol. Vis. Sci. 38:2576–2585).

7. EXAMPLE

Sequence and Characterization of the HKNG1 Gene

As demonstrated in the Example presented in Section 6, above, the HKNG1 gene is involved in the neuropsychiatric disorder BAD. The results presented in this Section further characterize the HKNG1 gene and gene product. In particular, isolation of additional cDNA clones and analyses of genomic and cDNA sequences have revealed both the full length HKNG1 amino acid sequence and the HKNG1 genomic intron/exon structure. In particular, the nucleotide and predicted amino acid sequence of the HKNG1 gene identified by these analyses disclose new HKNG1 exon sequences, including new HKNG1 protein coding sequence, discovered herein. Further, the expression of HKNG1 in human tissue, especially neural tissue, is characterized by Northern and in situ hybridization analysis. The results presented herein are consistent with the HKNG1 gene being a gene which mediates neuropsychiatric disorders such as BAD.

7.1. Materials and Methods

HKNG1 cDNA Clone Isolation: Hybridization of a human brain and kidney cDNA library was performed according to standard techniques and identified a full-length HKNG1 cDNA clone. In addition, a HKNG1 cDNA derived from a splice variant was isolated, as described in Section 7.2, below.

Northern Blot Analysis: Standard RNA isolation techniques and Northern blotting procedures were followed. The HKNG1 probe utilized corresponds to the complementary sequence of base pairs 1367 to 1578 of the full length HKNG1 cDNA sequence (SEQ ID NO. 1). Clontech multiple tissue northern blots were probed. In particular, Clontech human I, human II, human III, human fetal II, human brain II and human brain III blots were utilized for this study.

In Situ Hybridization Analysis: Standard in situ hybridization techniques were utilized. The HKNG1 probe utilized corresponds to the complementary sequence of base pairs 910 to 1422 of the full length HKNG1 cDNA sequence (SEQ ID NO. 1). Brains for in situ hybridization analysis were obtained from McLean Hospital (The Harvard Brain Tissue Resource Center, Belmont, Mass. 02178).

Other techniques: The remaining techniques described in Section 7.2, below, were performed according to standard techniques or as discussed in Section 6.1, above.

7.2. Results

7.2.1. HKNG1 Nucleotide and Amino Acid Sequence

A human brain cDNA library was screened and a full-length clone of HKNG1 was isolated from this library, as described above. By comparing the isolated cDNA sequence to sequences in the public databases, a clone was identified which had been previously identified as GS4642, or rod photoreceptor protein (RPP) gene (GenBank Accession No. D63813; Shimizu-Matsumoto, A. et al., 1997, Invest. Ophthalmol. Vis. Sci. 38:2576–2585). Although Shimizu-Matsumoto et al. refer to GS4642 as a full-length cDNA sequence, the isolated HKNG1 cDNA extends approximately 200 bp beyond the 5'end of the identified GS4642 clone.

Importantly, the HKNG1 clone isolated herein reveals that, contrary to the amino acid sequence described in Shimizu-Matsumoto et al., the full length HKNG1 amino acid sequence contains an additional 29 amino acid residues N-terminal to what had previously been identified as the full-length RPP (SEQ ID NO:64). The full-length HKNG1 nucleotide sequence (SEQ ID NO: 1) and the derived amino acid sequence of the full-length HKNG1 polypeptide (SEQ ID NO: 2) encoded by this sequence are depicted in FIGS. 1A–1C.

The full-length HKNG1 polypeptide was found to contain two clusterin similarity domains: clusterin similarity domain 1 which corresponds to amino acid residues 134 to amino acid residue 160, and clusterin similarity domain 2 which corresponds to amino acid residue 334 to amino acid residue 362. Such cluterin domains are typically characterized by five shared cysteine residues. In clusterin domain 1, these shared cysteine residues correspond to Cys 134, Cys145, Cys148, Cys158, and Cys 160. The shared cysteine residues in clusterin domain 2 correspond to the residues Cys334, Cys344, Cys351, Cys354, and Cys362.

Full-length HKNG1 cDNA sequence was compared with the genomic contig completed by random sheared library sequencing. Exon-intron boundaries were identified manually by aligning the two sequences in Sequencher 3.0 and by observing the conservative splicing sites where the alignments ended. This sequence comparison revealed that the additional cDNA sequence discovered through isolation of the full-length HKNG1 cDNA clone actually belongs within three HKNG1 exons.

Prior to the isolation and analysis of HKNG1 cDNA described herein, nine exons were predicted to be present within the corresponding genomic sequence. As discovered herein, however, the HKNG1 gene, in contrast, actually contains 13 exons, with the new cDNA containing sequence which corresponds to a new exon 1, exon 2 and a 5' extension of what had previously been designated exon 1. Splice variants, discussed in Section 9 below, also exist which comprise additional exons 2' and 2". The genomic sequence and intron/exon structure of the HKNG1 gene is shown in FIGS. 3A–3CC.

The breakdown of exons was confirmed by the perfect alignment of the cDNA sequence with the genomic sequence and by observation of expected splicing sites flanking each of the additional, newly discovered exons.

HKNG1 nucleotide sequence was used to search databases of partial sequences of cDNA clones. This search identified a partial cDNA sequence derived from IMAGE clone R61493 having similarity to the human HKNG1 sequence. IMAGE clone R61493 was obtained and consists of a cDNA insert, the Lafmid BA vector backbone, and DNA originating from the oligo dT primer and Hind III adaptors used in cDNA library construction. The Lafmid BA vector nucleotide sequence is available at the URL http://image.rzpd.de/lafmida_seq.html and descriptions of the oligo dT primer and Hind III adaptors are available in the GENBANK record corresponding to accession number R61493.

The sequence of the cDNA insert revealed that the insert was derived from an alternatively spliced HKNG1 mRNA variant, referred to herein as HKNG1-V1. In particular, this HKNG1 variant is deleted for exon 3 of the full length 13 exon HKNG1 sequence. The nucleotide sequence of this HKNG1 variant (SEQ ID NO:3) is depicted in FIGS. 2A–2C. The amino acid sequence encoded by the HKNG1 variant (SEQ ID NO:3) is also shown in FIGS. 2A–2C.

Preferably therefore, the nucleic acids of the invention include nucleic acid molecules comprising the nucleotide sequence of HKNG1-V1 or encoding the polypeptide encoded by HKNG1-V1 in the absence of heterologous sequences (e.g., cloning vector sequences such as Lafmid BA; oligo dT primer, and Hind III adaptor).

7.2.2. HKNG1 Gene Expression

HKNG1 gene expression was examined by Northern blot analysis in various human tissues. A transcript of approximately 2 kb was detected in fetal brain, lung and kidney, and in adult brain, kidney, pancreas, prostate, testis, ovary, stomach, thyroid, spinal cord, lymph node and trachea. An approximately 1.5 kb transcript was also seen in trachea. In addition, a larger transcript of approximately 5 kb was detected in all adult neural regions tested (that is, cerebellum, cortex, medulla, spinal cord, occipital pole, frontal lobe, temporal, putamen, amygdala, caudatte nucleus, corpus callosum, hippocampus, whole brain, substantia nigra, subthalamic nucleus and thalamus). Once again, this is in direct contrast to previous Northern analysis of the RPP gene, which reported that expression was limited to the retina (Shimizu-Matsumoto, A. et al., 1997, Invest. Ophthalmal. Vis. Sci. 38:2576–2585).

Analysis of HKNG1 the tissue distribution was extended through an in situ hybridization analysis. In particular, the HKNG1 mRNA distribution in normal human brain tissue was analyzed. The results of this analysis are depicted in FIGS. 4A–4B. As summarized in FIGS. 4A–4B, HKNG1 is expressed throughout the brain, with transcripts being localized to neuronal and grey matter cell types.

Finally, expression of HKNG1 in recombinant cells demonstrates that the HKNG1 gene encodes a secreted polypeptide(s).

8. A Missense Mutation within HKNG1 Correlates with BAD

The Example presented in Section 6, above, shows that the BAD disorder maps to an interval completely contained within the HKNG1 gene of the short arm of human chromosome 18. The Example presented in Section 7, above, characterizes the HKNG1 gene and gene products. The results presented in this Example further these studies by identifying a mutation within the coding region of a HKNG1 allele of an individual exhibiting a BAD disorder.

Thus, the results described herein demonstrate a positive correlation between a mutation which encodes a non-wild-type HKNG1 polypeptide and the appearance of the neuropsychiatric disorder BAD. The results presented herein, coupled with the results presented in Section 6, above, identify HKNG1 as a gene which mediates neuropsychiatric disorders such as BAD.

8.1. Materials and Methods

Pairs of PCR primers that flank each exon (see TABLE 1, above) were made and used to PCR amplify genomic DNA isolated from BAD affected and normal individuals. The amplified PCR products were analyzed using SSCP gel electrophoresis or by DNA sequencing. The DNA sequences and SSCP patterns of the affected and controls were compared and variations were further analyzed.

8.2. Results

In order to more definitively show that the HKNG1 gene mediates neuropsychiatric disorders, in particular BAD, a study was conducted to explore whether a HKNG1 mutation that correlates with BAD could be identified.

First, exon scanning was performed on all eleven exons of the HKNG1 gene using chromosomes isolated from three affected and one normal individual from the Costa Rican population utilized for the LD studies discussed in Section 6, above. No obvious mutations correlating with BAD were found through this analysis.

Next, HKNG1 intron and 3'-untranslated regions within the 27 kb BAD interval were scanned by sscp and/or sequencing for all variants among three affected and one normal individual from the same population. Approximately 60 variants were identified after scanning approximately two-thirds of the 27 kb genomic interval, which can be genotyped and analyzed by haplotype sharing and LD analyses, as described above, in order to identify ones which correlate with bipolar affective disorder. FIGS. 5A-5C lists selected variants identified through this study.

Exon scanning using chromosomal DNA from the general population of Costa Rica, however, successfully identified a HKNG1 missense mutation in an individual affected with BAD who did not share the common diseased haplotype identified by the LD analysis provided above. In particular, exon scanning was done on exons 1–11 of HKNG1 nucleic acid from 129 individuals from the general population affected with BAD.

This analysis identified a point mutation in the coding region of exon 7 not seen in non-bipolar affected disorder individuals. Specifically, the guanine corresponding to nucleotide residue 604 of SEQ ID No:1 (or nucleotide residue 550 of SEQ ID NO:3) had mutated to an adenine. HKNG1 protein expressed from this mutated HKNG1 allele comprises the substitution of a lysine residue at amino acid residue 202 of SEQ ID NO:2 (or amino acid residue 184 of SEQ ID NO:4) in place of the wild-type glutamic acid residue.

Additional HKNG1 polymorphisms relative to the HKNG1 wild-type sequence, and which, therefore, represent HKNG1 alleles, were identified through sequence analysis of the HKNG1 alleles within a collection of schizophrenic patients of mixed ethnicity from the United States and within a BAD collection from the San Francisco area. These variants are depicted in FIGS. 5A–5C, respectively. Statistical analysis indicated that there were significantly more variants in the collection of schizophrenic patients of mixed ethnicity from the United States and the San Francisco BAD and Costa Rican BAD samples than in a collection of 242 controls ($p<0.05$).

9. EXAMPLE

Identification of Additional HKNG1 Splice Variants

This example describes the isolation and identification of three novel splice variants of the human gene HKNG1. First, a novel HKNG1 clone was isolated from a human retinal cDNA library. This clone, which completely lacks exon 7 of the full length HKNG1 cDNA sequence, is referred to herein as HKNG1Δ7. Because the deletion of exon 7 from the full length HKNG1 sequence leads to an immediate frameshift, the clone HKNG1Δ7 encodes a truncated form of the HKNG1 protein. The HKNG1Δ7 cDNA sequence (SEQ ID NO:65) is depicted in FIGS. 18A–18C along with the predicted amino acid sequence (SEQ ID NO:66) of the HKNG1Δ7 gene product it encodes.

Two other novel splice variants, referred to herein as HKNG1-V2 and HKNG1-V3, were isolated and identified by using RT-PCR analysis to isolate additional HKNG1 sequences. The following primer sequences were used:

5'-AGTTGCGTCCCTCTCTGTTG-3' (SEQ ID NO:67)

5'-GCTTCATGTTCCCGCTGTTA-3' (SEQ ID NO:68)

These splice variants included additional exons between exons 2 and 3 of the full length HKNG1 sequence (SEQ ID NO:1).

The RT-PCR product derived from HKNG1-V2 includes a novel exon referred to as "exon 2'", whereas the RT-PCR product derived from HKNG1-V3 includes a novel exon referred to as "exon 2''". The sequence of these novel exons are provided in Table 2 below. The nucleotide sequence of the HKNG1-V2 RT-PCR product containing novel exon 2' is depicted in FIG. 6A (SEQ ID NO:36), whereas the HKNG1-V3 RT-PCR product containing novel exon 2'' is depicted in FIG. 6B (SEQ ID NO:37). Both exon 2' and 2'' are part of the 5'-untranslated region of the HKNG1 cDNA.

TABLE 2

| Exon 2' | 5'-TTCCCTCCCTTTGGAACGCAGCGTGGGCACC TGCAACGCAGAGACCACTGTATCCCCGGTGCAGA ATGTAATGAGTGCCTGATACATTTGCCGAATAAA CTATTCCAAGGGTTGAACTTGCTGGAAGCAAGAG AAGCACTATTCTGG-3' | (SEQ ID NO:34) |
|---|---|---|
| Exon 2'' | 5'-ATGGAGTCTTGCTCTCGTTGCCCAGACTGGA GTGCACTGCTGCGATCTCAGCTCACTGCAACCTC TACCTCCCAGGTTCAAGCGATTCTCCTGCCTCAG CCTCTCGAGTGGCTGGGACTATAG-3' | (SEQ ID NO:35) |

10. EXAMPLE

Identification of HKNG1 Orthologs

This example describes the isolation and characterization of genes in other mammalian species which are orthologs to human HKNG1. Specifically, both guinea pig and bovine HKNG1 sequences are described.

10.1. Guinea Pig HKNG1 Orthologs

A guinea pig HKNG1 ortholog, referred to as gphkng1815, was isolated using RT-PCR. The cDNA sequence (SEQ ID NO:38) and predicted amino acid sequence (SEQ ID NO:39) are depicted in FIGS. 7A–7C. Both the nucleotide and the predicted amino acid sequence of gphkng 1815 are similar to the human HKNG1 nucleotide and amino acid sequences. Specifically, the program ALIGNv2.0 identified a 71.5% nucleotide sequence identity and a 62.8% amino acid sequence identity using standard parameters (Scoring Matrix: PAM120; GAP penalties: −12/−4).

Like the human HKNG1 polypeptide, the predicted gphkng 1815 polypeptide also contains two clusterin similarity domains, which correspond to amino acid residues 105 to 131 (clusterin domain 1), and amino acid residues 305–333 (clusterin domain 2), respectively. Both of these domains contain the five conserved cysteine residues typically associated with clusterin domains. Specifically, these conserved cysteines correspond to Cys105, Cys116, Cys119, Cys124 and Cys131 (clusterin similarity domain 1) and Cys305, Cys315, Cys322, Cys325, and Cys333 (clusterin similarity domain 1) of the gphkng 1815 polypeptide sequence.

Three allelic variants of gphkng 1815, referred to as gphkng 7b, gphkng 7c, and gphkng 7d, respectively, were also identified by RT-PCR. Their nucleotide [SEQ ID NO:40 (gphkng 7b), SEQ ID NO:42 (gphkng 7c), and SEQ ID NO:44 (gphkng 7d)] and amino acid [SEQ ID NO:41 (gphkng 7b), SEQ ID NO:43 (gphkng 7c), and SEQ ID NO:45 (gphkng 7d)] sequences are depicted in FIGS. 8A–8C through 10A–10C, respectively. Each of these three allelic variants contains a deletion within a region homologous to exon 7 of human HKNG1. The allelic variants retain the open reading frame of the gene, however, each allelic variant contains a deletion, relative to gphkng 1815, of 16, 92, and 93 amino acid residues, respectively.

An alignment of the predicted amino acid sequences of gphkng1815, gphkng 7b, gphkng 7c, and gphkng7d is shown in FIGS. 14A–14M. An alignment of the predicted amino acid sequences of the human HKNG1 gene product, the guinea pig HKNG1 ortholog gphkng1815, and the bovine HKNG1 ortholog described in Subsection 10.2 below are shown in FIG. 16.

10.2. Bovine HKNG1 Orthologs

Bovine orthologs of HKNG1 were also cloned by screening a cDNA library made from pooled bovine retinal tissue using a nucleotide sequence that corresponded to the complementary sequence of base pairs 910–1422 of the full length human HKNG1 cDNA sequence (SEQ ID NO:1) as a probe. Three independent bovine cDNA species, referred to as bhkng1, bhkng2, and bhkng3 (SEQ ID NOS: 46 to 48, respectively) were isolated. Each of these allelic variants contains several single nucleotide polymorphisms (SNPs). None of the SNPs results in an altered predicted amino acid sequence. Thus all three bovine cDNAs encodes the same predicted amino acid sequence (SEQ ID NO:49). These SNPs apparently reflect the natural allelic variation of the pooled cDNA library from which the sequences were isolated. Each of the three bovine HKNG1 allelic variants is depicted in FIGS. 11A–C to 13A–13C, respectively, along with the predicted amino acid sequence which they encode.

The predicted bovine HKNG1 polypeptide also contains two clusterin similarity domains, corresponding to amino acid residues 105–131 and amino acid residues 304–332, respectively, of SEQ ID NO:49. Clusterin domain 1 contains the five shared cysteine amino acid residues typically associated with this type of domain: Cys105, Cys116, Cys119, Cys124, and Cys131. Clusterin domain 2 of the bovine HKNG1 polypeptide contains four conserved cystein residues: Cys314, Cys321, Cys324, and Cys332.

11. Expression of Human HKNG1 Gene Product

Described in this example is the construction of expression vectors and the successful expression of recombinant human HKNG1 sequences. Expression vectors are described both for native HKNG1 and for various HKNG1 fusion proteins.

11.1. Expression of Human HKNG1:Flag

A human HKNG1 flag epitope-tagged protein (HKNG1:flag) vector was constructed by PCR followed by ligation into an vector for expression in HEK 293T cells. The full open-reading frame of the full length HKNG1 cDNA sequence (SEQ ID NO:5) was PCR amplified using the following primer sequences:

5' primer 5'-TTTTTCTGAATTCGCCACCATGAAAATTAAAGCAGAGAAAAACG-3' (SEQ ID NO:52)

3' primer 5'-TTTTTGTCGACTTATCACTTGTCGTCGTCGTCCTTGTAGTCCCAGGTTTTAAAATGTTCCTTAAAATGC-3' (SEQ ID NO:53)

the 5' primer incorporating a Kozak sequence upstream of and including the upstream initiator methionine and the 3' primer including the nucleotide sequence encoding the flag epitope DYKDDDDK (SEQ ID NO:50) followed by a termination codon.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an M2 anti-flag polyclonal antibody (1:500, Sigma) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Flag immunoreactivity appeared as a doublet of bands that migrated by SDS-PAGE between 60 and 95 kDa as determined by Multimark molecular weight markers (Novex), demonstrating secretion of the HKNG1:Flag protein. The double band indicates at least two different species with different mobilities on SDS-PAGE. Such doublets most commonly arise with posttranslational modifications to the protein, such as glycosylation and/or proteolysis. Treatment of the PNGase F (Oxford Glycosciences) according to the manufacturer's directions resulted in a single band of increased mobility, indicating that two original bands contain N-linked carbohydrate. When run in the absence of a reducing agent, the relative mobility of the immunoreactive bands was greater than 100 kDa relative to the same markers, indicating that HKNG1:flag fusion proteins may be a disulfide linked dimer or higher oligomer.

11.2. Expression of Human HKNG1-V1:Flag

A human HKNG1-V1 flag epitope-tagged protein (HKNG1-V1:flag) vector was also constructed by PCR followed by ligation into an expression vector, pMET stop. The full length open-reading frame of the HKNG1-V1 cDNA sequence (SEQ ID NO:6) was PCR amplified using the following primer sequences:

5' primer 5'-TTTTTCTGAATTCACCATGAGGACCTGGGACTACAGTAAC-3' (SEQ ID NO:54)

3' primer 5'-TTTTTGTCGACTTATCACTTGTCGTCGTCGTCCTTGTAGTCCCAGGTTTTAAAATGTTCCTTAAAATGC-3' (SEQ ID NO:53)

The 5' primer incorporated a Kozak sequence upstream of and including the upstream initiator methionine. The 3' primer included the nucleotide sequence encoding the flag epitope DYKDDDDK (SEQ ID NO:50) followed by a termination codon.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an M2 anti-flag polyclonal antibody (1:500, Sigma) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Flag immunoreactivity appeared as a doublet of bands that migrated by SDS-PAGE between 60 and 95 kDa as determined by Multimark molecular weight markers (Novex), demonstrating secretion of the HKNG1:Flag protein. When run in the absence of reducing agent, the relative mobility of the immunoreactive bands was greater than 100 kDA relative to the same markers, suggesting that the HKNG1 -V1:flag fusion protein may be a disulfide linked dimer or higher oligomer.

11.3. Expression of Human HKNG1:Fc

A human HKNG1/hIgG1Fc fusion protein vector was constructed by PCR. The full-length open-reading frame of the full length HKNG1 cDNA (SEQ ID NO:5) was PCR amplified using the following primer sequences:

5' primer 5'-TTTTTCTCTCGAGACCATGAAAATTAAAGCAGAGAAAAACG-3' (SEQ ID NO:55)

3' primer 5'-TTTTTGGATCCGCTGCTGCCCAGGTTTTAAAATGTTCCTTAAAATGC-3' (SEQ ID NO:56)

The 5' primer incorporated a Kozak sequence before the upstream methionine to the amino acid residue before the stop codon. The 3' PCR primer contained a 3 alanine linker at the junction of HKNG1 and the human IgG1 Fc domain, which starts at residues DPE. The genomic sequence of the human IgG1 Fc domain was ligated along with the PCR product into a pCDM8 vector (Invitrogen, Carlsbad Calif.) for transient expression.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an M2 anti-Fc polyclonal antibody (1:500, Jackson ImmunoResearch Laboratories, Inc.) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Human IgG1 Fc immunoreactivity appeared as a doublet of bands that migrated by SDS-PAGE between 148 and 60 kDa standards of the Multimark molecular weight markers (Novex), demonstrating secretion of the HKNG1:Fc fusion protein.

11.4. Expression of Human HKNG1-V1:Fc

A human HKNG1-V1/hIgG1Fc fusion protein (HKNG1-V1:Fc) vector was also constructed by PCR. The full-length open reading frame of HKNG1-V1 cDNA (SEQ ID NO:6) was PCR amplified using the following primer sequences:

5' primer 5'-TTTTTCTCTCGAGACCATGAGGAC CTGGGACTACAGTAAC-3' (SEQ ID NO:57)

3' primer 5'-TTTTTGGATCCGCTGCTGCCCAGG TTTTAAAATGTTCCTTAAAATGC-3' (SEQ ID NO:56)

The 5' primer incorporated a Kozak sequence before the upstream methionine to the amino acid residue before the stop codon. The 3' PCR primer contained a 3 alanine linker at the junction of HKNG1-V1 and the human IgG1 Fc domain, which starts at residues DPE. The genomic sequence of the human IgG1 Fc domain was ligated along with the PCR product into a pCDM8 vector for transient expression.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an anti-human Fc polyclonal antibody (1:500, Jackson ImmunoResearch Laboratories, Inc.) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Human IgG1 Fc immunoreactivity appeared as a doublet of bands that migrated by SDS-PAGE between 148 and 60 kDa standards of the Multimark molecular weight markers (Novex) centered approximately between 125 and 150 kDa, demonstrating secretion mediated by the HKNG1 signal peptide.

11.5. Expression of Human HKNG1Δ7:Fc

A human HKNG1Δ7:hIgG1Fc fusion protein vector was also constructed by PCR. The sequence of the HKNG1Δ7 splice variant was amplified by PCR amplification using Exons 1 through 6 of the full length HKNG1 cDNA sequence (SEQ ID NO:1) as a template with the following primer sequences:

5' primer 5'-TTTTTCTGAATTCACCATGAAGCC GCCACTCTTGGTG-3' (SEQ ID NO:58)

3' primer 5'-TTTTTGGATCCGCTGCGGCCTCCG TGGTCAGGAGCTTATTTTCACAGAGGACC AGCTAG-3' (SEQ ID NO:59)

The 5' primer incorporated a Kozak sequence upstream of and including the upsream initiator methionine. The 3' primer included the first17 (coding) nucleotides of exon 8 followed by nucleotides encoding a 3 alanine linker.

The genomic sequence of the human IgG1 Fc domain was ligated along with the PCR product into a pCDM8 vector for transient expression.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an anti-human Fc polyclonal antibody (1:500, Jackson ImmunoResearch Laboratories) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Human IgG1 Fc immunoreactivity appeared as a band that migrated by SDS-PAGE between 42 and 60 kDa relative to Multimark molecular weight markers (Novex) centered approximately between 36.5 and 55.4 kDa relative to Mark 12 molecular weight markers (Novex).

11.6. Expression of Native Human HKNG1

A human HKNG1 expression vector was constructed by PCR amplification of the human HKNG1 cDNA sequence (SEQ ID NO:1) followed by ligation into an expression vector, pcDNA3.1 (Invitrogen, Carlsbad Calif.). The full open-reading frame of the HKNG1 cDNA sequence (SEQ ID NO:5) was PCR amplified using the following primer sequences:

5' primer 5'-TTTTTCTCTCGAGGACTACAGGAC ACAGCTAAATCC-3' (SEQ ID NO:60)

3' primer 5'-TTTTTGGATCCTTATCACCAGGTT TTAAAATGTTCCTTAAAATGC-3' (SEQ ID NO:61)

The 5' primer incorporated a Kozak sequence upstream of and including the upstream initiator methionine. The 3' primer included a tandem pair of termination codons.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an anti-HKNG1 polyclonal antibody (#84, 1:500) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). HKNG1 immunoreactivity appeared as a doublet of bands that migrated by SDS-PAGE between 60 and 95 kDa as determined by Multimark molecular weight markers (Novex).

11.7. Expression of Native Human HKNG1-V1

A human HKNG1-V1 expression vector was also constructed by PCR amplification of the human HKNG1-V1 cDNA sequence (SEQ ID NO:3) followed by ligation into an expression vector, pcDNA3.1. The full open-reading frame of the HKNG1 cDNA sequence (SEQ ID NO:6) was PCR amplified using the following primer sequences:

5' primer 5'-TTTTTCTGAATTCACCATGAAGCC GCCACTCTTGGTG-3' (SEQ ID NO:62)

5' primer 5'-TTTTTCTCTCGAGACCATGAGGAC CTGGGACTACAGTAAC-3' (SEQ ID NO:63)

3' primer 5'-TTTTTGGATCCTTATCACCAGGTT TTAAAATGTTCCTTAAAATGC-3' (SEQ ID NO:61)

The 5' primer incorporated a Kozak sequence upstream of and including the upstream initiator methionine. The 3' primer included a tandem pair of termination codons.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an M2 anti-HKNG1 polyclonal antibody (#84, 1:500) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). HKNG immunoreactivity appeared as a doublet of bands that migrated by SDS-PAGE between 70 and 95 kDa as determined by Multimark molecular weight markers (Novex), demonstrating secretion mediated by the HKNG1 signal peptide.

11.8. Expression of Human HKNG:AP Fusion Proteins

Expression vectors were also constructed for human HKNG1 alkaline phosphatase C-terminal fusion protein (HKNG1:AP), human HKNG1-V1 alkaline phosphatase C-terminal fusion protein (HKNG1-V1:AP), and human HKNG1 alkaline phosphatase N-terminal fusion protein (AP:HKNG1).

The expression vector for human HKNG1:AP was constructed by PCR amplification followed by ligation into a vector for suitable for expression in HEK 293T cells. The full-length open-reading frame of human HKNG1 (SEQ ID NO:5) was PCR amplified using a 5' primer incorporating an EcoRI restriction site followed by a Kozak sequence prior to the upstream initiator methionine. The 3' primer included a XhoI restriction site immediately following the final codon of HKNG1. Thus, the open reading frame of the construct includes the HKNG1 signal peptide and the full HKNG1 sequence followed by the full sequence of human placental alkaline phosphatase.

The expression vector for human HKNG1-V1:AP was constructed by PCR amplification followed by ligation into pMEAP3 vector. The full length open reading frame of human HKNG1-V1 (SEQ ID NO:6) was PCR amplified using a 5' primer incorporating an EcoRI restriction site followed by a Kozak sequence prior to the upstream initiator methionine. The 3' primer included a XhoI restriction site immediately following the final codon of HKNG1-V1. Thus, the open reading frame of the construct includes the HKNG1-V1 signal and the full length HKNG1-V1 sequence followed by the full sequence of human placental alkaline phosphatase.

The expression vector for human AP:HKNG1 was constructed by PCR amplification followed by ligation into the AP-Tag3 vector reported by Cheng and Flanagan, 1994, *Cell* 79:157–168. The full-length open-reading frame of human HKNG1 (SEQ ID NO:5) was PCR amplified using a 5' primer incorporating a BamHI restriction site prior to the nucleotides encoding the first amino acids (i.e., APT) of the mature HKNG protein, and a 3' primer that included a XhoI restriction site immediately following the termination codon of HKNG1. Thus, the open reading frame of the complete construct includes the AP signal peptide and the full sequence of human placental alkaline phosphatase, followed by the full HKNG1 sequence.

The sequenced DNA constructs were transiently transfected in HEK 293T cells in 150 mM plates using Lipofectamine (GIBCO/BRL) according to the manufacturer's protocol. 72 hours post-transfection, the serum-free conditioned media (OptiMEM, Gibco/BRL) were harvested, spun and filtered. Alkaline phosphatase activity in the conditioned media was quantitated using an enzymatic assay kit (Phospha-Light, Tropix) according to the manufacturer's instructions. When alkaline phosphatase fusion protein concentrations below 2 nM were observed, conditioned medium was concentrated by centrifugation using a 30 kDa cut-off membrane. Conditioned medium samples before and after concentration were analyzed by SDS-PAGE followed by Western blot using anti-human alkaline phosphatase antibodies (1:250, Genzyme) and chemiluminsecent detection. A band at 140 kDa was observed in concentrated supernatant of HKNG1:AP, HKNG1-V1:AP, and AP:HKNG1 transfections. Conditioned medium samples were adjusted to 10% fetal calf serum and stored at 4° C.

11.9. Purification of Flag-Tagged HKNG1 Proteins

The secreted flag-tagged proteins described in subsections 12.1 and 12.2 above were isolated by a one step purification scheme utilizing the affinity of the flag epitope to M2 anti-flag antibodies. The conditioned media was passed over an M2-biotin (Sigma)/streptavidin Poros column (2.1×30 mm, PE Biosystems). The column was then washed with PBS, pH 7.4, and flag-tagged protein was eluted with 200 mM glycine, pH 3.0. Fraction was neutralized with 1.0 M Tris pH 8.0. Eluted fractions with 280 nm absorbance greater than background were then analyzed on SDS-PAGE gels and by Western blot. The fractions containing flag taged protein were pooled and dialyzed in 8000 MWCO dialysis tubing against 2 changes of 4 L PBS, pH 7.4 at 4° C. with constant stirring. The buffered exchanged material was then sterile filtered (0.2 μm, Millipore) and frozen at −80° C.

11.10. Purification of HKNG1 Fc Fusion Proteins

The secreted Fc fusion proteins described in Subsections 12.3–12.5 above were isolated by a one step purification scheme utilizing the affinity of the human IgG1 Fc domain to Protein A. The conditioned media was passed over a POROS A column (4.6×100 mm, PerSeptive Biosystems); the column was then washed with PBS, pH 7.4 and eluted with 200 mM glycine, pH 3.0. Fractions were neutralized with 1.0 M Tris pH 8.0. A constant flow rate of 7 ml/min was maintained throughout the procedure. Eluted fractions with 280 nm absorbance greater than background were then analyzed on SDS-PAGE gels and by Western blot. The fractions containing Fc fusion protein were pooled and dialyzed in 8000 MWCO dialysis tubing against 2 changes of 4 L PBS, pH 7.4 at 4° C. with constant stirring. The buffered exchanged material was then sterile filtered (0.2 μm, Millipore) and frozen at −80° C.

12. Production of Anti-HKNG1 Antibodies

Described in the example presented in this Section is the production and characterization of polyclonal and monoclonal antibodies directed against HKNG1 proteins.

12.1. Production of Polyclonal Antibodies

Polyclonal antisera were raised in rabbits against each of the three peptides listed in Table 3 below. Each of the peptides was derived from the HKNG1 amino acid sequence (SEQ ID NO:2) by standard techniques (see, in particular, Harlow&Lane, 1988, *Antibodies: A Laboratory Manual*, Cold Spring Harbor Laboratory Press, the contents of which is incorporated herein by reference in its entirety). Each of the peptides is also represented in the HKNG1-V1 polypeptide sequence (SEQ ID NO:4). Antisera was subsequently affinity purified using the peptide immunogens.

TABLE 3

| Antibody | Peptide/Immunogen | a.a. residues (SEQ ID NO:2) |
|---|---|---|
| Antibody 84 | APTWKDKTAISENLK | 50–64 |
| Antibody 85 | KAIEDLPKQDK | 304–314 |
| Antibody 86 | KALQHFKEHFKTW | 483–495 |

12.2. Production of Monoclonal Antibodies

Monoclonal antibodies were raised in mice by standard techniques (see, Harlow & Lane, supra) against the HKNG-Fc fusion protein described in Section 11.3 above. Wells were screened by ELISA for binding to the HKNG-Fc fusion protein. Those wells reacting with the Fc protein were identified by ELISA for binding to an irrelevant Fc fusion protein and discarded. HKNG-Fc specific wells were tested for their ability to immunoprecipitate HKNG-Fc and subjected to isotype analysis by standard techniques (Harlow & Lane, supra), and eight wells were selected for subcloning. The isotype of the subcloned monoclonal antibodies was confirmed and is presented in Table 4 below.

Based on Western blotting, immunoprecipation and immunostaining data discussed in SubSection 12.3 below, two monoclonal antibodies (3D17 and 4N6) were selected for large scale production.

TABLE 4

| Clone | Isotype |
|---|---|
| 1F24 | 2a |
| 1J18 | 2a |
| 2O20 | 1 |
| 3D17 | 1 |
| 3D24 | 2a |
| 4N6 | 1 |
| 4O16 | 2b |
| 10C6 | 2a |

12.3. Western Blotting and Immunoprecipitation of Recombinant HKNG Protein

The polyclonal antisera and all eight monoclonal antibodies described in subsection 12.1 and 12.2 above were tested for their ability to recognize recombinant HKNG1 proteins on Western blots using standard techniques (see, in particular, Harlow & Lane, 1988, *Antibodies: A Laboratory Manual*, Cold Spring Harbor Laboratory Press). Polyclonal antisera 84 and 85 and monoclonal antibodies 3D17 and 4N6 were able to recognize all forms of the mature (i.e., secreted) recombinant HKNG proteins tested (i.e., HKNG1:Fc, HKNG1:flag, AP:HKNG1, and native HKNG1) in Western blots.

Table 5 indicates the ability of each monoclonal antibody to immunoprecipitate recombinant HKNG1, as assessed by Western blotting of immunoprecipitates with the polyclonal antisera 84 and 85. None of the polyclonal antisera were able to immunoprecipitate recombinant HKNG1 proteins. All eight monoclonal antibodies immunoprecipitated HKNG1:Fc. Immunoprecipitation of the other recombinant HKNG1 proteins was variable.

TABLE 5

| | Protein | | | |
|---|---|---|---|---|
| Monoclonal Antibody | HKNG1:Fc | HKNG1:flag | AP:HKNG1 | HKNG1 (native) |
| IF24 | + | + | + | −/+ |
| 1J18 | + | − | −/+ | +/+ |
| 2O20 | + | − | + | − |
| 3D17 | +/+ | +/+ | − | +/+ |
| 3D24 | + | − | − | − |
| 4N6 | + | + | + | + |
| 4O16 | + | − | − | +/+ |
| 10C6 | + | − | − | + |

13. Confirmation of the HKNG N-Terminus and Disulfide Bond Structure

The experiments described in this section provide data identifying the N-terminus of the mature secreted human HKNG protein. The experiments also provide data identifying the disulfide bond linkages between cysteine amino acid residues in the mature, secreted protein.

Specifically, mature, secreted HKNG:flag, HKNG, and HKNG:FC recombinant proteins were produced and purified as described in Section 11 above. The mature recombinant proteins were digested with trypsin, and the tryptic fragments were identified and sequenced using reverse-phase liquid chromatography coupled with electrospray ionization tandem mass spectrometry (LC/MS/MS). The N-terminus of all mature secreted proteins tested was unambiguously identified as APTWKDKT, which corresponds to the amino acid sequence starting at alanine 50 of the HKNG1 amino acid sequence (FIGS. 1A–1C; SEQ ID NO:2) or alanine 32 of the HKNG1-V1 amino acid sequence (FIGS. 2A–2C; SEQ ID NO:4). Thus, although the cDNA sequences of HKNG1 and HKNG1-V1 encode distinct amino acid sequences, the mature secreted proteins produced by these two splice variants of the human HKNG1 gene are identical, since the alternative splicing that gives rise to HKNG1-V1 (i.e., the deletion of exon 3) affects the amino acid sequence of the proteolytically cleaved signal peptide. The amino acid sequence of the mature secreted HKNG1 protein is shown in FIGS. 17A–17B (SEQ ID NO:51)

The mature secreted HKNG protein is also distinct from the RPP amino acid sequence disclosed by Shimizu-Matsumo et al. (1997, *Invest. Ophthalmal. Vis. Sci.* 38:2576–2585). In particular, amino acid residues 1 to 20 of the RPP amino acid sequence disclosed in FIG. 3 of Shimizu-Matsumo et al., supra, correspond to the cleaved signal peptide of HKNG1-V1. The amino acid sequence of the mature secreted form of the HKNG1 gene product is depicted in FIG. 17 (SEQ ID NO:51).

Disulfide bond linkages for 8 of the 13 cysteine residues in the mature, secreted HKNG protein were also identified from LC/MS/MS of peptides recovered from tryptic digestion of the unreduced protein. In particular, the following disulfide bonded pairs of cysteines were identified (numbering refers to the HKNG1 protein shown in FIGS. 1A–1C; SEQ ID NO:2):

Cys 134 to Cys 145;
Cys 148 to Cys 153;
Cys 160 to Cys 334; and
Cys 354 to Cys 362.

14. EXAMPLE

Localization of HKNG mRNA and Protein Expression

This example describes experiments wherein the HKNG gene product is shown to be expressed in human brain and retinal tissue. Specifically, in situ hybridization experiments performed using standard techniques with a probe that corresponded to the complementary sequence of base pairs 910–1422 of the full length HKNG1 cDNA sequence (SEQ ID NO:1) detected HKNG messenger RNA in the photoreceptor layer (outer nuclear layer) of human retina in eyes obtained from the New England Eye Bank.

The polyclonal antisera and all eight monoclonal antibodies described in Section 12 above were tested for immunostaining of human retina. Polyclonal antiserum 85 and monoclonal antibodies 1F24, 4N6 and 4O16 showed immunostaining of HKNG protein in the photoreceptor layer and adjacent layers of the retina. The immunostaining in these tissues with polyclonal antiserum was blocked by 85 peptide immunogen, but not by the other two peptide immunogens (i.e., 84 and 86), confirming that the immunostaining was due to HKNG protein expressed in the photoreceptor layer.

The same antibodies were then used to localize HKNG protein by immunostaining in sections of human and monkey brain. HKNG protein was observed in cortical neurons in the frontal cortex. The majority of pyramidal neurons in layers IV–V were immunoreactive for HKNG protein. A subpopulation of neurons was also labeled in layers I–III. HKNG immunoreactivity was also observed in the pyramidal cell layer of the hippocampus and in a small number of neurons in the striatum.

These data further support the fact that HKNG is, indeed, a gene which mediates neuropsychiatric disorders such as BAD. Furthermore, the fact that HKNG is also expressed in human retinal tissue suggests that the gene also plays a role in myopia conditions. Specifically, Young et al. (1998, *American Journal of Human Genetics* 63:109–119) report a strong linkage (LOD=9.59) for primary myopia and secondary macular degeneration and retinal detachment in the telomeric region of human chromosome 18p. Through fine mapping analysis, this candidate region has been narrowed to a 7.6 cM haplotype flanked by markers D18S59 and D18S1138 (Young et al., supra). However, the marker D18S59 lies within the HKNG1 gene. This fact, coupled with the finding the HKNG is expressed in high levels in the retina, strongly suggests that the HKNG1 gene is also responsible for human myopia conditions and/or other eye related diseases such as primary myopia, secondary macular degeneration, and retinal detachment.

15. EXAMPLE

Immature Protein Products of the HKNG1 cDNA Sequences

This section describes experiments which were performed to determine which of the two putative initiator methionines encoded by both the full length HKNG1 cDNA and the alternatively spliced HKNG1-V1 cDNA are used in the synthesis of immature HKNG1 protein. The results indicate that both initiator methionines are used at varying levels, resulting in the production of three different forms of the immature HKNG1 protein, referred to herein as immature protein form 1 (IPF1), immature protein form 2 (IPF2), and immature protein form 3 (IPF3).

Both the full length HKNG1 cDNA sequence shown in FIGS. 1A–1C (SEQ ID NO:1) and the alternatively spliced HKNG1-V1 cDNA sequence shown in FIGS. 2A–2C (SEQ ID NO:3) encode predicted proteins that have methionines in close proximity to their predicted initiator methionines. The predicted protein sequence encoded by the full length HKNG1 cDNA sequence has a second methionine at amino acid residue number 30 of the amino acid sequence depicted in FIGS. 1A–1C (SEQ ID NO:2). Thus, although FIGS. 1A–1C indicates that the full length HKNG1 cDNA encodes the first immature form of the HKNG1 protein depicted in FIGS. 1A–1C (referred to herein as IPF1), the full length HKNG1 cDNA may additionally encode a second immature protein form (referred to herein as IPF2), whose sequence (SEQ ID NO:64) is provided on the third line of the protein alignment depicted in FIGS. 17A–17B. IPF2 is initiated at methionine 30 of the IPF1 protein sequence, and is identical to the RPP polypeptide sequence taught by Shimizu-Matsumoto et al (1997, *Invest. Ophthalmol. Vis. Sci.* 38:2576–2585). Likewise, the alternatively spliced HKNG1-V1 cDNA sequence encodes the predicted immature protein form, referred to herein as IPF3, depicted in FIGS. 2A–2C (SEQ ID NO:4). However, the HKNG1-V1 cDNA may also encoded another immature protein form, identical to IPF2, that is initiated at methionine 12 of the IPF3 protein sequence. FIGS. 17A–17B illustrates an alignment of the three immature HKNG1 protein sequences IPF1 (second row), IPF2 (third row), and IPF3 (bottom row). As explained is Section 13 above, the mature HKNG1 gene product secreted by cells expressing the HKNG1 constructs described in Section 11, above, is in fact the same cleaved product (SEQ ID NO:51), regardless of the immature HKNG1 protein (IPF1, IPF2, or IPF3) from which it is produced. An alignment of the mature secreted HKNG1 protein is therefore also depicted in FIGS. 17A–17B (top row).

Modified HKNG1:flag and HKNG1-V1:flag expression vectors were constructed as described in Sections 12.1 and 12.2, respectively. However, the nucleotide sequence of full length HKNG1 was modified, using standard site directed mutagenesis techniques, so as to introduce an additional base pair between the upstream methionine (i.e., met 1 in SEQ ID NO:2) and the downstream methionine (i.e., met 30 in SEQ ID NO:2). The nucleotide sequence of HKNG1-V1 was likewise modified, using standard site directed mutagenesis techniques, to introduce an additional base between its upstream methionine (i.e., met 1 in SEQ ID NO:4) and downstream methionine (i.e., met 12 in SEQ ID NO:4). Thus, in both modified constructs, the C-terminal flag epitope tag was no longer in the same reading frame as the upstream methionine but was in frame with the downstream methionine. Consequently, exclusive translation initiation at the first methionine of a construct would lead to the production of non-flag immunoreactive proteins. However, exclusive translation initiation at the second methionine of a construct would lead to the production of flag immunoreactive proteins.

Unmodified HKNG1:flag, unmodified HKNG1-V1:flag, modified HKNG1:flag, and modified HKNG1-V1:flag constructs were transfected into cells, and their resulting gene products were harvested, blotted onto a PVDF membrane, and probed with an M2 anti-flag polyclonal antibody, and developed according to the methods described in Sections 12.1 and 12.2 above.

Flag immunoreactivity was detected in all four samples. The unmodified HKNG1:flag and HKNG1-V1:flag expression vectors produced amounts of mature secreted HKNG1:flag protein consistent with the levels detected in Sections 12.1 and 12.2 above. Further, the flag immunoreactive band detected for the modified HKNG1:flag construct was indistinguishable in intensity from the band detected for the unmodified HKNG1:flag construct, indicating that the immature HKNG1 protein produced by full length HKNG1 cDNA is predominantly IPF2, while IPF1 is produced by full length HKNG1 cDNA in relatively minor amounts.

The flag immunoreactive band from the modified HKNG1-V1:flag construct had dramatically reduced intensity relative to the band from the unmodified HKNG1-V1:flag construct. Thus, HKNG1-V1 produces primarily the immature HKNG1 protein IPF3, while the immature HKNG1 protein IPF2 is produced by HKNG1-V1 in relatively minor amounts. These results are summarized below in Table 6.

TABLE 6

| Construct | Immature Protein | Prominance |
| --- | --- | --- |
| HKNG1 | IPF1 (SEQ ID NO:2) | Minor |
|  | IPF2 (SEQ ID NO:64) | Predominant |
| HKNG1-V1 | IPF2 (SEQ ID NO:64) | Minor |
|  | IPF3 (SEQ ID NO:4) | Predominant |

Thus, the HKNG1 gene products of the invention include gene products corresponding to the immature protein forms IPF1 and IPF3. However, preferably the HKNG1 gene products of the invention do not include amino acid sequences consisting of the IPF2 sequence (SEQ ID NO:64).

16. REFERENCES CITED

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings.

All publications, patents, and patent applications mentioned in this specification are herein incorporated by reference to the same extent as if each individual publication or patent application was specifically and individually indicated to be incorporated by reference.

What is claimed is:

1. An isolated nucleic acid molecule comprising a nucleotide sequence that encodes a HKNG1 gene product comprising:

(a) the amino acid sequence of SEQ ID NO:2;

(b) the amino acid sequence of SEQ ID NO:4;

(c) the amino acid sequence of SEQ ID NO:39;

(d) the amino acid sequence of SEQ ID NO:41;

(e) the amino acid sequence of SEQ ID NO:43;

(f) the amino acid sequence of SEQ ID NO:45;

(g) the amino acid sequence of SEQ ID NO:49; or (h) the amino acid sequence of SEQ ID NO:66.

2. The isolate nucleic acid molecule of claim 1, wherein the isolate nucleic acid molecule comprises:

(a) the nucleotide sequence of SEQ ID NO:1;

(b) the nucleotide sequence of SEQ ID NO:3;

(c) the nucleotide sequence of SEQ ID NO:7;

(d) the nucleotide sequence of SEQ ID NO:34; or (e) the nucleotide sequence of SEQ ID NO:35.

3. The isolated nucleic acid molecule of claim 1, wherein the isolated nucleic acid molecule comprises:

(a) the nucleotide sequence of SEQ ID NO:38;
(b) the nucleotide sequence of SEQ ID NO:40;
(c) the nucleotide sequence of SEQ ID NO:42; or
(d) the nucleotide sequence of SEQ ID NO:44.

4. The isolated nucleic acid molecule of claim 1, wherein the isolated nucleic acid molecule comprises:
(a) the nucleotide sequence of SEQ ID NO:46;
(b) the nucleotide sequence of SEQ ID NO:47; or
(c) the nucleotide sequence of SEQ ID NO:48.

5. An isolated nucleic acid molecule consisting of a nucleotide sequence that encodes a mature HKNG1 protein having the amino acid sequence of SEQ ID NO:51.

6. An isolated nucleic acid molecule which hybridizes to the complement of the nucleic acid molecule of any one of claims 1–5 under highly stringent conditions comprising washing in 0.1×SSC/0.1% SDS at 68° C.

7. An isolated nucleic acid molecule which hybridizes to the complement of the nucleic acid molecule of any one of claims 1–5 under stringent conditions comprising washing in 0.2×SSC/0.1% SDS at 50–65° C.

8. The isolated nucleic acid molecule of claims 6 or 7, wherein said isolated nucleic acid molecule encodes a functionally equivalent HKNG1 gene product.

9. A vector comprising the nucleotide sequence of any one of claims 1–5.

10. An expression vector comprising the nucleotide sequence of any one of claims 1–5 operatively associated with a regulatory nucleotide sequence controlling the expression of the nucleotide sequence in a host cell.

11. A host cell genetically engineered to contain the nucleotide sequence of any one of claims 1–5.

12. A host cell genetically engineered to express the nucleotide sequence of any one of claims 1–5 operatively associated with a regulatory nucleotide sequence controlling expression of the nucleotide sequence in said host cell.

* * * * *

SEQUENCE LISTING

<160> NUMBER OF SEQ ID NOS: 84

<210> SEQ ID NO 1
<211> LENGTH: 2055
<212> TYPE: DNA
<213> ORGANISM: Homo sapiens
<220> FEATURE:
<221> NAME/KEY: CDS
<222> LOCATION: (285)...(1769)

<400> SEQUENCE: 1

```
tgcgtcacct gcaggcccgg gccgcggggt tggtttccac cctggaggtt gctgacaccc      60
tgtgccctcg gctgacttcc agccggtggc acagacgcct ccaggggca gcactcaagc     120 gcatcttagg aatgacagag ttgcgtccct ctctgttgcc aggctggagt tcagtggcat    180
gttcttagct cactgaagcc tcaaattcct gggttcaagt gaccctccca cctcagcccc    240
atgaggacct gggactacag gacacagcta aatccctgac acgg atg aaa att aaa    296
                                                Met Lys Ile Lys
```

-continued

```
                                 1
gca gag aaa aac gaa ggt cct tcc aga agc tgg tgg caa ctt cac tgg    344
Ala Glu Lys Asn Glu Gly Pro Ser Arg Ser Trp Trp Gln Leu His Trp
 5              10                  15                  20 gga gat att gca aat aac agc ggg aac atg aag ccg cca ctc ttg gtg    392
Gly Asp Ile Ala Asn Asn Ser Gly Asn Met Lys Pro Pro Leu Leu Val
                25                  30                  35 ttt att gtg tgt ctg ctg tgg ttg aaa gac agt cac tgc gca ccc act    440
Phe Ile Val Cys Leu Leu Trp Leu Lys Asp Ser His Cys Ala Pro Thr
                    40                  45                  50 tgg aag gac aaa act gct atc agt gaa aac ctg aag agt ttt tct gag    488
Trp Lys Asp Lys Thr Ala Ile Ser Glu Asn Leu Lys Ser Phe Ser Glu
            55                  60                  65 gtg ggg gag ata gat gca gat gaa gag gtg aag aag gct ttg act ggt    536
Val Gly Glu Ile Asp Ala Asp Glu Glu Val Lys Lys Ala Leu Thr Gly
        70                  75                  80 att aag caa atg aaa atc atg atg gaa aga aaa gag aag gaa cac acc    584
Ile Lys Gln Met Lys Ile Met Met Glu Arg Lys Glu Lys Glu His Thr
 85                 90                  95                 100 aat cta atg agc acc ctg aag aaa tgc aga gaa gaa aag cag gag gcc    632
Asn Leu Met Ser Thr Leu Lys Lys Cys Arg Glu Glu Lys Gln Glu Ala
                105                 110                 115 ctg aaa ctt ctg aat gaa gtt caa gaa cat ctg gag gaa gaa gaa agg    680
Leu Lys Leu Leu Asn Glu Val Gln Glu His Leu Glu Glu Glu Glu Arg
                    120                 125                 130 cta tgc cgg gag tct ttg gca gat tcc tgg ggt gaa tgc agg tct tgc    728
Leu Cys Arg Glu Ser Leu Ala Asp Ser Trp Gly Glu Cys Arg Ser Cys
            135                 140                 145 ctg gaa aat aac tgc atg aga att tat aca acc tgc caa cct agc tgg    776
Leu Glu Asn Asn Cys Met Arg Ile Tyr Thr Thr Cys Gln Pro Ser Trp
        150                 155                 160 tcc tct gtg aaa aat aag att gaa cgg ttt ttc agg aag ata tat caa    824
Ser Ser Val Lys Asn Lys Ile Glu Arg Phe Phe Arg Lys Ile Tyr Gln
165                 170                 175                 180 ttt cta ttt cct ttc cat gaa gat aat gaa aaa gat ctc ccc atc agt    872
Phe Leu Phe Pro Phe His Glu Asp Asn Glu Lys Asp Leu Pro Ile Ser
                185                 190                 195 gaa aag ctc att gag gaa gat gca caa ttg acc caa atg gag gat gtg    920
Glu Lys Leu Ile Glu Glu Asp Ala Gln Leu Thr Gln Met Glu Asp Val
                    200                 205                 210 ttc agc cag ttg act gtg gat gtg aat tct ctc ttt aac agg agt ttt    968
Phe Ser Gln Leu Thr Val Asp Val Asn Ser Leu Phe Asn Arg Ser Phe
            215                 220                 225 aac gtc ttc aga cag atg cag caa gag ttt gac cag act ttt caa tca   1016
Asn Val Phe Arg Gln Met Gln Gln Glu Phe Asp Gln Thr Phe Gln Ser
        230                 235                 240 cat ttc ata tca gat aca gac cta act gag cct tac ttt ttt cca gct   1064
His Phe Ile Ser Asp Thr Asp Leu Thr Glu Pro Tyr Phe Phe Pro Ala
245                 250                 255                 260 ttc tct aaa gag ccg atg aca aaa gca gat ctt gag caa tgt tgg gac   1112
Phe Ser Lys Glu Pro Met Thr Lys Ala Asp Leu Glu Gln Cys Trp Asp
                265                 270                 275 att ccc aac ttc ttc cag ctg ttt tgt aat ttc agt gtc tct att tat   1160
Ile Pro Asn Phe Phe Gln Leu Phe Cys Asn Phe Ser Val Ser Ile Tyr
                    280                 285                 290 gaa agt gtc agt gaa aca att act aag atg ctg aag gca ata gaa gat   1208
Glu Ser Val Ser Glu Thr Ile Thr Lys Met Leu Lys Ala Ile Glu Asp
            295                 300                 305 tta cca aaa caa gac aaa gct cct gac cac gga ggc ctg att tca aag   1256
```

```
Leu Pro Lys Gln Asp Lys Ala Pro Asp His Gly Gly Leu Ile Ser Lys
    310                 315                 320 atg tta cct ggg cag gac aga gga ctg tgt ggg gaa ctt gac cag aat    1304
Met Leu Pro Gly Gln Asp Arg Gly Leu Cys Gly Glu Leu Asp Gln Asn
325                 330                 335                 340 ttg tca aga tgt ttc aaa ttt cat gaa aaa tgc caa aaa tgt cag gct    1352
Leu Ser Arg Cys Phe Lys Phe His Glu Lys Cys Gln Lys Cys Gln Ala
                345                 350                 355 cac cta tct gaa gac tgt cct gat gta cct gct ctg cac aca gaa tta    1400
His Leu Ser Glu Asp Cys Pro Asp Val Pro Ala Leu His Thr Glu Leu
            360                 365                 370 gac gag gcg atc agg ttg gtc aat gta tcc aat cag cag tat ggc cag    1448
Asp Glu Ala Ile Arg Leu Val Asn Val Ser Asn Gln Gln Tyr Gly Gln
        375                 380                 385 att ctc cag atg acc cgg aag cac ttg gag gac acc gcc tat ctg gtg    1496
Ile Leu Gln Met Thr Arg Lys His Leu Glu Asp Thr Ala Tyr Leu Val
    390                 395                 400 gag aag atg aga ggg caa ttt ggc tgg gtg tct gaa ctg gca aac cag    1544
Glu Lys Met Arg Gly Gln Phe Gly Trp Val Ser Glu Leu Ala Asn Gln
405                 410                 415                 420 gcc cca gaa aca gag atc atc ttt aat tca ata cag gta gtt cca agg    1592
Ala Pro Glu Thr Glu Ile Ile Phe Asn Ser Ile Gln Val Val Pro Arg
                425                 430                 435 att cat gaa gga aat att tcc aaa caa gat gaa aca atg atg aca gac    1640
Ile His Glu Gly Asn Ile Ser Lys Gln Asp Glu Thr Met Met Thr Asp
            440                 445                 450 tta agc att ctg cct tcc tct aat ttc aca ctc aag atc cct ctt gaa    1688
Leu Ser Ile Leu Pro Ser Ser Asn Phe Thr Leu Lys Ile Pro Leu Glu
        455                 460                 465 gaa agt gct gag agt tct aac ttc att ggc tac gta gtg gca aaa gct    1736
Glu Ser Ala Glu Ser Ser Asn Phe Ile Gly Tyr Val Val Ala Lys Ala
    470                 475                 480 cta cag cat ttt aag gaa cat ttt aaa acc tgg taagaagatc taatgcatcc   1789
Leu Gln His Phe Lys Glu His Phe Lys Thr Trp
485                 490                 495 tatatccagt aagtagaatt atctcttcat ctgggacctg gaaatcctga aataaaaaag   1849
gataatgcaa taaacacagt tgcaggaaag tatgttagct atatactatg aagtactctt   1909
agtttactta tgttgaatgg cttagctatt aatactcaaa ttgagttaaa atgaaaattc   1969
ctccttaaaa aatcaaacgt aatatgtatt acatttcatg gtacattagt agttctttgt   2029
atattgaata aatactaaat caccta                                       2055

<210> SEQ ID NO 2
<211> LENGTH: 495
<212> TYPE: PRT
<213> ORGANISM: Homo sapiens

<400> SEQUENCE: 2

Met Lys Ile Lys Ala Glu Lys Asn Glu Gly Pro Ser Arg Ser Trp Trp
1               5                   10                  15

Gln Leu His Trp Gly Asp Ile Ala Asn Asn Ser Gly Asn Met Lys Pro
                20                  25                  30

Pro Leu Leu Val Phe Ile Val Cys Leu Leu Trp Leu Lys Asp Ser His
            35                  40                  45

Cys Ala Pro Thr Trp Lys Asp Lys Thr Ala Ile Ser Glu Asn Leu Lys
        50                  55                  60

Ser Phe Ser Glu Val Gly Glu Ile Asp Ala Asp Glu Glu Val Lys Lys
65                  70                  75                  80
```

-continued

```
Ala Leu Thr Gly Ile Lys Gln Met Lys Ile Met Met Glu Arg Lys Glu
                85                  90                  95
Lys Glu His Thr Asn Leu Met Ser Thr Leu Lys Lys Cys Arg Glu Glu
            100                 105                 110
Lys Gln Glu Ala Leu Lys Leu Leu Asn Glu Val Gln Glu His Leu Glu
        115                 120                 125
Glu Glu Glu Arg Leu Cys Arg Glu Ser Leu Ala Asp Ser Trp Gly Glu
    130                 135                 140
Cys Arg Ser Cys Leu Glu Asn Asn Cys Met Arg Ile Tyr Thr Thr Cys
145                 150                 155                 160
Gln Pro Ser Trp Ser Ser Val Lys Asn Lys Ile Glu Arg Phe Phe Arg
                165                 170                 175
Lys Ile Tyr Gln Phe Leu Phe Pro Phe His Glu Asp Asn Glu Lys Asp
            180                 185                 190
Leu Pro Ile Ser Glu Lys Leu Ile Glu Glu Asp Ala Gln Leu Thr Gln
        195                 200                 205
Met Glu Asp Val Phe Ser Gln Leu Thr Val Asp Val Asn Ser Leu Phe
    210                 215                 220
Asn Arg Ser Phe Asn Val Phe Arg Gln Met Gln Gln Glu Phe Asp Gln
225                 230                 235                 240
Thr Phe Gln Ser His Phe Ile Ser Asp Thr Asp Leu Thr Glu Pro Tyr
                245                 250                 255
Phe Phe Pro Ala Phe Ser Lys Glu Pro Met Thr Lys Ala Asp Leu Glu
            260                 265                 270
Gln Cys Trp Asp Ile Pro Asn Phe Phe Gln Leu Phe Cys Asn Phe Ser
        275                 280                 285
Val Ser Ile Tyr Glu Ser Val Ser Glu Thr Ile Thr Lys Met Leu Lys
    290                 295                 300
Ala Ile Glu Asp Leu Pro Lys Gln Asp Lys Ala Pro Asp His Gly Gly
305                 310                 315                 320
Leu Ile Ser Lys Met Leu Pro Gly Gln Asp Arg Gly Leu Cys Gly Glu
                325                 330                 335
Leu Asp Gln Asn Leu Ser Arg Cys Phe Lys Phe His Glu Lys Cys Gln
            340                 345                 350
Lys Cys Gln Ala His Leu Ser Glu Asp Cys Pro Asp Val Pro Ala Leu
        355                 360                 365
His Thr Glu Leu Asp Glu Ala Ile Arg Leu Val Asn Val Ser Asn Gln
    370                 375                 380
Gln Tyr Gly Gln Ile Leu Gln Met Thr Arg Lys His Leu Glu Asp Thr
385                 390                 395                 400
Ala Tyr Leu Val Glu Lys Met Arg Gly Gln Phe Gly Trp Val Ser Glu
                405                 410                 415
Leu Ala Asn Gln Ala Pro Glu Thr Glu Ile Ile Phe Asn Ser Ile Gln
            420                 425                 430
Val Val Pro Arg Ile His Glu Gly Asn Ile Ser Lys Gln Asp Glu Thr
        435                 440                 445
Met Met Thr Asp Leu Ser Ile Leu Pro Ser Ser Asn Phe Thr Leu Lys
    450                 455                 460
Ile Pro Leu Glu Glu Ser Ala Glu Ser Ser Asn Phe Ile Gly Tyr Val
465                 470                 475                 480
Val Ala Lys Ala Leu Gln His Phe Lys Glu His Phe Lys Thr Trp
                485                 490                 495
```

-continued

```
<210> SEQ ID NO 3
<211> LENGTH: 1957
<212> TYPE: DNA
<213> ORGANISM: Homo sapiens
<220> FEATURE:
<221> NAME/KEY: CDS
<222> LOCATION: (241)...(1671)

<400> SEQUENCE: 3
tgcgtcacct gcaggcccgg gccgcggggt tggtttccac cctggaggtt gctgacaccc      60
tgtgccctcg gctgacttcc agccggtggc acagacgcct caggggca gcactcaagc      120 gcatcttagg aatgacagag ttgcgtccct ctcggttgcc aggctggagt tcagtggcat     180
gttcatagct cactgaagcc tcaaattcct gggttcaagt gacctccta cctcagcccc      240 atg agg acc tgg gac tac agt aac agc ggg aac atg aag ccg cca ctc      288
Met Arg Thr Trp Asp Tyr Ser Asn Ser Gly Asn Met Lys Pro Pro Leu
 1               5                  10                  15 ttg gtg ttt att gtg tgt ctg ctg tgg ttg aaa gac agt cac tcc gca      336
Leu Val Phe Ile Val Cys Leu Leu Trp Leu Lys Asp Ser His Ser Ala
             20                  25                  30 ccc act tgg aag gac aaa agt gct atc agt gaa aac ctg aag agt ttt      384
Pro Thr Trp Lys Asp Lys Ser Ala Ile Ser Glu Asn Leu Lys Ser Phe
 35                  40                  45 tct gag gtg ggg gag ata gat gca gat gaa gag gtg aag aag gct ttg      432
Ser Glu Val Gly Glu Ile Asp Ala Asp Glu Glu Val Lys Lys Ala Leu
 50                  55                  60 act ggt att aag caa atg aaa atc atg atg gaa aga aaa gag aag gca      480
Thr Gly Ile Lys Gln Met Lys Ile Met Met Glu Arg Lys Glu Lys Ala
65                  70                  75                  80 aac cag gcc cca gaa aca gag atc atc ttt aat tca ata cag gta gtt      528
Asn Gln Ala Pro Glu Thr Glu Ile Ile Phe Asn Ser Ile Gln Val Val
                 85                  90                  95 cca agg att gaa cac acc aat cta atg agc acc ctg aag aaa tgc aga      576
Pro Arg Ile Glu His Thr Asn Leu Met Ser Thr Leu Lys Lys Cys Arg
            100                 105                 110 gaa gaa aag cag gag gcc ctg aaa ctt ctg aat gaa gtt caa gaa cat      624
Glu Glu Lys Gln Glu Ala Leu Lys Leu Leu Asn Glu Val Gln Glu His
        115                 120                 125 ctg gag gaa gaa gaa agg cta tgc cgg gag tct ttg gca gat tcc tgg      672
Leu Glu Glu Glu Glu Arg Leu Cys Arg Glu Ser Leu Ala Asp Ser Trp
    130                 135                 140 ggt gaa tgc agg tct tgc ctg gaa aat aac tgc atg aga att tat aca      720
Gly Glu Cys Arg Ser Cys Leu Glu Asn Asn Cys Met Arg Ile Tyr Thr
145                 150                 155                 160 acc tgc caa cct agc tgg tcc tct gtg aaa aat aag att gaa cgg ttt      768
Thr Cys Gln Pro Ser Trp Ser Ser Val Lys Asn Lys Ile Glu Arg Phe
                165                 170                 175 ttc agg aag ata tat caa ttt cta ttt cct ttc cat gaa gat aat gaa      816
Phe Arg Lys Ile Tyr Gln Phe Leu Phe Pro Phe His Glu Asp Asn Glu
            180                 185                 190 aaa gat ctc ccc atc agt gaa aag ctc att gag gaa gat gca caa ttg      864
Lys Asp Leu Pro Ile Ser Glu Lys Leu Ile Glu Glu Asp Ala Gln Leu
        195                 200                 205 acc caa atg gag gat gtg ttc agc cag ttg act gtg gat gtg aat tct      912
Thr Gln Met Glu Asp Val Phe Ser Gln Leu Thr Val Asp Val Asn Ser
    210                 215                 220 ctc ttt aac agg agt ttt aac gtc ttc aga cag atg cag caa gag ttt      960
Leu Phe Asn Arg Ser Phe Asn Val Phe Arg Gln Met Gln Gln Glu Phe
225                 230                 235                 240
```

```
gac cag act ttt caa tca cat ttc ata tca gat aca gac cta act gag   1008
Asp Gln Thr Phe Gln Ser His Phe Ile Ser Asp Thr Asp Leu Thr Glu
            245                 250                 255 cct tac ttt ttt cca gct ttc tct aaa gag ccg atg aca aaa gca gat   1056
Pro Tyr Phe Phe Pro Ala Phe Ser Lys Glu Pro Met Thr Lys Ala Asp
        260                 265                 270 ctt gag caa tgt tgg gac att ccc aac ttc ttc cag ctg ttt tgt aat   1104
Leu Glu Gln Cys Trp Asp Ile Pro Asn Phe Phe Gln Leu Phe Cys Asn
    275                 280                 285 ttc agt gtc tct att tat gaa agt gtc agt gaa aca att act aag atg   1152
Phe Ser Val Ser Ile Tyr Glu Ser Val Ser Glu Thr Ile Thr Lys Met
290                 295                 300 ctg aag gca ata gaa gat tta cca aaa caa gac aaa gct cct gac cac   1200
Leu Lys Ala Ile Glu Asp Leu Pro Lys Gln Asp Lys Ala Pro Asp His
305                 310                 315                 320 gga ggc ctg att tca aag atg tta cct ggg cag gac aga gga ctg tgt   1248
Gly Gly Leu Ile Ser Lys Met Leu Pro Gly Gln Asp Arg Gly Leu Cys
            325                 330                 335 ggg gaa ctt gac cag aat ttg tca aga tgt ttc aaa ttt cat gaa aaa   1296
Gly Glu Leu Asp Gln Asn Leu Ser Arg Cys Phe Lys Phe His Glu Lys
        340                 345                 350 tgc caa aaa tgt cag gct cac cta tct gaa gac tgt cct gat gta cct   1344
Cys Gln Lys Cys Gln Ala His Leu Ser Glu Asp Cys Pro Asp Val Pro
    355                 360                 365 gct ctg cac aca gaa tta gac gag gcg atc agg ttg gtc aat gta tcc   1392
Ala Leu His Thr Glu Leu Asp Glu Ala Ile Arg Leu Val Asn Val Ser
370                 375                 380 aat cag cag tat ggc cag att ctc cag atg acc cgg aag cac ttg gag   1440
Asn Gln Gln Tyr Gly Gln Ile Leu Gln Met Thr Arg Lys His Leu Glu
385                 390                 395                 400 gac acc gcc tat ctg gtg gag aag atg aga ggg caa ttt ggc tgg gtg   1488
Asp Thr Ala Tyr Leu Val Glu Lys Met Arg Gly Gln Phe Gly Trp Val
            405                 410                 415 tct gaa ctg cat gaa gga aat att tcc aaa caa gat gaa aca atg atg   1536
Ser Glu Leu His Glu Gly Asn Ile Ser Lys Gln Asp Glu Thr Met Met
        420                 425                 430 aca gac tta agc att ctg cct tcc tct aat ttc aca ctc aag atc cct   1584
Thr Asp Leu Ser Ile Leu Pro Ser Ser Asn Phe Thr Leu Lys Ile Pro
    435                 440                 445 ctt gaa gaa agt gct gag agt tct aac ttc att ggc tac gta gtg gca   1632
Leu Glu Glu Ser Ala Glu Ser Ser Asn Phe Ile Gly Tyr Val Val Ala
450                 455                 460 aaa gct cta cag cat ttt aag gaa cat ttt aaa acc tgg taagaagatc   1681
Lys Ala Leu Gln His Phe Lys Glu His Phe Lys Thr Trp
465                 470                 475 taatgcatcc tatatccagt aagtagaatt atctcttcat ctgggacctg gaaatcctga   1741
aataaaaaag gataatgcaa taaacacagt tgcaggaaag tatgttagct atatactatg   1801
aagtactctt agtttactta tgttgaatgg cttagctatt aatactcaaa ttgagttaaa   1861
atgaaaattc ctccttaaaa aatcaaacgt aatatgtatt acatttcatg gtacattagt   1921
agttctttgt atattgaata aatactaaat caccta                            1957

<210> SEQ ID NO 4
<211> LENGTH: 477
<212> TYPE: PRT
<213> ORGANISM: Homo sapiens

<400> SEQUENCE: 4

Met Arg Thr Trp Asp Tyr Ser Asn Ser Gly Asn Met Lys Pro Pro Leu
```

-continued

```
  1               5                    10                    15
Leu Val Phe Ile Val Cys Leu Leu Trp Leu Lys Asp Ser His Ser Ala
             20                  25                  30

Pro Thr Trp Lys Asp Lys Ser Ala Ile Ser Glu Asn Leu Lys Ser Phe
         35                  40                  45

Ser Glu Val Gly Glu Ile Asp Ala Asp Glu Val Lys Lys Ala Leu
     50                  55                  60

Thr Gly Ile Lys Gln Met Lys Ile Met Glu Arg Lys Glu Lys Ala
 65              70                  75                  80

Asn Gln Ala Pro Glu Thr Glu Ile Ile Phe Asn Ser Ile Gln Val Val
                 85                  90                  95

Pro Arg Ile Glu His Thr Asn Leu Met Ser Thr Leu Lys Lys Cys Arg
             100                 105                 110

Glu Glu Lys Gln Glu Ala Leu Lys Leu Leu Asn Glu Val Gln Glu His
             115                 120                 125

Leu Glu Glu Glu Arg Leu Cys Arg Glu Ser Leu Ala Asp Ser Trp
     130                 135                 140

Gly Glu Cys Arg Ser Cys Leu Glu Asn Cys Met Arg Ile Tyr Thr
 145                 150                 155                 160

Thr Cys Gln Pro Ser Trp Ser Val Lys Asn Lys Ile Glu Arg Phe
             165                 170                 175

Phe Arg Lys Ile Tyr Gln Phe Leu Phe Pro Phe His Glu Asp Asn Glu
             180                 185                 190

Lys Asp Leu Pro Ile Ser Glu Lys Leu Ile Glu Glu Asp Ala Gln Leu
             195                 200                 205

Thr Gln Met Glu Asp Val Phe Ser Gln Leu Thr Val Asp Val Asn Ser
     210                 215                 220

Leu Phe Asn Arg Ser Phe Asn Val Phe Arg Gln Met Gln Gln Glu Phe
 225                 230                 235                 240

Asp Gln Thr Phe Gln Ser His Phe Ile Ser Asp Thr Asp Leu Thr Glu
             245                 250                 255

Pro Tyr Phe Phe Pro Ala Phe Ser Lys Glu Pro Met Thr Lys Ala Asp
             260                 265                 270

Leu Glu Gln Cys Trp Asp Ile Pro Asn Phe Phe Gln Leu Phe Cys Asn
             275                 280                 285

Phe Ser Val Ser Ile Tyr Glu Ser Val Ser Glu Thr Ile Thr Lys Met
 290                 295                 300

Leu Lys Ala Ile Glu Asp Leu Pro Lys Gln Asp Lys Ala Pro Asp His
 305                 310                 315                 320

Gly Gly Leu Ile Ser Lys Met Leu Pro Gly Gln Asp Arg Gly Leu Cys
             325                 330                 335

Gly Glu Leu Asp Gln Asn Leu Ser Arg Cys Phe Lys Phe His Glu Lys
             340                 345                 350

Cys Gln Lys Cys Gln Ala His Leu Ser Glu Asp Cys Pro Asp Val Pro
             355                 360                 365

Ala Leu His Thr Glu Leu Asp Glu Ala Ile Arg Leu Val Asn Val Ser
             370                 375                 380

Asn Gln Gln Tyr Gly Gln Ile Leu Gln Met Thr Arg Lys His Leu Glu
 385                 390                 395                 400

Asp Thr Ala Tyr Leu Val Glu Lys Met Arg Gly Gln Phe Gly Trp Val
                 405                 410                 415

Ser Glu Leu His Glu Gly Asn Ile Ser Lys Gln Asp Glu Thr Met Met
             420                 425                 430
```

Thr Asp Leu Ser Ile Leu Pro Ser Ser Asn Phe Thr Leu Lys Ile Pro
        435                 440                 445

Leu Glu Glu Ser Ala Glu Ser Ser Asn Phe Ile Gly Tyr Val Val Ala
    450                 455                 460

Lys Ala Leu Gln His Phe Lys Glu His Phe Lys Thr Trp
465                 470                 475

<210> SEQ ID NO 5
<211> LENGTH: 1485
<212> TYPE: DNA
<213> ORGANISM: Homo sapiens

<400> SEQUENCE: 5

| | | | | | |
|---|---|---|---|---|---|
| atgaaaatta | aagcagagaa | aaacgaaggt | ccttccagaa | gctggtggca | acttcactgg | 60 |
| ggagatattg | caaataacag | cgggaacatg | aagccgccac | tcttggtgtt | tattgtgtgt | 120 |
| ctgctgtggt | tgaaagacag | tcactgcgca | cccacttgga | aggacaaaac | tgctatcagt | 180 |
| gaaaacctga | agagtttttc | tgaggtgggg | gagatagatg | cagatgaaga | ggtgaagaag | 240 |
| gctttgactg | gtattaagca | aatgaaaatc | atgatggaaa | gaaagagaa | ggaacacacc | 300 |
| aatctaatga | gcaccctgaa | gaaatgcaga | gaagaaaagc | aggaggccct | gaacttctg | 360 |
| aatgaagttc | aagaacatct | ggaggaagaa | gaaaggctat | gccgggagtc | tttggcagat | 420 |
| tcctggggtg | aatgcaggtc | ttgcctggaa | ataactgca | tgagaattta | tacaacctgc | 480 |
| caacctagct | ggtcctctgt | gaaaaataag | attgaacggt | ttttcaggaa | gatatatcaa | 540 |
| tttctatttc | cttccatga | agataatgaa | aaagatctcc | ccatcagtga | aaagctcatt | 600 |
| gaggaagatg | cacaattgac | ccaaatggag | gatgtgttca | gccagttgac | tgtggatgtg | 660 |
| aattctctct | ttaacaggag | ttttaacgtc | ttcagacaga | tgcagcaaga | gtttgaccag | 720 |
| acttttcaat | cacatttcat | atcagataca | gacctaactg | agccttactt | ttttccagct | 780 |
| ttctctaaag | agccgatgac | aaaagcagat | cttgagcaat | gttgggacat | tcccaacttc | 840 |
| ttccagctgt | tttgtaatt | cagtgtctct | atttatgaaa | gtgtcagtga | acaattact | 900 |
| aagatgctga | aggcaataga | agatttacca | aaacaagaca | agctcctga | ccacggaggc | 960 |
| ctgatttcaa | agatgttacc | tgggcaggac | agaggactgt | gtggggaact | tgaccagaat | 1020 |
| ttgtcaagat | gtttcaaatt | tcatgaaaaa | tgccaaaaat | gtcaggctca | cctatctgaa | 1080 |
| gactgtcctg | atgtacctgc | tctgcacaca | gaattagacg | aggcgatcag | gttggtcaat | 1140 |
| gtatccaatc | agcagtatgg | ccagattctc | cagatgaccc | ggaagcactt | ggaggacacc | 1200 |
| gcctatctgg | tggagaagat | gagagggcaa | tttggctggg | tgtctgaact | ggcaaaccag | 1260 |
| gccccagaaa | cagagatcat | ctttaattca | atacaggtag | ttccaaggat | tcatgaagga | 1320 |
| aatatttcca | acaagatga | aacaatgatg | acagacttaa | gcattctgcc | ttcctctaat | 1380 |
| ttcacactca | agatccctct | tgaagaaagt | gctgagagtt | ctaacttcat | tggctacgta | 1440 |
| gtggcaaaag | ctctacagca | ttttaaggaa | cattttaaaa | cctgg | | 1485 |

<210> SEQ ID NO 6
<211> LENGTH: 1431
<212> TYPE: DNA
<213> ORGANISM: Homo sapiens

<400> SEQUENCE: 6

| | | | | | |
|---|---|---|---|---|---|
| atgaggacct | gggactacag | taacagcggg | aacatgaagc | cgccactctt | ggtgtttatt | 60 |
| gtgtgtctgc | tgtggttgaa | agacagtcac | tccgcaccca | cttggaagga | caaaagtgct | 120 |

```
atcagtgaaa acctgaagag tttttctgag gtgggggaga tagatgcaga tgaagaggtg      180
aagaaggctt tgactggtat taagcaaatg aaaatcatga tggaaagaaa agagaaggca      240
aaccaggccc cagaaacaga gatcatcttt aattcaatac aggtagttcc aaggattgaa      300
cacaccaatc taatgagcac cctgaagaaa tgcagagaag aaaagcagga ggccctgaaa      360
cttctgaatg aagttcaaga acatctggag gaagaagaaa ggctatgccg ggagtctttg      420
gcagattcct ggggtgaatg caggtcttgc ctggaaaata actgcatgag aatttataca      480
acctgccaac ctagctggtc ctctgtgaaa aataagattg aacggttttt caggaagata      540
tatcaatttc tatttccttt ccatgaagat aatgaaaaag atctccccat cagtgaaaag      600
ctcattgagg aagatgcaca attgacccaa atggaggatg tgttcagcca gttgactgtg      660
gatgtgaatt ctctctttaa caggagtttt aacgtcttca gacagatgca gcaagagttt      720
gaccagactt tcaatcaca tttcatatca gatacagacc taactgagcc ttactttttt       780
ccagctttct ctaaagagcc gatgacaaaa gcagatcttg agcaatgttg ggacattccc      840
aacttcttcc agctgttttg taatttcagt gtctctattt atgaaagtgt cagtgaaaca      900
attactaaga tgctgaaggc aatagaagat ttaccaaaac aagacaaagc tcctgaccac      960
ggaggcctga tttcaaagat gttacctggg caggacagag gactgtgtgg ggaacttgac     1020
cagaatttgt caagatgttt caaatttcat gaaaaatgcc aaaaatgtca ggctcaccta     1080
tctgaagact gtcctgatgt acctgctctg cacacagaat tagacgaggc gatcaggttg     1140
gtcaatgtat ccaatcagca gtatggccag attctccaga tgacccggaa gcacttggag     1200
gacaccgcct atcggtggga agatgagag gggcaatttg ctgggtgtc tgaactgcat       1260
gaaggaaata tttccaaaca agatgaaaca atgatgacag acttaagcat tctgccttcc     1320
tctaatttca cactcaagat ccctcttgaa gaaagtgctg agagttctaa cttcattggc     1380
tacgtagtgg caaaagctct acagcatttt aaggaacatt ttaaaacctg g              1431
```

<210> SEQ ID NO 7
<211> LENGTH: 72604
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g, or t

<400> SEQUENCE: 7

```
acattttaag ctactatag tccttggaaa tagcaacaaa tatcttagtt attggactat      60
tataacctta gtcatcttat tactgcttga ttatgagaca ctctccctgc taatccttag    120
aacatcttgg ttcttggtac ttgacttta gcccctctga catatagttg atgtcagagt    180
gtctgcatt tcagtagtgc tctattttac aaatcccagt aaactgctcc actgtggctt    240
gtttatgtgt taatactgct tgttttctgt tataaattat tttttgcttt ggagtaagat    300
atcatcattt tgcatagcta caaatctgaa gttaaagaaa attttaaaaa tgtaattgtg    360
ggaaaataac aaatagatct gctgagatgg aggctttgac taatgtttta ataacaggca    420
acaaaacaaa gaggcaggat attttggtca caactaaaac taaattaaat cctcatacaa    480
agccccatta agataaatgc tcaaattctg ggaacatttc acttgctttg ccagcaattt    540
taccccttcag agggtgtgga tctaatcagg ggaacaaact accctgggct taattctcat   600
taacaggggac taatttgtca aagcggcagt actagctgaa gtgatgggta tggaagcatt   660
cactgtgagg attttgctga ggtgcctggc acagggtagg ggaactcacc caggctgcaa   720
gatgctaaca gttcaggttc aaggtcttag tgtggactaa ggtcagtca ggatgggaac    780
aggtgcaact tgggccaaca tcagtatgaa gggcctgatc tgagggcagg ggaaggaggg   840
ggcattctgg gaagcaagag ttcctggtat cctgttgacc agagtcttgg cccaaggatc    900
aacgtatgaa ttaaagtaga ataccagaa acaaagaaag ttggcagaaa ctaggagaag    960
cagagtctca gccaactgga ctgggctcag ccttggctac tggcccggca gatgatagaa   1020
gagaaaacca ggaacccagg ctgaagccca gtggttgggc tggccacaca ccatgcatag   1080
ccttaaaggg gtggcctaag ggcatggtcc gctccaaaaa aggaaagggg gccccagaat   1140
atttctgaat cccactcact gccagggaag aacctctcaa ttcactcaat agtgcattct   1200
cctgcttctc aataggctaa tactctagag aatatgggga caaggggagg agggtctagt   1260
ggaacaggtc taaactggcg tttgaatttt aagataagtt aatcatacat tggctgggtc   1320
```

```
agccatgtct cttagtcttt acaaaagtag aacacaaaaa aattcaatgg aaatctacag    1380
acacctattt gcagatgagg aaaacacggct atgaagattg ggaagattgg gaagaactgg    1440
ccaggtgtgg tgctcacgcc tgtaatccca gcactttggg aggccgagge tggtggatca    1500
cttgaggtca ggagttggag accagcctgg gcaacatagt aaaaccctgt ctctactcaa    1560
attacaaaaa tcagcagggc gttgtggtgc ccacctgtaa tcccagctat gcaggaggct    1620
gaggcaggac aatcacttga acctggtagg cggaggttgc agtgagccaa aatcacgcca    1680
ctgtactcca gcctgggtga cagagcaaga ctttgtttaa aaaaaaaaaa aaaaagggaa    1740
gaactaaaaa tgtaattttc aagggggctat cacaaatggt cccaataaag agaaagcagg    1800
actcatgttt aagaaaccca tgagatgtgt atggacctca tggaagagct cttgctttct    1860
aatgatctac gtaacagatg aaaagcagag catagggcta aggatgaaaa tacaacagta    1920
ataaggtatt aatatattat taagaaagct aatgctccac ataagcagag gacattaaag    1980
ggactttttt ttcttaagga tatcttaatg ttttaaatga gaagacatag aaagggatag    2040
gtccaactct tgggattgtt gcaggttggt ttccatcgga agcactctga gtctgagatt    2100
tgtatgcaga aaattaattt gaatgtgctt ttcagatcac ccaggtgggg gagggaggaa    2160
accaggactg ggcagagaga ggctgggctg taaccaagtc acaacaaagg tgtcagctgg    2220
tcccatggtg aattctggac ctaggatggc tgatcccaag gcattccaaa ctggggcaag    2280
gaagttgtgc tttaaaactt ctcattgact gtcagtcact gggcatgagc agtccccagg    2340
aagggggat gaccttgagc aaggtggatg tcttcagcca agggcaayca ctgggaagga    2400
gaacccagct atgaactgtc agctgccaac actcccagca tctgagagga tgagggcttc    2460
aattctaagg gcaggggctc caagggcagg ggtacggatg gtggaatctg ggcagtacct    2520
tgtggcttcc actacagtcc acccccttgca ccacttagtt ccactggctt ttttttttt    2580
tttcttttct gagacagtct cactctgtca cccaggctgg agtgcggtgg cacgatctcg    2640
gctcgctgca acctccgcct cccaggttca agcaattctt gaacctcctg agtagctggg    2700
actacagatg tgtgccacca cacccagcta attttttgta ttttttagtag agacgggtt    2760
ttaccgtgtt agccagattg gtctcgatct cctgacctca tgatccgcct gctttggcct    2820
cccaaagtgc tgggattaca ggtgtgagcc accgcacaca gccagatcca ctggcttcta    2880
tataatttct gggtgaagct aattcaggat tctgatggac ctgtcttccc gagggaaact    2940
tgtaaaagga aagttagagg gacaaactat agcccctgcc acagcagctg ctgtcgagga    3000
caaaaatggt gctcctcatt tcccttaacc acctgaccta gattcccta accccttagtg    3060
ggcacctctg tggatggaag tggtggctca cykgkkggrw krwycmrrwy ycwymycect    3120
gagtggtctg agctcccagt taccaggccc ttctcaggct gtggctgttg cacttacctc    3180
cccagccatc ccccactttt tttcttgag actgggtctt gctctgtcac ccaggctgaa    3240
atgcagtggc ataacctcag ctcactgcag ccttgatctc ccaagctcaa gccatcttct    3300
cacctctgcc tcccaagtgg ctgggactac aggcacatgc caccatgccc agctaatatt    3360
ttttattttt tatttttttg tagcaatggg attttgccat gtttcccagg ctgggcttga    3420
actcctaagc tcaagctatc ctcccacctc tgcttcccaa agtgctggga ttacaggctt    3480
gagtcactgc atctggccac atttattcct tttaaacgtt aaaattgaat gcaggatcac    3540
tgagagacag gtgagtgatt accagggtgc caaacatacc cttctcctcc tttcctgcag    3600
ctctacctcc tcctgatgat caggacaatc atgtatgatg actcctttcc ttgactgctg    3660
ctctctcaga aggaacccat tgtgttgggt gagaaccaat catttgaaat ttagtaagac    3720
tcttgctgtg cctatggtag aagcattccc tctctgggge caagatcttt aaatgcacag    3780
agtccaaagt cgtgggaacc aaagcagaaa ttaaaaagga gatgactggg attatggtaa    3840
gaactgtttc cacccttgat ttgctgcacc catgtgttct acctaggaga tagcacacca    3900
tatactggtt attcattgg attacatgct gcatcccgga gaatgggcac tgcattctca    3960
ctggtcatca tgtcagagcc tgcgctgcag aggctttccc attgctctgt cagtgtgtta    4020
tagggtcagt ggatttcatg gtcatgtgcc cactgctgca cctccattct tgtaaaatgg    4080
gtcctctggt tcaatgtgat gccatgtggg atcttgtgtc aatagaataa atactcagat    4140
gttctggctg aagcttttaca agcagaaaag gccaaccgat gactgaaata agcgttgagc    4200
ccagtcaaga tgagttcctg ctcttttccag gatagacgga gtctagtgta gatcacttga    4260
catcaagaga ctggctggtc tccttgaggg atggtgctgt tctgcattca tcatccttga    4320
tgaatgaggg accctgctat tgggctcatg tacagccccc atctctgcca caatgagcgc    4380
tccattcatg ttcctattgt gccaacacta gggtgtctgt aatcactgaa acattattg    4440
ctatcattat tattatttt ttttttgag acagagtcgtc gctctgtcgc caaggctgga    4500
gtgcagtggc acgatctcag ctcactgcaa cctctgcctc ccggcttcaa gtgattctcc    4560
cgcctcagcc tccagagtag ctgggattat aggcatgcgc caccacgcct ggctaattt    4620
tgtatttta gtagagacag tcttttgcca tattagtctg tctggtctcg aactcctgac    4680
ctcaggtgat ctgcccgcct tggccttccg gagtgctagg attataggcg tgagccacca    4740
cttgctatta ttatgttgag aaaactgttt tcaattataa ataagaaaaa ataaaagatt    4800
atattttgcc tttattcctt ctctaatgct gttctttaag tagatgtgaa tttctgaact    4860
acatactttt tctttactct tgagaggttg tttggaggtt ccagcagggg accacagcta    4920
ctcgtatacc cttgaccaaa gactggtcct tgtctatcaa ggatggtcgt cttcttccac    4980
caagcacaca gcttctggag ggacgcacat ggagtggtga gggaggaagg ggacaccgc    5040
ctagccagct agatcagcca agcagaataa accctggtag tcaatgggt gacagtgtcg    5100
cagccagatt gccctcacat ccaactctta gtgatcttct cttaacattt cttgcaaggc    5160
aggtctactg gtacaaattc tctaattttt gcttgttttga gaaagtcttt gtttcttctt    5220
cacctttttt tttttttttt tggagacaga gtctccctct gttgtccagg ctgagtgca    5280
gtggcctgat cttggctcac tgcaaactct gcctccaggg ttcaagtgat cctcattcct    5340
cagccatctg agtagctgtg gttacaggcg tgtgccacca tgcctagcta attttgtat    5400
ttttagtaga acgaggttt taccgtgttg gccaggatgg tcttcagcct tcttaacttt    5460
taaaggataa tttcacgggg agaattctag ggttagttat ttytcttttca atactttaaa    5520
tattttcactc cactttcttc ttgcttgtgt ggttctgaag ataatgatat aattcttatt    5580
cttgtttctc tgcaggtaag gtggtttcat acctctggct tctttcgaga atttctcttt    5640
gtctttgatt tcctacagtt tgaatatgat ataattatgt atagacttgg ggctatttat    5700
cctttctgtg gtagtctgag ctccctaagt ctgtggtatg gtgtcttgta attgattttgg    5760
gaaaattctc agtcattatt acttcaaata tttcttctgt tcctttgtgt tttttttaact    5820
tgtgccaact ttttaattga tacatagtat tttacatatt tatggggtac atgtgatact    5880
tcattacctg catagaatgt gtaaatgatc tagtgaaggt gtttggacta ttaccttgag    5940
tatgtatcgt ttctatgtgt tgggagcttt tcaagtcctc tcttgtaaca attttgaaat    6000
atacaatgcc ttgttgttaa ctagtcaccc tgctctgctc tcaaacacta ggatttattc    6060
```

-continued

```
cttctgtcta actgggtgtt tgtacccatt aaccaacctg tcttcatccc ctctacccac      6120
ataccttttcc cagccttggg tatctatcat tctactcttt acctccatga gatcagcctt     6180
tttaactccc acatatgagt gagaacatgt agtacttgtt ttgccgtgtc tggcttattt     6240
cacttaagat aatgaccttt tattccatcc aggtcactgc aaataacaag atttcattgc      6300
ttttttctttt tatggccaaa tagtgttcca ttgtttatat agaccacatt ttactttatc    6360
catttgtaca ttgatgaaca ctgaggttga tccatatctt ggctattgtg aatagtgctg      6420
caataaacat gggggtgcag tgatcccttt aaatatccga tttcttttcc tttggataaa     6480
tacccagtaa tgggattgct ggatcatgtg gtagatgtat tttaagttttt ttgagaaacc    6540
tccatactct tccatcatgg ctgtattaat ttacattccc atcaatagta tatgagttcc     6600
ctttttttttc tgcatcctca ccagcatcta ttattttgt ctttataata atggcctttc     6660
taaccagggt aagatgatat ctcattgtgg ttttgatttg catctccctg atgagtagtg     6720
atgtcaagcg tttttccata tgcccattgg ccatttgtat gtcttctttt gatgaagtct     6780
gtttgtgtcc tttgcccact gtttatgctc cttttttttct tctctctctg gtatcccct    6840
cacacatata tcagaccttt tttaattgtc ccacaattcc tgcattttct gttcttttc      6900
attcttttctt ctctttgtat ttcagttttg gaagttctcta ttgatattca agctcactga   6960
ttcttcctct ggctctgttc agtctattaa taagcccttc aaagcctttc tctctctttc     7020
ttttctttctc tctctctctt tctctctttc gttcttcttt tctctatttc cttcctttct    7080
ttcttctctct ttcttttcttt ctttctcttt cttttctttct ttttcttttcc ttccttcctt 7140
ccttccttcc ttccttcctt cctttcttttc cttccttcct tccttccttt                7200
cttttctttct ccttccttcc ttccttcctt ccttccttcc ttccttcctt ccttccttcc    7260
tttcttttctt tcttttcttttc ttttctttctt tctttttctttc tttctttcttt tccttcttttc 7320
tttcgaccag ttctcactat gttgctcagg ctagcctaga acccctgggc tcaagttatc     7380
ctctcagctc agcctttcaa gtaggtggga caaatgcgcc attctatcat acccaacaat     7440
tcctcattttc tgttacagtg gttttttattt ctagcatttt cttttgattc tttcctagag   7500
tttccatctc tctgcttaca tacacatttg ttctctcata ttttccactt tttccattag     7560
ggccttcagc atattaatta gttatttttca attctagcct gataattcca aaatctcggt   7620
tatatttgag tctgtatcta tgcttggttt gtctcctcag actgcgtttt ttccttttag    7680
gatgtccctt atcattttttt gttgaaaaca agacatgatg tatcagataa aagtaattga    7740
ggtaaacagg cctttaatat gaggttttat gtttatctgg cttggagtta ggctgtgttt    7800
actctttgct gtaactttgg tgccagaggc taaaatttcc tctggtgccc ttgttttttgt  7860
ctctcctgtt atgtttgtgt ttccacagag tctccgtgaa tatggtgtga ggcttgaagt    7920
tctttagctg taaccctctct tattatacag gagccttacg gatgtggtgg taatgtggga    7980
gggtgggctt aagtattcag cagtcctgtg atcaggcctc agtctttttaa taagcctgag   8040
tacttccctt tccctttctg catgttagag tggcctgagg ttgggggtat ccattacccc    8100
aggttggtag gctttggtaa aaccacagtc tatcaagctg tggtaaaata gtttccctgc     8160
agtctggctt tgttaaggat aacagagggc tctgggggtg tttcaaaatt gctacttttc    8220
ctctctccct gtcagaagca caaggagatt tctcttgatc ttcaccctga gagtctggtg    8280
gggttcctgg aggtaaaact caggaaagtg tgagggcctc cacacaaagg gtctgctgaa   8340
gtttgttcca tagcctcagt tctctaatgg atctaagaag agttattgat tttcaatttg    8400
tccaacttaa ttcttgtttt gaagcagaca gtgatgactt ccaagctctt tatatgttga    8460
acccaaccccc atattatttt caattagcaa ttgcatatag caatggtaca ttgcatttat   8520
agaaatataa ttgatgtttg cctgtgtatc tttttttccta ttatgttgct gaattcattt   8580
cttagttcta ggaattttttc aaatacatcc cttaggatat tctgtataca taatcatgtc   8640
atctgcacat agggacagtt ttatttcttt ttctagtctg tatttcttat ttccttttct   8700
tgccttattg cagtggctag aacttgcagc actatattaa aataagagtg gtaaaagtga    8760
acattctttc tttgttgctg atcttggggg gaaagtattc agtctttcac cattgagcat    8820
aatgttagct gtaggtgttt taaatctttta tccagttgac gaagttaccc tttattccaa   8880
tttttctgag agtttatatc ataaatgtgt taaattttgt caaattttttt tgcatgtatt    8940
gatatgatta tgtggtttt cttctttagt tactgcagtg ggttgcattg attgatttct     9000
attattgaac cagcctgcat tcctggaata aaccccatttt ggtcatgatg tataattctt   9060
ttttttatat tgctgaattc tatttgctaa tattttgtta aggattttttg catctgtgtt   9120
catgagggat ctgggctggt aggttttttt ccccctgca atgtctctgt ctggttttgg   9180
tattaaggta atttttttttk ttttkttttt gagatggagt ctcgctctgc tcacccaggc   9240
tggagtgcag tggcacgatc ttggctcact gcaacctcca cctcccaggt ttaagcgatt   9300
ctcctgcctc aggctcctga gtagctggga ctacaggtca caccaccacg cccgactaat   9360
ttggtattaa ggtaatatta tcatcataaa atgaactggg aagtgtgccc tcttcttgta    9420
tttcttttttt tttttttgag acagtcttgc tgttgcccag gctggagtac agtggtaga   9480
tcatggctca ctgcagcctc aaactcccag gctcaagtga tcttcctgcc tcagccttcc   9540
cagtacaggg gcaggctacc acatctgcc aattttttaaa tttttcttttt gtagagaggg   9600
gtctcactat gttgcccaga ggatctcaag caattcacct accttggccc ctcttcttgt   9660
atttttatgga agaattattg gtgtcaattc ttcttgaaag tttcgttaga attcttcagt   9720
gaagctgtat gggcttgaag attactttttt tttcttttttt ttttgagatg gaatttcact   9780
cttgtcgccc aggctgtagt gcagtggtgt gacctctgct cactacaacc tctgcctccc    9840
acgttcaggt gattcccctg ccttactcag cctctggagg agctgggatt acaggcaccc   9900
gccaccatgc ccggctaatt ttttgtattt ttagtagaga cggggttttca ccatgttgac   9960
cagactggtc tcgaactcct gacctcaagt gatcccaccg cctcggcctc tcaaagtgct  10020
gggattacag gcatgagcca ccgcgcccag ctgaagattt cttttggggg agttttaaat   10080
tatacaatca atttgcttaa taggtataag ctattcaagt tatctatttt atactggatg   10140
agttgcaata gtttgtggtt tatgagttta tatggtccat ttcatctgag gtataaaatt   10200
tayttgtgta gtattgttgg tagtattccc ttgttatctt ttgttatgttc acatggtata  10260
tggtgacagt cctggtttaa ttcctagtat tagtaactgg ctctctctct ctctctctct   10320
ctctctctct ctctggtcag tctttccaga ggttttgtcaa ttttgttgac ttttttcccc   10380
caaagaatca gctctttgtt tcatggattt tctgcttttc tgttttcaac ttcattgatt   10440
tctgctgttt attatttctc tccttctgtt ggttgtgatt ttgtttcttttc              10500
tacatattcg atgtgaaatc ttacattatt cactcgggac ttttcttctt ttttgatgta   10560
tgcatttagt attctaaatt tacttctkag tactgcatac tgcttgaact atgtctgaca   10620
aatattaata tattgttttt aaatctttat tcagttcagt gtattttttaa aatttccttc   10680
tctgcctctt ctttgatttg ttatttagaa ttgtgttgtt attttccgag tatttacatt    10740
ttcctcttat ctttctgcat tgattccatc gtagtcagag tgcatgctct gtacagtttc   10800
```

```
agttctttca aatttattga gctttgttta atggatctgg atacagttta tcttggcata   10860
tatatatata tacacacaca tatgtatgtg ggcgcttgaa aagaaagcgt atctgctgtt   10920
tggtggaatg tttggagtgt tctataagcg gtgattagat actgttggtt gatgatgtca   10980
ttgagggtcc gataaccctc ctgatttaaa tttatttagt ctgtcaatta ttcagagaga   11040
gaggtgttga actctgcaat gtgaattgtg gatttgtcaa tttctccttt cagttctatt   11100
agtttttcct tcacatattt tacaactctg ttgtttggtg catacacatt tatgcaccaa   11160
atttaggatt gctataactt cttggtggat tgacccttta acattatata atgtcttttt   11220
ctgtccctgg taattgtggt tgctctgaag tctatgttat ctcaatataa atagacaact   11280
ctgctttctt ttgattaatg tttacatgat acatcttttt ctattctttt actttcaact   11340
tacttatatt attatgtttg aagtgagctt cttgtagaca gcatgtagta ggtcatatat   11400
gtacatagat atatattttt ttttgagatg gtgtactctg tcacccaggc tggagtacag   11460
tagtgctcac tgcaacctct gcctcctggg tcaagtgatc tcgtgcckca gcckcccag   11520
tagctgggat tacaggcacg caccaccatg cccagctaat ttttgtattt ttagtagaga   11580
cgggtttaac catgatggac aggctggtct cgaactcccg acctcagcg attagcccac   11640
cttggcctcc caaagtgctg gcattacagg tgtgagccac cgtgcctggt ttaatatttt   11700
taatccactc agtctttgtc ttctactggt gtacatagac attcgcatgt aatgtaaatg   11760
ttgatatgta agagcttgaa tctgttatgt ttttgctttc tctatgtttt ctcaattttt   11820
aatttctctg ttttcttttt ttctgcttca tattggctaa tgaacacttt gaatcattcc   11880
attttgattt acctatagtg tttttttagtg tgtctctttg catagctttt ttaggggtta   11940
ctttaagtat ttcattatat gtacataact tatcacagta tattggtatc gttattttac   12000
cagttcaagt aaagtatgga aatgtttcct ctctacattc ctttacctca tttataatat   12060
aattgtctta ggtatttctt gtacatacat tttaaaccgg atgagtgtta tttttgattt   12120
agctatcaaa taattccaaa aactcaagaa aaaaaggaaa gcttactata ttgacccata   12180
ttttcattca ccatgttgtt tcttccctct ttatgcccca tagttccttc ttctattgtt   12240
ttcgtttaga gaacttccta gccattctat tgggtagaa ctcctagtga caaattctct   12300
tagctttctt ttctctgtga atgtctttat ttccctcttt gttcctggag gacattctca   12360
ctggatatag gattcttggc tattgggtct tttctttttgg cactttttgta agtgtgcagc   12420
ctgctgtcaa aataaaaatt aaaataaaat aaaaatgaat gttttccttt gctacgttca   12480
tgaaagtata attcactgaa tgaggaggga cacccatctc tataatctgg aggcccatgc   12540
tcacctctga atagtacatt tgcagagaaa ttggggaaat caaagtctgt tgagaccagc   12600
aagataaata aggcaaaagg atacaaaacc atatccaaag agaaatggtt taaggaact   12660
aaggctgttt ctcctaaaaa gaaaatagtt ggagacatgt gacctccaaa gaaacaggac   12720
tttttctatg gggctccaag gggtttctat gagagaatga taaggagag atttcagctt   12780
agtctcagga agacttttca acaaccaaac ctgcccaaaa atggactgcc ctgcctaagg   12840
attgtgttct gacattaagg gtatgaggt atggttaga tgaatatttt accaaaatgc   12900
catagatatt tcaggctatt gatgttgtaa tatcatacta ggcaactcca cttcaatatg   12960
agtctctatg atgtaaaatg aaataggatg tgtttcgata gagagttgca gatttcattt   13020
tgatgttagc gaccacacaa aattactttc cctacataag aacatgttat tactctagtt   13080
gatgatgact gcttatggga aatgtgtctg ctttgttagg aatcttgcct aatatatgta   13140
taattcaaga tggtattata aagtgacata tatgatttta acatttgcac ttaaaataac   13200
acttattctg taccatgmas tgtctaggag cttctacata ttccattatt atctttattt   13260
tacaagacag ggaactaagg catggagaga ttgagtaatt tgtgcaatat tacctaccta   13320
gtaagtggta aaggaaagat tggaacccat tctggctcca ggatccaggc tcaaagccaa   13380
tatactatcc accacccccaa ctctttagtt tgatcaattt gtcaaattat tttacagtta   13440
tttatctgta aattaaggggg ataattgccc agtcaataaa tgtgtccct tcaaaggtta   13500
catacttaac caatggtgct actgggctca gaacatttt ggaactacga ttttggtggc   13560
aaccaaaaaa cctccagtac attcctctga acattctcca gaggcaagtc tttctccatg   13620
gagactgggc ttcatttttt gaattagcct gaagttgttt gaggtcaaat ctgatgaaaa   13680
gagcggctgg ggaagctgaa tattttcgtt cgtgatttaa aacagtaaat gccacctaaa   13740
tgagaaggct actttctttg aatgttttgt aaactggctt tgaaggtact tctttaaaaa   13800
agaagcacaa gaaagacggt gactggcaac agcctcactg gaatacgtct ctaatcatca   13860
aggcaaccca cactcatttg gatgtgtgca tccggtgatg ttattatttt taagttatg   13920
tgccacaaag atgcattctt tgctatacaa aagagctgtt gttaaattta taaagatata   13980
aaaaggggaa aggagaaggc accaaatgga agattcttag gcattaagtg ctcagacagc   14040
atagatcttc attagatgac gtcagggaga agagacacag actttgccat ctcaggtaga   14100
agtatcaaag tcatcagcct cctagtaaga cagacctggg tttgaagctc tgcacagcca   14160
tttcctagct ggtctgggga aaaattactt cttgaagcct cagtgtcttt attttgtaag   14220
taagtggaat tatattacct tgtcaggatg ttgtcagaat tagaaataat ttaaagaggt   14280
ccagcacgag caggtcaatc aagggaagat gttaaaaata caacaggtg aaatgtactc   14340
ccaaaagata aagtggatac atagatgaat cttcctcaca cacagagtat aataacctca   14400
gaaaaatatt gcctagagta aacatgcctc ccaagccaac gttcatcatc caggaatacg   14460
gagaggatgt ttgggatatg gggggcatga aatttacaa ttgtagggcc ctttaacaag   14520
ggtagacttg caagttgcac tgmctttcct gccctcctct ggctaccgtg tccagcatcc   14580
agagtttgtg aacctggggm ccaaggacag cacccctggca tgggcaggcc cactnggcga   14640
ctctctcagg gctgctcag ctgtgtcagt gtccccacag ggagnctgac atccagccat   14700
gaccatcgca ttaagcccac cagtcagggc caggagcaa ctgctcagag gcaccttga   14760
cccactactt ttttcccctc ctgctttatc tgccagagc gaggctctct ttctaatgtg   14820
tacaaggcgt tctacctatg actcgtggtc ctgccataga aatgcttttt ttttttttaa   14880
ctgaattaag ttgccaagtt tgaaaaatca gaatttcaca taagatccct atttctgtct   14940
tcttttgaaa aactgaatgt tcttcccaca gtgagcccac attccttcct gacgaccatc   15000
accgttcagc tggagtagag agggctctgc tggcttcaga tccggacgcg caggtcctct   15060
gcaggccccg cccacccggc gtcacctgca ggtcccgccc accggcgtc tgcaggcccc   15120
gcccacccgg cgtcacctgc aggccccgcc caccggcgt ctgcaggccc cgcccacccg   15180
gcgtcacctg caggccccgc ctgcaggccc caccggcgtc tgcaggccac catc          15240
gcaggccccg cccacccggc gtctgcaggc cccgccaccc ctgcgtcacc tgcaggcccg   15300
ggccgcgggg ttgttttcca ccmtggaggt tgctgacacc ctgtgccctc ggctgacttc   15360
cagccggtgt cacagacgcc tccaggggc agcactcaag cgcatcttag gaatgacagg   15420
tgagarcatc ctccgggccc cagatttctc tcctcgccgc tcttgcccat ttctccggag   15480
agccagagaa agccgctccc aagtccaagg ccgagctccg cagacgcccg gcccctccgg   15540
```

```
cgcggacaga acaaagccat tgttcttgcc ggggaaggta gaaatactgt gggctgcttc  15600
agaggctgcc gagcaaaact caggcaatct cctgggctgt tccaatacgt ttattctctt  15660
tttcaaaaca ggaggaggag gtagaggcgg ggagacacac catccctgca aaactactgg  15720
caaaaactaa gcggagccgg gtgtggtggc tcacgcctgt aatctcaaca ctttgggagg  15780
ccgaggggg ccgatcactt gaggtcagga gttggaggcc agcctggccg gcatggtgaa  15840
acacaaaaat tagtcgattg tggtggtgca tgcttgtaat cccatctact tgggaggctg  15900
aggcaggaga atcgcttgaa cccgggaggc ggaggttgca gtgagccgag attgcgccac  15960
tgcactccag cctggacaac acaagtgaga ttctgtctca aaataaataa ataaataaac  16020
ccaagcagaa aaagaatcac tctgaaaacg atcacatcta actatcaatg ctcatacagt  16080
ttatggaatt atcagcccaa cttgataaaa tcagtatttg aggaaactgt ggataagccc  16140
cctgatttca atccccattg tgccaggtcc tggttaactg aggttaacga agtaaagagc  16200
tgcagacact attaactgct accttaaacc gattactcta gcttagccta ctttccacgt  16260
acagatttta ccagtggaca acatgatgct ttatcttgtt tttctctccc tgggactttt  16320
ctccagacat tgaaaacaga aatactaata aggccacttt tacctgcctg atgcaagaac  16380
agaattttca aactcaacat taatgcaact cctcagtccc tgacaatggc gggtggaaaa  16440
gtttctaaaa atatgcagca gcacaattat cgggaagaga tgagatactg ttacctaata  16500
aaaatgccat aaatagagaa tgatgaacta ccatgggaaa tgaatgcata gaagaggaca  16560
tgctggaatg tgggacagta aaaatcactt aaactttgcg tgaccttgaa gaaagtcacg  16620
atgatctgtt tttccaggtc cctcaaacag tgagatgtgg ctgtttccca agtcttcctc  16680
tccagtgtaa agggtctgaa tttagacgct ttgtgagtct tccttctttc gacagcctgg  16740
agtctctctt gagtctcaag gctgcctgag ttcctctcta acatcctcta ggcagtatca  16800
gctaatgaga caatgaattc catggaggca gcagtgggaa cagaagtacc tctcttggat  16860
aatttacaac actggtgagc agagggtcag atcaccctgg ggtttgtgtc acaaccaaaa  16920
aagtggctgt ggcactgagt tcttggatgg ttttctacag ctggtccaga tttttccatgg  16980
gctcaccttt aaattaaaag aatttctgca ctttgaagaa tttgaaaaca aagccatgtg  17040
tgagaatatg gatccactc atatgccctt gcaagaaata ggttgcattc cttttttccgg  17100
acttaaaaaa aaagcacccc ctctttcttt ttttcagaag gcatatatgt aaatgattcc  17160
aaattaatct ttagcatgtg cctatgttgt tctgatttac taaactttaa aaatatgtcc  17220
attgttgtct gttaacagct tttggcaact ttttcagaga ttgaaatatg tgagcaaatt  17280
agagaaatga gtacaattat tagctagtac cattcaacaa gcgctaaaga tacaaatacc  17340
tctacaaatac ataaaaggaa tgattatagt agattttata atgccatata aggtttctta  17400
tttaacttca ttcttaattc tcaaaataaa atgaaattac atagaagcaa agtaatatag  17460
ttaccagaat agtattttta catgtcttta agtgtatgtt gttgttgttg tttttaaggt  17520
aattatgtga tgttgtggaa agaacagaga cctgggttag ataaaattcc ggttgtctac  17580
cagattgtga tagtgagcaa attacttaac ctctatgatc cttatcttat ttatctatga  17640
aacaggattg gtaatactca tatcataagg ttgaaaggat taaatgaggc actatggaaa  17700
atttctaaca tggtggtgcc tgggacagta gaagatgctt aataaagata gcttttcatta  17760
ttattattag ctttttcagg tgatggtgat tgtaaatgtt taggtaattt tttaaacttt  17820
agaaataatt gattttcaaa tgattaagac tgcttatttt aatcatttat ttttatcacc  17880
agatttattt ttattaccca aaatgtcaca gactgtcata aagataaaaa ttaataataa  17940
ttggccaggt gcggtggttc acgcctgtaa tcccagcact tgggagctg aggtgggtag  18000
atcacaaggt caggagattg agaccatcct ggctaacgcg gtgaaacccc atctctacta  18060
aaaatacaaa aaattagctg ggtgtgttgg cgggcgcctg tagtcccagc tactcatagt  18120
cccagctact caggaggctg aggcaggaga atggtgtgaa cccggggaggc ggagcttgca  18180
gtgagccgag atcgcgccac tgcactccag tctgggctac agagccagac ttcatctcaa  18240
aaaaaaaaaa aaattaataa taatttaaac ccgaagtatg aactgaatta ttttcccttag  18300
tagcacatca cataggctga tgatagtttt ggtgactggt ttatctattc ttcctaaaag  18360
caaactgttg ttagatggat gatcacttgc atgttgtgac tgaactcagc agttgggttt  18420
tatttttttat ttttttatttg cttcagtagc attadccttt cctaccaaga ttcgaacaat  18480
ccatttgcct ttttttccct aaaatctctc atacattgta aatactacat attggctaaa  18540
tatttcctgg acagacatga aggacacata aatcagtctc tgtatgatgt ttctcactgt  18600
aatggagttt atctggctca agaccaggac atttattgca tatcaggttt ctacagttca  18660
ggcaaaagtt tgaggataag gacttactgc aaaaagtctt ctattgttct caaccatttt  18720
ctcgcttagc acatgcagag atttgaaatg gtccgtggta cagtagttgt gtctgtatat  18780
ttctcttgta gaatattaga acaagggatt tgcagtttac agagaagaag gcttggcgag  18840
gtgtttggaa atacactcag aaacctgagg aaatttgtgg aaagagaggc ttattatttc  18900
tagaaatatg ctagagtwcg tttttgattgt gcacctgagg aattaataga ttaagtagtt  18960
ttataaggac tgggggttaat agaatactgg cagtgaagtt tgtcttagga cttcttaatt  19020
ggataatcag tgaagtcacc agatcccagt tagagacagt tccaagtttt acaaaacgca  19080
agataactgt ccaagagctg taatggctta atcatctttg aataatacct ctcactgaag  19140
ctatatcata agaaataaaa atctacattt taaaaaattg gctgtaatca tagggtgact  19200
aactgtccct gtttacccag gactcagggt ttcccaggct gagggacaat gggtactaaa  19260
accaggacag tccaggcaa actgggacgg ttgatcaccc tacccaatgg cctcatctgt  19320
ctcattaaaa tatctggatt acttcgtgcc tcaaaaatat cctcggctta cctgactcta  19380
gacagtcaag aagcttttat taattgtcta atgtatgcca ctttctggag gtgatattgt  19440
tcaactgata gatgagcatc actgattgaa atatttgtg gttttcatgc ttttgtatctt  19500
gtgctgatag ccccacatgg atatttctgt ttccaagttt gtgtcacttc tggagatatt  19560
agcctgaact cagcaaaata ggatgatcaa aatgaacctt tccagtgaat tctgtccttc  19620
ttgtgctgtt gtcatctgac ttagatatac tggccgggcg cggtggctca cacctgtaat  19680
cccagtactt tgggaggctg aggtggttgg atcccttggg atcaggagtt tgagaccagc  19740
ctggccaata tggtgaatga agcccgtgtct ctactaaaaa tacaaaaatt agttgtgcgt  19800
ggtgaagtgt gcctgtaatc ccaggtactc aggaggttga ggcaggagaa ctgcttgaac  19860
cagggagtcg gaggttgcag tgagcccaga tcacaccact gcactccagc ctggcaacag  19920
agtgagactc catctcaaaa aaaaaaaaaa ttagctgagt gtggtggcac gtgcctgtaa  19980
tcccagctac ctgaaggct gaggcaggag aatcgcttga acccaggaga cggaggttgc  20040
agtgggacga gatcgtgcca ctgcactcca gcctgggtgt cacagcgaga ctccatctca  20100
aaaaataaaa atcaataaaa aataaataaa tacataaata aatgaacaca taaattagat  20160
ataccaagaa agtataaaaa agtcttgtg tgaacataaa tgaaaattgg ccaaaatagg  20220
taacagacag ggtcaggcgt ggtggctcat gcctggaatc ccagtacttt gggaggctga  20280
```

```
                                              -continued ggtgggagga ccacttgagg ccaggagctc aagaccagct tgggcaacaa agcgagacct   20340
catctctatg aaagaaaaaa aaatttaaaa gacgtaatga caaacttgct tgccttcctg   20400
cctgccttcc ctaaaatact aagttaaatg caatacagtc cctgacattg tagtttgctt   20460
tcacaaagat ttactgaata cttactctag gctaaacctt gtgctacatg ttggggctac   20520
agggatgaaa garaattggt cttgccctcc aggaaccttt catttagtac agagatttag   20580
tgtgtgctgg ttggtctctg ttctccccct ctcctccaga tctattctct atttcttccc   20640
ctctccctgc ctccaggaag gggggctgga tcactgtggc tcattgctct gtggcttctg   20700
attgagttca gccaatggga ggcatmattt tggcgtggca gctctggctg ttcctctgca   20760
attgcagttc cctcctccaa ggctctggct ctcactgggt tcctgtatcc aataacagac   20820
tcccttaact gcccacttct gaaaacagtt tctgcataaa gctattttca taatttcctc   20880
tgatgtgcct tctgtttcct gtgtagaccc tgattcaata ggaaaataaa ttattgaaat   20940
agaggaagag acaggtaata atagaggtat acacaagtag aatggggcaa taaatggcgc   21000
attttcgcac catcaagagt gcccatgtaa cagagataag taaatgcatc ttgagctgaa   21060
cactgaagga taagaaacaa aggggagaaa gacctagaag gggcaatata cagcaaggag   21120
ggaaaataaa ctactgtgca ttcatgccag tgttagcatt taggacatct ggaagctaga   21180
ggtggagtgg aaaaggagag agtgatagga gctgggggtca gagagtttca gggtggggaa   21240
ggtcttgcag gaccttgtag gtaattgtaa agcatttgga ttttattctg agggtcactg   21300
gggtgtcatt agagactttt gagcaaagag gtacatgctc tgactgaact ttattctgtg   21360
aacaatcaga atcaactaga tggatttaag tatgggtata ccatgaaaga aaattactta   21420
agatccttgc tactcaaagt atgagccagg accagctaca ctggcatmag ctgggaactt   21480
gttagaaatg cagaatccca agtccccgag acaaactgaa tcagaacctg cactttaaca   21540
agatcccagg tggcccattt gtatggtaga gtttaagaag cattggttta aaagatccct   21600
cttgatagga gcatggaaga tacatttgag acagaataga caagtcagag acaggtggga   21660
agggcctaaa acagggcaga agtagggagg taaatgagga gacaaataca aaggaagaaa   21720
atgcacagca cagtgtagac aattcctaaa tacttaaaaa aatttttttt gaaataatga   21780
tagattcaca ggaggttgca aagaaatgcg tagggaagaa caatgcaccc tttacccagc   21840
ctcctccatc attaacatct tatgcaacta tattataata tcgaaaacaa tcaagtgaca   21900
ttgctacaac ccatagagct tattcagatt tcaccagtta ttagatgcac tcgtgtgtgt   21960
gtatgcatat agctctgtgt aattttatca tatgtgaagc tttgctacca caatcaagat   22020
attcaagcca ttagcagaag attttctggt gttacctcct tatagccaca cgcattcctc   22080
catcattaac ccctgggaac aactaatctg ttcatctcta taattattct atttcacgaa   22140
cattttgtag atgggtacat gcagtgtgta tcttttggga ttggtaacag agcaagacag   22200
gatctcactc tgtcacccag gctggagtgc agtgtcgtga tcttggctca ttgcagcctc   22260
cacctcctgg gctcaggtga tccttccacc ccagcctcct gagtagctgg gactacagac   22320
acacgccacc tcacctggct aatttttttgt attttttataa tgatgggggtt tcaccatttt   22380
gcctaggcta gtctagaact cctgggctca agtgatccaa ccgccttggc ctcccaaaat   22440
gctgggagta caggcatgag ccaccacctc caccagcttt ttcattcata ctttctttga   22500
agttcatcca agttgtgtgt atcaatactt cactccttcc agttgctgag tagtattcca   22560
tggcttggag gtgctagagt ttattcatca cattcaaccc attgaaggmc atttgggtgg   22620
cttccaagtt tccagttttg ggctattatg aacaaagtta ctatgaacat tcatatacaa   22680
tggatacttt ttgtatgaat gaatggaata gaatgagatag gatttagtga tcagctatgt   22740
gggatgaaga gtggcataag tagtaaaaag taacccctcaa tgcaatgtgc agccagcaag   22800
taccacaaaa agagtttatt ttgtttcata catatatttc tatatataca tacacacact   22860
ttattaataa ccaaatagta tccttttcaa atgaaaacag taatttaaca taaactatga   22920
acttaaaatc taaagtaaaa cttgacaaca gtgatgcaga atttttttgct ccttagcta   22980
gttaggtctg tgttcttatc ttatgaccag gaagaactag gtaccctgac atcaaagaat   23040
gagtggcata gaatttatta agcaaaaagg aaagctctca ggaaagagtg gggtcctgaa   23100
agcaggttgc tggttgcccc ttcgtagttg aatacaaggg cttctatata aaacctgatg   23160
gggccgagtt ccctgttcgt ataaggcatg aattcctggc ggctccaccg ccctccccca   23220
gtgcgtatgt gggaccttcg tccactaggg acatgtttag acaagctccc tgtgcacgtt   23280
cccttatctg cacaaaacat gggttggagg ttctccgggg accccttcctt tactttctgc   23340
ctaaagcaag ctggctaact cctttcaaca atactaaaga catacagaca atggttctca   23400
gtacaatcat tttaaatatt taagtaaact aaaatggtg tttgttttga tttgacattt   23460
taaaagatat cgctgttcta aaaattctgt gttttttagtt gtttgggctc ctattctaca   23520
atgtgctatt actattaagc attcttgtat catggcattc ctcaaaatagt ttttaaatta   23580
ctttttaattt gaagaaggaa cattctgtac agtcacggaa agtgtcaaaa atgaaaatga   23640
ggcaggggtgt ggtggctcac gcctgtaatc ccggcacttt gggaggccta ggtgggtgga   23700
ttgcttgagc ctaagaattt gagaccagcc tgggcaatat ggtataaccc tgtgtgtaca   23760
aaaaatacaa aaattagcca ggtgtggtgg cccaagcctg tagtcccagc tacttgggaa   23820
gttagggtgg gaaatcctag gtgacagaat gagaccttgt ctcaaaaaaa aaagaaaaa   23880
agaaaatgat aaaggataca tatcaggaaa acatgcatgt tattttgtat catctacttt   23940
agagtaattc cagtatagtg ttttttttgt tgttgtttgt tttattttttg agaaagggtc   24000
ttgcgctgtc acccaggctg gagtgcagtg gtacgatctt ggctcactgc aacctccgcc   24060
taccaggttc aagccatcct cccaactcag cctccagagt agctgggact acaggtgtgc   24120
gccaccatgt ccagataatt ttgtattttt tgtagagatg ggattttgcc atgttgtcca   24180
aatgcctggc ctcaagcaat ccaccctcct cagcctccca aagtgctggg attgcaggcg   24240
tgagccacca cacccagccc cagtgtagtc gttttttctt ttcttttttt ttctatgttt   24300
taatgaattt acacgttacc caaatgttcc ctagttttc tgccttccaa gatcactctg   24360
gaagaatatt taagaatata ccaaataaga atatgcaagt cctcccctaa gggtggcagg   24420
aagaacaccc ctccccccaga tggtatttag cgcctctggc tgggaacggc ttccccatgc   24480
tcctaggtca gggtcctctc ttggcatgac actaccacca cagtgcagac ccacaacagg   24540
gagaaggacg gccacagtcc ctcaatcccc ctttccaag atgtgcacag cctgactcct   24600
aactccccac cactgactct aggggaaaaa cagcacaggg caggaaacga ttttccatgt   24660
caccaacctt tctctgaggg aacctactgg ccacctccct cttaggacca ggccatcgtc   24720
cacaacgtgg aagtccagct tccgttcaaa tcggagttct ttcttcatga catttctttg   24780
caaagtcccg gaaccacag ctctgagact ctggctgtcc cccaacccac cccatcttcc   24840
ttgtcctcac ccctggtcag gagaagccaa acatcagtc agcttccag taatcaagcc   24900
tggctttctc acccagggct cgccccagaa caaccaccg cttctttcag tgtagccaaa   24960
aggctattgg agtcttctca aatgaaagag attttatcaa aggcttggag aagaaaagaa   25020
```

```
aaagaggatt atataataaa acgtaaaaca acaaacatat acacacaaac aaaaataaac   25080
gtgagatatg attctcccgg agtgtttaga gcaggaatgt tcttgggcat ctgccttccc   25140
ccaccagcac cccccacaag gcaaggccag ttcaccctca gtgctcacta ctttgcagtg   25200
ttcatagaat atttgtaata attttaggcg gctccctaaa atttcttttc ttttcttttc   25260
tttcttttaga gttgcgtccc tctcggttgc caggctggag ttcagtggca tgttcatagc   25320
tcactgaagc ctcaaattcc tgggttcaag tgaccctcct acctcagccc catgaggacc   25380
tgggactaca ggtatgcacc gctataccccg tctatctttat atttatttat ttatttagag   25440
acagagtcta gctctgtcac ccaggccaga atgcagtgac acgatctcag ctcactgcaa   25500
cttctgcctc ccagatttaa gggtttctct tgcctcagcc tccctactag ctgggattac   25560
aggcttgcac cacctacgtc cggctaattt ttgtattttt agtagagatg tggtttcacc   25620
atgttggcca ggcaggtctc gagctcctga cctcaagtga tccacccggc ctggcctccc   25680
aaagtgctgg gattacaggc gtgagccact acgcccagcc tattttattt tataattttg   25740
ttttagacaa ggtctagctc tgttgcctgg gctggagtgt agtggtgcaa tcacgattca   25800
gtgcggccct gatctcctgg gttcgagtga gccttagcct cctgtttagc tggtactaca   25860
ggtgcatgcc accacctagc taattttttta aaattttttt gtagagacgg ggtctcaccc   25920
tggtgtccag gctggtctca aactcctggg ctccagtgat gctcccacat tggcgtccca   25980
aagtgctggg attataggag tgaactactg tgcccagtct ttttaaaaaa ttttcaagag   26040
attggggtct tgctatattg cccaggctgg tctccactcc tggtgttaag cgatcctccc   26100
acctcagcct ccttgagtag ctgggatgac attacaggca cacactgcca ccactggctc   26160
taaaacttct tctgtgccat ttgtgcactt caccccaattg cctctttgta gtaattaatt   26220
aggatctagg gtgaaaaaaa agtcaacagc tatatatagt cctcaaagtt ttgtacgtat   26280
ctgagcagtc atcagttgca cagtgcagag ggatgaactg ccgtcccgcc acctaaaaag   26340
cattagtgac catcagggaa ccgtcagatg catgccagac taaagcagag tgaggctgtg   26400
ctgggtgctc tgtctgtggc tgcccgtgct ctcacttccc tgtcttgctc tgtgccttttg   26460
ggaggttgac cctgagttgg catctcaggg tctcagtctg ctggtttcct gsgttcccct   26520
tgaaggctac tgctcccaca aggcaaccac ggtcccgct ctggctctca ctgagctcca   26580
gaatcattgt ttcctccct tacccaagtg agaataatta tgttttattc cagaaccctg   26640
acaaatgaag aggcctaaaa acccccctagg tattatccga tcttggtgat cagggaggtg   26700
tttgtttttgt ttttttaatgc agacacatag ttttaaaaat tattcacttc atctactgta   26760
agaaaagtca tattaattca caattttgat taaaacaaac aaacaaacaa acaacttctg   26820
tgacattttg gctaacaagt ggttcaatat taaagctttg tccaccaggt gcagtggctc   26880
atgcctgtag tctcagtgct ttaggaggct gaggtgggag gatcacttga ggccaggagg   26940
tcgaggctgc agtgaaccat gatctcacta ctacactcca gcctgggcaa cagagtgaga   27000
ctctgtctct aacaaacaaa caaacaaata agtatagttc tttcaagcat ggcagacaat   27060
ctgtctcctt tggcctgggt ctctcactgc cttttagata aaaatctggc aataaccaaa   27120
gagttttcat aaggcctgtt gatctattta taagacatgc atataattta cttgaccatt   27180
ataataccat tataataatc taaatctatt ttctttatcg tccaataatc cacagagtca   27240
gcacacaagg attcttttttt ccatatatag gctgagtatt cctatctta catgcgtgac   27300
gccaaagtgt ttcaggttct ggatgttttg ggattttgaa atatttgcat atacacaatg   27360
agatatcttg gggatagaac ctacatctaa acacaaaatt catttatgtt tcatatacac   27420
cttatacacg tagcctgaag gtaaatttac acaatatttt taataatttt ccacataaaa   27480
caaagtttgt atacattgaa ccatcaggaa gcaaggtgtc cctgtctcag ccacccacaa   27540
ggacactctg tagttgtctt tcattcctga ttccgaattt atacgctact gacaagcaat   27600
cattttctta cacttattca cacaagagca cttagtaaaa aatatgacat atatatctgg   27660
catgctcaga aaagctattt tgcagcagaa aggagctggg agggtccttt ttttccctttg   27720
gggacacgga ataaattgtg tattatgtgc ctgcattttg actgtgaccc catcacatga   27780
ggttaagtgt agaattttcc acttgtctct ctgtgcttaa aaagtttaga ttggccaggc   27840
atggtggctc atgcctgcaa tcccatcact ttaggaggcc aaagcaggtg ggtcatttga   27900
ggtcaggagt caaaaccagc ctggccaaca tggtgaaacc ctgtctctac taaaaataaa   27960
aaagttagcc tggcatgttg gtgcatgctt gtaatcccag ctactcggga ggccgaggca   28020
ggagaatctc ttgaacctgg gaggcagagg ttgcagagag cagagatcac tccattgcac   28080
tccagcctgg gtgacaaagc gagactctgt ctcaaaaaaa aaaaaaaaaa aaggttagat   28140
tttggagcat tttggatttt ggattttgca ttaagtgtgt tcaagctgaa aagaaaatcc   28200
gatttgctca ggacaaactt aacaaaacaa gtgagatatt ccaatactat atatatgctc   28260
ctgtttatat ttccttaatt aatttggact tgaacaact tggccaatta tggattagag   28320
gatgagactt aaatgttact gtacaaggga tagaacgatt cattcctcta tgttatcaaa   28380
tacttatggt attttmccca tcctgctgtc atgcagatcc agaaccaaa ttaaaacaca   28440
tttgccgggg tcataataat gtggccagaa tttaaagaaa aacttgattt ttaattatgt   28500
atgattttgc ttgtttagtc taccgatttc tatttgcttt agcttactca aaaataaagc   28560
gcggcactc gaagactcaa tagtcttcca ttcatgtggg ccttatatat gcacgggccc   28620
agatgcaata catctggcgg tctgcttggg ttggccactg gattgaagga ggcagagaag   28680
tctgggatga ttcccaaatg tctgatctg gtgacaggga gatatggcag ggcgagctta   28740
ggggaaaaag ctgggttagg aactgttgaa actgaaatcc ctgaggsytk tgccgacaga   28800
gagacagccg gtagaaggtt gtctttgcct gtctgtggtt ccaggtaact tcatcgaaag   28860
agagtttcag gcagtagaaa taagagcacc caggaacaca ccccagggaa gagaaacatc   28920
tgacggagga cagaggaaga aggtcagga atgagactga gcaggtgtca tgtgtctgac   28980
accagagcct gacacatagt acgtagtaga cactcagcaa ataccgtaac agagatgaat   29040
ccaaggctgg gggaggtggc tcacgcctgt aatcccaca ccttgagagg cctaagtggg   29100
aggatctctt gagtccagga gttcgagacc agcctggaa acatggtgag accttgcctc   29160
taaaaaaata aaaattaaac attaaaaaaa gagatgaata cataacctgg ctgctggagc   29220
caacatgggt tgggtgagcc cactcttacc agcagctaat caaaaattttg cctgaattc    29280
tgaggctcct gtcctacgtc ttggctgctc ctcccagatc accttctggc cggtcccaag   29340
tccacttccc gtgctccttg ctcccttcct cctggtctcc ctcacacttt cctttcctac   29400
tcccttcccc tctgtgggcc tggctcagcc cagcacaggg agagccctgt gccacctatt   29460
acagctcacc tgcaccttg catctttcag aaaggagcac ctacaagata acccacccc   29520
cacctttttt tttttttttt tagtagtaca gattgcctct catagcataa ttgggcttca   29580
ttattatcct taaagaccct ctttctgtgg cggattggga tggataaaat aaagaagatc   29640
gagaggttga agaaccccatc ctgttttgcc agtgagaagg ggatagaatt aaaaggatta   29700
ggagggctca ggcatggtgg ctccagngtg tcatcccagc tactcaggag gctgaggcgg   29760
```

```
gaggatcact tgagcccagg agttggagac tatagagcac tatgattaca cctgtgaata   29820
gccactgcac tctagcctgg gcaacatatc aagaccctgt ttctagggac aaaaatatnn   29880
tttaataaat ttaaaaatta agggaaaggt aaccacatcc tgctacaaan aaaagaagnt   29940
ggagaggtan gangaggacc aagagctaat ggcatcattt acacaaaaag agatgcttta   30000
aaatcagttg ctcatccaat tccacaagga caataagtaa gaaagaggat agaaagtcac   30060
cggtggattt ggtcatcatt ggcttcttga tgactttagc aacaaaaatt cttgttgta    30120
gtgagagtta gaccctggtg gactgggtag ggggttcctg gatcatgagc aaaggcctgt   30180
gccagccaat ggcccccact acactctgcc ccggcctttc tcatctcaaa aaatggcatc   30240
ccccatccaa agctcaagtc aagaatccag cagccacctt tgattctgca cttcccctca   30300
cctcacagtc cagtcccatc tccaaaataa gttccaaaty tcaccacttc tcattctcca   30360
aagaggmacm attatctctt tcctggtgat taaaacagct tcctaactgg sttcccttct   30420
accttgcttt cccatagtcc attcttctca ggacaacaac agtggccttt taaaaccagt   30480
gcattattgt tgcccttttgg gaaatcctcc acaattatcc agtcttgctt caaaaaatgt   30540
atgtatttct gactttttac cctgccctac ttacaggata tgcacatttc tgatctccag   30600
ccaatatcac acttcttctc tcactgcact ctgccacct tggccaagtt tgttcccact    30660
cctcttgcac ttgctctcag atctcagaag aggcgtgctc cttgtctttc aggccagccg   30720
gcttcacaca tgtgccacgt gcgcccctcg ctcagaaggg atctgtactc ggtttggatc   30780
tattgttgcc atcttgaaac tcttaatact cttttgaacac ggggcccgta ttttcatttt   30840
gcactgggtc ctgaaaattg tgtagctggc tctactttca gggattgtat cagaagtctc   30900
ctcctcaaag aggccttcct cggccactta tcctcaagta gctcctcccc ttctaagtta   30960
ctggctatcc catcattccc acttaatttt cttcataaca gttgtcatgc ttttatacat   31020
tctggcttct atatttattt gtgtattgtc cagttccctc cctttggaac gcagcgtggg   31080
cacctgcaac gcagagacca ctgtatcccc ggtgcagaat gtaatgagtg cctgatacat   31140
ttgccgaata aactattcca caggtttgaac ttgctggaag caagaagaag actattctgg   31200
gtaaaatgga aatttttaaat gtacttgata tttatataca tccctaatcaa taattaaatt   31260
tgtgtagtgc tgatctaaac agataaattc tggcttcatg atgatggtga agtggaatat   31320
aattttctca ttttgtattc aaactagatc ttttttcatga aaggatttga agtctagatt   31380
caatgcctac ttttgctact tatgttatat gaaactaaaca caattttttt attgtatttt   31440
tttgagatgg agtcttgctc tcgttgccca gactggagtg cactgctgcg atctcagctc   31500
actgcaacct ctacctccca ggttcaagcg attctcctgc ctcagcctct cgagtggctg   31560
ggactatagg tgcgtgccac cacacccagc taattttttgt attttttagta aagatgggct   31620
ttcaccatgt tggccaggct ggtcttgaac tcctgaccca agtgatctgc ctgcctcggc    31680
ctcccaaagt gttggattac aggcatgagc cactgtgcct ggcaataatt ttagtttagt   31740
ctgaatttt ttttttttttt gagatggagt ctcgctctgt tgcccaggct ggagtgcagt   31800
gacgctatct cagctcacag aaacctccgc ctccaggtt taagcaatcc tcctgtctca   31860
gcctcccgag tagccaagat tacaggcacc tgccaccacc cccagctaat tttttgtattt   31920
ttagtagaga tggggtttca ccatgttgac caggctggtc tcaaactcct gacccaagtg   31980
atgtgtctgc ctcagcctcc caaaatgctg ggattacagg cctgagccac tgtgcctggc   32040
ctagtctgaa tttttttaaaa aggttattgg tctaccttcc aatgacattg cactctgtgt   32100
ggctcaataa aacattttca tttataataa ctaatttgac ctgctcagca atctctaagc   32160
aagatagagt agctgtaatt cttcattttta caggtcatgt caaatcatt cgtacattcc    32220
agctatgtac gagagcttgg tgagaatatg tgaataataa tcacagaact tcagagctgg   32280
gagtaacagc tggaaatatt tcttccaata attgcatttt ttatgagagg acgatgaggt   32340
ccaagtggac aggaccatga gacaatcgtg tggcaaggaa gttgatgcaa tttgaccctct   32400
taagtcagtg atcttttatgt ccatcggtcc tttccagcaa gtgagttagc caacctttgc   32460
ctgcaaagga ggaaattttt aattgaggat ttacactctg cttctaaaat tttgcttatt    32520
attgtgaata attttcttta agtttattaa atgaatggct gaataaatgg acataaggaa   32580
agaaggaagg gaggaaggaa gggagggagg kaaggaaggg agggaaggaa ggaaggaagg   32640
aaagaaggaa ggaaggaagg aaaaagaaga gaggaaggaa agtctgatga   32700
cagctgctat tatattctac gtggataatt tatttagatc tttatacttt atcttttgtt   32760
ttacttctct tatgcatatt ctcctcaact ttttttcagt gggccagagg aggaggactg   32820
cctcttgtga ctgtggaagg acttctacca ggctaacacc cctggcctct caccctccca   32880
ttctcaccc tgcaaagcag agtgctattt gattcatgtt cttagtctgt ggatctcagt    32940
tgaggagaac tcgttagaga tttgccctct ttctgtcttt ttgagacctt actggtgcaa   33000
gacagcaaat cctagctggt gtctacagga cacatgcact cttaggttac ataactgcag   33060
ggaccactgt cattgtatcc tggagctggt tctatataag acacagcctg agcagtatat   33120
aggcttccta gtctgctcct ggccaaatgt cccagttgga agcccagagg ttgtctggat   33180
atgccagtgg caggatgggc aagtctaact caagggtgac atattagcaa gacctttatg   33240
gccatgcatc taagatgctc tgtccaagcc tgaacttagc aacaataaac ctgacatttt   33300
gaaatccatc tgattcctct atttttccagt tgatgccaca tgcatcctct tgccatcttt   33360
cttaattaag atgactttgc ttctaaatct ccttaattat caagcagcta tctacaatat   33420
tttgtaatcc ccttaaatct tgagcataat gatgtcataa ttatgaaagt gmccggwttc   33480
acatgaagta ttgcttaatc ttaagaacaa aatggcagct gtgaaaacag atgaagtaat   33540
tagaggaaga gccttttttgg aagcttcgag atattttcaa agtaattagt actagttagc   33600
aataaagttc tgttctgaga aattgctctt aaaggaggaa catggattaa agaaaaaaat   33660
ctgctactag gaagtaagcc atcttcctat gtgtgtgatt ggttttgctt cctgaaaact   33720
ggttccgttt tcaacaaaat ttgggtctgt tgaaaagaa cacgcagatg ccagccttga   33780
tgtcaaacgg gcccaaactt ggacagtggt aaactaatga gcaatggtgc acagagtcag   33840
ggtaaaagct ggacaatttc ctatgaccaa cttttccagg actctgctct gctcttcctg   33900
agaaaaatac ccaaagtgct gcctcttcca ttggcccaac catgcatctt tcaggatagg   33960
mcacatctgt ttataggtgt ggattgtagt tgctcataag tgacattagg ctgtttaaaa   34020
taataatagt tcgagttttg ctatgagctg atctgttttc caagagagct aagagttttc   34080
cagctaaaag agggaattag tgggtaatca aggcagctga catgggtgt ggctgggcct    34140
tgaatgtgtg tcactctctg tgcccaggca gagcaaagat aaactccaga ctgcatgttg   34200
ctcagagacc aggaccaacg tcataggcgc cctaaaaggc aggtggccca gttcagaatt   34260
gtcaaggtct gacctgcttg gacaagtgct gagtacatag taaggatgga ttggctagtc   34320
tctcaaaact tgcaaacagg gcgcaggtga tcttgagatt tcaggtgccg gagagaccca   34380
tcgtgtgat tccagagttg gctatcatga ctaacagctg tctaagttgt tttttaaatga   34440
atcattaagg gctacatttt cagttcagct aatcaagtag caaattacgg tgggtctaaa   34500
```

```
atacttatct attgcattat gtatatgcta gactttatca ctttagttgg ttatatcgct  34560
tcatatacta acagtcaaaa aatgccaaac gagaaaacaa acaaacaaaa atgccacatg  34620
actgtgtaaa tacacttttc aaactgtttt atctaagagt ttactcactt tcacattgtg  34680
gcttatagta ttttcaatct aagagactaa ttttgcttac ataggaaact acatatttta  34740
aattgaaaat taaaaaaata ttttttaaggt tttaatgagt cctatcaaaa cacatttgta  34800
tataggaagg tagcccaagg tcactgttgc caattgtgta cacagcctgc cctmtagtgt  34860
tttcttctaa acagcaccaa attttagatc atagttgtaa atctcaaaat gttgggttaa  34920
taggattaaa cactgtgtca tcaaattgat aggacacagc taaatccctg acacggatga  34980
aaattaaagc agagaaaaac gaaggtcctt ccagaagctg gtggcaactt cactggggag  35040
atattgcaaa gttagtggta aatacactat attaaaaagt tttgttttgt aaatagagta  35100
atgatagaag aagagttagt tgaaatgatg tatgtaaaat gtgataactg cataattact  35160
agtacagttg ctagtttacg actgtattaa aaagacattc caaatgttga tcaaataatg  35220
gaggtttctg tggttgtttt cttttttaaaa tagtaaatat acgtaaagca gataaatatc  35280
cccctttgtg gagttaaaat aatctaactt attttatagt tttaacttta ttaaagcata  35340
cgactattct aacttattta accttttctta gtaaagtttt aacctctgta tttagaaatat  35400
ttgtaactaa tgtgtatcga attaaactca aagggaaatt cattaactga gaagaaaaaa  35460
ttttaactgt gcactattca catagcataa tgggtttat aaggagtatg agaaaaatgt  35520
gtgtggttgg ttttgctttc tttaaaaata atagcgaacc acgtaggtaa aaactcactt  35580
gagaacatag acttttggag ggaaatgcca gtgtggtgg ctcacgcctg taatcccagc  35640
actttgggag gccgaggggg gcggatcacc tgaggtcagt agttcgagac cagcctgacc  35700
cacatggaga aactccatct ctactaaaaa tacaaaatta accgggcttg gtggcgcatg  35760
cctataatcc cagctacttg ggaaggctga ggcaggagaa tcacttgaac ctgggaggtg  35820
gaggttgcgg tgggccgaga tcacgccatt gcactccagc ctgggcaaca agagcaaaac  35880
tccgtctcaa aaaaaaaaa aaaaaaaaag aattttgagg aaaaaaaat ccctctaaca  35940
gattcgaatt aattcgtgt ttcgagatgt ttacaaaatg aagcttggac tctgagagga  36000
tgtgatctat cctctccatt gcattgagtt tcaagtactt cacatggcgg ctttttttaa  36060
ctgtcgtgaa gtttaaacca aatagggact agaatttgtt tgtttttta acttacattt  36120
caagcttcct tatgtctcag tgcacattagc ataagttgtc taaagtcata aggaaaaatt  36180
gacagaaaaa tgctttggag ccccaggtgt tttcaattga tgccaacaga aactaaccaa  36240
atggaagaca tttgatgcgg gttttattttt cctttgcagt aacagcggga acatgaagcc  36300
gccactcttg gtgtttattg tgtgtctgct gtggttgaaa gacagtcact gcgcacccac  36360
ttggaaggac aaaactgcta tcagtgaaaa cctgaagagt acgtttggtt tcttacctgt  36420
gctgtgtcct gtttgcatgt tggttgtcct gctggcgttt atagtgagtc gcagttgaga  36480
gataaccata ttcgctgttt tcacggtgaa acgttctcaa ggcgcttaaa ccaggtcatc  36540
ctgacgccaa acatctgggt aaaaatagaa aattccaatc acgtctctgc aggcgttcac  36600
ctttccagat gtttgtatca tgtagataca acttgccagt tttttcactg catttttttg  36660
tatcatccag atggttggtg tcatctcagc acagctctaa tgaacagtga aatacttttc  36720
tagcatttga aaaattttaaa ccattagagt aatctgtgca attgttctta aactagtgaa  36780
agaatggtt ataattacgt tgaatctggt tgttctgtgg ccattaactt gcaactttgc  36840
ttggtgatat atactttggg tacttaatat atagaagaac aaattagcta aaatgcagct  36900
gatttggggt ctgtaataat cagagtcaag aatgagctcc tcagtaggcc acgttggcta  36960
ttttgaacag ggaatgacaa tgaattttaa acttactaag ggcttattaa aggtgtataa  37020
gacacgtcca ttgagttatt aaggaagctc gtattacatg ggatacttc taggtctcgt  37080
gcctccttat taggtaactg aagctgaaag aaagagaaat tgctgactgt gtttgaggtc  37140
cccagctggg cacttaatat aaattatgaa gaaaatgcaa aattttctct aaatataaca  37200
cacttgagtc ttaaatgaaa gaaaaaaaat ggataaatga aaacagggcc tgagcaagtg  37260
acaagaatga ggttcagtga actctatttg tttaggcgct cacaagtgag gagtagaagg  37320
tatggtccgt gtggcagctg tgtccatgtg gcagctgaca gctaattcat tatgatctgc  37380
tttcagaata tgagcctata agagaacaat taagcctctc ttttggagac atgaaaggtt  37440
ggtgaacttg gtgtttttgta atctgatcag atctccaaga aaaaattgcc acatgtcttt  37500
taggtttttc tgaggtgggg gagatagatg cagatgaaga ggtgaagaag gctttgactg  37560
gtattaagca aatgaaaatc atgatggaaa gaaaagagaa ggaacacacc aatctaatga  37620
gcaccctgaa gaaatgcaga gaagaaaagc aggtacagtc attgaaaata atgtctgttc  37680
ttacacagat ctggaccaga aatactgcac ttgttagtgc gattgatgaa ttacttattt  37740
tccttagtaa taaatttcat gggtagctgc ttttatttga ggaaaagttt aagggaagct  37800
tcagatttcc ttgaagaaca tatttcgtgt aggataggc tctgcaagac tccacccgg  37860
aatctgggggg attcatctct gtttaagtgc tgctttctca aaaatagatt attcttggtc  37920
tcttctgagt taggatattg agtcaaaagt atttgaagag tttttttttt tactagatca  37980
gtggtctcca gagttttttgt tttttgtttt ttgtttgttt ctgttttttga gacagagtct  38040
cgctctgtca cccaggctgg agttgatccc gctcattgca acctccacct cctgggttca  38100
ggtgattctc ctgtctcagc ctccctagta gctgggatta caggctccta ccaccagcc  38160
tggctaattt ttgtattttt agaagagacg gggtttcacc atgctggcca ggctggtccc  38220
gaactctggg gctcaagtga tccacctgcc tcagcctccc aaagtgctgg aattacaggc  38280
atggaccacc gtgcctggcc cagagatttt tggtctctca ttcctatgac taaaaaattt  38340
gttaccactc actcctaaat atatgcatat tcatttactc atgaattaga tacatgaatt  38400
gctaccattg atatctcaag gcacaatatg tatttaaggt gagattcatc attagcgagt  38460
gtggatataa gtccacattt caaataatct tctagatatt ttgaaacttt tagccgactt  38520
gccagatctg attagatcac catagttttc ccttgtcact tggccaataa agagctcata  38580
atgatcaagt gtcagctctg ccatttgctt ttggtccgct tgagcttaaa ttattcattt  38640
ttaaaatctg ccaagttttt ttttttttca aagaatcttg ttaagcctcc tgtccattta  38700
gtgaaggtta ctttagttaa aactagataa taaaatccat cagtctacct gagttctctt  38760
acatgcaac tcattacaat tgggtgcatg tgaacagagc aagggaacta tagttgattc  38820
ttctggaatg tagaggatcc ccttttcccc aaggtcatca catacagttg ggcacacaca  38880
gtatctgaca tatgcatctc aagagagtac catgtatgca tcagcctaat tcagcctaat  38940
cacttttca aattcaaata gctttattta acagcctatg cttgaactac atatttatc  39000
catggagaat acatattata ttcaaatgtc tttggaagat gtaaaaaatt gttcatatgc  39060
cacagtataa agttcagtaa atttctaaat tatagacatt gaatagcttg cagtttaatg  39120
acattaataa ttaacatcac actcaaaaca atgactttt taaaaaggt tatcttcaam  39180
cattmccctt aaatcaaaga ggaaattaaa actgtaacaa aaataatttg gaaatatttt  39240
```

```
tcaattttaa tgttgagagt aaattacttt ttaaatktat ttttatttt tgaaaaatgt    39300
taagttgtaa aatacatata acaaaattta ccatcataac catttttaag tgtaacgttc    39360
agtagtgtta aatacattca tactgttgtg caaccaatct ccagaattat tttcatcttg    39420
caaaaactga aagtctatac atattaaaca atgccccatt cccccaccc cagtcagatt    39480
tttaatttaa aaatacaagt ggaagttcta atattttcta tctatccctc tatctataaa    39540
gttgggggcc actgaattcc agattgctgc ttgcatcttt ttacttctga gcatcatggc    39600
ctctggagt ccgttaagca actggagccg ggtagtgtga caggctgacc ccaaagctgc    39660
gtgtcagcgt caccggactg gttgatgttg cagcctcacc tactgccctg agtcagtcag    39720
ggttctggca aggaaaggag aatgcctgac cagcagctgc aaaccttct cccttttggc    39780
agcaatcaaa agattttgag gaaatctaaa atagctcctc atcaggaaaa tgtggaagcc    39840
cctccagctg ggatcttccc tggtgggctt gtgagcctgg ccatctggga atagagacac    39900
tagatagcac tcatacactc ttcacaaaac acattatcac atggaatgtt ttgaacatct    39960
gggtaaacca ctactttcat tttatagcta agaaaactgg ggtttgagat gtttgttaat    40020
taacatgtta ctccaacact gtaatgaatg aactgagata aagtcagcag atgtgtgcac    40080
gggggaccca gtgattttct gcttttctca cttccctgaa cctcctggca aggaggacag    40140
ggtatacagc tttaacaaga atattccact ttgggtgggt caagtaagca aatgtggatt    40200
tcacttctgg ccctgaagaa tccaagcaac tagtagaatt tttgtttatt cttaaaaatc    40260
ttattgtaca aaaattcatt gaattatact cttaagtttg aggcactcaa ttagaaagtt    40320
aatcggaaaa aaaaaatctg tttaaccctg agtatccctc cctaaaatta cttaaagcct    40380
agaataaagg tcagtttaga caaattatga attggcaaat atggtgttag caaccctagt    40440
ctcccagtat tgagccccac ccattctcaa gagtactgct cagtggtgac ccagcatcct    40500
cactgtcccc ttcctccacc cctccttatt aatatttagt gagactatct gaacttatt    40560
aagtaggaaa ccctagagaa ggttagagtg acttgacctc caaatcaggt tttatttgta    40620
tgtgtttta atgaaatggg gtcttgctat gttgctcaag ctggtcttga actcctggtc    40680
tcaagggatc ctcctgcctc acttcccgag tagctgggac tacaggcact agccaccatg    40740
cctggctcaa tgccaggtta atatagcgct tttgataaac tgtcaactat aggaatagag    40800
ttataagcgt gaatctgcca gttggtacaa tgtctagcag gaaacggaag gcgtcgatag    40860
gatattcctt aggaatgttt aatagacaga ggtctacttc ttccatgcca atgtttcact    40920
tccaaaactt gggacctgtg atttggtaac tgtttttttgt cctgcttctg ggcagtgaat    40980
ggaaggaagc ctgagagata ctagttatta tactggacta gttataataa cagatgtctt    41040
gcctatgata atggatacta ggtataataa tagatgcctt gcttgtttag ctcatttaat    41100
gcaaagacct tgagaagtag atactattat tcctattatt cttatttgca aatgaggaga    41160
ctaaggctta tatgtattaa gtaatttgcc caagggtaca cagccactgt agtttggaat    41220
tgggaatatt aggattttgg cttatgagga caatgagcag aatatgtaaa attgggactg    41280
attgagaaaa tcctggaggt attgttactt gccttgagaa acaacttt tttttttttt    41340
tttgagacag agtcttactc ttgttgccca ggctaaagga caatggcacg atcttggctc    41400
actgcaacct ccgcctcctg ggttcaagcg attctcctgc ttcagcctct gaagtggctg    41460
ggattacagg cacccaccat catgaccagc taatttttgt atttctagca gagacagggt    41520
tttactatgt tggccaggct gttctcaaac tcctgacatc aggtgatcca cccgcctcca    41580
gcctcccaaa atgctggaat tacagtgttg agccactgca ccctgccgaa aaacaaccac    41640
tttaagatgt tagattccag ccaagtgaag tggctcatgc ctgcaatccc aagcactttg    41700
ggaggtcaac ctgggcagat cacttgaggc caggagttcg agntcagcct gggnaaantg    41760
gtgnaactcc gtctctanta naacatacaa aaattngccc ggcatggtgg cacgcacctg    41820
tactcccagc tactgggggag gctgaggcag gagaatctct taaacctggg agatggaggt    41880
tgcagtgagc tgagattgca ccactgcact ccagcctggg cgacacagcg agactctgtc    41940
tcaaaaaaaa aaaaaaaaaaa aaaagatgta agattccaaa attgttctac aaagtscaag    42000
gacacacaca cactcctgtc tgggtcaaaa tgtatattgg caagctgggg ccctggcagt    42060
tttcttacgt ggatcatagc aaatgctacg tggcttagca gccaaacttt acaatgagga    42120
caackgacaa atcctagcca ggcagagaag atgtggaaga ttgtcagtgc ccaggtgatt    42180
ctttgggctt aatactccag gaaagggtca tttccattag ctctgaggct gtcttcttat    42240
ggccagatcc actatactca cttcattccc ctgcacgata tctcggcatg gagggggctg    42300
gggttcagaa gtccacactt gcagggaagc cagaggtttg ggcaggggca caggaagaaa    42360
ggtctgttgc accatggtgc tgacccgtga ggcactccag gggcagggct gaggctcgca    42420
gggacaggtg ccactgctgc tgggctcctc accacccaga gcaggacttg gccaagtaca    42480
gcaagcacca aaggggggag cactgggaat ataacaaga agaacaaagc ttgtttatat    42540
tcccatttat atttatttaa tattacatta tatataaata tatttattat attacattct    42600
aattgcagag atgccatcct gcgtctcagg aattacaatg taactcaacg ggaacattta    42660
acttgacata caagaattgt actttcttgc aatgtttaag gatatacaac aattaaagac    42720
agcataaatg aaagaattaa aatgtaccag ctttataaac tgtaaagccc actttcccca    42780
tgcaccagtg gatgagaatt gaagacagac ttaccggtaa ataggtaaat cacagttgtt    42840
cccagatcgg gatggcatct tcattgtcag gtcacccaca cctagagtaa tgtctgtcac    42900
atagcaaaca ctcagtaaat acttagtgca caaatgaatg aacagatgaa taagattac     42960
agtcttcaat aggaatcaat cagtgctctt ttcttaaact aaaacagaaag ctttggggag    43020
atctgacagc tgcgaggcac ctgaaggaga aagaatgaaa aagcagttta gaatgtgtac    43080
atttcaaagg gtgaaatcaa ctaaggtgca catagatcat gaaatggaaa ttggactttt    43140
gtttctactt ttaactagga ggccctgaaa cttctgaatg aagttcaaga acatctggag    43200
gaagaagaaa ggctatgccg ggagtcttg gcagattcct ggggtgaatg caggtcttgc    43260
ctggaaaata actgcatgag aatttataca acctgccaac ctagctggtc ctctgtgaaa    43320
aataaggtaa gagaaaaaga gagctcaaga tttcacagtt cttaaggcac ctatttcagc    43380
ttactttttt attaatttat gttaatattt agaacggaga tgcctgatct gatagggggcc    43440
ttttgctttc tagaatctaa tactaatgtt tacataccat cacctgtgta tacgcaattt    43500
ataaggtaga gcaccattca gtggtcactg aatgcatctc ttaaaatatc ctggcttct    43560
gccttgtatt tgttatttgt gaacatgttc ccactagata gtaagctctt tgagggcagg    43620
gatcatatct tatttgtctt cacttatgca ttggtagtga ccagtaaatg tttaccaaat    43680
tgcatttgga atcatagcat tgcagtctct gatttcaatc cacattaatt tttccttctg    43740
gaggccaaat atttaaagat actctctgcc tcccaaatct taccttcaac atgcttgcct    43800
ccttatgcat aacacacaca cacacacaca cacacacaca cacacacccc ttcatgtccc    43860
cttttgccct acccatgtat gtagactgcc atgttttctt ttttgtaccc tttggttatc    43920
ttctgagcag agggatcaca gagggtggtg acctgaatag gatgagctct gccccactaa    43980
```

```
cggctccaat taagctagat ttttctcccc cttcaagaag tgagctgaat acaaaattga  44040
gtggaatttc acgctccata ttagagcaca tactaattag ggtatgctcc tggcttggca  44100
atgccatact caattacaaa gggagcaact actaagataa tgaatgcgcc aagttaattt  44160
gcctccacta ttaattgcat ctgctctatt tttagagcta ctgtcgcctg ctaatacacc  44220
agaatatggt gtaatcagca ccagcaggaa gtcaggagat atgggggacca ttcccatctg  44280
ggtcagttgt gtgatcttat gaacatttct tggggcttta aaggtttgtt tttgtggatg  44340
aagagtcaag taaacagaag ctggtagagg gagaggcaga caatccaccc aaattcttta  44400
cttttatttt tttcatgaga cagggtctgg ctcttttgcc ctggctagag ggcagtggtg  44460
ccatcttggc ttactgcagc ctccacctcc tgggttcaag tgattctcct gcctcagcct  44520
cctgagtagc tgggattaca ggcgcccacc accacgccta gctaattttt gtattttttag 44580
tagagacagg gtttaccat gttggccagg ctggtgacct caggtgatcc acacaccttg   44640
gcctcccaaa gtgaaaactt gacctttta ggctattggt gggcaatgta aaccaggaga   44700
aatttcagat cctgtttcca taggcaaagg caaagtcagg tataagaggg ttaagaaatt   44760
atcttaaagt taattgcctc atactagctt gcccagaatt attattgatt tgaaatgact   44820
actgtaagtt gactttaaaa tttgcaataa gaaatggtcc agggccgggt gcagtggctc   44880
acccctgtta tccctagcac tttgggaggc ctaggcatgt ggattmcctg agctcaggag   44940
ttcgagacca gcctgggcaa cacggtaaaa ccctgtctgt actaaaatac aaaaaaaatt   45000
agccaggcat ggcggtgtgc aactgtaatc ccagctactc ggaaggctga gacagaagaa   45060
tcacttgaac ccaggaggcg gaggttgcag tgagccgaga tggtgccatt gcactccagc   45120
ctgagtgaca gagcaagact ccatctcaaa taagaaagaa agaaagaaag agagagagaa   45180
agagaaagaa agagaaagaa agaaagaaag aaagaaagaa agaaagaaag aaagaaagaa   45240
agaaagaaag aaagraagra agaaagaaag aaagaaagaa agaaagaaag agagaaaaga   45300
agagagaaga agaaagaaaa gaaaagagaa aagaaagagt tgagaaagaa aataattttt   45360
tattccattt ctgtccccta ctctactcca cagattgagc ggtttttcag gaagatatat   45420
caatttctat ttccttttcca tgaagataat gaaaagatc tccccatcag tgaaaagctc   45480
attgaggaag atgcacaatt gacccaaatg gaggatgtgt ymagccagtt gactgtggat   45540
gtgaattctc tctttaacag gagttttaac gtcttcagac agatgcagca agagtttgac   45600
cagacttttc aatcacattt catatcagat acagaccta ctgagcctta ctttttttcca   45660
gctttctcta aagagccgat gacaaaagca gatcttgagc aatgttggga cattcccaac   45720
ttcttccagc tgtttgtaa tttcagtgtc tctatttatg aaagtgtcag tgaaacaatt   45780
actaagatgc tgaaggcaat agaagattta ccaaaacaag acaaaggcaa gtattaaaag   45840
attacttta cttagaggtt tacactaaag tcaagttta tttagcttca gaaatggtag   45900
acatttctga gtcacattgt atagcgtttc ttgaagagac aatttatgga aaatgtttca   45960
gagcctctta aaagaagctt tgaagtctgc taaacactat ccctcttcca tcatcgttga   46020
gaactgaact ctttctagag caaattttca aagcagaaag aaaaaaatgct aataggttga   46080
gaacttgaaa aaaaaaaaaacc agttccctca tttattattt ctttatttat ttatttttgt 46140
gacggagtct cactctgcca cccagcctgg agtacagtgg tgtgatcttg gctcactgca   46200
acctctgcct cccaggttca agcaattctc ctgcctcagc ctcccaagta gctgggacta   46260
cagttgtgca ccaccacgcc cagctaattt tttttgtattt ttagtagaga cggggggtgtc 46320
agtatcttgg ccaagctggt ctcaaactcc cgacctcagg tgatccaccc gccttggcct   46380
cccaaagtgc tgggattgca ggcgtgagcc accatgcatg gccatttccc tcatttatta   46440
aagctcatgt agatgctcag ctctattctg ctaaagcatc agagagcttc tttaaaattg   46500
atctggaatc ctcaactccc agtttgagaa gcccactctc acatataacc agagcaattt   46560
agtgcctcc tctgaatcac tacaatcatt ccttaaatca taaatgtat gcataaaacc    46620
acaaaaaatg ctcataaacc ccaaactaca gaaatattag ataagaattg ccttctacca   46680
acactaatca tgcctcatgg catccatgtt ggagacacaa tgctgcttta tgttttaagg   46740
cggcagatat cttctgtggg cttctatgga gtaagttaga taccgcattc gagaatgaga   46800
attgccacga gggtcaagtg taggatctgc atttcctttg tcactgtatt gacccctaag   46860
ccaggttgaa ggctgctccc ctctgagatg aaaaataaaa tgggctcctt ctatctattt   46920
ttcttttttct tttttctttt tttttttttt tgagatggag tgttgctctg ttgtccaggc   46980
tgtattggtg tgatctcggc tcactgcaac ctctgcctcc tgggttcaat caattctcct   47040
gcctcagctt cccgagtagt ggggattaca ggtgcccgcc accacgcctg gctaattttt   47100
gtattttttag tagagacagg ggtttcacca tgttggccag gctggtctcg aactcctgac   47160
ctcaagtgat ctgctcacct tggcttccca aagtgctgga attacaagca tgagccacca   47220
cacccagcca gccaccacac ccagccagcc accactcctg accctatctg actatttttc   47280
aattatatta gctgtagctg gcaacatctg aatcagattc tcaaaatcgc catgacatta   47340
cataactggc ctctacatag gagaggttta cctttcagaa actgaagctg acatgttaca   47400
cattacatcc ttcaggtgcc atcgttccat gaacagagaa cagccatcat tactggaatt   47460
gttgggttct atttcagagt ccagtggact ttttttataa gtcaattatt tggtctggta   47520
gtccattctg aggttgcaaa ttcatcaaat attcaggata aacaccaggc gagtagacta   47580
aatctatcca ggctgggtgg tattaagtga tttttagcctg actgttttaca tggatatcaa   47640
ctgtcttgga ataacactga gaatatgttc attagaacaa aagggctcct ccctccatg    47700
ttgtgtagca gccttacaca agcattggtt acattcccat gtgcacagga ctgtcagtag   47760
tgattcagac atgccacaat ctagataatt tttcaaccac tgtaacccc tcccacacac   47820
cagctacgaa cataggtttc cactgtctgc caccattgcc ttctcattca cacgctggg   47880
ggccagccct actccagct gcctcacacg caccctcccc agcccctctg cgccacttcc   47940
atctcagtga tgacctggaa agccaaggtc cctgtgaatg caaatagta aagacaaaaa   48000
caaaatagca accaaaaaag tctgtgttac actattgtac tcttcttct ccagtatccc    48060
tccccctagcc agacagtaca cagaagctac cgcagaggag acactgtctt cccagatgag   48120
caaatgtgca ctgtttatca agaatagtca ggcaggcgct ctacagccact tgaatgtgg   48180
ttccatcact tttctggaca ggtagttggt gaggaataag cctactgccc ctagaaaatc   48240
tgcctaatga cttgacactt tgagttttgc ccctttgtggt aggcaaaata atgactgccc   48300
acaatatccc caccctaatc cccagaacct gtgaatttat gttatcgggc aaaggggaaag   48360
taaggatgca gatgaaaatc aatttgttaa tcaactgact ttattttttat ttatttattt   48420
tttgagacag agtcttgctc tgtcacccag gctggagtgc agtggaatga tcttggctca   48480
ctgcaacctc cacctccggg gtttaagtga ttctcctgcc tcagcctccc gagtagctgt   48540
gattacaggc actcaccacc atacctggct aattttttgta tttgagtag aggcagggtt   48600
tcgccatgtt gtccaggctg gtctcgaact tctgacctca aatgatccgc ccacctcggc   48660
ctcccaaagt gctgggatta caggcatgag ccatcatgcc cggcctcaac tgatttttaaa   48720
```

```
atagagagag tatgctggat tatccagatg gattcaatgt aatcacaggg tccttaaaag  48780
tggaagaagg aggcagaaaa gaattaatag tagcagccac aagagaagga cttggctcga  48840
ctttgacgac cttgaagaca gaggaagggg ccaggagcg agtaatgtag gtggcctcga   48900
ggaactggaa atggtataga aatgaattct cctctagagc ctccgcaaaa aactagccct  48960
actgacatct tttttttttt tttttttttt tttttttttt gagacagagt ctcgctctgt  49020
cttcaggctg gagtgcagtg gtgcgatctt ggctcagtac aacctcgcc tcctaggttc    49080
aagcgattct tctgcctcag ccacctgagt agctgggact acaggcacgt gccaccacgc   49140
ccagctaatt tttgcatttt tttttttttg agacagatga catcttgatt ttagcctagg   49200
gagacccact tcagacttct gacctaaaag accaaacaat aatgaatttg tgctgtttca   49260
agccactgaa tctgtggtag ctgtagcaga gctaataata atagtaactg accaacattt   49320
actgagcaag ttccgtgtgg caaccttcat ggatgggcct tattggtcat gattgtttaa   49380
agggccaaaa ttagaaaaat agctaacact gaattatgaa caccaggaaa aggagagcgg   49440
aaataaaaag aatcagaaat atcttgataa ttaatgctat ttttgttgag tataggttca   49500
ttttgttctc atatttcttt cctaccttgg tctttctgga cctcagttcc tgaatctgtt   49560
gaaagcgaat aggtccagga aagtagctct tggaattatc ttcatttgcc ttatgaatcc   49620
ctggaaggaa cagatgagat tgagttctac tgtagcttga cccgtgcggg ggccgggaga   49680
cctggttcta atgctgcctt agagagtgtt agttaacatt aattttcgcg tgggagaaac   49740
agacaggcag gtgggagagt agatgattta gctcagtgac tgcactggaa gtagctccct   49800
ggaagggttc tgaggttctg tcaaggctag actaagcgag gtgatggatt gtgctgtggc   49860
tgcaggatgg ggaattagtg tcatatgggc ctagaatttg tcatccttgg tgtacatacc   49920
aggtattaat ctagatgcta gagataaaat gatgattatg acacagcctc tgacttccag   49980
gagctcagtc cagagaaagg aaaacagatt agtgaacaat tacatcacca tattgtgggt   50040
aaaatggcag aagaaggtat ggaagaatga caagattaaa atggcaagac caagtcccctt  50100
ccctcaagag gctacagtc taatgaaaa gataagaaca caaacactac ataaagcgag    50160
aattaattct acactggaaa ttctcacagg gggctataca gggcaaagaa gagggtccag   50220
gaaagcagct gggagaaact gactttctgg tcaccaaagg ggatgggtgc cttacatgcc   50280
attctatcaa acagtgcttc actgttttta aactatggac tttgcaattt atctcaaaat   50340
aaaacgtttc atttttaaat gctgaggatt taatatgaca gaaaatcatc aggttgtaaa   50400
ttagtaatac atgtttccta atgtcaaaca ctctattggg aaccgccaat tttctgttgg   50460
atagacttct cttttacaca ttttttatatg gattgttaat tctcctaggg gaaaaaactt   50520
ctcaaaactt gattggcttt agatattttc ctaaatcttt gacccctgt tcataacagt     50580
atatgcatct ccacacacac atactcgcac acatatgtgt gtatatatat gtgtgtgtgt   50640
gtgtgtgtgt gtatacat atatatgaga aatgcaaaaa aagaatagta ataaaataac      50700
cacctatcac ccactttaag aaacagacat ttctaatatc tttgaaactt cttcccaatt   50760
atagctttaa aaattaatta ttaaagagtt ttttaaaata cagaaaagtc caagagaaaa   50820
agtggttcac aatcacctat ttacttaatc ctattgacat cagaaatact aatgatataa   50880
gacaaatgat ttttaaagta atcaaatata taaagaaca aaataaatga aagctgccct      50940
ctcctacctt atcaactccc tcttctaaaa gatagttatt aataattctt catgactcct   51000
cctagaaaat aaaattacat gcattaatat atgtgtgtat atactactaa taaatttcta   51060
gtaatgagat tcttggattc aagagtgtgc aatttttaat agctgttcag ttgtcccaga   51120
aaattattgc accaacgtgc atttctgtgt ctaaatatag gaaaagggc caggggcggt    51180
ggctcatgcc tgtaatccca gcactttggg aggccgaggc gggtggatca tttgaggtca   51240
ggagttcaag aaaccggcct ggacaacatg gcgcaacccc atctctacta aaagtacaaa   51300
gattagctgg gcttggtggc tctcacctgt aatcccagct acttgggagc ctgaggcagg   51360
agaatcactt gaacccggga ggcagaggtt gcagtgagcc aagatcccgc cactgcactt   51420
tagcctgggc aacaagcaag actctgtctc aaaaataaat aaattaaata catacataca   51480
tataggaaaa agattttgaa agcactggta agaaaaagct gcggcattgt ctccacttct   51540
tcaaagtgca aactcttatg acactaacgt gtaaatgtta tgttccctgt agctcctgac   51600
cacggaggcc tgatttcaaa gatgttacct gggcaggaca gaggactgtg tggggaactt   51660
gaccagaatt tgtcaagatg tttcaaattt catgaaaaat gccaaaaatg tcaggctcac   51720
ctatctgaag gtaaataatt gctatttgt ttttattct actttaagtt ctcaggtaca      51780
ttttgttata aagtttcggt gccacaaaag aaatagcact cgaatataaa attttctttt   51840
taattctcag caaggaaagt tacttctata gaagggtgcg ccctacaga tgggacgaatg    51900
gtgagcgtgc acttgccaag ggaggggaag gggttcttaa ccctgacaat gcacgtggcc   51960
cctgctgctg tgtggttccc ctattggcta gggttagacc gcacaggcta gactaattcc   52020
cattggctaa tttaaagaga gtgacgaggt gagtggtctg gagggaaaaa tggttatgac   52080
agagcatgta atcggaatga atcagggcgg agcgtgtaat cagaatgaat caggggcggag  52140
catgtaatcg gaatgaatca gggtggagcg tgtaatcgaa aaaggttgct ttacgaggaa   52200
attaagttta aaagtagaag gcaaagaatt gaacatactg acatactgat tctttggaaa   52260
gaaattagaa actcacatct aacaatttt tagggtttct ttagtattct ggacagagga    52320
caaaatctca ttctcacaag catagtggat tcattttctt tcctccaagc actttttttgg  52380
aggctcattt ccatctgggg gcgttcaatg taggtttata aactggtgtt ttgtttgttt   52440
gttttatgag acagagtctt gctctgttgc ccaggctggn gtggcacaat ctcggctcac   52500
tgcaacctcc acctctcggg ttcaagcaat tctcctgcct cagcctgcca agtagctggg   52560
attacaggca tgtgcacca cgcccggcta atttttttg tatttttagt agggacgaatg    52620
gtttcaccat attggccagg ctggtctcga actcctgacc ttgtgatccg cccacctcgg   52680
cctcccaaag tgctgggatt acaggcatga accaccgtgc ctggcctggt ttataaactt   52740
ttattattcc aaagtatgtc attctttcac tttctttaat tccctaattg ttcttgtgat   52800
tttttttatg attaatgacc aaacactatt gtgtgcaaaa gaaaaacctt gagcaaatta   52860
gcgcaactcc ttccttctta ccgcaagcaa aaagaacccc tgccccaac catgaaagaa   52920
acctttcatt ctgtaaatca gtgtttagac aagtgaaata ttttttttgaa agtggcattg  52980
gctctttccc attggtgggt taatgaacta attagcattt aaataggggaa agtggcttct  53040
cctcccaagc cccaggaatc cttttccctc ctttctagt tccttcccca ggaaggaaat     53100
cattctccct ttcctccatc cctccctca ttcccttc cttccaga ctaaagtcac        53160
tcctccaacc ccaccaggc caaattacaa cttttcttac ataaaacaag gctttttgat    53220
tcctatgctt ctgcatttta tctcactaaa gccctaaggg aaggaaattt tcaaagtgtg   53280
actaatggct tacagtagga aattggaaga tacagaaggg acagaaatca acatgtcagt   53340
aaattctaca acactagcta gagatttggg gcaagtcatt tatgctgtct aggcctcagt   53400
tgagtaattt gtaaataaag gacccaagat aatcttggg ttctaacaaa attcttctgt    53460
```

```
aaaacagtgg tccccagcct tctggcacca gggactagat tcctggaaga caattttttcc    53520
aaagatggtg gggcagggggg cacgtttggg gatgatcatc aggcattatt ctcctaagga    53580
gcgctcaacc tgaccctttt gcatgcacag ttcacaatag ggttttgtgct cccgtgagaa    53640
tggaatgcct ccgctgatct gacagcaggc ggggctcagg cagtcatgct tgctcacctg    53700
ccgctcacct cctgctgtac agctccgttc ctaagaggct acaggctgat atgggtccgt    53760
ggcccagggg ttgggaccc  ctgctataaa ggaagttcag aaaaatcaga ttataattct    53820
gattttttata aatcagaatt tataaaattc agattataat ttactaccaa gtaatagctc    53880
ttttgcccttt aacttcccac agtgaagacc actggagtaa tttatatcaa cgcaaagaac    53940
aaaaagcatg gtcagtggaa actcctgccc ctccccttggc tttctctcct caatctaaca    54000
gtgagcaagt tgcaacaaat cgcgccgttc agagaaaagg gaggatgaa  ttgttacaac    54060
cgtttctgtc gcccaggctg gagtgcagtg gcgcgatctt cgctcactga aacctctacc    54120
tcctgagttc aagcgattct gctgcctcag cctcctgagt agctgggatt acaggcacgc    54180
gccaccatac ctggctgatt tttgtatttt tagtagagat ggggtttcac catattggcc    54240
aggctggtct cgaactcctg acctcgkgat cctcccacct cagcctccca aagcgctggg    54300
attacaggtg tgagccatcg cgcctggcca acaaattgtt acaatgttaa acaacataat    54360
atcctaaaca tattggcttt taaagtatca ttagatacac cacaatacta ataaaggtta    54420
cctttggggtt ttaagattaa agatgatttt taaaaatact tcttttctgta ttttccaaac    54480
tcttaaccat aaacataaga tattccttga cttaggatag gattatgtca caacccatca    54540
taagtttgaa aaatcataag ttgaaccatt gtaaattggg gaccatatgt acatgtatgc    54600
atatatgata ttaaaaatta ttagacgtct ttaaaatttg acttttttaac atattacttt    54660
tatttaatca ccttgctcaa ggagcctgta aattacatat taatattctc cattatgaaa    54720
taagtctttc cattgtgcaa attaatgcat tgcagaggtt ctaaacatct atatgctttg    54780
caactcgaaa ggagtaagtt tcccttttcta attttttttat tcaattaaat aaaaaaatga    54840
gtttaataga gtcattaaaa ttagatcatt attcggagtg gttagtaaac ctgtttagag    54900
tcgacaacac tcccttttctc tctttttttt ttttttttttt tttgtgccag agtctcgctc    54960
tgtcgccgag gctggagtgc aatggcacga tctcggctca ctgcaacctc cacttcccag    55020
gttcaagtga ttctcctgcc tcagcctctc gagtagctgg gattacaggc aaccgccacc    55080
atgcccagct actttgttgt atttttagta gagatgggt  ttcaccatgt tggttaggct    55140
ggtggcgaac tcctgacctc aagtgatttg cctgcctctg cctcccaaag tgctgggatt    55200
acaggcgtga gccaccatgc ccagcccctt tctcctttttt aaatatcacc agcctgggtt    55260
ctttgttcttt tttgtttttgt ttygttttttg tttttgtttt tttgagacg  gagtcttgct    55320
ccgtngccca ggctggaggg cagtggcaca atcttggctc agtgcaacct ccgccttctg    55380
ggttcatgcc attctcctgc ctcagcctcc tgagtagctg ggactacagg cgcccgccac    55440
catgcccggc taaatttttg tatttttagt agagacgggg tttcaccgtg ttagccagga    55500
tggtctcgat ctcctgacct tgtgatccac ctgcctcggc ctcccaaagt cctgggatta    55560
caggcttgag ccaccatccc tggcctccag ctcgggttct tattgcacact gaattctcaa    55620
gttagttggg ctagtgagga agtcaggtta cacgggccac agaacaagaa caaggattgt    55680
tctttctctc tctcttccac ttcattctct gtcagcctct cccgacctca gtagttggtc    55740
ttttctcccc cttcttttga aagcagagtc cattatacaa atggacttgt ttacttctcc    55800
acatccctct tgtgcaaatt ttctgccatg gacacctcta cccaccttta gaatgtatat    55860
tagacaattt tgacatctag aatgtccttgt tgggcagaaa agcgtttgga aagcgttgct    55920
ccaggtagct ctgattacaa actggacctt ttcgcgggggt tacctagagc agttgagagt    55980
gctctttctc ctggccaggt gcagttgctc atggctgtaa tcccagcact ctggaaggcc    56040
gaggcgggcg gatcacctgc ggtcaggagt ttgagaccag cctggccaac atggcgaaac    56100
cccgttctac taaaaataca aaaattagcc agatatggtg gtatgaacct gtaatcccag    56160
ctactcagga ggctgaggca agagaattgc ttgaacctgg gaggcagagg ttgcagtgag    56220
ctgagatcaa gcctccagcc tgggcctcag agcgagactc tgtctgtcttgaaa aataataat    56280
aataataaac agataaataa aatttaaaaa aataaaaaag gagtgctctc tctcctgaac    56340
tgctgactcg aggactctct cagcctgttt tatcatttgg aagaggaaat aatatatctg    56400
cttcgtacac atctttagaa gtttaaataa aatgtctgaa atatcaatga ttctcattat    56460
tcaaatatttt gttttttaag tcacagttgc aaggttatat acagaagcat aggttttat    56520
aacagaaaaa tagacactta atatactgac ctcttacaaa aatagtcctg ctcaagcatc    56580
ccatctatgt atcattamca tctatttctt tctacccagc taaaatagtt tattaataat    56640
ccttgaatgt cacaagtnga atacagaata aatcagataa tacattaaaa tgcacctgat    56700
aatcaatatg caccagataa tggacacagt atacatcaga taatacagta caaattcaat    56760
gaaagtttag tgttgcaaag gtaaaatgta aagaatgtcc taatgtgctc ccatgctgct    56820
taaaactgtt attataaatt gcttttttatt ataaatatat aaagaatgat gtaatagtcc    56880
agccatggtg gctcatccct gtaattccag gtctttggga ggctgaggca ggtgaatcac    56940
ttgaggttag gagtttgaga ccagcctggc caacatggtg aaaccccgtc tctactaaaa    57000
atataaaaaat tagccaggtg tggtggtacg cacctgtagt ctcagctact ccggaggctg    57060
aggcaggaga atcgcttgaa accagaagcc ggaggttgca gtgggtcaag atcaagcaac    57120
tgcactccag cctaggtgac agagcgagac tttgtctcag gaaaaaaaaa aaattccag    57180
tcacctagat tgagaaatag aacattacca aaacagataa agcccactg tgttcccatc    57240
cacatcacat tcacttttatc tcctcaaaag gaaagtgcta ttttgaattt agtattaatt    57300
atttccttgc atttcttcct actcatatca tgtgcctata tacatataat atatacaaat    57360
gccgatatca tacatagcaa tgtttttacat ttcgatttt gcattgtcaa tgtagaattt    57420
ttaaacttaa aaacatgctt catacagccg gtgtggtgg ctcatgcctg taatcccagc    57480
attttgggag gccaaggcag gcggatcgac gaggtcagga gttcgagacc agcctgacca    57540
acatggtgaa accccatctc tattaaaaat acaaaaaaaa atattagctg gtcatggtgg    57600
cgcgtgcctg taatcccagc tactcaggag gctgaggcag gagaattgtt gaacccagg    57660
aggcagaggt tgcagtgagc cgagatcgca ccattgcact ccagcctggg tgacagagcg    57720
agactccatc tcaaaaaaaa aaaaaaaaag cttcatacaa acatgaaacg ggcacatgtc    57780
tggctgggtg cggtggctca tgcctgtaat cccagcactt tgggaggcca aggcgggcaa    57840
tcacttaagg ccaggagttc gagaccagcc tggtcagcat ggtgaaaccc cgtctctact    57900
aaaactacaa aaattagcca ggcatggtgg catgcgcctg tagtcccagc tactcgggag    57960
gctgaggcac aagtatcact tgatcccagg aagcagaggt tgcagtgagc caagattgtg    58020
tcactgcact cctgcctggg taacagagtg atactctgtc tcaaacaaac aaacaaaaaa    58080
aacaaagaaa agaaaaagaa aaagaaaatg ggcacatgtc aaatgttaat ttgactatgt    58140
aacttattaa tgaaggaacc agcagggtgt tagagctggg tcaaagaagt ataagagaga    58200
```

```
ctggagtgct tacagtcaag cagagacaga atgctgaaag gttatgaaat tagatatgtt  58260
agttaatatt cgaaagggca actaaactgt aaatcttgcc attatctttt ctatcagacc  58320
aaaataattt acatctctac tagacaaaca tttgccactt ttcaatccat aatctatggg  58380
taatttcatg gagtctggcc ctaatcaaca gtaaatagta aagccaacaa aggatctctt  58440
ccctagacct tgaagtgatc tttgggtgga cccccttagac aataatttag tatgacattg  58500
agaggacacg caagcctggg cagcatagtg agacccgcct ctacaaaaaa attaaaaatt  58560
agccggtgcat ggtggtgtga gcctgtagtc ctagctactc aggaggctaa ggtggaaata  58620
ccacttgagc ccgggagttc gaggctgtag tgagctatga tcatgccatt gcactccagc  58680
ctgggtaaca gagcgagaac ctgtcttgaa aaaaagaaa agaaaaaga aaagaaaca    58740
aaaggaaatg cagccatttt ttttttgcct tatttccaag ttctggataa ttttttcttt   58800
ttaacaatat aaatattatc acttatgtat tcttttgcaa tatggcttt cactcagtgt   58860
agtttgcaag gggttagcca tgtgaatgca tgctgctcta gttcattaat tcactgttgt   58920
atgttggtct atgtaggcat atcacaatwt atycattccc tagctgaagt acatttgctt   58980
tcaaggtatt gctattataa acaaatctca tacctttaat caaataataa ttttgtctct  59040
tcaatcagct ntgatttact ttgttcnaan acnaagcaca caactataat tanaatttca   59100
ttactgataa atataaaata ttttccaaaa catcacaaat cttttntnnt ncactattta   59160
ctatacactt tnggtctnaa tttaaagcgg cttcactata tgtggttctt ttcctctctt   59220
cccatactaa ttactggtac tggacatata catccaaaat caaatagtar tgtccttttt   59280
aagggataaa tgggatgtga tgtagaaggg gcatagtagg gacttcatct gttttggcaa   59340
atttttttctt aatataggtg gtaggcatgt ggaatttata acaaaagttc tgtctccagc   59400
ccagtttctg ttacataaaa ccatataatt aacagttaaa ctggatctgg tttgacacag   59460
atgtagacga tattaataat tactccagaa caacaggcat aactaaaaac taccacaggc   59520
aaaaggggaa aatagagaat gtaagggctg ggacttaagc ccatgttgcc cacctccaag   59580
tttcatggac ttttttcctt c tccacattac tttcttctct gctagactgt cctgatgtac  59640
ctgctctgca cacagaatta gacgaggcga tcaggttggt caatgtatcc aatcagcagt   59700
atggccagat tctccagatg acccggaagc acttggagga caccgcctat ctggtggaga   59760
agatgagagg gcaatttggc tgggtgtctg aactggcaaa ccaggcccca gaaacagaga   59820
tcatctttaa ttcaatacag gtaaaggaga gacccaagag cagatacgga agtgacacgt   59880
gcataccttg atttcactgt taatttactt atgaattgtg tctgaatttg aaaacaagct   59940
gtaggaggta ttcatatttc cattgtgatt gccttcaggc tgacttgatt taacgtagtt   60000
catggtcttt agaaaacaag aaagtccata aagaaaatca atttaaaaca caaatactt   60060
tctaatctag aaatggctat ttctgcttag agttatagggg ctataactga tagaggtaac   60120
cttgaagaaa tatggccaat gtaggttttta ggagagaaga cttacaaata aagcaatttg   60180
agttcaaaat ttgactctga aacttaccag ctgagtaagc ttgggaaagt acctcaacca   60240
ttctaggcct cagtgttcca cctgtaaaat ggtaacaatc atagctatct taacgtgtac   60300
acctataag tgattagtat agatttctta tacaaaacaa gagctctgta aattatagct   60360
cttattagtt gctgacacaa taaagccact gagttatctt gagaattaaa catttatatg   60420
ttactcgtca cataaaaata cattgccagc tgggcgcagt ggcttatgcc tgtaatccca   60480
gcactttggg aggctgaggt gggtggatca cttgaggtca ggagtttgag accagcctgg   60540
ctaatgtggc gaaaccccgt ctctaccaaa aacataaaaa attagccaag tgtgatggca   60600
cacacttgta atcccagcta ctcaggaggc tgaggcagga gaatcacttg aacccggaag   60660
gcagaggttg cagtgagctg agatcgtgcc actgcactcc agcctgggcg acagaaggag   60720
actctgtctc aaaaaaaaaca aaaataaara catattgcca tcttaaattc cacctatacc   60780
atgactccca gattcagtca ataattttt gcataacgtc caagtgactt ttcttcctaa   60840
gacatccccc ctccaacaca cacacattac cttaatctac aaatgcgcca ggctagtgat   60900
tcctgatgag gctggttttg agggttccca aaaagacttg gatacaaaaa ttactgggca   60960
gagcaattga agatgcaata ttctgtgtgt agtatgttag gttatgttgg tgccctatcc   61020
agatccctgg ggatcccttt taccagctcc cactggtgct ggtgctgctg ctaactgctt   61080
atctctgaaa cttttctccca aagattgccc ttggagcact tatgccccag agcttcctgc   61140
aggatcaggc tgaggctaac agtcatctga agccatatcc ttgcttagct tctttcactt   61200
ctctagttttg cttttcctcat ccccttaaaa gttgcacctg agagcattct ttataaacca   61260
cttctgtcag aatctcaggc actgcttcta ggaaattaga cttatggcat tctataatcc   61320
agcatttccc tctttttttca aactacaaag ctgtggatca tgcctgattt gagaaataag   61380
tttagaaagt cacagcaagc tcattaaaaa acaaaattaa aaaccataca aaaaatagaa   61440
taggacaaag tagaaaatat tagcatgcat tgcatttcat aagtcatatg cacatcatgg   61500
aatttcattt ccattttgta tgtgtatatg tgtgtaaaca tatatacaca tatgtagaca   61560
tacgtgtgtg ttttgaatca tgatgtcaag tgtattcatt actgcagacc acagtcaaag   61620
ggttttgaaa gccactgttc caatccctgc cagctctctg attctataac tctattagat   61680
tacacttgag gaaggtaaaa taattcaata tatttgatca tcctcgcata tatagacttt   61740
tagtttaacg aggaaaaagt cttgtattga agaataaaac ttgaagaaaa attttagcag   61800
tgcttttcaac cttttagaaat ctacagtcaa tattttagttg ttttttaccat tgtcagtatt   61860
ttctattctg tgctttgatt tacttccatt ctagtgtctc ttgagtaaca taacagattt   61920
atctaaaatt ctttatgctg ataacaaagg cacttctata taaaaccctc cacataaaat   61980
aaaattatgg ttttcaatta tacatttta taacaattat taccacttaa gagcatttac   62040
tgggtgtcag gcaatgttct aagcttttt ccatatatca gatcatttaa taccctcaat   62100
gaccctataa gggaagtaga attctttccc cagttttca aatgaggcac agaggaggtt   62160
aagcaacttg tctgagctca cacagctagt aaatggtaga actagaattc aaactcaagc   62220
agtatttctc tagaatcagt gaacgtaacc actttgctaa actgcctgtg aagttacttt   62280
tctcaaaaca gctcctattt caccatgtaa agaaaagtaa aaacccataa aatagcaagt   62340
gctgaagaga agccttatga aagaaatata caattccgac caagtgaaca cggttgtggt   62400
ccctggttgt ataatagtta catggtgtt gactttacaa ttattttaaac caaacataaa   62460
tacttttatgc agtttttatg tatgttatac tcacagaaag agaagggaaa aattttttaaa   62520
tcattctctt aaggttacat caagttgcgt atcagttcag ttccatttaa atgattcaaa   62580
tcaaagtctg tgcatttgag aattcattaa gagagtaaca tacatgttat tcattaagag   62640
taacataaat tttgcattga ttcttgccaa aatcacacct acaaccataa attgtaaatt   62700
tctaggaaaa ctcagtacaa aacttggtgc aatgcaataa agtttgtggc acagacagta   62760
atactcagca aacatcccac ctcctctctc atattttcca gctccccttg tggttaaacg   62820
ttgccatgtg gcaagttctg gccagtgaag cgtgagcaaa actgaaaagg gttcttgta    62880
gattgagaca gtgaagagcc tatgtgtgct catctattct ctttttctgc tgagggcaca   62940
```

-continued

```
aagaaagtcc tgaaatcatg tgctacagct atgagataat gtgcctttgc ctaccaggct    63000
tctcagtgtt tactggtgtg gagcccttgt aatggacaca taacatgaac aagaaataaa    63060
tctttgttgc atgaagccct aggaatgcca ggactaatct gttacctcag cacaaaccca    63120
ggcctatcct gactaaggtg gtattaaatt actattgaat gtgtattggg atttagtaaa    63180
cttctactgt ataatccttc ttctgtaggt agttccaagg attcatgaag gaaatatttc    63240
caaacaagat gaaacaatga tgacagactt aagcattctg ccttcctcta atttcacact    63300
caagatccct cttgaagaaa gtgctgagag ttctaacttc attggctacg tagtggcaaa    63360
agctctacag cattttaagg aacattttaa aacctggtaa gcagagtgcc tggttaggaa    63420
tgccttgttg acaggaatag ttaattctca aaagggaaaa acaaaacttg tttcaaaata    63480
cctgaaaaac atgtttaacc tcattaataa agacatgaaa acaaacaaga tggcattttc    63540
tgcctatcag atttgcaaat taaaaaaaaa cccaggaaaa cctgatagga atgtgatgaa    63600
atgggaattc tcatatatca tgtattggtg ggaacataat tggttttgca ttttttgaaag   63660
ctatttgatt atgcatatga agagccataa aatttccttt tgatataata attccacttc    63720
cgaaatcaat cctaaggrat aaatctaaat ttgatgaama ktctccctcc aagatctaga    63780
tttgcagcat tatttaaata ttaaaagttg gccgggcgca gtggctcatg cctgtaatcc    63840
cagcactttg ggaggctgag gcgggcggat cacgaggtca ggagattgag accatcctgg    63900
ataacacgga gaaactgcgt ctctactaaa ataaaaaaaa ttagccgggc atggtggcgg    63960
gcgcctgtag tcccagctac tcgggaggct gaggcaggag aatggcgtga cccgggagg     64020
cagarcttgc agtgagcaga gatcgcgcca ctgcactcca gcctgggcga cagagcaaga    64080
ctctgtttaa aaaaaaaaaa aaaaaaaaaa atatatatat atatatatat atatatatat    64140
atatatatat atgttaaaca tactcttaat gtgtaaaaac aagagaatga ttaagtakat    64200
tatgactaaa tacactcaat acattttatg aaacgttaaa aatattcaaa aaatttaaat    64260
aatgacttgc taactacttt aacaagagct ttattatcag ctagtcttgg aggtaatagt    64320
attatcatga tttttcagaa aaagatcctg aggctcagtg tccaaggtcc aatgaactac    64380
tcaggtcgga ggtggtagag cagcatgtgg agccagttct ctctccgact ccatcatcac    64440
actgcacggc ttcctgttaa gatatttgct caaaaaatgc gagatataaa aatctgggta    64500
atatgatcaa ccttaaagaa taattacatt ttaaattatt catgagacct tgttagtagg    64560
tcaccatcaa tgtgtaatta agccagatgt gacaggattt gttgcctctc cttttacttc    64620
tgaatttttgg aggccttttt ttttttctag ttgtatcagt cagccaacca atatctttt    64680
agcatctact aagtttagat acgggaactg gtactctgaa agagaaaatg agaaatttga    64740
caagatcctg tccccaagga gcttcctatc caacaggggc acaagacaga tagatagaca    64800
cacacacaca cacacacaca cacacacaca ctataaagca aggcaagatt    64860
tagagagtgc acaggagtgg gctctggag ttcaggggag ggtcgttcac attctggtag    64920
ggaagatact tctgagctca gtatattccc tttctcactg tccttctatc ccctctcttc    64980
ctctcctcct ctcttttcct ctttcttctc cctcctccca ctctgtcctc tccctttctt    65040
tccttttttc tttctttctt tttttttttg agacagagtc ttgttctgtc acccatactg    65100
gagtacagtg gcacgatctc ggctcactgc aacctcggcc tcccaggttc aaatgattct    65160
tgtgcctcag cctcctgagt agctgggatt acaggcgcac accaccatgc ctggctaatt    65220
tttgtgtttt tagtagaga cagggtttca ccatgttggc caggctggtc ttgaactcct    65280
gacctcaagt aatccaccca ccttggcctc ccaaagtgct gggatcacag gcatgagcca    65340
ccacactggc ctcctctccc tttcttaaaa atacatcaat taattaaata tataaatgta    65400
gatacacaca caggcagaat caaagtgtat aggttggaga ggagactgtt ccaaaagggg    65460
ggatggcatg ggcaaatacg gcaagaaaga gtagagcatc taggtactga gggtgctggg    65520
aagtcctgct aaaaatacgg caagaaagag tagagcatct aggtactgag ggtgctggga    65580
agtcctgcta aagtggtccc ctcccactgt ggggcctttg agtttccctg tgccagggta    65640
cctgccctct gtgagtttga gttctttctt tggttgcaag caaccaagac cagctcagct    65700
aaaagaaatg gatggatacc gactcatgag tcagagggga agctgacgt ctatgcccag     65760
agccaggcag aaacgggtca ggtctagagt ctgggaggag gaaaccgatg gacactgct    65820
tcagggccca gcgctcaggg tgaagcagct gcagttgttt ttagtcctca gatcactctg    65880
ctcaagatgt gacttgccag gaggaatctg gctggcccag ctgggacatg tgtgtctacc    65940
tctagaccag gagagaggag agtcttggtt gacagtcccc atgtagtacc cctttgttta    66000
ggttactgag tcatcaacag atctcagttc aaatagtcac ttcttcaggg gcaatatacc    66060
ctcttctacc cataaactag gggcaacata ccctctctcc ccttcacac atgaccataa    66120
caccatgtag cactcaactc ttgtaagttg acatttaccc atgtgactct ttatgaacgt    66180
tcatctccat cccgagacct acagtccatg agggtaccac cgttctaggg ttttttgctct   66240
tctctttgtc agtggggact taggactctg cctggcacag ggcaaaccct caatatttgt    66300
tgaataaatt aattaataaa cacgtgtaaa tgaatatcag tagactacaa caagagtaac    66360
agtaggcgaa ggtggaaggc aaaggtggga agaggtcagg gctctgagtg ctgggctgtg    66420
gagtctgagg ttcactctac agcgctggtg agacacgata ggttttagag aaaggaagcc    66480
tcatgctggt gccccagtgg gtactgacta tgcatttgta gccaaatcaa agtatttccc    66540
ataaagtcat ctatctcttc ccagttgttg ggacttccaa tggcaatggg aattaagata    66600
ctgagtaatt gggagatcaa gcaaattatt tactaacaag gcacacgaag tgattttttca   66660
caggcaatgt taatgttttt cttttttatg tagttttaaa attctaaaag taacaaaatc    66720
acaactacca aacatttaga cgacaaaaat tatccataat cccaccatct taacacaacc    66780
actattatca tttgtttttcc ttattcacat tttctaccta ttttcttaag ttyccaagaa    66840
atagaattac ttgtttagag gttattaaca tcttattgtt ctggatatat atatatatat    66900
agctatatat agctaaattt aataacagca atgtctgcag taccactttc tcaaatgcta    66960
actggcattt caatttttg agacagtctc tctctgttgc ccaggcagga ttgcagtggc    67020
atgatctcgg ctcacggcaa cctccacctc ccaggttcaa gcgactctca tgcctcagcc    67080
tcccaagtag ctgggattac aggtgtgcac caccacactt gtgtattttt tgtatttttt    67140
agtagagatg tgttttttacc atgttggccg ggctggtctc aaactcctgg cctcaagtga    67200
tccttccacc tcagcctccc aagggctgg tattacaggc atgagccact gcctggcctg     67260
gcatttcaat tttttaaaatc ttcagtaata aatgaaaatt tttatcttat tgttataatt    67320
tttatgtttt tttattattc atgagaataa acattttcca agtttgttta tgactgaatt    67380
ttcttttttg tgcaccttac ttggtatcat ggataaaatt ttgtcaattt tctgattata    67440
tcaatgcatt caggtcccca aacctgccaa agtttaaaga gaaagatact aagggaaaaa    67500
ccaggaaaag atggtagaaa agaatcaccc tggcattttc aatcacgtaa acatttgcta    67560
ggtgccctag ctgcaggtat acagctcact gaaacatgaa ttccaatttt ataggtgaa     67620
atatatattt agaaccctct tctggaactt tcttctagtt atctagcatc ctaagtgcct    67680
```

```
ggacgttcct gattggtttg caatgtgttt tatttcccat ccccaagttt catagctgcc  67740
ggccctggga tctacagtca caggctgtaa cacaatatct tgcacatcct gagtctttaa  67800
taagcttttg tagatgggct cttaccatca tcatcatcgt gaaaggcaaa tatacaaaat  67860
ttgttgacta atgtaatgag tcatgagtaa cagaagttta ctgaccaaac actacgtgca  67920
tgtagagttc agaataaaca ctttattatc acatcagagg aaaagaccat cttagaggct  67980
caacaaccca ggaaagctgt gacgattict tcaaattgtt aagaatatcc atgcatatgg  68040
gtttcacatt atttttgctac acacagtacc aatttttcca aaagccaaca gcaggtattc  68100
tattacccat cctggacttt tactccaaga aaaaatacac tgagtctgtg agtaatttat  68160
tagtatttg atcattgctg cttttttttt tttttaagg taagaagatc taatgcatcc  68220
tatatccagt aagtagaatt atctcttcat ctgggacctg gaaatcctga aataaaaaag  68280
gataatgcaa taaacacagt tgcaggaaag tatgttagct atatactatg aagtactctt  68340
agtttactta tgttgaatgg cttagctatt aatactcaaa ttgagttaaa atgaaaattc  68400
ctccttaaaa aatcaaacgt aatatgtatt acatttcatg gtacattagt agttctttgt  68460
atattgaata aatactaaat cacctaggtg tctatgttct atcacatcta caaacatgtc  68520
acttcctaat taacaaaatg ttcttccttt agtttgcttt tgcacttaaa atatatataa  68580
ttgactttt tggaaaaaaa tctaagattc attgctttgt tttgtaaaga ccaataggtt  68640
ctgtatagtc ttttttttaaa ttgtggtaaa atacacatgg cattaattta ccattttaac  68700
cattttaaag tgcacaattt gtggcattaa gtacactcac gttgctgtgc aaccatcacc  68760
accgtccatc ttcagaacct ttttatcttc ctaaactgaa actctgtact cgttaagcac  68820
tcacttcccg tttccccatc ccccagcccg tagcaaccac gactgtactt tctatgaatt  68880
tgactactct aggtactgca tgtaggtgga atcatacagt atttgtcttt tgcttcattt  68940
tgttttgttt tttgttttct aagacagggt ctcactctgt cgcccaggct ggagtgcagt  69000
ggtgcaatca cagtgtcctt ttgtgactgg tttatttcac ttagtgccat gttttcaagg  69060
ttcatccatg ttgttgcatg tctcagaact tccttttca ggctaatatt cttgcatgta  69120
tttacctagt tttgcttatc cattcagcca ttgatggaca cttgggttgc ttccatcttt  69180
tggctattgt gaataatgct gtttttgaacg tgggtgtgct acatagttac tttttaaaat  69240
tggcacaaca gcgctgtctt ttgacatacg tattttatgg aaaacacaag attttcctgg  69300
ctgacgctca acctcataat ttggaccttg gtgcaacaca ataataggag agctatgtgt  69360
cagtatatat cactaaggat tacaatgaga gtgtatacag tcagtattac aaattataaa  69420
aagaaatgta ggccaggcac ggtgcctcac acctgtaatc ccagcacttt gggaggccaa  69480
cgtggggtgga ttacctgagg acaggagttc gaaaccagcc tggccaacat ggtgaaaacc  69540
tgtatctact aaaaatacaa aaattggcca ggtgtggtgg cgcatgcctg taatcccagc  69600
tactcaggag gctgagatgg gagaattgct tgaacctggg aggcagaggt tgcactgagc  69660
caagattgtg ccactgtact ccagcctggg caacagagcg agactctttt ttaataaata  69720
aataaataaa taaatatata aaagaaacgt aatgaaagag agaactct gaacttttaa  69780
agaactttc acccagtctt gatctatctg acagaaaggc ttgtcagaga aagttagagt  69840
tcagaggcag ccaattgaat ataattaact ccaaatgaag ataaacctt tctaaatcat  69900
actgaaggct ataaaaaatg agaattagt tatttttttt ttgagacagg gtcttactct  69960
attgcccagg ctggagtgca gtggcatgat ctgggctcac tgaagcctga cctccttggc  70020
tcaggtgatc ctcccacctc agcctcctga gtagctggga ctacaggtac taccatgccc  70080
gtctatttt gtatttttt agtagagatg gggtttctcc atgttgtcca ggctggtctc  70140
aaactcccag gctcaagcaa tctgcccgcc tcagcctcca aaagtgctgt aattacaggc  70200
atgagccact gctcctggca gggaactaat agaatcctgg gttcttcggt gtgcaataaa  70260
yctcaaatac agctattcaa ccatagattt taaatatttg ttagtgaagg tgacaaaaaa  70320
ataagtgatt aagagaacct attttctatc caatgagcta tcaaaagctt atagagtgaa  70380
aagagagtgg gggaagtgag gctcaaaaca gctaaatgga aagaagattt tgcatgcagg  70440
ctgaactgga ttttcatcct ggctactata ttctccagat gtgtcacttt ggccaagatc  70500
cttaatctca gtgtcatcta taaggtaatt aaagtacact agtgccccac taatctgtgg  70560
ttttgcttc caagctttca gttacccgag atcaactgcg gttttaaaat attatgtgga  70620
aaattccaga aatacatagt aagttttcaa ttgcatgcca ttaaatctca tgctgtccct  70680
gacccttcc tctccggagg tgaatgctcc ctttgtccag tggctccacg atgactacat  70740
tccccaaatt gttctcttag gaacccttc tgtgttcaag gaacccttac tttacttaat  70800
tatggcccca aagcacaaga tagggatgcc ggcatactgt tataattgtt ctattttatt  70860
attagttatt gttgttcatc tctacctgtg actaatttat gaattcaact ttatcatagg  70920
tatgtaggta taggaaaaaa acatggtatg tataaggttc agtactatct gcagtttcag  70980
acatcccctt ggggtcttgg aacatatccc ccgtggataa sgggaaacta ctgtaaaagt  71040
ttgtstttta tagagtagtt stsagaacta cattaatcca taatgtgtgs ctcatgatac  71100
tcattgatag atggtagtag caacaataaa aaataatatt atcaagtaac tgattcataa  71160
ttgactctca aaaacgttaa ttttctgctt tcctttacct aagtttacct acatgtttga  71220
atttgtaaag ggaaggtttt tctagaccaa taattttcaa atatttttgc tctcatactt  71280
cctcaaagga aactgaaaaa gttgcaacat acttgcatgt catttttcta taaagttga  71340
aagaatagca aattgttatt ttcccacgca tcgtaaagat tagcaggtca tccctcttta  71400
aaatgtacca aatggaatct aaatatcatc gcaatttgac ccagcatcat ccatttaaac  71460
aaatatacaa gttttctttt aacaatgaga aattttatct cattacattt tctccctaaa  71520
ctcttatttc aatctacatt cctaagaatt ttatcctaat gtagtatatt tttatgctta  71580
aatatctttt gttgatcaac acaatttga tcatttttaa attttaaaaa ttaagaacat  71640
cctgtgacat caaattctag gtatgaaata tttattctag attgggtgat cattataatt  71700
attttttgta cataattgat caaaataaca taaatatact acaaatttct atgactacta  71760
aacatataaa agtaaaattt taaacaaata tatctcttaa tgaaggaa gagctttta  71820
tactccaata agttaacgta tccactaata attatttt cttcctagaa caagacagga  71880
ttaagcatca tgaccgtccc tattggggga tgttttata gatgcaagca ctgtggcacc  71940
tactggtata aatgcacctg ctgattgaa tgttcttcc ccagatcttc cctgctggt  72000
ttcttcccag tattcaggtc tcagctcaaa tgtgacttcc tcaatgaggc ctcctggtga  72060
tcagatcaa agcaccctct acacaatcac tgtttagtgc tatacccatt aattactat  72120
catcacactt gtcactatct gcagatgtct tgtttggtta ctttttgtngt gtttgtcact  72180
gccagaatat cagttctatg aagaaaaggg ccttgtctat tttgacactt atagaatga  72240
tgnaggnacg acatacaaat ggccaatggg catatgcaaa aacgcttgac ttcaagagta  72300
ctnatgnta tnaccaacat ttatggagta actactttga aaagaaccat tctgtctta  72360
ctatcaagcc aagtactca aggaaggcag cagaagtgga agctccatgt gggcagagga  72420
```

```
gcctagtctt gagatgtgat ttagctggta tttgggtgaa acaaataaac cagcctcaaa    72480
ataacacaag gggccgggtg cagtggctca cgcctgtatc ccagcacttt gggaggctcg    72540
aggcaggcag attacttcag gtgaggagtt cgagaccagc ctggctaaca tggtgaacct    72600
ccat                                                                 72604
```

<210> SEQ ID NO 8
<211> LENGTH: 17
<212> TYPE: DNA
<213> ORGANISM: Artificial Sequence
<220> FEATURE:
<223> OTHER INFORMATION: Primer

<400> SEQUENCE: 8

```
cggggttggt ttccacc                                                      17
```

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9

```
gcgaggagag aaatctggg                                                    19
```

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10

```
tgctcactac tttgcagtgt tc                                                22
```

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11

```
tgagatcgtg tcactgcatt ct                                                22
```

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12

```
gtaaatctca aaatgttggg ttaatag                                           27
```

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13

```
ctaactcttc ttctatcatt actc                                              24
```

<210> SEQ ID NO 14

```
<211> LENGTH: 22
<212> TYPE: DNA
<213> ORGANISM: Artificial Sequence
<220> FEATURE:
<223> OTHER INFORMATION: Primer

<400> SEQUENCE: 14
tgtttattgt gtgtctgctg tg                                              22

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gaacaaccaa catgcaaaca g                                               21

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
cccaggtgtt ttcaattgat gc                                              22

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
agcagttttg tccttccaag tg                                              22

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
gtgttttgta atctgatcag atctc                                           25

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gcagtatttc tggtccagat c                                               21

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
```

```
ggtgcacata gatcatgaaa tgg                                              23

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
taagctgaaa taggtgcctt aag                                              23

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
tttattccat ttctgtcccc tac                                              23

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
aaggctcagt taggtctgta tc                                               22

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
caggagtttt aacgtcttca gac                                              23

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
gactcagaaa tgtctaccat ttc                                              23

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
tgtctccact tcttcaaagt gc                                               22

<210> SEQ ID NO 27
<211> LENGTH: 24
<212> TYPE: DNA
```

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
caaaatgtac ctgagaactt aaag                                    24

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
cacctccaag tttcatggac                                         20

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
caaggtatgc acgtgtcatt tc                                      22

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
gaatgtgtat tgggatttag taaac                                   25

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
ttgagaatta actattcctg tcaac                                   25

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ccatcctgga cttttactcc                                         20

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
ctttcctgca actgtgttta ttg                                     23

<210> SEQ ID NO 34
<211> LENGTH: 147
<212> TYPE: DNA
<213> ORGANISM: Homo sapiens

<400> SEQUENCE: 34
ttccctccct tggaacgca gcgtgggcac ctgcaacgca gagaccactg tatccccggt      60
gcagaatgta atgagtgcct gatacatttg ccgaataaac tattccaagg gttgaacttg     120
ctggaagcaa gagaagcact attctgg                                         147

<210> SEQ ID NO 35
<211> LENGTH: 123
<212> TYPE: DNA
<213> ORGANISM: Homo sapiens

<400> SEQUENCE: 35
atggagtctt gctctcgttg cccagactgg agtgcactgc tgcgatctca gctcactgca      60
acctctacct cccaggttca agcgattctc ctgcctcagc ctctcgagtg gctgggacta     120
tag                                                                   123

<210> SEQ ID NO 36
<211> LENGTH: 398
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g, or t

<400> SEQUENCE: 36
agttgcgtcc ctctctgttg ccaggctgga gttcagtggc atgttcatag ctcactgaag      60
cctcaaattc ntgggttcaa gtgaccctcc tacctcagcc ccatgaggac ctgggactac     120
agttccctcc ctttggaacg cagcgtgggc acctgcaacg cagagaccac tgtatctccg     180
gtgcagaatg taatgagtgc tgatacatt tgccgaataa actattccaa gggttgaact     240
tgctggaagc aanagaagca ctattctggt aacagcggga acatgaagcc gccactcttg     300
gtgtttattg tgtgtctgct gtggttgaaa gacagtcact gcgcacccac ttggaaggac     360
aaaactgcta tcagtgaaaa cctgaagagt ttttctga                             398

<210> SEQ ID NO 37
<211> LENGTH: 372
<212> TYPE: DNA
<213> ORGANISM: Homo sapiens

<400> SEQUENCE: 37
agttgcgtcc ctctctgttg ccaggctgga gttcagtggc atgttcttag ctcactgaag      60
cctcaaattc ctgggttcaa gtgaccctcc cacctcagcc ccatgaggac ctgggactac     120
agatggagtc ttgctctcgt tgcccagact ggagtgcact gctgcgatct cagctcactg     180
caacctctac ctcccaggtt caagcgattc tcctgcctca gcctctcgag tggctgggac     240
tatagtaaca gcgggaacat gaagccgcca ctcttggtgt ttattgtgtg tccgctgtgg     300
ttgaaagaca gtcactgcgc acccacttgg aaggacaaaa ctgctatcag tgaaaacctg     360
aagagttttt ct                                                         372

<210> SEQ ID NO 38

-continued

```
<211> LENGTH: 1815
<212> TYPE: DNA
<213> ORGANISM: Cavia sp.
<220> FEATURE:
<221> NAME/KEY: CDS
<222> LOCATION: (145)...(1542)

<400> SEQUENCE: 38
```

| | |
|---|---|
| cttggagtca actgagtgtg gactgaaact tccaaaaact gacatgagga gtcactggag | 60 |
| aatcatgatc aaggagctac acactctgac ttaactttat tctgtggaca atgagagaca | 120 |
| actgcaagga ttaacagtga gaac atg aag ctg cca ctt ttg atg ttt ccc<br>　　　　　　　　　　　　　　 Met Lys Leu Pro Leu Leu Met Phe Pro<br>　　　　　　　　　　　　　　　 1　　　　　　　 5 | 171 |
| gtg tgt ctg cta tgg ttg aaa gac tgt cat tgt gca cct act tgg aag<br>Val Cys Leu Leu Trp Leu Lys Asp Cys His Cys Ala Pro Thr Trp Lys<br>　10　　　　　　　　　 15　　　　　　　　　 20　　　　　　　　　 25 | 219 |
| gac aaa act gcc atc agt gaa aac gcg aac agt ttt tct gag gct ggg<br>Asp Lys Thr Ala Ile Ser Glu Asn Ala Asn Ser Phe Ser Glu Ala Gly<br>　　　　　　　　　　 30　　　　　　　　　 35　　　　　　　　　 40 | 267 |
| gag ata gac gta gat gga gag gtg aag ata gct ttg att ggc att aaa<br>Glu Ile Asp Val Asp Gly Glu Val Lys Ile Ala Leu Ile Gly Ile Lys<br>　　　　　　　　 45　　　　　　　　　 50　　　　　　　　　 55 | 315 |
| cag atg aaa atc atg atg gaa agg aga gag gaa gaa cac agc aaa cta<br>Gln Met Lys Ile Met Met Glu Arg Arg Glu Glu Glu His Ser Lys Leu<br>　　　　　 60　　　　　　　　　 65　　　　　　　　　 70 | 363 |
| atg aaa acc ttg aag aag tgc aaa gaa gaa aag cag gag gcc ctg aaa<br>Met Lys Thr Leu Lys Lys Cys Lys Glu Glu Lys Gln Glu Ala Leu Lys<br>　 75　　　　　　　　　 80　　　　　　　　　 85 | 411 |
| ctt atg aat gaa gtt cat gaa cac ctg gag gag gaa gaa agc tta tgc<br>Leu Met Asn Glu Val His Glu His Leu Glu Glu Glu Glu Ser Leu Cys<br>　 90　　　　　　　　　 95　　　　　　　　　 100　　　　　　　　 105 | 459 |
| cag gtt tct ctg gca gat tcc tgg gat gaa tgc agg gct tgc ctg gaa<br>Gln Val Ser Leu Ala Asp Ser Trp Asp Glu Cys Arg Ala Cys Leu Glu<br>　　　　　　　　 110　　　　　　　　　 115　　　　　　　　 120 | 507 |
| agt aac tgc atg agg ttt gat acc acc tgc caa cct gca tgg tcc tct<br>Ser Asn Cys Met Arg Phe Asp Thr Thr Cys Gln Pro Ala Trp Ser Ser<br>　　　　　 125　　　　　　　　　 130　　　　　　　　 135 | 555 |
| gtg aaa aat atg gtg gaa cag ttt ttc agg aag atc tat cag ttt ctg<br>Val Lys Asn Met Val Glu Gln Phe Phe Arg Lys Ile Tyr Gln Phe Leu<br>　 140　　　　　　　　 145　　　　　　　　 150 | 603 |
| ttt cct ctc cag gaa aat gac aga agt ggc cct gtc agc aaa ggg gtc<br>Phe Pro Leu Gln Glu Asn Asp Arg Ser Gly Pro Val Ser Lys Gly Val<br>　 155　　　　　　　　 160　　　　　　　　 165 | 651 |
| act gag gaa gat gcg cag gtg tca cac ata gag cat gtg ttc agc cag<br>Thr Glu Glu Asp Ala Gln Val Ser His Ile Glu His Val Phe Ser Gln<br>170　　　　　　　　 175　　　　　　　　 180　　　　　　　　 185 | 699 |
| ctg agc gca gat gtg aca tct ctc ttc aac aga agc ctt tac gtc ttc<br>Leu Ser Ala Asp Val Thr Ser Leu Phe Asn Arg Ser Leu Tyr Val Phe<br>　　　　　　　　 190　　　　　　　　 195　　　　　　　　 200 | 747 |
| aaa cag ctg cgg cga gaa ttt gac cag gct ttt cag tca tat ttc aca<br>Lys Gln Leu Arg Arg Glu Phe Asp Gln Ala Phe Gln Ser Tyr Phe Thr<br>　　　　　 205　　　　　　　　 210　　　　　　　　 215 | 795 |
| tcg ggg act gac gtt aca gag cct ttc ttt ttt cca tct ttg tcc aag<br>Ser Gly Thr Asp Val Thr Glu Pro Phe Phe Phe Pro Ser Leu Ser Lys<br>　 220　　　　　　　　 225　　　　　　　　 230 | 843 |
| gag cca gcc tac aga gca gat gct gag cca agc tgg gcc att ccc aat<br>Glu Pro Ala Tyr Arg Ala Asp Ala Glu Pro Ser Trp Ala Ile Pro Asn<br>　 235　　　　　　　　 240　　　　　　　　 245 | 891 |
| gtc ttc cag ctg ctc tgc aac ttg agt ttc tca gtt tat caa agt gtc<br>Val Phe Gln Leu Leu Cys Asn Leu Ser Phe Ser Val Tyr Gln Ser Val | 939 |

```
                250                 255                 260                 265
agt gaa aaa ctc atc aca acc ctg cgt gcc aca gag gac cct cca aaa        987
Ser Glu Lys Leu Ile Thr Thr Leu Arg Ala Thr Glu Asp Pro Pro Lys
                270                 275                 280 caa gac aaa gac tcc aac cag gga ggc ccg att tca aag ata cta cct       1035
Gln Asp Lys Asp Ser Asn Gln Gly Gly Pro Ile Ser Lys Ile Leu Pro
            285                 290                 295 gag caa gac aga ggc tca gat ggg aaa ctt ggc cag aat ttg tct gat       1083
Glu Gln Asp Arg Gly Ser Asp Gly Lys Leu Gly Gln Asn Leu Ser Asp
            300                 305                 310 tgc gtt aat ttt cgc aag aga tgc cag aaa tgc cag gat tat cta tct       1131
Cys Val Asn Phe Arg Lys Arg Cys Gln Lys Cys Gln Asp Tyr Leu Ser
        315                 320                 325 gat gac tgc cct aat gtg cct gaa cta tac aga gaa ctc aat gag gcc       1179
Asp Asp Cys Pro Asn Val Pro Glu Leu Tyr Arg Glu Leu Asn Glu Ala
330                 335                 340                 345 ctc cga ctg gtc agt aga tcc aat cag caa tac gac cag gtg gtg cag       1227
Leu Arg Leu Val Ser Arg Ser Asn Gln Gln Tyr Asp Gln Val Val Gln
                350                 355                 360 atg acc cag tat cac ctg gaa gac acc acg ctt ctg atg gag aag atg       1275
Met Thr Gln Tyr His Leu Glu Asp Thr Thr Leu Leu Met Glu Lys Met
            365                 370                 375 aga gag cag ttt ggc tgg gtt tct gaa ctg gca tac cag tcc cca gga       1323
Arg Glu Gln Phe Gly Trp Val Ser Glu Leu Ala Tyr Gln Ser Pro Gly
            380                 385                 390 gct gag gac atc ttt aat cca gtg aaa gta atg gta gcc cta agt gct       1371
Ala Glu Asp Ile Phe Asn Pro Val Lys Val Met Val Ala Leu Ser Ala
        395                 400                 405 cat gaa gga aat tct tct gat caa gat gac aca gtg gtt cct tca agc       1419
His Glu Gly Asn Ser Ser Asp Gln Asp Asp Thr Val Val Pro Ser Ser
410                 415                 420                 425 ctc ctg cct tcc tct aac ttc aca ctc agc agc cct ctt gaa aag agt       1467
Leu Leu Pro Ser Ser Asn Phe Thr Leu Ser Ser Pro Leu Glu Lys Ser
                430                 435                 440 gct ggc aac gct aac ttc att gat cac gtg gta gag aag gtt ctt cag       1515
Ala Gly Asn Ala Asn Phe Ile Asp His Val Val Glu Lys Val Leu Gln
            445                 450                 455 cac ttt aag gag cac ttt aaa act tgg taagaagatt tagtccatcc             1562
His Phe Lys Glu His Phe Lys Thr Trp
            460                 465 tataatcagc aagaattaca ccttcggcca agacctgaga attctgaaaa tacaaagcag     1622
gctaacacaa tgaacacagc tgcatgaaag ttaggtatat attaggaagc actattggtt     1682
tactttgttg aatggaagtt taatagctat tcaaattgag ttaatataaa aatttcttcc     1742
taaaaagtaa aatgtacata tgtagaatat gatgcattag ttctttgtat actaaataaa    1802
tactgagtcc cct                                                        1815

<210> SEQ ID NO 39
<211> LENGTH: 466
<212> TYPE: PRT
<213> ORGANISM: Cavia sp.

<400> SEQUENCE: 39

Met Lys Leu Pro Leu Leu Met Phe Pro Val Cys Leu Leu Trp Leu Lys
 1               5                  10                  15

Asp Cys His Cys Ala Pro Thr Trp Lys Asp Lys Thr Ala Ile Ser Glu
            20                  25                  30

Asn Ala Asn Ser Phe Ser Glu Ala Gly Glu Ile Asp Val Asp Gly Glu
```

-continued

```
                    35                  40                  45
Val Lys Ile Ala Leu Ile Gly Ile Lys Gln Met Lys Ile Met Met Glu
 50                  55                  60

Arg Arg Glu Glu Glu His Ser Lys Leu Met Lys Thr Leu Lys Lys Cys
 65                  70                  75                  80

Lys Glu Glu Lys Gln Glu Ala Leu Lys Leu Met Asn Glu Val His Glu
                     85                  90                  95

His Leu Glu Glu Glu Glu Ser Leu Cys Gln Val Ser Leu Ala Asp Ser
                    100                 105                 110

Trp Asp Glu Cys Arg Ala Cys Leu Glu Ser Asn Cys Met Arg Phe Asp
                115                 120                 125

Thr Thr Cys Gln Pro Ala Trp Ser Ser Val Lys Asn Met Val Glu Gln
130                 135                 140

Phe Phe Arg Lys Ile Tyr Gln Phe Leu Phe Pro Leu Gln Glu Asn Asp
145                 150                 155                 160

Arg Ser Gly Pro Val Ser Lys Gly Val Thr Glu Glu Asp Ala Gln Val
                165                 170                 175

Ser His Ile Glu His Val Phe Ser Gln Leu Ser Ala Asp Val Thr Ser
            180                 185                 190

Leu Phe Asn Arg Ser Leu Tyr Val Phe Lys Gln Leu Arg Arg Glu Phe
            195                 200                 205

Asp Gln Ala Phe Gln Ser Tyr Phe Thr Ser Gly Thr Asp Val Thr Glu
        210                 215                 220

Pro Phe Phe Phe Pro Ser Leu Ser Lys Glu Pro Ala Tyr Arg Ala Asp
225                 230                 235                 240

Ala Glu Pro Ser Trp Ala Ile Pro Asn Val Phe Gln Leu Leu Cys Asn
                245                 250                 255

Leu Ser Phe Ser Val Tyr Gln Ser Val Ser Glu Lys Leu Ile Thr Thr
            260                 265                 270

Leu Arg Ala Thr Glu Asp Pro Pro Lys Gln Asp Lys Asp Ser Asn Gln
            275                 280                 285

Gly Gly Pro Ile Ser Lys Ile Leu Pro Glu Gln Asp Arg Gly Ser Asp
        290                 295                 300

Gly Lys Leu Gly Gln Asn Leu Ser Asp Cys Val Asn Phe Arg Lys Arg
305                 310                 315                 320

Cys Gln Lys Cys Gln Asp Tyr Leu Ser Asp Asp Cys Pro Asn Val Pro
                325                 330                 335

Glu Leu Tyr Arg Glu Leu Asn Glu Ala Leu Arg Leu Val Ser Arg Ser
            340                 345                 350

Asn Gln Gln Tyr Asp Gln Val Val Gln Met Thr Gln Tyr His Leu Glu
            355                 360                 365

Asp Thr Thr Leu Leu Met Glu Lys Met Arg Glu Gln Phe Gly Trp Val
        370                 375                 380

Ser Glu Leu Ala Tyr Gln Ser Pro Gly Ala Glu Asp Ile Phe Asn Pro
385                 390                 395                 400

Val Lys Val Met Val Ala Leu Ser Ala His Gly Asn Ser Ser Asp
                405                 410                 415

Gln Asp Asp Thr Val Val Pro Ser Ser Leu Leu Pro Ser Ser Asn Phe
            420                 425                 430

Thr Leu Ser Ser Pro Leu Glu Lys Ser Ala Gly Asn Ala Asn Phe Ile
            435                 440                 445

Asp His Val Val Glu Lys Val Leu Gln His Phe Lys Glu His Phe Lys
        450                 455                 460
```

```
Thr Trp
465

<210> SEQ ID NO 40
<211> LENGTH: 1767
<212> TYPE: DNA
<213> ORGANISM: Cavia sp.
<220> FEATURE:
<221> NAME/KEY: CDS
<222> LOCATION: (145)...(1494)

<400> SEQUENCE: 40
cttggagtca actgagtgtg gactgaaact tccaaaaact gacatgagga gtcactggag         60
aatcatgatc aaggagctac acactctgac ttaactttat tctgtggaca atgagagaca       120
actgcaagga ttaacagtga gaac atg aag ctg cca ctt ttg atg ttt ccc          171
                          Met Lys Leu Pro Leu Leu Met Phe Pro
                            1               5 gtg tgt ctg cta tgg ttg aaa gac tgt cat tgt gca cct act tgg aag         219
Val Cys Leu Leu Trp Leu Lys Asp Cys His Cys Ala Pro Thr Trp Lys
 10              15                  20                  25 gac aaa act gcc atc agt gaa aac gcg aac agt ttt tct gag gct ggg         267
Asp Lys Thr Ala Ile Ser Glu Asn Ala Asn Ser Phe Ser Glu Ala Gly
                 30                  35                  40 gag ata gac gta gat gga gag gtg aag ata gct ttg att ggc att aaa         315
Glu Ile Asp Val Asp Gly Glu Val Lys Ile Ala Leu Ile Gly Ile Lys
             45                  50                  55 cag atg aaa atc atg atg gaa agg aga gag gaa gaa cac agc aaa cta         363
Gln Met Lys Ile Met Met Glu Arg Arg Glu Glu Glu His Ser Lys Leu
         60                  65                  70 atg aaa acc ttg aag aag tgc aaa gaa gaa aag cag gag gcc ctg aaa         411
Met Lys Thr Leu Lys Lys Cys Lys Glu Glu Lys Gln Glu Ala Leu Lys
     75                  80                  85 ctt atg aat gaa gtt cat gaa cac ctg gag gag gaa gaa agc tta tgc         459
Leu Met Asn Glu Val His Glu His Leu Glu Glu Glu Glu Ser Leu Cys
 90                  95                 100                 105 cag gtt tct ctg gca gat tcc tgg gat gaa tgc agg gct tgc ctg gaa         507
Gln Val Ser Leu Ala Asp Ser Trp Asp Glu Cys Arg Ala Cys Leu Glu
                110                 115                 120 agt aac tgc atg agg ttt gat acc acc tgc caa cct gca tgg tcc tct         555
Ser Asn Cys Met Arg Phe Asp Thr Thr Cys Gln Pro Ala Trp Ser Ser
            125                 130                 135 gtg aaa aat atg gaa aat gac aga agt ggc cct gtc agc aaa ggg gtc         603
Val Lys Asn Met Glu Asn Asp Arg Ser Gly Pro Val Ser Lys Gly Val
        140                 145                 150 act gag gaa gat gcg cag gtg tca cac ata gag cat gtg ttc agc cag         651
Thr Glu Glu Asp Ala Gln Val Ser His Ile Glu His Val Phe Ser Gln
    155                 160                 165 ctg agc gca gat gtg aca tct ctc ttc aac aga agc ctt tac gtc ttc         699
Leu Ser Ala Asp Val Thr Ser Leu Phe Asn Arg Ser Leu Tyr Val Phe
170                 175                 180                 185 aaa cag ctg cgg cga gaa ttt gac cag gct ttc cag tca tat ttc aca         747
Lys Gln Leu Arg Arg Glu Phe Asp Gln Ala Phe Gln Ser Tyr Phe Thr
                190                 195                 200 tcg ggg act gac gtt aca gag cct ttc ttt ttt cca tct ttg tcc aag         795
Ser Gly Thr Asp Val Thr Glu Pro Phe Phe Phe Pro Ser Leu Ser Lys
            205                 210                 215 gag cca gcc tac aga gca gat gct gag cca agc tgg gcc att ccc aat         843
Glu Pro Ala Tyr Arg Ala Asp Ala Glu Pro Ser Trp Ala Ile Pro Asn
        220                 225                 230
```

-continued

```
gtc ttc cag ctg ctc tgc aac ttg agt ttc tca gtt tat caa agt gtc    891
Val Phe Gln Leu Leu Cys Asn Leu Ser Phe Ser Val Tyr Gln Ser Val
    235                 240                 245 agt gaa aaa ctc atc aca acc ctg cgt gcc aca gag gac cct cca aaa    939
Ser Glu Lys Leu Ile Thr Thr Leu Arg Ala Thr Glu Asp Pro Pro Lys
250                 255                 260                 265 caa gac aaa gac tcc aac cag gga ggc ccg att tca aag ata cta cct    987
Gln Asp Lys Asp Ser Asn Gln Gly Gly Pro Ile Ser Lys Ile Leu Pro
                270                 275                 280 gag caa gac aga ggc tca gat ggg aaa ctt ggc cag aat ttg tct gat   1035
Glu Gln Asp Arg Gly Ser Asp Gly Lys Leu Gly Gln Asn Leu Ser Asp
            285                 290                 295 tgc gtt aat ttt cgc aag aga tgc cag aaa tgc cag gat tat cta tct   1083
Cys Val Asn Phe Arg Lys Arg Cys Gln Lys Cys Gln Asp Tyr Leu Ser
        300                 305                 310 gat gac tgc cct aat gtg cct gaa cta tac aga gaa ctc aat gag gcc   1131
Asp Asp Cys Pro Asn Val Pro Glu Leu Tyr Arg Glu Leu Asn Glu Ala
    315                 320                 325 ctc cga ctg gtc agt aga tcc aat cag caa tac gac cag gtg gtg cag   1179
Leu Arg Leu Val Ser Arg Ser Asn Gln Gln Tyr Asp Gln Val Val Gln
330                 335                 340                 345 atg acc cag tat cac ctg gaa gac acc acg ctt ctg atg gag aag atg   1227
Met Thr Gln Tyr His Leu Glu Asp Thr Thr Leu Leu Met Glu Lys Met
                350                 355                 360 aga gag cag ttt ggc tgg gtt tct gaa ctg gca tac cag tcc cca gga   1275
Arg Glu Gln Phe Gly Trp Val Ser Glu Leu Ala Tyr Gln Ser Pro Gly
            365                 370                 375 gct gag gac atc ttt aat cca gtg aaa gta atg gta gcc cta agt gct   1323
Ala Glu Asp Ile Phe Asn Pro Val Lys Val Met Val Ala Leu Ser Ala
        380                 385                 390 cat gaa gga aat tct tct gat caa gat gac aca gtg gtt cct tca agc   1371
His Glu Gly Asn Ser Ser Asp Gln Asp Asp Thr Val Val Pro Ser Ser
    395                 400                 405 ctc ctg cct tcc tct aac ttc aca ctc agc agc cct ctt gaa aag agt   1419
Leu Leu Pro Ser Ser Asn Phe Thr Leu Ser Ser Pro Leu Glu Lys Ser
410                 415                 420                 425 gct ggc aac gct aac ttc att gat cac gtg gta gag aag gtt ctt cag   1467
Ala Gly Asn Ala Asn Phe Ile Asp His Val Val Glu Lys Val Leu Gln
                430                 435                 440 cac ttt aag gag cac ttt aaa act tgg taagaagatt tagtccatcc         1514
His Phe Lys Glu His Phe Lys Thr Trp
            445                 450 tataatcagc aagaattaca ccttcggcca agacctgaga attctgaaaa tacaaagcag   1574
gctaacacaa tgaacacagc tgcatgaaag ttaggtatat attaggaagc actattggtt   1634
tactttgttg aatggaagtt taatagctat tcaaattgag ttaatataaa aatttcttcc   1694 taaaagtaa aatgtacata tgtagaatat gatgcattag ttctttgtat actaaataaa   1754
tactgagtcc cct                                                      1767

<210> SEQ ID NO 41
<211> LENGTH: 450
<212> TYPE: PRT
<213> ORGANISM: Cavia sp.

<400> SEQUENCE: 41

Met Lys Leu Pro Leu Leu Met Phe Pro Val Cys Leu Leu Trp Leu Lys
 1               5                  10                  15

Asp Cys His Cys Ala Pro Thr Trp Lys Asp Lys Thr Ala Ile Ser Glu
            20                  25                  30
```

-continued

```
Asn Ala Asn Ser Phe Ser Glu Ala Gly Glu Ile Asp Val Asp Gly Glu
             35                  40                  45

Val Lys Ile Ala Leu Ile Gly Ile Lys Gln Met Lys Ile Met Met Glu
 50                  55                  60

Arg Arg Glu Glu Glu His Ser Lys Leu Met Lys Thr Leu Lys Lys Cys
 65                  70                  75                  80

Lys Glu Glu Lys Gln Glu Ala Leu Lys Leu Met Asn Glu Val His Glu
                 85                  90                  95

His Leu Glu Glu Glu Ser Leu Cys Gln Val Ser Leu Ala Asp Ser
            100                 105                 110

Trp Asp Glu Cys Arg Ala Cys Leu Glu Ser Asn Cys Met Arg Phe Asp
            115                 120                 125

Thr Thr Cys Gln Pro Ala Trp Ser Ser Val Lys Asn Met Glu Asn Asp
    130                 135                 140

Arg Ser Gly Pro Val Ser Lys Gly Val Thr Glu Glu Asp Ala Gln Val
145                 150                 155                 160

Ser His Ile Glu His Val Phe Ser Gln Leu Ser Ala Asp Val Thr Ser
                165                 170                 175

Leu Phe Asn Arg Ser Leu Tyr Val Phe Lys Gln Leu Arg Arg Glu Phe
            180                 185                 190

Asp Gln Ala Phe Gln Ser Tyr Phe Thr Ser Gly Thr Asp Val Thr Glu
            195                 200                 205

Pro Phe Phe Pro Ser Leu Ser Lys Glu Pro Ala Tyr Arg Ala Asp
        210                 215                 220

Ala Glu Pro Ser Trp Ala Ile Pro Asn Val Phe Gln Leu Leu Cys Asn
225                 230                 235                 240

Leu Ser Phe Ser Val Tyr Gln Ser Val Ser Glu Lys Leu Ile Thr Thr
                245                 250                 255

Leu Arg Ala Thr Glu Asp Pro Pro Lys Gln Asp Lys Asp Ser Asn Gln
            260                 265                 270

Gly Gly Pro Ile Ser Lys Ile Leu Pro Glu Gln Asp Arg Gly Ser Asp
        275                 280                 285

Gly Lys Leu Gly Gln Asn Leu Ser Asp Cys Val Asn Phe Arg Lys Arg
    290                 295                 300

Cys Gln Lys Cys Gln Asp Tyr Leu Ser Asp Asp Cys Pro Asn Val Pro
305                 310                 315                 320

Glu Leu Tyr Arg Glu Leu Asn Glu Ala Leu Arg Leu Val Ser Arg Ser
                325                 330                 335

Asn Gln Gln Tyr Asp Gln Val Val Gln Met Thr Gln Tyr His Leu Glu
            340                 345                 350

Asp Thr Thr Leu Leu Met Glu Lys Met Arg Glu Gln Phe Gly Trp Val
            355                 360                 365

Ser Glu Leu Ala Tyr Gln Ser Pro Gly Ala Glu Asp Ile Phe Asn Pro
    370                 375                 380

Val Lys Val Met Val Ala Leu Ser Ala His Glu Gly Asn Ser Ser Asp
385                 390                 395                 400

Gln Asp Asp Thr Val Val Pro Ser Ser Leu Leu Pro Ser Ser Asn Phe
                405                 410                 415

Thr Leu Ser Ser Pro Leu Glu Lys Ser Ala Gly Asn Ala Asn Phe Ile
            420                 425                 430

Asp His Val Val Glu Lys Val Leu Gln His Phe Lys Glu His Phe Lys
            435                 440                 445
```

```
Thr Trp
    450

<210> SEQ ID NO 42
<211> LENGTH: 1539
<212> TYPE: DNA
<213> ORGANISM: Cavia sp.
<220> FEATURE:
<221> NAME/KEY: CDS
<222> LOCATION: (145)...(1266)

<400> SEQUENCE: 42
cttggagtca actgagtgtg gactgaaact tccaaaaact gacatgagga gtcactggag      60
aatcatgatc aaggagctac acactctgac ttaactttat tctgtggaca atgagagaca     120
actgcaagga ttaacagtga gaac atg aag ctg cca ctt ttg atg ttt ccc        171
                         Met Lys Leu Pro Leu Leu Met Phe Pro
                           1               5 gtg tgt ctg cta tgg ttg aaa gac tgt cat tgt gca cct act tgg aag       219
Val Cys Leu Leu Trp Leu Lys Asp Cys His Cys Ala Pro Thr Trp Lys
 10              15                  20                  25 gac aaa act gcc atc agt gaa aac gcg aac agt ttt tct gag gct ggg       267
Asp Lys Thr Ala Ile Ser Glu Asn Ala Asn Ser Phe Ser Glu Ala Gly
                 30                  35                  40 gag ata gac gta gat gga gag gtg aag ata gct ttg att ggc att aaa       315
Glu Ile Asp Val Asp Gly Glu Val Lys Ile Ala Leu Ile Gly Ile Lys
             45                  50                  55 cag atg aaa atc atg atg gaa agg aga gag gaa gaa cac agc aaa cta       363
Gln Met Lys Ile Met Met Glu Arg Arg Glu Glu Glu His Ser Lys Leu
         60                  65                  70 atg aaa acc ttg aag aag tgc aaa gaa gaa aag cag gag gcc ctg aaa       411
Met Lys Thr Leu Lys Lys Cys Lys Glu Glu Lys Gln Glu Ala Leu Lys
 75                  80                  85 ctt atg aat gaa gtt cat gaa cac ctg gag gag gaa gaa agc tta tgc       459
Leu Met Asn Glu Val His Glu His Leu Glu Glu Glu Glu Ser Leu Cys
 90                  95                 100                 105 cag gtt tct ctg gca gat tcc tgg gat gaa tgc agg gct tgc ctg gaa       507
Gln Val Ser Leu Ala Asp Ser Trp Asp Glu Cys Arg Ala Cys Leu Glu
                110                 115                 120 agt aac tgc atg agg ttt gat acc acc tgc caa cct gca tgg tcc tct       555
Ser Asn Cys Met Arg Phe Asp Thr Thr Cys Gln Pro Ala Trp Ser Ser
            125                 130                 135 gtg aaa aat atg gag cca gcc tac aga gca gat gct gag cca agc tgg       603
Val Lys Asn Met Glu Pro Ala Tyr Arg Ala Asp Ala Glu Pro Ser Trp
        140                 145                 150 gcc att ccc aat gtc ttc cag ctg ctc tgc aac ttg agt ttc tca gtt       651
Ala Ile Pro Asn Val Phe Gln Leu Leu Cys Asn Leu Ser Phe Ser Val
    155                 160                 165 tat caa agt gtc agt gaa aaa ctc atc aca acc ctg cgt gcc aca gag       699
Tyr Gln Ser Val Ser Glu Lys Leu Ile Thr Thr Leu Arg Ala Thr Glu
170                 175                 180                 185 gac cct cca aaa caa gac aaa gac tcc aac cag gga ggc ccg att tca       747
Asp Pro Pro Lys Gln Asp Lys Asp Ser Asn Gln Gly Gly Pro Ile Ser
                190                 195                 200 aag ata cta cct gag caa gac aga ggc tca gat ggg aaa ctt ggc cag       795
Lys Ile Leu Pro Glu Gln Asp Arg Gly Ser Asp Gly Lys Leu Gly Gln
            205                 210                 215 aat ttg tct gat tgc gtt aat ttt cgc aag aga tgc cag aaa tgc cag       843
Asn Leu Ser Asp Cys Val Asn Phe Arg Lys Arg Cys Gln Lys Cys Gln
        220                 225                 230 gat tat cta tct gat gac tgc cct aat gtg cct gaa cta tac aga gaa       891
```

```
Asp Tyr Leu Ser Asp Asp Cys Pro Asn Val Pro Glu Leu Tyr Arg Glu
        235                 240                 245 ctc aat gag gcc ctc cga ctg gtc agt aga tcc aat cag caa tac gac       939
Leu Asn Glu Ala Leu Arg Leu Val Ser Arg Ser Asn Gln Gln Tyr Asp
250                 255                 260                 265 cag gtg gtg cag atg acc cag tat cac ctg gaa gac acc acg ctt ctg       987
Gln Val Val Gln Met Thr Gln Tyr His Leu Glu Asp Thr Thr Leu Leu
                270                 275                 280 atg gag aag atg aga gag cag ttt ggc tgg gtt tct gaa ctg gca tac      1035
Met Glu Lys Met Arg Glu Gln Phe Gly Trp Val Ser Glu Leu Ala Tyr
            285                 290                 295 cag tcc cca gga gct gag gac atc ttt aat cca gtg aaa gta atg gta      1083
Gln Ser Pro Gly Ala Glu Asp Ile Phe Asn Pro Val Lys Val Met Val
        300                 305                 310 gcc cta agt gct cat gaa gga aat tct tct gat caa gat gac aca gtg      1131
Ala Leu Ser Ala His Glu Gly Asn Ser Ser Asp Gln Asp Asp Thr Val
    315                 320                 325 gtt cct tca agc ctc ctg cct tcc tct aac ttc aca ctc agc agc cct      1179
Val Pro Ser Ser Leu Leu Pro Ser Ser Asn Phe Thr Leu Ser Ser Pro
330                 335                 340                 345 ctt gaa aag agt gct ggc aac gct aac ttc att gat cac gtg gta gag      1227
Leu Glu Lys Ser Ala Gly Asn Ala Asn Phe Ile Asp His Val Val Glu
                350                 355                 360 aag gtt ctt cag cac ttt aag gag cac ttt aaa act tgg taagaagatt      1276
Lys Val Leu Gln His Phe Lys Glu His Phe Lys Thr Trp
            365                 370 tagtccatcc tataatcagc aagaattaca ccttcggcca agacctgaga attctgaaaa   1336
tacaaagcag gctaacacaa tgaacacagc tgcatgaaag ttaggtatat attaggaagc   1396
actattggtt tactttgttg aatggaagtt taatagctat tcaaattgag ttaatataaa   1456
aatttcttcc taaaaagtaa aatgtacata tgtagaatat gatgcattag ttctttgtat   1516
actaaataaa tactgagtcc cct                                          1539

<210> SEQ ID NO 43
<211> LENGTH: 374
<212> TYPE: PRT
<213> ORGANISM: Cavia sp.

<400> SEQUENCE: 43

Met Lys Leu Pro Leu Leu Met Phe Pro Val Cys Leu Leu Trp Leu Lys
1               5                   10                  15

Asp Cys His Cys Ala Pro Thr Trp Lys Asp Lys Thr Ala Ile Ser Glu
            20                  25                  30

Asn Ala Asn Ser Phe Ser Glu Ala Gly Glu Ile Asp Val Asp Gly Glu
        35                  40                  45

Val Lys Ile Ala Leu Ile Gly Ile Lys Gln Met Lys Ile Met Met Glu
    50                  55                  60

Arg Arg Glu Glu Glu His Ser Lys Leu Met Lys Thr Leu Lys Lys Cys
65                  70                  75                  80

Lys Glu Glu Lys Gln Glu Ala Leu Lys Leu Met Asn Glu Val His Glu
                85                  90                  95

His Leu Glu Glu Glu Ser Leu Cys Gln Val Ser Leu Ala Asp Ser
            100                 105                 110

Trp Asp Glu Cys Arg Ala Cys Leu Glu Ser Asn Cys Met Arg Phe Asp
        115                 120                 125

Thr Thr Cys Gln Pro Ala Trp Ser Ser Val Lys Asn Met Glu Pro Ala
    130                 135                 140
```

-continued

```
Tyr Arg Ala Asp Ala Glu Pro Ser Trp Ala Ile Pro Asn Val Phe Gln
145                 150                 155                 160

Leu Leu Cys Asn Leu Ser Phe Ser Val Tyr Gln Ser Val Ser Glu Lys
                165                 170                 175

Leu Ile Thr Thr Leu Arg Ala Thr Glu Asp Pro Lys Gln Asp Lys
            180                 185                 190

Asp Ser Asn Gln Gly Gly Pro Ile Ser Lys Ile Leu Pro Glu Gln Asp
        195                 200                 205

Arg Gly Ser Asp Gly Lys Leu Gly Gln Asn Leu Ser Asp Cys Val Asn
    210                 215                 220

Phe Arg Lys Arg Cys Gln Lys Cys Gln Asp Tyr Leu Ser Asp Asp Cys
225                 230                 235                 240

Pro Asn Val Pro Glu Leu Tyr Arg Glu Leu Asn Glu Ala Leu Arg Leu
                245                 250                 255

Val Ser Arg Ser Asn Gln Gln Tyr Asp Gln Val Val Gln Met Thr Gln
                260                 265                 270

Tyr His Leu Glu Asp Thr Thr Leu Leu Met Glu Lys Met Arg Glu Gln
            275                 280                 285

Phe Gly Trp Val Ser Glu Leu Ala Tyr Gln Ser Pro Gly Ala Glu Asp
290                 295                 300

Ile Phe Asn Pro Val Lys Val Met Val Ala Leu Ser Ala His Glu Gly
305                 310                 315                 320

Asn Ser Ser Asp Gln Asp Asp Thr Val Val Pro Ser Ser Leu Leu Pro
                325                 330                 335

Ser Ser Asn Phe Thr Leu Ser Ser Pro Leu Glu Lys Ser Ala Gly Asn
                340                 345                 350

Ala Asn Phe Ile Asp His Val Val Glu Lys Val Leu Gln His Phe Lys
                355                 360                 365

Glu His Phe Lys Thr Trp
            370

<210> SEQ ID NO 44
<211> LENGTH: 1536
<212> TYPE: DNA
<213> ORGANISM: Cavia sp.
<220> FEATURE:
<221> NAME/KEY: CDS
<222> LOCATION: (145)...(1263)

<400> SEQUENCE: 44
cttggagtca actgagtgtg gactgaaact tccaaaaact gacatgagga gtcactggag      60
aatcatgatc aaggagctac acactctgac ttaactttat tctgtggaca atgagagaca     120
actgcaagga ttaacagtga gaac atg aag ctg cca ctt ttg atg ttt ccc        171
                         Met Lys Leu Pro Leu Leu Met Phe Pro
                           1               5 gtg tgt ctg cta tgg ttg aaa gac tgt cat tgt gca cct act tgg aag       219
Val Cys Leu Leu Trp Leu Lys Asp Cys His Cys Ala Pro Thr Trp Lys
 10              15                  20                  25 gac aaa act gcc atc agt gaa aac gcg aac agt ttt tct gag gct ggg       267
Asp Lys Thr Ala Ile Ser Glu Asn Ala Asn Ser Phe Ser Glu Ala Gly
                30                  35                  40 gag ata gac gta gat gga gag gtg aag ata gct ttg att ggc att aaa       315
Glu Ile Asp Val Asp Gly Glu Val Lys Ile Ala Leu Ile Gly Ile Lys
            45                  50                  55 cag atg aaa atc atg atg gaa agg aga gag gaa gaa cac agc aaa cta       363
Gln Met Lys Ile Met Met Glu Arg Arg Glu Glu Glu His Ser Lys Leu
```

```
                    60                  65                  70
atg aaa acc ttg aag aag tgc aaa gaa gaa aag cag gag gcc ctg aaa      411
Met Lys Thr Leu Lys Lys Cys Lys Glu Glu Lys Gln Glu Ala Leu Lys
     75                  80                  85 ctt atg aat gaa gtt cat gaa cac ctg gag gag gaa gaa agc tta tgc      459
Leu Met Asn Glu Val His Glu His Leu Glu Glu Glu Glu Ser Leu Cys
 90                  95                 100                 105 cag gtt tct ctg gca gat tcc tgg gat gaa tgc agg gct tgc ctg gaa      507
Gln Val Ser Leu Ala Asp Ser Trp Asp Glu Cys Arg Ala Cys Leu Glu
                 110                 115                 120 agt aac tgc atg agg ttt gat acc acc tgc caa cct gca tgg tcc tct      555
Ser Asn Cys Met Arg Phe Asp Thr Thr Cys Gln Pro Ala Trp Ser Ser
             125                 130                 135 gtg aaa aat atg cca gcc tac aga gca gat gct gag cca agc tgg gcc      603
Val Lys Asn Met Pro Ala Tyr Arg Ala Asp Ala Glu Pro Ser Trp Ala
         140                 145                 150 att ccc aat gtc ttc cag ctg ctc tgc aac ttg agt ttc tca gtt tat      651
Ile Pro Asn Val Phe Gln Leu Leu Cys Asn Leu Ser Phe Ser Val Tyr
     155                 160                 165 caa agt gtc agt gaa aaa ctc atc aca acc ctg cgt gcc aca gag gac      699
Gln Ser Val Ser Glu Lys Leu Ile Thr Thr Leu Arg Ala Thr Glu Asp
170                 175                 180                 185 cct cca aaa caa gac aaa gac tcc aac cag gga ggc ccg att tca aag      747
Pro Pro Lys Gln Asp Lys Asp Ser Asn Gln Gly Gly Pro Ile Ser Lys
                 190                 195                 200 ata cta cct gag caa gac aga ggc tca gat ggg aaa ctt ggc cag aat      795
Ile Leu Pro Glu Gln Asp Arg Gly Ser Asp Gly Lys Leu Gly Gln Asn
             205                 210                 215 ttg tct gat tgc gtt aat ttt cgc aag aga tgc cag aaa tgc cag gat      843
Leu Ser Asp Cys Val Asn Phe Arg Lys Arg Cys Gln Lys Cys Gln Asp
         220                 225                 230 tat cta tct gat gac tgc cct aat gtg cct gaa cta tac aga gaa ctc      891
Tyr Leu Ser Asp Asp Cys Pro Asn Val Pro Glu Leu Tyr Arg Glu Leu
     235                 240                 245 aat gag gcc ctc cga ctg gtc agt aga tcc aat cag caa tac gac cag      939
Asn Glu Ala Leu Arg Leu Val Ser Arg Ser Asn Gln Gln Tyr Asp Gln
250                 255                 260                 265 gtg gtg cag atg acc cag tat cac ctg gaa gac acc acg ctt ctg atg      987
Val Val Gln Met Thr Gln Tyr His Leu Glu Asp Thr Thr Leu Leu Met
                 270                 275                 280 gag aag atg aga gag cag ttt ggc tgg gtt tct gaa ctg gca tac cag     1035
Glu Lys Met Arg Glu Gln Phe Gly Trp Val Ser Glu Leu Ala Tyr Gln
             285                 290                 295 tcc cca gga gct gag gac atc ttt aat cca gtg aaa gta atg gta gcc     1083
Ser Pro Gly Ala Glu Asp Ile Phe Asn Pro Val Lys Val Met Val Ala
         300                 305                 310 cta agt gct cat gaa gga aat tct tct gat caa gat gac aca gtg gtt     1131
Leu Ser Ala His Glu Gly Asn Ser Ser Asp Gln Asp Asp Thr Val Val
     315                 320                 325 cct tca agc ctc ctg cct tcc tct aac ttc aca ctc agc agc cct ctt     1179
Pro Ser Ser Leu Leu Pro Ser Ser Asn Phe Thr Leu Ser Ser Pro Leu
330                 335                 340                 345 gaa aag agt gct ggc aac gct aac ttc att gat cac gtg gta gag aag     1227
Glu Lys Ser Ala Gly Asn Ala Asn Phe Ile Asp His Val Val Glu Lys
                 350                 355                 360 gtt ctt cag cac ttt aag gag cac ttt aaa act tgg taagaagatt          1273
Val Leu Gln His Phe Lys Glu His Phe Lys Thr Trp
             365                 370 tagtccatcc tataatcagc aagaattaca ccttcggcca agacctgaga attctgaaaa   1333
```

-continued

```
tacaaagcag gctaacacaa tgaacacagc tgcatgaaag ttaggtatat attaggaagc    1393
actattggtt tactttgttg aatggaagtt taatagctat tcaaattgag ttaatataaa    1453
aatttcttcc taaaaagtaa aatgtacata tgtagaatat gatgcattag ttctttgtat    1513
actaaataaa tactgagtcc cct                                            1536
```

<210> SEQ ID NO 45
<211> LENGTH: 373
<212> TYPE: PRT
<213> ORGANISM: Cavia sp.

<400> SEQUENCE: 45

```
Met Lys Leu Pro Leu Leu Met Phe Pro Val Cys Leu Leu Trp Leu Lys
1               5                   10                  15

Asp Cys His Cys Ala Pro Thr Trp Lys Asp Lys Thr Ala Ile Ser Glu
            20                  25                  30

Asn Ala Asn Ser Phe Ser Glu Ala Gly Glu Ile Asp Val Asp Gly Glu
        35                  40                  45

Val Lys Ile Ala Leu Ile Gly Ile Lys Gln Met Lys Ile Met Met Glu
    50                  55                  60

Arg Arg Glu Glu Glu His Ser Lys Leu Met Lys Thr Leu Lys Lys Cys
65                  70                  75                  80

Lys Glu Glu Lys Gln Glu Ala Leu Lys Leu Met Asn Glu Val His Glu
                85                  90                  95

His Leu Glu Glu Glu Glu Ser Leu Cys Gln Val Ser Leu Ala Asp Ser
            100                 105                 110

Trp Asp Glu Cys Arg Ala Cys Leu Glu Ser Asn Cys Met Arg Phe Asp
        115                 120                 125

Thr Thr Cys Gln Pro Ala Trp Ser Ser Val Lys Asn Met Pro Ala Tyr
    130                 135                 140

Arg Ala Asp Ala Glu Pro Ser Trp Ala Ile Pro Asn Val Phe Gln Leu
145                 150                 155                 160

Leu Cys Asn Leu Ser Phe Ser Val Tyr Gln Ser Val Ser Glu Lys Leu
                165                 170                 175

Ile Thr Thr Leu Arg Ala Thr Glu Asp Pro Pro Lys Gln Asp Lys Asp
            180                 185                 190

Ser Asn Gln Gly Gly Pro Ile Ser Lys Ile Leu Pro Glu Gln Asp Arg
        195                 200                 205

Gly Ser Asp Gly Lys Leu Gly Gln Asn Leu Ser Asp Cys Val Asn Phe
    210                 215                 220

Arg Lys Arg Cys Gln Lys Cys Gln Asp Tyr Leu Ser Asp Asp Cys Pro
225                 230                 235                 240

Asn Val Pro Glu Leu Tyr Arg Glu Leu Asn Glu Ala Leu Arg Leu Val
                245                 250                 255

Ser Arg Ser Asn Gln Gln Tyr Asp Gln Val Val Gln Met Thr Gln Tyr
            260                 265                 270

His Leu Glu Asp Thr Thr Leu Leu Met Glu Lys Met Arg Glu Gln Phe
        275                 280                 285

Gly Trp Val Ser Glu Leu Ala Tyr Gln Ser Pro Gly Ala Glu Asp Ile
    290                 295                 300

Phe Asn Pro Val Lys Val Met Val Ala Leu Ser Ala His Glu Gly Asn
305                 310                 315                 320

Ser Ser Asp Gln Asp Asp Thr Val Val Pro Ser Ser Leu Leu Pro Ser
                325                 330                 335
```

Ser Asn Phe Thr Leu Ser Ser Pro Leu Glu Lys Ser Ala Gly Asn Ala
            340                 345                 350

Asn Phe Ile Asp His Val Val Glu Lys Val Leu Gln His Phe Lys Glu
            355                 360                 365

His Phe Lys Thr Trp
        370

<210> SEQ ID NO 46
<211> LENGTH: 2464
<212> TYPE: DNA
<213> ORGANISM: Bos sp.

<400> SEQUENCE: 46

| | | | | | |
|---|---|---|---|---|---|
| gcaacctcgt | tggtgagagc | ctgcagttag | tgtcacggcg | gaaacatgaa | gccgccactc | 60 |
| ttggtgttta | ttgtgtatct | gctgcggctg | agagactgtc | agtgtgcgcc | tacagggaag | 120 |
| gaccgaactt | ccatccgtga | agacccgaag | ggttttttcca | aggctgggga | gatagacgta | 180 |
| gatgaagagg | tgaagaaggc | tttgattggc | atgaagcaga | tgaaaatcct | gatggaaaga | 240 |
| agagaggagg | aacatagcaa | actaatgaga | acactgaaga | aatgcagaga | agaaaagcag | 300 |
| gaggccctga | agcttatgaa | tgaagttcaa | gaacatctag | aagaggaaga | aaggctatgc | 360 |
| caggtgtctc | tgatgggttc | ctgggacgaa | tgcaaatctt | gcctggaaag | tgactgcatg | 420 |
| agatttttata | caacctgcca | aagcagttgg | tcctctatga | aatccacgat | tgaacgggtt | 480 |
| ttccggaaga | tatatcagtt | tctctttcct | ttccatgaag | acgatgaaaa | agagcttcct | 540 |
| gttggtgaga | agttcactga | ggaagatgta | cagctgatgc | agatagagaa | tgtgttcagc | 600 |
| cagctgaccg | tggatgtggg | atttctctat | aacatgagct | tcacgtcttc | caaacagatg | 660 |
| cagcaagaat | tgacctggc | ttttcaatca | tactttatgt | cagacacaga | ctccatggag | 720 |
| ccttactttt | ttccagctttt | ttccaaagag | ccagcaaaaa | aagcacatcc | tatgcagagt | 780 |
| tgggacattc | ccagcttctt | ccagctgttt | tgtaatttca | gcctctctgt | ttatcaaagt | 840 |
| gtcagcgcaa | cagttacaga | gatgctgaag | gccattgagg | acttatccaa | acaagacaaa | 900 |
| gattctgccc | acggtggacc | gagttccacg | acgtggcctg | tgcggggcag | agggctgtgt | 960 |
| ggagaacctg | gccagaactc | gtccgaatgt | ctccaatttc | atgcaagatg | ccagaaatgt | 1020 |
| caggattacc | tatgggcaga | ctgccctgct | gttcctgaac | tatacacaaa | ggcggatgag | 1080 |
| gcccttgagt | tggtcaacat | atccaatcag | cagtatgccc | aggtactcca | gatgacccag | 1140 |
| catcacttgg | aggacaccac | gtatctgatg | gagaagatga | gagagcagtt | tggttgggta | 1200 |
| acagagctgg | ccagccagac | cccaggaagc | gagaacatct | tcagtttcat | aaaggtagtt | 1260 |
| ccaggtgttc | acgaaggaaa | tttctccaaa | caagatgaaa | agatgataga | cataagcatt | 1320 |
| ctgccttcct | ctaatttcac | actcaccatc | cctcttgaag | aaagtgctga | gagttccgac | 1380 |
| ttcattagct | acatgctggc | caaagctgta | cagcatttta | aggaacattt | taaatcttgg | 1440 |
| taagcagagt | atttgattag | ggacgtttgc | tgataggaat | agatggttct | taaaagggaa | 1500 |
| aaatgacaaa | actagctttt | gaataccttg | aaaacgtatt | caacctcatt | aataatcaaa | 1560 |
| ggcatgaaaa | ctaagacaag | ttagcagttt | ttacctattg | aattttcaaa | ttaaaaaaaa | 1620 |
| aaatcctgat | agaatgcaat | gaaatgagaa | ttcttatatg | tgattgccag | aaacaaactg | 1680 |
| gttttgtctt | tttgaaaagt | tattcaatta | tacatatcaa | gagtcatcaa | atttcttttt | 1740 |
| aatataataa | ttccacttct | ggaatcaatc | caaaggagta | aatctaaaat | tgaattgaag | 1800 |
| ttccacccc | aagatcaata | tttgcaaatt | atttaaaata | gtaaactgtt | aaaaactgaa | 1860 |

```
tgtcatctga atgtctaaaa accagaaatg gttaaaagct gtggctaaat atgctccaaa    1920
tatcttataa aaccattaaa aatatttata aaatttaaat catgacatga catctgctgg    1980
aacaagagtt tattctaagc ctatctataa ggcaaatatt attattacta tcttccagaa    2040
aagaaacttg agactcaggg tccaagtgtt agttgctcag tcatgtctga ctctttggga    2100 cccttggac tgtagcccac caggctcctc tgtccgtggg attcttcaga caggaatact     2160
ggggcaggtt gctatttcct tctccaggaa atcttcccta tccagggatg gaacccaggt    2220
ctcctgcatt gcaggtagat gctttactat ctgagcaacc aaatgaatta ctcaagtcag    2280 taggggtag aggcaaattt taacttagtt ttctctgaat cataattgcc acattaaact     2340
ggttcctgtt gggacatttg gttgaaaaaa ataaagtgaa aaatgagtat aaaactctat    2400
aaatgtaatg atcaaaacga aaaaaaatct acaatctgca ttaaaaataa aaagggttgg    2460
cagg                                                                2464

<210> SEQ ID NO 47
<211> LENGTH: 3016
<212> TYPE: DNA
<213> ORGANISM: Bos sp.

<400> SEQUENCE: 47
cagaagctgg tggcaacctc gttggtgaga gcctgcagtt agtgtcacgg cggaaacatg      60
aagccgccac tcttggtgtt tattgtgtat ctgctgcggc tgagagactg tcagtgtgcg     120
cctacaggga aggaccgaac ttccatccgt gaagacccga agggtttttc caaggctggg     180
gagatagacg tagatgaaga ggtgaagaag ctttgattg gcatgaagca gatgaaaatc      240
ctgatggaaa gaagagagga ggaacatagc aaactaatga gaacactgaa gaaatgcaga     300
gaagaaaagc aggaggccct gaagcttatg aatgaagttc aagaacatct agaagaggaa     360
gaaaggctat gccaggtgtc tctgatgggt tcctgggacg aatgcaaatc ttgcctggaa     420
agtgactgca tgagatttta tacaacctgc caaagcagtt ggtcctctat gaaatccacg     480
attgaacggg ttttccggaa gatatatcag tttctctttc ctttccatga agacgatgaa     540
aaagagcttc ctgttggtga gaagttcact gaggaagatg tacagctgat gcagatagag     600
aatgtgttca gccagctgac cgtggatgtg ggatttctct ataacatgag ctttcacgtc     660
ttcaaacaga tgcagcaaga atttgacctg gcttttcaat catactttat gtcagacaca     720
gactccatgg agccttactt ttttccagct ttttccaaag agccagcaaa aaaagcacat     780
cctatgcaga gttgggacat tcccagcttc ttccagctgt tttgtaattt cagcctctct     840
gtttatcaaa gtgtcagcgc aacagttaca gagatgctga aggccattga ggacttatcc    900
aaacaagaca aagattctgc ccacggtgga ccgagttcca cgacgtggcc tgtgcggggc    960
agagggctgt gtggagaacc tggccagaac tcgtccgaat gtctccaatt tcatgcaaga   1020
tgccagaaat gtcaggatta cctatgggca gactgccctg ctgttcctga actatacaca   1080
aaggcggatg aggcccttga gttggtcaac atatccaatc agcagtatgc ccaggtactc   1140
cagatgaccc agcatcactt ggaggacacc acgtatctga tggagaagat gagagagcag   1200
tttggttggg taacagagct ggccagccag accccaggaa gcgagaacat cttcagtttc   1260
ataaaggtag ttccaggtgt tcacgaagga aatttctcca acaagatgaa aagatgata    1320 gacataagca ttctgccttc ctctaatttc acactcacca tccctcttga agaaagtgct   1380
gagagttccg acttcattag ctacatgctg gccaaagctg tacagcattt taaggaacat   1440
```

-continued

| | |
|---|---|
| tttaaatctt ggtaagcaga gtatttgatt agggacgttt gctgatagga atagatggtt | 1500 |
| cttaaaaggg aaaaatgaca aaactagctt ttgaatacct tgaaaacgta ttcaacctca | 1560 |
| ttaataatca aaggcatgaa aactaagaca agttagcagt ttttacctat tgaattttca | 1620 |
| aattaaaaaa aaaaatcctg atagaatgca atgaaatgag aattcttata tgtgattgcc | 1680 |
| agaaacaaac tggttttgtc tttttgaaaa gttattcaat tatacatatc aagagtcatc | 1740 |
| aaatttcttt ttaatataat aattccactt ctggaatcaa tccaaaggag taaatctaaa | 1800 |
| attgaattga agttcccacc ccaagatcaa tatttgcaaa ttatttaaaa tagtaaactg | 1860 |
| ttaaaaactg aatgtcatct gaatgtctaa aaaccagaaa tggttaaaag ctgtggctaa | 1920 |
| atatgctcca aatatcttat aaaaccatta aaaatattta taaaatttaa atcatgacat | 1980 |
| gacatctgct ggaacaagag tttattctaa gcctatctat aaggcaaata ttattattac | 2040 |
| tatcttccag aaaagaaact tgagactcag ggtccaagtg ttagttgctc agtcatgtct | 2100 |
| gactctttga gacccttgg actgtggccc accaggctcc tctgtccatg ggattcttca | 2160 |
| gacaagaata ctggagcagg ttgctatttc cttctccagg aaatcttccc tatccaggga | 2220 |
| tggaacccag gtcctgca ttgcaggtag atgctttact atctgagcaa ccaaatgaat | 2280 |
| tactcaagtc agtaggggt agaggcaaat tttaacttag ttttctctga atcataattg | 2340 |
| ccacattaaa ctggttcctg ttgggacatt tggttgaaaa aaataaagtg aaaaatgagt | 2400 |
| ataaaactct ataatgtaa tgatcaaaac gaaaaaaaat ctacaatctg cattaaaaat | 2460 |
| aaaagggtt ggcaggaatt acggttggaa atggatgatt ttttttaacc ttttcatctt | 2520 |
| ttgatatttt acaattttct ataatgaata aataattttg agatttcaaa ttagaagata | 2580 |
| tgttgctaaa atagctaggt aaatgtagat tgaacactgt atcaatgtgt tctcatcttt | 2640 |
| aaactttagt ataagtactt ctattccatg gtaatcctac agtaagacga aatgtaaatc | 2700 |
| tgttcggtct acaggaaaaa caactaaatg acatttcaga cgtacattac catctctgtt | 2760 |
| aggataatct tctgaattaa tggcacaatt agaactgtac atagtattct cctttggtaa | 2820 |
| aatggtcaat cttaaagaag cattaaatgt taattctaag ttattactca taagggacct | 2880 |
| tgtaggtagg tccctatcaa tgtataatta agctgggtat ttctagattc gctgcctctc | 2940 |
| cctttatctc tgaatgttgg agaggttgtt ggtcatcaat caaccaatat cttttagca | 3000 |
| tcttctaagt gaaggc | 3016 |

<210> SEQ ID NO 48
<211> LENGTH: 2488
<212> TYPE: DNA
<213> ORGANISM: Bos sp.
<220> FEATURE:
<221> NAME/KEY: CDS
<222> LOCATION: (71)...(1465)

<400> SEQUENCE: 48

| | |
|---|---|
| gtgaaggtcc ttacagaagc tggtggcaac ctcgttggtg agagcctgca gttagtgtca | 60 |
| cggcggaaac atg aag ccg cca atc ttg gtg ttt atc gtg tat ctg ctg<br>           Met Lys Pro Pro Ile Leu Val Phe Ile Val Tyr Leu Leu<br>            1                  5                    10 | 109 |
| cag ctg aga gac tgt cag tgt gcg cct aca ggg aag gac cga act tcc<br>Gln Leu Arg Asp Cys Gln Cys Ala Pro Thr Gly Lys Asp Arg Thr Ser<br> 15                    20                   25 | 157 |
| atc cgt gaa gac ccg aag ggt ttt tcc aag gct ggg gag ata gac gta<br>Ile Arg Glu Asp Pro Lys Gly Phe Ser Lys Ala Gly Glu Ile Asp Val<br>30                   35                   40                   45 | 205 |

| | | |
|---|---|---|
| gat gaa gag gtg aag aag gct ttg att ggc atg aag cag atg aaa atc<br>Asp Glu Glu Val Lys Lys Ala Leu Ile Gly Met Lys Gln Met Lys Ile<br>50                         55                    60 | 253 |
| ctg atg gaa aga aga gag gag gaa cat agc aaa cta atg aga acc ctg<br>Leu Met Glu Arg Arg Glu Glu Glu His Ser Lys Leu Met Arg Thr Leu<br>65                       70                    75 | 301 |
| aag aaa tgc aga gaa gaa aag cag gag gcc ctg aag ctt atg aat gaa<br>Lys Lys Cys Arg Glu Glu Lys Gln Glu Ala Leu Lys Leu Met Asn Glu<br>80                       85                    90 | 349 |
| gtt caa gaa cat cta gaa gag gaa gaa agg cta tgc cag gtg tct ctg<br>Val Gln Glu His Leu Glu Glu Glu Glu Arg Leu Cys Gln Val Ser Leu<br>95                      100                 105 | 397 |
| atg ggt tcc tgg gac gaa tgc aaa tct tgc ctg gaa agt gac tgc atg<br>Met Gly Ser Trp Asp Glu Cys Lys Ser Cys Leu Glu Ser Asp Cys Met<br>110               115                120                125 | 445 |
| aga ttt tat aca acc tgc caa agc agt tgg tcc tct atg aaa tcc acg<br>Arg Phe Tyr Thr Thr Cys Gln Ser Ser Trp Ser Ser Met Lys Ser Thr<br>                         130                 135                140 | 493 |
| att gaa cgg gtt ttc cgg aag ata tat cag ttt ctc ttt cct ttc cat<br>Ile Glu Arg Val Phe Arg Lys Ile Tyr Gln Phe Leu Phe Pro Phe His<br>             145                 150                155 | 541 |
| gaa gac gat gaa aaa gag ctt cct gtt ggt gag aag ttc act gag gaa<br>Glu Asp Asp Glu Lys Glu Leu Pro Val Gly Glu Lys Phe Thr Glu Glu<br>160               165                170 | 589 |
| gat gta cag ctg atg cag ata gag aat gtg ttc agc cag ctg acc gtg<br>Asp Val Gln Leu Met Gln Ile Glu Asn Val Phe Ser Gln Leu Thr Val<br>175               180                185 | 637 |
| gac gtg gga ttt ctc tat aac atg agc ttt cac gtc ttc aaa cag atg<br>Asp Val Gly Phe Leu Tyr Asn Met Ser Phe His Val Phe Lys Gln Met<br>190               195                200                205 | 685 |
| cag caa gaa ttt gac ctg gct ttt caa tca tac ttt atg tca gac aca<br>Gln Gln Glu Phe Asp Leu Ala Phe Gln Ser Tyr Phe Met Ser Asp Thr<br>                         210                 215                220 | 733 |
| gac tcc atg gag cct tac ttt ttt cca gct ttt tcc aaa gag cca gca<br>Asp Ser Met Glu Pro Tyr Phe Phe Pro Ala Phe Ser Lys Glu Pro Ala<br>             225                 230                235 | 781 |
| aaa aaa gca cat cct atg cag agt tgg gac att ccc agc ttc ttc cag<br>Lys Lys Ala His Pro Met Gln Ser Trp Asp Ile Pro Ser Phe Phe Gln<br>240               245                250 | 829 |
| ctg ttt tgt aat ttc agc ctc tct gtt tat caa agt gtc agc gca aca<br>Leu Phe Cys Asn Phe Ser Leu Ser Val Tyr Gln Ser Val Ser Ala Thr<br>255               260                265 | 877 |
| gtt aca gag atg ctg aag gcc att gag gac tta tcc aaa caa gac aaa<br>Val Thr Glu Met Leu Lys Ala Ile Glu Asp Leu Ser Lys Gln Asp Lys<br>270               275                280                285 | 925 |
| gat tct gcc cac ggt gga ccg agt tcc acg acg tgg cct gtg cgg ggc<br>Asp Ser Ala His Gly Gly Pro Ser Ser Thr Thr Trp Pro Val Arg Gly<br>                         290                 295                300 | 973 |
| aga ggg ctg tgt gga gaa cct ggc cag aac tcg tcc gaa tgt ctc caa<br>Arg Gly Leu Cys Gly Glu Pro Gly Gln Asn Ser Ser Glu Cys Leu Gln<br>             305                 310                315 | 1021 |
| ttt cat gca aga tgc cag aaa tgt cag gat tac cta tgg gca gac tgc<br>Phe His Ala Arg Cys Gln Lys Cys Gln Asp Tyr Leu Trp Ala Asp Cys<br>320               325                330 | 1069 |
| cct gct gtt cct gaa cta tac aca aag gcg gat gag gcc ctt gag ttg<br>Pro Ala Val Pro Glu Leu Tyr Thr Lys Ala Asp Glu Ala Leu Glu Leu<br>335               340                345 | 1117 |
| gtc aac ata tcc aat cag cag tat gcc cag gta ctc cag atg acc cag<br>Val Asn Ile Ser Asn Gln Gln Tyr Ala Gln Val Leu Gln Met Thr Gln<br>350               355                360                365 | 1165 |

```
cat cac ttg gag gac acc acg tat ctg atg gag aag atg aga gag cag         1213
His His Leu Glu Asp Thr Thr Tyr Leu Met Glu Lys Met Arg Glu Gln
             370                 375                 380 ttt ggt tgg gta aca gag ctg gcc agc cag acc cca gga agc gag aac         1261
Phe Gly Trp Val Thr Glu Leu Ala Ser Gln Thr Pro Gly Ser Glu Asn
             385                 390                 395 atc ttc agt ttc ata aag gta gtt cca ggt gtt cac gaa gga aat ttc         1309
Ile Phe Ser Phe Ile Lys Val Val Pro Gly Val His Glu Gly Asn Phe
             400                 405                 410 tcc aaa caa gat gaa aag atg ata gac ata agc att ctg cct tcc tct         1357
Ser Lys Gln Asp Glu Lys Met Ile Asp Ile Ser Ile Leu Pro Ser Ser
         415                 420                 425 aat ttc aca ctc acc atc cct ctt gaa gaa agt gct gag agt tcc gac         1405
Asn Phe Thr Leu Thr Ile Pro Leu Glu Glu Ser Ala Glu Ser Ser Asp
430                 435                 440                 445 ttc att agc tac atg ctg gcc aaa gct gta cag cat ttt aag gaa cat         1453
Phe Ile Ser Tyr Met Leu Ala Lys Ala Val Gln His Phe Lys Glu His
                 450                 455                 460 ttt aaa tct tgg taagcagagt atttgattag ggacgtttgc tgataggaat            1505
Phe Lys Ser Trp
             465 agatggttct taaaagggaa aaatgacaaa actagctttt gaataccttg aaaacgtatt      1565 caacctcatt aataatcaaa ggcatgaaaa ctaagacaag ttagcagttt ttacctattg      1625 aattttcaaa ttaaaaaaaa aatcctgata gaatgcaatg aaatgagaat tcttatatgt      1685 gattgccaga acaaactgg ttttgtcttt ttgaaaagtt attcaattat acatatcaag       1745 agtcatcaaa tttctttta atataataat tccacttctg gaatcaatcc aaaggagtaa      1805 atctaaaatt gaattgaagt tcccaccca agatcaatat ttgcaaatta tttaaaatag      1865 taaactgtta aaaactgaat gtcatctgaa tgtctaaaaa ccagaaatgg ttaaaagctg      1925 tggctaaata tgctccaaat atcttataaa accattaaaa atatttataa aatttaaatc     1985 atgacatgac atctgctgga acaagagttt attctaagcc tatctataag gcaaatatta     2045 ttattactat cttccagaaa agaaacttga gactcagggt ccaagtgtta gttgctcagt     2105 catgtctgac tctttgagac cccttggact gtagcccacc aggctcctct gtccatggga     2165 ttcttcagac aagaatactg gagcaggttg ctatttcctt ctccaggaaa tcttccctat     2225 ccagggatgg aacccaggtc tcctgcattg caggtagatg ctttactatc tgagcaacca     2285 aatgaattac tcaagtcagt aggggtaga ggcaaatttt aacttagttt tctctgaatc      2345 ataattgcca cattaaactg gttcctgttg ggacatttgg ttgaaaaaaa taaagtgaaa     2405 aatgagtata aaactctata aatgtaatga tcaaaacgaa aaaaaatcta caatctgcat     2465 taaaaataaa aagggttggc agg                                              2488
```

<210> SEQ ID NO 49
<211> LENGTH: 465
<212> TYPE: PRT
<213> ORGANISM: Bos sp.

<400> SEQUENCE: 49

```
Met Lys Pro Pro Ile Leu Val Phe Ile Val Tyr Leu Leu Gln Leu Arg
 1               5                  10                  15

Asp Cys Gln Cys Ala Pro Thr Gly Lys Asp Arg Thr Ser Ile Arg Glu
             20                  25                  30

Asp Pro Lys Gly Phe Ser Lys Ala Gly Glu Ile Asp Val Asp Glu Glu
         35                  40                  45
```

```
Val Lys Lys Ala Leu Ile Gly Met Lys Gln Met Lys Ile Leu Met Glu
 50                  55                  60

Arg Arg Glu Glu Glu His Ser Lys Leu Met Arg Thr Leu Lys Lys Cys
 65                  70                  75                  80

Arg Glu Glu Lys Gln Glu Ala Leu Lys Leu Met Asn Glu Val Gln Glu
                 85                  90                  95

His Leu Glu Glu Glu Arg Leu Cys Gln Val Ser Leu Met Gly Ser
                100                 105                 110

Trp Asp Glu Cys Lys Ser Cys Leu Glu Ser Asp Cys Met Arg Phe Tyr
                115                 120                 125

Thr Thr Cys Gln Ser Ser Trp Ser Ser Met Lys Ser Thr Ile Glu Arg
        130                 135                 140

Val Phe Arg Lys Ile Tyr Gln Phe Leu Phe Pro Phe His Glu Asp Asp
145                 150                 155                 160

Glu Lys Glu Leu Pro Val Gly Glu Lys Phe Thr Glu Glu Asp Val Gln
                165                 170                 175

Leu Met Gln Ile Glu Asn Val Phe Ser Gln Leu Thr Val Asp Val Gly
                180                 185                 190

Phe Leu Tyr Asn Met Ser Phe His Val Phe Lys Gln Met Gln Gln Glu
                195                 200                 205

Phe Asp Leu Ala Phe Gln Ser Tyr Phe Met Ser Asp Thr Asp Ser Met
210                 215                 220

Glu Pro Tyr Phe Phe Pro Ala Phe Ser Lys Glu Pro Ala Lys Lys Ala
225                 230                 235                 240

His Pro Met Gln Ser Trp Asp Ile Pro Ser Phe Phe Gln Leu Phe Cys
                245                 250                 255

Asn Phe Ser Leu Ser Val Tyr Gln Ser Val Ser Ala Thr Val Thr Glu
                260                 265                 270

Met Leu Lys Ala Ile Glu Asp Leu Ser Lys Gln Asp Lys Asp Ser Ala
        275                 280                 285

His Gly Gly Pro Ser Ser Thr Thr Trp Pro Val Arg Gly Arg Gly Leu
290                 295                 300

Cys Gly Glu Pro Gly Gln Asn Ser Ser Glu Cys Leu Gln Phe His Ala
305                 310                 315                 320

Arg Cys Gln Lys Cys Gln Asp Tyr Leu Trp Ala Asp Cys Pro Ala Val
                325                 330                 335

Pro Glu Leu Tyr Thr Lys Ala Asp Glu Ala Leu Glu Leu Val Asn Ile
                340                 345                 350

Ser Asn Gln Gln Tyr Ala Gln Val Leu Gln Met Thr Gln His His Leu
        355                 360                 365

Glu Asp Thr Thr Tyr Leu Met Glu Lys Met Arg Glu Gln Phe Gly Trp
        370                 375                 380

Val Thr Glu Leu Ala Ser Gln Thr Pro Gly Ser Glu Asn Ile Phe Ser
385                 390                 395                 400

Phe Ile Lys Val Val Pro Gly Val His Glu Gly Asn Phe Ser Lys Gln
                405                 410                 415

Asp Glu Lys Met Ile Asp Ile Ser Ile Leu Pro Ser Ser Asn Phe Thr
                420                 425                 430

Leu Thr Ile Pro Leu Glu Glu Ser Ala Glu Ser Ser Asp Phe Ile Ser
        435                 440                 445

Tyr Met Leu Ala Lys Ala Val Gln His Phe Lys Glu His Phe Lys Ser
450                 455                 460
```

-continued

```
Trp
465

<210> SEQ ID NO 50
<211> LENGTH: 8
<212> TYPE: PRT
<213> ORGANISM: Homo sapiens

<400> SEQUENCE: 50

Asp Tyr Lys Asp Asp Asp Asp Lys
1               5

<210> SEQ ID NO 51
<211> LENGTH: 446
<212> TYPE: PRT
<213> ORGANISM: Homo sapiens

<400> SEQUENCE: 51

Ala Pro Thr Trp Lys Asp Lys Thr Ala Ile Ser Glu Asn Leu Lys Ser
1               5                   10                  15

Phe Ser Glu Val Gly Glu Ile Asp Ala Asp Glu Glu Val Lys Lys Ala
                20                  25                  30

Leu Thr Gly Ile Lys Gln Met Lys Ile Met Met Glu Arg Lys Glu Lys
            35                  40                  45

Glu His Thr Asn Leu Met Ser Thr Leu Lys Lys Cys Arg Glu Glu Lys
    50                  55                  60

Gln Glu Ala Leu Lys Leu Leu Asn Glu Val Gln Glu His Leu Glu Glu
65                  70                  75                  80

Glu Glu Arg Leu Cys Arg Glu Ser Leu Ala Asp Ser Trp Gly Glu Cys
                85                  90                  95

Arg Ser Cys Leu Glu Asn Asn Cys Met Arg Ile Tyr Thr Thr Cys Gln
                100                 105                 110

Pro Ser Trp Ser Ser Val Lys Asn Lys Ile Glu Arg Phe Phe Arg Lys
                115                 120                 125

Ile Tyr Gln Phe Leu Phe Pro Phe His Glu Asp Asn Glu Lys Asp Leu
            130                 135                 140

Pro Ile Ser Glu Lys Leu Ile Glu Glu Asp Ala Gln Leu Thr Gln Met
145                 150                 155                 160

Glu Asp Val Phe Ser Gln Leu Thr Val Asp Val Asn Ser Leu Phe Asn
                165                 170                 175

Arg Ser Phe Asn Val Phe Arg Gln Met Gln Gln Glu Phe Asp Gln Thr
                180                 185                 190

Phe Gln Ser His Phe Ile Ser Asp Thr Asp Leu Thr Glu Pro Tyr Phe
            195                 200                 205

Phe Pro Ala Phe Ser Lys Glu Pro Met Thr Lys Ala Asp Leu Glu Gln
210                 215                 220

Cys Trp Asp Ile Pro Asn Phe Gln Leu Phe Cys Asn Phe Ser Val
225                 230                 235                 240

Ser Ile Tyr Glu Ser Val Ser Glu Thr Ile Thr Lys Met Leu Lys Ala
                245                 250                 255

Ile Glu Asp Leu Pro Lys Gln Asp Lys Ala Pro Asp His Gly Gly Leu
                260                 265                 270

Ile Ser Lys Met Leu Pro Gly Gln Asp Arg Gly Leu Cys Gly Glu Leu
            275                 280                 285

Asp Gln Asn Leu Ser Arg Cys Phe Lys Phe His Glu Lys Cys Gln Lys
290                 295                 300
```

```
Cys Gln Ala His Leu Ser Glu Asp Cys Pro Asp Val Pro Ala Leu His
305                 310                 315                 320

Thr Glu Leu Asp Glu Ala Ile Arg Leu Val Asn Val Ser Asn Gln Gln
            325                 330                 335

Tyr Gly Gln Ile Leu Gln Met Thr Arg Lys His Leu Glu Asp Thr Ala
        340                 345                 350

Tyr Leu Val Glu Lys Met Arg Gly Gln Phe Gly Trp Val Ser Glu Leu
    355                 360                 365

Ala Asn Gln Ala Pro Glu Thr Glu Ile Ile Phe Asn Ser Ile Gln Val
    370                 375                 380

Val Pro Arg Ile His Glu Gly Asn Ile Ser Lys Gln Asp Glu Thr Met
385                 390                 395                 400

Met Thr Asp Leu Ser Ile Leu Pro Ser Ser Asn Phe Thr Leu Lys Ile
            405                 410                 415

Pro Leu Glu Glu Ser Ala Glu Ser Ser Asn Phe Ile Gly Tyr Val Val
        420                 425                 430

Ala Lys Ala Leu Gln His Phe Lys Glu His Phe Lys Thr Trp
        435                 440                 445
```

<210> SEQ ID NO 52
<211> LENGTH: 44
<212> TYPE: DNA
<213> ORGANISM: Artificial Sequence
<220> FEATURE:
<223> OTHER INFORMATION: Primer

<400> SEQUENCE: 52 ttttctgaa ttcgccacca tgaaaattaa agcagagaaa aacg      44

<210> SEQ ID NO 53
<211> LENGTH: 69
<212> TYPE: DNA
<213> ORGANISM: Artificial Sequence
<220> FEATURE:
<223> OTHER INFORMATION: Primer

<400> SEQUENCE: 53
tttttgtcga cttatcactt gtcgtcgtcg tccttgtagt cccaggtttt aaaatgttcc      60
ttaaaatgc      69

<210> SEQ ID NO 54
<211> LENGTH: 40
<212> TYPE: DNA
<213> ORGANISM: Artificial Sequence
<220> FEATURE:
<223> OTHER INFORMATION: Primer

<400> SEQUENCE: 54
tttttctgaa ttcaccatga ggacctggga ctacagtaac      40

<210> SEQ ID NO 55
<211> LENGTH: 41
<212> TYPE: DNA
<213> ORGANISM: Artificial Sequence
<220> FEATURE:
<223> OTHER INFORMATION: Primer

<400> SEQUENCE: 55
tttttctctc gagaccatga aaattaaagc agagaaaaac g      41

<210> SEQ ID NO 56

```
<211> LENGTH: 47
<212> TYPE: DNA
<213> ORGANISM: Artificial Sequence
<220> FEATURE:
<223> OTHER INFORMATION: Primer

<400> SEQUENCE: 56
tttttggatc cgctgctgcc caggttttaa aatgttcctt aaaatgc          47

<210> SEQ ID NO 57
<211> LENGTH: 40
<212> TYPE: DNA
<213> ORGANISM: Primer

<400> SEQUENCE: 57
tttttctctc gagaccatga ggacctggga ctacagtaac                  40

<210> SEQ ID NO 58
<211> LENGTH: 37
<212> TYPE: DNA
<213> ORGANISM: Artificial Sequence
<220> FEATURE:
<223> OTHER INFORMATION: Primer

<400> SEQUENCE: 58
tttttctgaa ttcaccatga agccgccact cttggtg                     37

<210> SEQ ID NO 59
<211> LENGTH: 60
<212> TYPE: DNA
<213> ORGANISM: Artificial Sequence
<220> FEATURE:
<223> OTHER INFORMATION: Primer

<400> SEQUENCE: 59
tttttggatc cgctgcggcc tccgtggtca ggagcttatt tttcacagag gaccagctag   60

<210> SEQ ID NO 60
<211> LENGTH: 36
<212> TYPE: DNA
<213> ORGANISM: Artificial Sequence
<220> FEATURE:
<223> OTHER INFORMATION: Primer

<400> SEQUENCE: 60
tttttctctc gaggactaca ggacacagct aaatcc                      36

<210> SEQ ID NO 61
<211> LENGTH: 45
<212> TYPE: DNA
<213> ORGANISM: Artificial Sequence
<220> FEATURE:
<223> OTHER INFORMATION: Primer

<400> SEQUENCE: 61
tttttggatc cttatcacca ggttttaaaa tgttccttaa aatgc             45

<210> SEQ ID NO 62
<211> LENGTH: 37
<212> TYPE: DNA
<213> ORGANISM: Artificial Sequence
<220> FEATURE:
<223> OTHER INFORMATION: Primer

<400> SEQUENCE: 62
tttttctgaa ttcaccatga agccgccact cttggtg                     37
```

<210> SEQ ID NO 63
<211> LENGTH: 40
<212> TYPE: DNA
<213> ORGANISM: Artificial Sequence
<220> FEATURE:
<223> OTHER INFORMATION: Primer

<400> SEQUENCE: 63
tttttctctc gagaccatga ggacctggga ctacagtaac        40

<210> SEQ ID NO 64
<211> LENGTH: 466
<212> TYPE: PRT
<213> ORGANISM: Homo sapiens

<400> SEQUENCE: 64

Met Lys Pro Pro Leu Leu Val Phe Ile Val Cys Leu Leu Trp Leu Lys
 1               5                  10                  15

Asp Ser His Cys Ala Pro Thr Trp Lys Asp Lys Thr Ala Ile Ser Glu
             20                  25                  30

Asn Leu Lys Ser Phe Ser Glu Val Gly Glu Ile Asp Ala Asp Glu Glu
         35                  40                  45

Val Lys Lys Ala Leu Thr Gly Ile Lys Gln Met Lys Ile Met Met Glu
 50                  55                  60

Arg Lys Glu Lys Glu His Thr Asn Leu Met Ser Thr Leu Lys Lys Cys
 65                  70                  75                  80

Arg Glu Glu Lys Gln Glu Ala Leu Lys Leu Leu Asn Glu Val Gln Glu
                 85                  90                  95

His Leu Glu Glu Glu Arg Leu Cys Arg Glu Ser Leu Ala Asp Ser
                100                 105                 110

Trp Gly Cys Arg Ser Cys Leu Glu Asn Asn Cys Met Arg Ile Tyr
             115                 120                 125

Thr Thr Cys Gln Pro Ser Trp Ser Ser Val Lys Asn Lys Ile Glu Arg
    130                 135                 140

Phe Phe Arg Lys Ile Tyr Gln Phe Leu Phe Pro Phe His Glu Asp Asn
145                 150                 155                 160

Glu Lys Asp Leu Pro Ile Ser Glu Lys Leu Ile Glu Glu Asp Ala Gln
                165                 170                 175

Leu Thr Gln Met Glu Asp Val Phe Ser Gln Leu Thr Val Asp Val Asn
            180                 185                 190

Ser Leu Phe Asn Arg Ser Phe Asn Val Phe Arg Gln Met Gln Gln Glu
        195                 200                 205

Phe Asp Gln Thr Phe Gln Ser His Phe Ile Ser Asp Thr Asp Leu Thr
    210                 215                 220

Glu Pro Tyr Phe Phe Pro Ala Ser Lys Glu Pro Met Thr Lys Ala
225                 230                 235                 240

Asp Leu Glu Gln Cys Trp Asp Ile Pro Asn Phe Phe Gln Leu Phe Cys
                245                 250                 255

Asn Phe Ser Val Ser Ile Tyr Glu Ser Val Ser Glu Thr Ile Thr Lys
            260                 265                 270

Met Leu Lys Ala Ile Glu Asp Leu Pro Lys Gln Asp Lys Ala Pro Asp
        275                 280                 285

His Gly Gly Leu Ile Ser Lys Met Leu Pro Gly Gln Asp Arg Gly Leu
    290                 295                 300

Cys Gly Glu Leu Asp Gln Asn Leu Ser Arg Cys Phe Lys Phe His Glu

```
305                 310                 315                 320
Lys Cys Gln Lys Cys Gln Ala His Leu Ser Glu Asp Cys Pro Asp Val
            325                 330                 335

Pro Ala Leu His Thr Glu Leu Asp Glu Ala Ile Arg Leu Val Asn Val
            340                 345                 350

Ser Asn Gln Gln Tyr Gly Gln Ile Leu Gln Met Thr Arg Lys His Leu
            355                 360                 365

Glu Asp Thr Ala Tyr Leu Val Glu Lys Met Arg Gly Gln Phe Gly Trp
            370                 375                 380

Val Ser Glu Leu Ala Asn Gln Ala Pro Glu Thr Glu Ile Ile Phe Asn
385                 390                 395                 400

Ser Ile Gln Val Val Pro Arg Ile His Glu Gly Asn Ile Ser Lys Gln
            405                 410                 415

Asp Glu Thr Met Met Thr Asp Leu Ser Ile Leu Pro Ser Ser Asn Phe
            420                 425                 430

Thr Leu Lys Ile Pro Leu Glu Glu Ser Ala Glu Ser Ser Asn Phe Ile
            435                 440                 445

Gly Tyr Val Val Ala Lys Ala Leu Gln His Phe Lys Glu His Phe Lys
            450                 455                 460

Thr Trp
465

<210> SEQ ID NO 65
<211> LENGTH: 1622
<212> TYPE: DNA
<213> ORGANISM: Homo sapiens
<220> FEATURE:
<221> NAME/KEY: CDS
<222> LOCATION: (3)...(1622)

<400> SEQUENCE: 65 tg cgt cac ctg cag gcc cgg gcc gcg ggg ttg gtt tcc acc ctg gag        47
   Arg His Leu Gln Ala Arg Ala Ala Gly Leu Val Ser Thr Leu Glu
   1               5                   10                  15 gtt gct gac acc ctg tgc cct cgg ctg act tcc agc cgg tgg cac aga       95
Val Ala Asp Thr Leu Cys Pro Arg Leu Thr Ser Ser Arg Trp His Arg
                20                  25                  30 cgc ctc cag ggg gca gca ctc aag cgc atc tta gga atg aca gag ttg      143
Arg Leu Gln Gly Ala Ala Leu Lys Arg Ile Leu Gly Met Thr Glu Leu
            35                  40                  45 cgt ccc tct ctg ttg cca ggc tgg agt tca gtg gca tgt tct tag ctc      191
Arg Pro Ser Leu Leu Pro Gly Trp Ser Ser Val Ala Cys Ser     Leu
        50                  55                  60 act gaa gcc tca aat tcc tgg gtt caa gtg acc ctc cca cct cag ccc      239
Thr Glu Ala Ser Asn Ser Trp Val Gln Val Thr Leu Pro Pro Gln Pro
        65                  70                  75 cat gag gac ctg gga cta cag gac aca gct aaa tcc ctg aca cgg atg      287
His Glu Asp Leu Gly Leu Gln Asp Thr Ala Lys Ser Leu Thr Arg Met
    80                  85                  90 aaa att aaa gca gag aaa aac gaa ggt cct tcc aga agc tgg tgg caa      335
Lys Ile Lys Ala Glu Lys Asn Glu Gly Pro Ser Arg Ser Trp Trp Gln
 95                 100                 105                 110 ctt cac tgg gga gat att gca aat aac agc ggg aac atg aag ccg cca      383
Leu His Trp Gly Asp Ile Ala Asn Asn Ser Gly Asn Met Lys Pro Pro
                115                 120                 125 ctc ttg gtg ttt att gtg tgt ctg ctg tgg ttg aaa gac agt cac tgc      431
Leu Leu Val Phe Ile Val Cys Leu Leu Trp Leu Lys Asp Ser His Cys
            130                 135                 140
```

```
gca ccc act tgg aag gac aaa act gct atc agt gaa aac ctg aag agt      479
Ala Pro Thr Trp Lys Asp Lys Thr Ala Ile Ser Glu Asn Leu Lys Ser
    145                 150                 155 ttt tct gag gtg ggg gag ata gat gca gat gaa gag gtg aag aag gct      527
Phe Ser Glu Val Gly Glu Ile Asp Ala Asp Glu Glu Val Lys Lys Ala
160                 165                 170 ttg act ggt att aag caa atg aaa atc atg atg gaa aga aaa gag aag      575
Leu Thr Gly Ile Lys Gln Met Lys Ile Met Met Glu Arg Lys Glu Lys
175                 180                 185                 190 gaa cac acc aat cta atg agc acc ctg aag aaa tgc aga gaa gaa aag      623
Glu His Thr Asn Leu Met Ser Thr Leu Lys Lys Cys Arg Glu Glu Lys
            195                 200                 205 cag gag gcc ctg aaa ctt ctg aat gaa gtt caa gaa cat ctg gag gaa      671
Gln Glu Ala Leu Lys Leu Leu Asn Glu Val Gln Glu His Leu Glu Glu
            210                 215                 220 gaa gaa agg cta tgc cgg gag tct ttg gca gat tcc tgg ggt gaa tgc      719
Glu Glu Arg Leu Cys Arg Glu Ser Leu Ala Asp Ser Trp Gly Glu Cys
                225                 230                 235 agg tct tgc ctg gaa aat aac tgc atg aga att tat aca acc tgc caa      767
Arg Ser Cys Leu Glu Asn Asn Cys Met Arg Ile Tyr Thr Thr Cys Gln
    240                 245                 250 cct agc tgg tcc tct gtg aaa aat aag ctc ctg acc acg gag gcc tga      815
Pro Ser Trp Ser Ser Val Lys Asn Lys Leu Leu Thr Thr Glu Ala
255                 260                 265 ttt caa aga tgt tac ctg ggc agg aca gag gac tgt gtg ggg aac ttg      863
Phe Gln Arg Cys Tyr Leu Gly Arg Thr Glu Asp Cys Val Gly Asn Leu
270                 275                 280                 285 acc aga att tgt caa gat gtt tca aat ttc atg aaa aat gcc aaa aat      911
Thr Arg Ile Cys Gln Asp Val Ser Asn Phe Met Lys Asn Ala Lys Asn
                290                 295                 300 gtc agg ctc acc tat ctg aag act gtc ctg atg tac ctg ctc tgc aca      959
Val Arg Leu Thr Tyr Leu Lys Thr Val Leu Met Tyr Leu Leu Cys Thr
                305                 310                 315 cag aat tag acg agg cga tca ggt tgg tca atg tat cca atc agc agt     1007
Gln Asn     Thr Arg Arg Ser Gly Trp Ser Met Tyr Pro Ile Ser Ser
                320                 325                 330 atg gcc aga ttc tcc aga tga ccc gga agc act tgg agg aca ccg cct     1055
Met Ala Arg Phe Ser Arg     Pro Gly Ser Thr Trp Arg Thr Pro Pro
                335                     340                 345 atc tgg tgg aga aga tga gag ggc aat ttg gct ggg tgt ctg aac tgg     1103
Ile Trp Trp Arg Arg     Glu Gly Asn Leu Ala Gly Cys Leu Asn Trp
        350                 355                 360 caa acc agg ccc cag aaa cag aga tca tct tta att caa tac agg tag     1151
Gln Thr Arg Pro Gln Lys Gln Arg Ser Ser Leu Ile Gln Tyr Arg
    365                 370                 375 ttc caa gga ttc atg aag gaa ata ttt cca aac aag atg aaa caa tga     1199
Phe Gln Gly Phe Met Lys Glu Ile Phe Pro Asn Lys Met Lys Gln
        380                 385                 390 tga cag act taa gca ttc tgc ctt cct cta att tca cac tca aga tcc     1247
    Gln Thr     Ala Phe Cys Leu Pro Leu Ile Ser His Ser Arg Ser
                    395                 400                 405 ctc ttg aag aaa gtg ctg aga gtt cta act tca ttg gct acg tag tgg     1295
Leu Leu Lys Lys Val Leu Arg Val Leu Thr Ser Leu Ala Thr     Trp
            410                 415                 420 caa aag ctc tac agc att tta agg aac att tta aaa cct ggt aag aag     1343
Gln Lys Leu Tyr Ser Ile Leu Arg Asn Ile Leu Lys Pro Gly Lys Lys
            425                 430                 435 atc taa tgc atc cta tat cca gta agt aga att atc tct tca tct ggg     1391
Ile     Cys Ile Leu Tyr Pro Val Ser Arg Ile Ile Ser Ser Ser Gly
                440                 445                 450
```

```
acc tgg aaa tcc tga aat aaa aaa gga taa tgc aat aaa cac agt tgc    1439
Thr Trp Lys Ser     Asn Lys Lys Gly     Cys Asn Lys His Ser Cys
        455                 460                         465 agg aaa gta tgt tag cta tat act atg aag tac tct tag ttt act tat    1487
Arg Lys Val Cys     Leu Tyr Thr Met Lys Tyr Ser     Phe Thr Tyr
            470                     475                     480 gtt gaa tgg ctt agc tat taa tac tca aat tga gtt aaa atg aaa att    1535
Val Glu Trp Leu Ser Tyr     Tyr Ser Asn     Val Lys Met Lys Ile
                485                         490 cct cct taa aaa atc aaa cgt aat atg tat tac att tca tgg tac att    1583
Pro Pro     Lys Ile Lys Arg Asn Met Tyr Tyr Ile Ser Trp Tyr Ile
495                         500                 505 agt agt tct ttg tat att gaa taa ata cta aat cac cta                1622
Ser Ser Ser Leu Tyr Ile Glu     Ile Leu Asn His Leu
510                 515                     520

<210> SEQ ID NO 66
<211> LENGTH: 61
<212> TYPE: PRT
<213> ORGANISM: Homo sapiens

<400> SEQUENCE: 66

Arg His Leu Gln Ala Arg Ala Ala Gly Leu Val Ser Thr Leu Glu Val
1               5                   10                  15

Ala Asp Thr Leu Cys Pro Arg Leu Thr Ser Ser Arg Trp His Arg Arg
            20                  25                  30

Leu Gln Gly Ala Ala Leu Lys Arg Ile Leu Gly Met Thr Glu Leu Arg
        35                  40                  45

Pro Ser Leu Leu Pro Gly Trp Ser Ser Val Ala Cys Ser
    50                  55                  60

<210> SEQ ID NO 67
<211> LENGTH: 208
<212> TYPE: PRT
<213> ORGANISM: Homo sapiens

<400> SEQUENCE: 67

Leu Thr Glu Ala Ser Asn Ser Trp Val Gln Val Thr Leu Pro Pro Gln
1               5                   10                  15

Pro His Glu Asp Leu Gly Leu Gln Asp Thr Ala Lys Ser Leu Thr Arg
            20                  25                  30

Met Lys Ile Lys Ala Glu Lys Asn Glu Gly Pro Ser Arg Ser Trp Trp
        35                  40                  45

Gln Leu His Trp Gly Asp Ile Ala Asn Asn Ser Gly Asn Met Lys Pro
    50                  55                  60

Pro Leu Val Phe Ile Val Cys Leu Leu Trp Leu Lys Asp Ser His
65                  70                  75                  80

Cys Ala Pro Thr Trp Lys Asp Lys Thr Ala Ile Ser Glu Asn Leu Lys
            85                  90                  95

Ser Phe Ser Glu Val Gly Glu Ile Asp Ala Asp Glu Val Lys Lys
                100                 105                 110

Ala Leu Thr Gly Ile Lys Gln Met Lys Ile Met Glu Arg Lys Glu
        115                 120                 125

Lys Glu His Thr Asn Leu Met Ser Thr Leu Lys Lys Cys Arg Glu Glu
    130                 135                 140

Lys Gln Glu Ala Leu Lys Leu Leu Asn Glu Val Gln Glu His Leu Glu
145                 150                 155                 160
```

```
Glu Glu Glu Arg Leu Cys Arg Glu Ser Leu Ala Asp Ser Trp Gly Glu
            165                 170                 175
Cys Arg Ser Cys Leu Glu Asn Asn Cys Met Arg Ile Tyr Thr Thr Cys
            180                 185                 190
Gln Pro Ser Trp Ser Ser Val Lys Asn Lys Leu Leu Thr Thr Glu Ala
            195                 200                 205
```

<210> SEQ ID NO 68
<211> LENGTH: 50
<212> TYPE: PRT
<213> ORGANISM: Homo sapiens

<400> SEQUENCE: 68

```
Phe Gln Arg Cys Tyr Leu Gly Arg Thr Glu Asp Cys Val Gly Asn Leu
1               5                   10                  15
Thr Arg Ile Cys Gln Asp Val Ser Asn Phe Met Lys Asn Ala Lys Asn
            20                  25                  30
Val Arg Leu Thr Tyr Leu Lys Thr Val Leu Met Tyr Leu Leu Cys Thr
        35                  40                  45
Gln Asn
    50
```

<210> SEQ ID NO 69
<211> LENGTH: 19
<212> TYPE: PRT
<213> ORGANISM: Homo sapiens

<400> SEQUENCE: 69

```
Thr Arg Arg Ser Gly Trp Ser Met Tyr Pro Ile Ser Ser Met Ala Arg
1               5                   10                  15
Phe Ser Arg
```

<210> SEQ ID NO 70
<211> LENGTH: 14
<212> TYPE: PRT
<213> ORGANISM: Homo sapiens

<400> SEQUENCE: 70

```
Pro Gly Ser Thr Trp Arg Thr Pro Pro Ile Trp Trp Arg Arg
1               5                   10
```

<210> SEQ ID NO 71
<211> LENGTH: 25
<212> TYPE: PRT
<213> ORGANISM: Homo sapiens

<400> SEQUENCE: 71

```
Glu Gly Asn Leu Ala Gly Cys Leu Asn Trp Gln Thr Arg Pro Gln Lys
1               5                   10                  15
Gln Arg Ser Ser Leu Ile Gln Tyr Arg
            20                  25
```

<210> SEQ ID NO 72
<211> LENGTH: 15
<212> TYPE: PRT
<213> ORGANISM: Homo sapiens

<400> SEQUENCE: 72

```
Phe Gln Gly Phe Met Lys Glu Ile Phe Pro Asn Lys Met Lys Gln
1               5                   10                  15
```

<210> SEQ ID NO 73
<211> LENGTH: 26
<212> TYPE: PRT
<213> ORGANISM: Homo sapiens

<400> SEQUENCE: 73

Ala Phe Cys Leu Pro Leu Ile Ser His Ser Arg Ser Leu Leu Lys Lys
 1               5                  10                  15

Val Leu Arg Val Leu Thr Ser Leu Ala Thr
            20                  25

<210> SEQ ID NO 74
<211> LENGTH: 18
<212> TYPE: PRT
<213> ORGANISM: Homo sapiens

<400> SEQUENCE: 74

Trp Gln Lys Leu Tyr Ser Ile Leu Arg Asn Ile Leu Lys Pro Gly Lys
 1               5                  10                  15

Lys Ile

<210> SEQ ID NO 75
<211> LENGTH: 18
<212> TYPE: PRT
<213> ORGANISM: Homo sapiens

<400> SEQUENCE: 75

Cys Ile Leu Tyr Pro Val Ser Arg Ile Ile Ser Ser Ser Gly Thr Trp
 1               5                  10                  15

Lys Ser

<210> SEQ ID NO 76
<211> LENGTH: 4
<212> TYPE: PRT
<213> ORGANISM: Homo sapiens

<400> SEQUENCE: 76

Asn Lys Lys Gly
 1

<210> SEQ ID NO 77
<211> LENGTH: 10
<212> TYPE: PRT
<213> ORGANISM: Homo sapiens

<400> SEQUENCE: 77

Cys Asn Lys His Ser Cys Arg Lys Val Cys
 1               5                  10

<210> SEQ ID NO 78
<211> LENGTH: 7
<212> TYPE: PRT
<213> ORGANISM: Homo sapiens

<400> SEQUENCE: 78

Leu Tyr Thr Met Lys Tyr Ser
 1               5

<210> SEQ ID NO 79
<211> LENGTH: 9
<212> TYPE: PRT
<213> ORGANISM: Homo sapiens

<400> SEQUENCE: 79

-continued

```
Phe Thr Tyr Val Glu Trp Leu Ser Tyr
 1               5

<210> SEQ ID NO 80
<211> LENGTH: 7
<212> TYPE: PRT
<213> ORGANISM: Homo sapiens

<400> SEQUENCE: 80

Val Lys Met Lys Ile Pro Pro
 1               5

<210> SEQ ID NO 81
<211> LENGTH: 20
<212> TYPE: PRT
<213> ORGANISM: Homo sapiens

<400> SEQUENCE: 81

Lys Ile Lys Arg Asn Met Tyr Tyr Ile Ser Trp Tyr Ile Ser Ser Ser
 1               5                  10                  15

Leu Tyr Ile Glu
            20

<210> SEQ ID NO 82
<211> LENGTH: 5
<212> TYPE: PRT
<213> ORGANISM: Homo sapiens

<400> SEQUENCE: 82

Ile Leu Asn His Leu
 1               5

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
agttgcgtcc ctctctgttg                                                    20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
gcttcatgtt cccgctgtta                                                    20
```